United States Patent [19]

Tsushima et al.

[11] Patent Number: 4,962,113
[45] Date of Patent: Oct. 9, 1990

[54] PYRIDINIUM DERIVATIVES, THEIR PRODUCTION AND USE

[75] Inventors: Susumu Tsushima, Osaka; Muneo Takatani; Kohei Nishikawa, both of Kyoto, all of Japan

[73] Assignee: Takeda Chemical Industries, Ltd, Osaka, Japan

[21] Appl. No.: 224,352

[22] Filed: Jul. 26, 1988

[30] Foreign Application Priority Data

Jul. 31, 1987 [JP] Japan ................... 62-193479
Jun. 6, 1988 [JP] Japan ................... 63-138908

[51] Int. Cl.$^5$ ................... A61K 31/47; C07D 401/12
[52] U.S. Cl. ................... 514/307; 514/314; 540/471; 540/575; 544/131; 544/310; 544/360; 544/365; 546/146; 546/147; 546/148; 546/285; 546/286; 546/287; 546/288; 546/289; 546/296; 546/297; 546/298; 546/300; 546/301; 546/302; 546/303; 546/304; 546/306; 546/307; 546/308; 546/309; 546/310; 546/312
[58] Field of Search ................ 546/146, 147, 148, 156; 514/307, 314

[56] References Cited

FOREIGN PATENT DOCUMENTS 0147768 7/1985 European Pat. Off. .
0157609 10/1985 European Pat. Off. .
0238202 9/1987 European Pat. Off. .

*Primary Examiner*—Richard L. Raymond
*Assistant Examiner*—James H. Turnipseed
*Attorney, Agent, or Firm*—Wegner & Bretschneider

[57] ABSTRACT

Novel pyridinium derivatives represented by the formula (I):

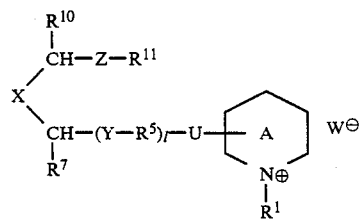

wherein

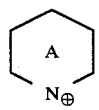

is an optionally substituted pyridinium ring;
$R^1$ is a lower alkyl group or aralkyl group;
$R^7$ and $R^{10}$ are independently hydrogen, a lower alkyl group, aryl group or aralkyl group;
$l$ is 0 or 1;
$R^5$ is a phenylene group or an alkylene group which may be substituted;
$R^{11}$ is an alkyl group or aryl group;
X is a group of the formula: $-CH_2OCH_2-$ or a group of the formula:

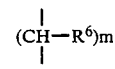

wherein $R^6$ is hydrogen, a lower alkyl or a lower alkoxy, and m is an integer of 0 to 3;
U is a group of the formula:

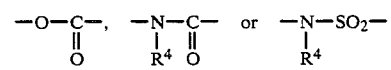

wherein
$R^4$ is hydrogen, a lower alkyl group, aryl group or aralkyl group;
Y and Z are independently a divalent chain group consisting of one to six members which is selected from the class consisting of groups of the formulae:

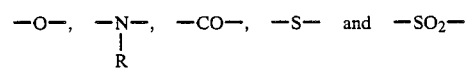

wherein R is hydrogen, a lower alkyl group, acyl group or aryl group and at least one of which is a group of the formula:

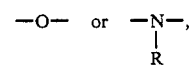

with the proviso that R may be the same or different from each other, or may form a ring together when two or more groups of the formula:

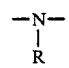

are present, that R may be bonded to $R^4$ when Y contains a group of the formula:

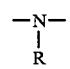

and that R may be bonded to $R^{11}$ when Z contains a group of the formula:

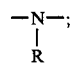

and $W^\ominus$ is a counter anion;
are useful as a platelet activating factor antagonist.

24 Claims, No Drawings

PYRIDINIUM DERIVATIVES, THEIR PRODUCTION AND USE

BACKGROUND OF THE INVENTION

This invention relates to pyridinium derivatives useful as medicines. More specifically, the present invention relates to compounds useful as antagonists of the platelet activating factor (PAF), the compounds being represented by the following formula:

$$X \begin{cases} CH-Z-R^{11} \\ | \\ R^{10} \\ \\ CH-(Y-R^5)_l-U \end{cases} \underset{\underset{R^1}{N_\oplus}}{\overset{A}{\bigcirc}} \quad W^\ominus \quad (I)$$

wherein $\underset{\underset{R^1}{N_\oplus}}{\overset{A}{\bigcirc}}$ stands for an optionally substituted pyridinium ring; $R^1$ stands for a lower alkyl group or aralkyl group; $R^7$ and $R^{10}$ each stand for hydrogen, a lower alkyl group, aryl group or aralkyl group; l denotes 0 or 1; $R^5$ stands for a phenylene group or an alkylene group which may be substituted; $R^{11}$ stands for an alkyl group or an aryl group; X stands for a group of the formula —CH$_2$OCH$_2$— or a group of the formula $$(CH-R^6)_m$$

(wherein $R^6$ stands for hydrogen, a lower alkyl or a lower alkoxy, and m denotes an integer of 0 to 3); U stands for a group of the formula $$-O-\underset{O}{\overset{\parallel}{C}}-, \quad -\underset{R^4}{\overset{|}{N}}-\underset{O}{\overset{\parallel}{C}}- \quad \text{or} \quad -\underset{R^4}{\overset{|}{N}}-SO_2-$$

(wherein $R^4$ stands for hydrogen, a lower alkyl group, aryl group or aralkyl group); Y and Z each stand for a divalent chain group consisting of one to six members which are selected from the class consisting of groups of the formulae —O—, $$-\underset{R}{\overset{|}{N}}-,$$

—CO—, —S— and —SO$_2$— (wherein R stands for hydrogen, a lower alkyl group, acyl group or aryl group) and at least one of which is a group of the formula —O— or $$-\underset{R}{\overset{|}{N}}-,$$

with the proviso that the R groups may be the same or different from each other, or may form a ring together when two or more groups of the formula $$-\underset{R}{\overset{|}{N}}-$$

are contained, that R may be bonded to $R^4$ when Y contains a group of the formula $$-\underset{R}{\overset{|}{N}}-$$

and that R may be bonded to $R^{11}$ when Z contains a group of the formula $$-\underset{R}{\overset{|}{N}}-;$$

and $W^\ominus$ stands for a counter anion.

PAF has a phospholipid structure and is a chemical transmitter existing in a living body. It has been made clear that PAF is, in a living body, closely concerned with allergy, anaphylaxis, inflammation, etc. and it is also known that PAF has a strong hypotensive activity and platelet agglutinating activity. On administering PAF to an animal, the animal may, in some cases, be killed from shock. Symptoms caused by the shock from PAF have much resemblance to those caused by the shock from endotoxin, and it has been demonstrated that PAF is concerned with the endotoxin shock.

On the other hand, while a variety of compounds having PAF-antagonistic activity are known, very few of them are satisfactory in PAF-antagonistic activity in a living body. And, even when the PAF-antagonistic activity in a living body is satisfactory, not a few of those compounds have some restrictions in the administration method.

DETAILED DESCRIPTION

The present invention is to provide pyridinium compounds represented by the above-mentioned formula(I).

In the formula(I), the group $$\overset{4}{\underset{2\underset{\underset{1}{N_\oplus}}{\bigcirc}6}{\overset{3\overset{}{\bigcirc}5}{A}}}$$

shows an optionally substituted pyridinium ring. To the 1-position of the pyridinium ring is bonded the group $R^1$, and to the 2- to 6- positions is attached one side chain represented by the following formula:

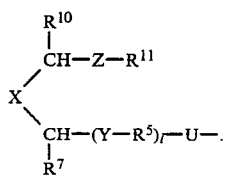

The pyridinium ring may have, at a position other than its 1-position and the position to which the side chain is bonded, 1 to 4(preferably 1 to 2) substituents such as a halogeno group, a lower alkyl group, a lower alkoxy group, a nitro group, a cyano group, a lower alkoxycarbonyl group, a carbamoyl group, a lower alkyl carbamoyl group, etc. or may have an aromatic ring bonded thereto. The side chain is preferably bonded to the 2- to 4-position, and the substituents are preferably bonded to one or two of the 3- to 5-position of the pyridinium ring.

Examples of the lower alkyl group as $R^1$, $R^4$, $R^6$, $R^7$, $R^{10}$ or a substituent at the pyridinium ring include straight-chain or branched alkyl groups having 1 to 6 carbon atoms, such as methyl, ethyl, propyl, isopropyl, butyl, isobutyl, sec-butyl, tert-butyl, pentyl hexyl, etc. The lower alkyl groups may optionally have an unsaturated bond and are exemplified by lower alkenyl groups having 2 to 6 carbon atoms, such as vinyl, allyl, 2-butenyl, 3-butenyl, etc.

Examples of the lower alkoxy group as $R^6$ or a substitutent at the pyridinium ring include straight-chain or branched alkoxy groups having 1 to 6 carbon atoms, such as methoxy, ethoxy, propoxy, isopropoxy, butoxy, pentoxy, etc. The lower alkoxy group as $R^6$ may have substituents, which may be combined together to form a 5- to 7- membered hetero ring (e.g., imidazolyl, oxazolyl, isoxazolyl, thiazolyl, etc.), and said hetero ring may have substituents such as a lower alkyl group, acyl group, aryl group, aralkyl group, etc.

Examples of the halogeno group as a substituent at the pyridinium ring include fluoro, bromo, chloro and iodo.

Examples of the lower alkoxycarbonyl group as a substituent at the pyridinium ring include alkoxycarbonyl groups whose alkoxy moiety has about 1 to about 6 carbon atoms, such as methoxycarbonyl ethoxycarbonyl, propoxycarbonyl, butoxycarbonyl, etc.

Examples of the lower alkylcarbamoyl group as a substituent at the pyridinium ring include N-alkyl carbamoyl groups whose alkyl moiety has about 1 to about 6 carbon atoms, such as methyl carbamoyl, ethyl carbamoyl, propyl carbamoyl, butyl carbamoyl, etc., and N,N-dialkyl carbamoyl groups, the carbon number of each alkyl moiety being about 1 to about 6, such as dimethyl carbamoyl, diethyl carbamoyl, dibutyl carbamoyl, methyl ethy carbamoyl, etc.

Examples of the aryl group as $R^4$, $R^7$ or $R^{10}$ include aromatic monocyclic, dicyclic or tricyclic hydrocarbon residue, such as phenyl, 1-naphthyl, 2-naphthyl, phenanthryl, anthryl, etc., or aromatic monocyclic or dicyclic heterocyclic ring such as thienyl, furyl, benzothienyl, benzofuranyl, etc. The aryl group may have 1 to 4(preferably 1 to 2) substituents such as a halogeno group, a lower alkyl group, a lower alkoxy group, a nitro group, a cyano group, an oxo group, a hydroxy group, an amino group, a lower alkoxy carbonyl group, a carbamoyl group, a lower alkyl carbamoyl group, etc. Examples of the lower alkyl group include alkyl groups whose carbon number is about 1 to about 6, and the said lower alkyl groups may have an unsaturated bond. Examples of the lower alkyl groups include lower alkenyl groups whose carbon number ranges from about 2 to about 6. Examples of the alkyl groups whose carbon number ranges from about 1 to about 6 and of the lower alkenyl groups whose carbon number ranges from about 2 to about 6 include, as practical ones, lower alkyl groups mentioned as the substituents at the abovementioned pyridinium ring. As the lower alkoxy group, mention is made of alkoxy groups whose carbon number ranges from about 1 to about 6. As the lower alkoxycarbonyl group, mention is made of alkoxycarbonyl group, the carbon number of the alkoxy moiety of which ranges from about 1 to about 6. As the lower alkylcarbamoyl group, mention is made of N-alkylcarbamoyl group, the carbon number of the alkyl moiety of which ranges from about 1 to about 6, and of N,N-dialkylcarbamoyl, the carbon number of each alkyl moiety of which ranges from about 1 to about 6. Practical examples of these groups include groups like the lower alkoxy groups, lower alkoxycarbonyl groups and lower alkylcarbamoyl groups set forth as substituents of the above-mentioned pyridinium ring. As the aryl group having an oxo group, mentioned is made of, for example, benzoquinonyl, naphthoquinonyl, anthraquinonyl, etc.

Examples of the aralkyl groups as $R^1$, $R^4$, $R^7$ and $R^{10}$ include the phenyl-lower alkyl group, the carbon number of the alkyl moiety of which ranges from about 1 to about 6, and naphthyl-lower alkyl group, the carbon number of the alkyl moiety of which ranges from about 1 to about 6. The phenyl moiety of phenyl-lower alkyl groups and the naphthyl moiety of naphthyl-lower alkyl groups may have 1 to 4 (preferably 1 or 2) substituents such as a halogeno group, a lower alkyl group, a lower alkoxy group, nitro group, cyano group, oxo group, hydroxyl group, amino group, a lower alkoxycarbonyl group, carbamoyl group, a lower alkylcarbamoyl group, etc. As these substituents, mention is made of groups as the above-mentioned substituents at the aryl groups.

Examples of the phenylene groups as $R^5$ include o-phenylene(1,2-phenylene), m-phenylene(1,3-phenylene) and p-phenyllene(1,4-phenylene).

Examples of the alkylene groups as $R^5$ include alkylene groups whose carbon number ranges from about 1 to about 6, such as methylene, ethylene, trimethylene, tetramethylene, pentamethylene, hexamethylene, etc. Said alkylene groups may have substituents such as lower alkyl groups whose carbon number ranges about 1 to 5, etc.

The alkyl groups shown by $R^{11}$ are exemplified by straightchain or branched alkyl groups whose carbon number ranges from about 1 to about 30 (preferably $C_{1-18}$), such as methyl, ethyl, propyl, butyl, pentyl, hexyl, heptyl, octyl, nonyl, decyl, undecyl, tridecyl, tetradecyl, pentadecyl, hexadecyl, heptadecyl, octadecyl, nonadecyl, eicosanyl, heneicosanyl, docosanyl, tricosanyl, tetracosanyl, pentacosanyl, hexacosanyl, heptacosanyl, octacosanyl, nonacosanyl, triacontanyl, farnesyl, dihydrophytyl, etc.; cycloalkyl groups whose carbon number ranges from about 3 to about 8, such as cyclopropyl, cyclobutyl, cyclopentyl, cycloheptyl, cyclooctyl, etc.; bicycloalkyl groups whose carbon number ranges from about 7 to about 12, such as norbornyl, bicyclo[2,2,2]octyl, bicyclo[3,3,1]nonyl, bicyclo[3,3,0]octyl, etc.; tricycloalkyl groups whose carbon number ranges from about 7 to about 12, such as adamantyl, etc.; bicyclic hydrocarbon residues formed by condensation of 5- to 8-membered ring, such as perhydropentalenyl, perhydroindenyl, perhydroazulenyl, perhydrocyclopentacyclooctenyl, perhydronaphthyl, perhydrobenzocycloheptenyl, perhydrobenzocyclooctenyl, perhydroheptalenyl, perhydrocycloheptacyclooctenyl, etc.; tricyclic hydrocarbon residues formed by condensation of 5- to 8-membered ring, such as perhydroindacenyl(asymetric or symetric) perhydroacenaphthylenyl, perhydrophenanthryl, perhydroanthryl, etc. The above-mentioned alkyl groups may optionally have an unsaturated bond, and the unsaturated alkyl groups are exemplified by alkenyl groups whose carbon number ranges from about 2 to about 30, such as vinyl, allyl, 9-octadecenyl, etc.; cycloalkenyl groups whose carbon number ranges from about 5 to about 8, such as cyclopentenyl, cyclohexenyl, etc.; bicycloalkenyl groups whose carbon number ranges from about 7 to about 12, such as bicyclo[2,2,2]-oct-2-enyl, etc.; tricycloalkenyl groups whose carbon number ranges from about 7 to about 12; bicyclic hydrocarbon residues formed by condensation of a benzene ring with 5- to 8-membered ring, such as indanyl(1-indanyl, 2-indanyl, etc.), indenyl(1H-inden-1-yl, 1H-inden-2-yl, 1H-inden-3-yl, etc.), dihydronaphthyl(1,2-dihydro-1-naphthyl, 1,2-dihydro-2-naphthyl, etc.), tetrahydronaphthyl(5,6,7,8-tetrahydro-1-napthyl, 5,6,7,8-tetrahydro-2-naphthyl, etc.), 5H-benzocycloheptenyl(5H-5-benzocycloheptenyl, 5H-8-benzocycloheptenyl, etc.), dihydro-5H-benzocycloheptenyl(6,7-dihydro-5H-8-benzocycloheptenyl, etc., tetrahydrobenzocyclooctenyl (5,6,7,8-tetrahydro-9-benzocyclooctenyl, etc.); tricyclic hydrocarbon residue formed by condensation of two benzene ring with a 5- to 8-membered ring, such as acenaphthenyl(1-acenaphthenyl, etc.), tetrahydroanthryl(1,2,3,4-tetrahydro-1-anthryl, etc.

The above-mentioned alkyl groups whose carbon number ranges from about 1 to about 30 and alkenyl groups whose carbon number ranges from about 2 to about 30 may have about one to about four (preferably one or two) substituents which are exemplified by a cycloalkyl group, the carbon number of which ranges from 3 to about 8, phenyl group, naphthyl group, halogeno or a lower alkoxy group, whose carbon number ranges from about one to about six, etc. The phenyl groups as the substituents on the alkyl groups and the alkenyl groups may have about one to about four substituents which are exemplified by a lower alkyl group whose carbon number ranges from 1 to about 6, a lower alkoxy group whose carbon number ranges from about 1 to about 6, hydroxy group, nitro group, halogeno group, etc.

Cycloalkyl group, bicycloalkyl group, tricycloalkyl group, bicyclic hydrocarbon residue, tricyclic hydrocarbon residue as well as these groups having an unsaturated bond, which are included in the alkyl groups shown by $R^{11}$, may have about 1 to about 4 (preferably 1 or 2) substituents such as a lower alkyl group, a halogeno lower alkyl group, a hydroxy lower alkyl group, an acyloxy lower alkyl group, a lower alkoxy lower alkyl group, a lower alkoxy, a halogeno lower alkoxy group, a lower alkoxycarbonyl lower alkoxy group, a lower alkenyloxy group, aralkyloxy group, a lower alkoxy lower alkoxy group, a lower alkoxycarbonyl group, carboxyl group, carbamoyl group, an N,N-di-lower alkylcarbamoyl group, an N-lower alkyl carbamoyl group, halogeno group, cyano group, nitro group, hydroxyl group, acyloxy group, amino group, a lower alkylsulfonylamino group, acylamino group, a lower alkoxycarbonylamino group, acyl group, mercapto group, a lower alkylthio group, a lower alkyl sulfinyl group, a lower alkylsulfonyl group, oxo group, etc. When they have two or more substituents, the kinds of these substituents may be the same or different from one another.

Lower alkyl groups as the above-mentioned substituents are exemplified by alkyl groups whose carbon number ranges from about 1 to about 6, such as methyl, ethyl, propyl, isopropyl, butyl, isobutyl, sec-butyl, tert-butyl, etc. As the halogeno lower alkyl group, mention is made of alkyl groups whose carbon number ranges from about 1 to about 6, which are substituted with 1 to 3 halogeno groups, such as trifluoromethyl, fluoromethyl, chloromethyl, chloroethyl, fluoroethyl, etc. As the hydroxy lower alkyl group, mention is made of hydroxy alkyl groups whose carbon number ranges from about 1 to about 6, such as hydroxymethyl, hydroxyethyl, hydroxypropyl, hydroxybutyl, etc. As the acyloxy lower alkyl group, mention is made of alkyl groups whose carbon number ranges from about 1 to about 6, which are substituted with, for example, a lower alkanoyloxy group whose carbon number ranges from about 2 to about 6 or a benzoyloxy group such as acetoxy ethyl, benzoyloxyethyl, etc. As the lower alkoxylower alkyl group, mention is made of alkyl groups whose carbon number ranges from about 1 to about 6, which are substituted with, for example, an alkoxy group whose carbon number ranges from about 1 to about 6 such as methoxyethyl, ethoxyethyl, propoxyethyl, butoxyethyl, methoxypropyl, methoxybutyl, ethoxypropyl, ethoxybutyl, etc. As the lower alkoxy group, mention is made of alkoxy groups whose carbon number ranges from about 1 to about 6, such as methoxy, ethoxy, propoxy, isopropoxy, butoxy, isobutoxy, sec-butoxy, tert-butoxy, etc. As the halogeno lower alkoxy group, mention is made of alkoxy groups whose carbon number ranges from about 1 to about 6, which are substituted with 1 to 3 halogeno groups such as chloroethoxy, fluoroethoxy, difluoroethoxy, trifluoroethoxy, chloropropoxy, chlorobutoxy, etc. As the lower alkoxy carbonyl-lower alkoxy group, mention is made of alkoxy groups whose carbon number ranges from about 1 to about 6, which are substituted with an alkoxycarbonyl group, the carbon number of the alkoxy moiety of which ranges from about 1 to about 6, such as methoxycarbonylmethoxy, ethoxycarbonylmethoxy, butoxycarbonylmethoxy, methoxycarbonylpropoxy, ethoxycarbonylethoxy, etc. Examples of the lower alkenyloxy group include alkenyloxy groups whose carbon number ranges from about 2 to about 6, such as vinyloxy, allyloxy, butenyloxy, etc. As the aralkyloxy group, mention is made of phenyl lower alkyloxy groups, the carbon number of the lower alkyl moiety of which ranges from about 1 to about 6, such as benzyloxy, phenethyloxy, 3-phenylpropyloxy, α-methylphenethyloxy, α-methylbenzyloxy, α-ethylbenzyloxy, β-ethylphenethyloxy, β-methylphenethyloxy, etc. As the lower alkoxy-lower alkoxy group, mention is made of alkoxy groups whose carbon number ranges from about 1 to about 6, which are substituted with, for example, an alkoxy group whose carbon number ranges from about 1 to about 6, such as ethoxymethoxy, methoxyethoxy, butoxyethoxy, ethoxypropoxy, etc. Examples of the lower alkoxycarbonyl group include alkoxycarbonyl groups, the carbon number of the alkoxy moiety of which ranges from about 1 to about 6, such as methoxycarbonyl, ethoxycarbonyl, propoxycarbonyl, butoxycarbonyl, etc. As the N,N-di-lower alkylcarbamoyl group, mention is made of N,N-dialkylcarbamoyl groups, the carbon number of each alkyl moiety of which ranges from about 1 to about 6, such as N,N-dimethylcarbamoyl, N,N-diethylcarbamoyl, N,N-dipropylcarbamoyl, N,N-dibutylcarbamoyl, N-ethyl-N-methylcarbamoyl, etc., and groups forming 5- or 6-membered ring structure (e.g. N-pyrrolidinylcarbonyl, piperidinocarbonyl) by combining dialkyl moieties together. As the N-lower alkylcarbamoyl group, mention is made of N-alkylcarbamoyl groups, the carbon number of the alkyl moiety of which ranges from about 1 to about 6, such as N-methylcarbamoyl, N-ethylcarbamoyl, N-propylcarbamoyl, N-butylcarbamoyl, etc. As the halogeno group, mention is made of halogeno groups such as chloro, fluoro, bromo, iodo, etc. As the acyloxy group, mention is made of alkanoyloxy groups, the carbon number of which ranges from about 2 to about 6, such as the acetoxy, propanoyloxy, butyryloxy, pivaloyloxy. etc., and benzoyloxy group. As the lower alkylsulfonylamino group, mention is made of alkylsulfonylamino groups, the carbon number of which ranges from about 1 to about 6, such as methanesulfonylamino, ethanesulfonylamino, etc. Examples of the acylamino group include alkanoylamino groups, whose carbon number ranges from about 2 to about 6, such as acetamido, propanoylamino, butyrylamino, pivaloylamino, etc. and benzamido group. As the lower alkoxycarbonylamino group, mention is made of alkoxycarbonylamino groups, the carbon number of the alkoxy moiety of which ranges from about 1 to about 6, such as methoxycarbonylamino, ethoxycarbonylamino, propoxycarbonylamino, butoxycarbonylamino, etc. As the acyl group, mention is made of alkanoyl groups, the carbon number of which ranges from about 2 to about 6, such as acetyl, propanoyl, butyryl, pivaloyl, etc., and benzoyl group. As the lower alkylthio group, mention is made of alkylthio groups, the carbon number of which ranges from about 1 to about 6, such as methylthio, ethylthio, propylthio, butylthio, etc. As the lower alkylsulfinyl group, mention is made of alkylsulfinyl groups, whose carbon number ranges form about 1 to about 6, such as methylsulfinyl, ethylsulfinyl, propylsulfinyl, butylsulfinyl, etc. As the lower alkylsulfonyl group, mention is made of alkylsulfonyl groups, the carbon number of which ranges from about 1 to about 6, such as methylsulfonyl, ethylsulfonyl, propylsulfonyl, butylsulfonyl, etc.

As the aryl group shown by $R^{11}$, mention is made of, for example, phenyl group, aromatic condensed di- or tri-cyclic hydrocarbon residue formed by 5- to 8-membered ring, such as naphthyl(1-naphthyl, 2-naphthyl), azulenyl, heptalenyl, indacenyl(as,s), acenaphthylenyl, phenanthryl, anthryl, banzocyclooctenyl, etc., hetero monocycle such as thienyl, furanyl, etc., hetero dicycles such as benzothienyl, isobenzothienyl, benzofuranyl, isobenzofuranyl, benzoxepinyl, benzothiepinyl. etc. The above-mentioned aryl groups may be partially saturated, and the partially saturated aryl groups are exemplified by indanyl(4-indanyl, 5-indanyl, etc.), indenyl(1H-inden-4-yl, 1H-inden-5-yl, etc.), dihydronaphthyl (5,6-dihydro-1-naphthyl, 5,6-dihydro-2-naphthyl, 7,8-dihydro-1-naphthyl, 7,8-dihydro-2-naphthyl, etc.), tetrahydronaphthyl (5,6,7,8-tetrahydro-1-naphthyl, 5,6,7,8-tetrahydro-2-naphthyl, etc.), 1,2,3,4-tetrahydro-1-quinolyl, 1,2,3,4-tetrahydro-2-isoquinolyl, etc.

The aryl group and the partially saturated aryl groups may have about 1 to about 4 substituents (preferably 1 or 2), such as a lower alkyl group, a halogeno lower alkyl group, a hydroxy lower alkyl group, an acyloxy lower alkyl group, a lower alkoxy lower alkyl group, a lower alkoxy group, a halogeno alkoxy group, a halogeno lower alkoxy group, a lower alkoxy carbonyl lower alkoxy group, a lower alkenyloxy group, an aralkyloxy group, a lower alkoxy lower alkoxy group, a lower alkoxycarbonyl, carboxyl group, carbamoyl group, an N,N-di-lower alkylcarbamoyl group, N-lower alkylcarbamoyl group. halogeno group, cyano group, nitro group, hydroxyl group, acyloxy group, amino group, a lower alkylsulfonylamino group, acylamino group, a lower alkoxycarbonylamino group, acyl group, mercapto group, a lower alkylthio group, a lower alkylsulfinyl group, a lower alkylsulfonyl group, oxo group, etc. When the aryl group and the partially saturated aryl groups have two or more substituents, the kinds of these substituents may be the same or different from one another. Practical examples of the above substituents include those shown by $R^{11}$, such as a cycloalkyl group, bicycloalkyl group, tricycloalkyl group, a bicyclic hydrocarbon residue, a tricyclic hydrocarbon residue or groups as the substituents at those groups having unsaturated bond.

A divalent chain group shown by Y includes divalent functional gorups shown by the following formulae:

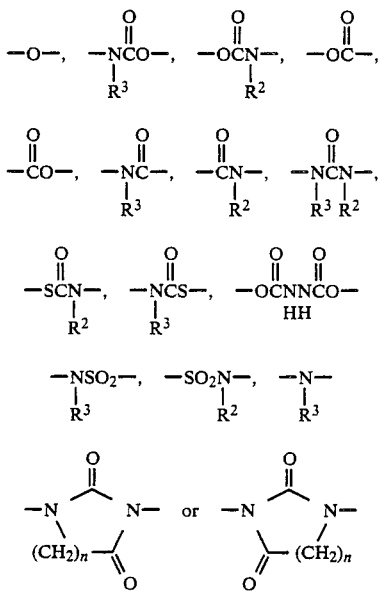

wherein n denotes 1 or 2, $R^2$ and $R^3$ each stand for hydrogen, a lower alkyl group, acyl group or aryl group, and $R^3$ may be combined with $R^4$ to form a ring.

A divalent chain group shown by Z includes divalent functional groups are shown by the following formulae:

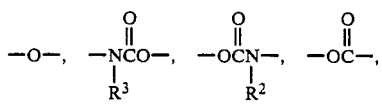

-continued

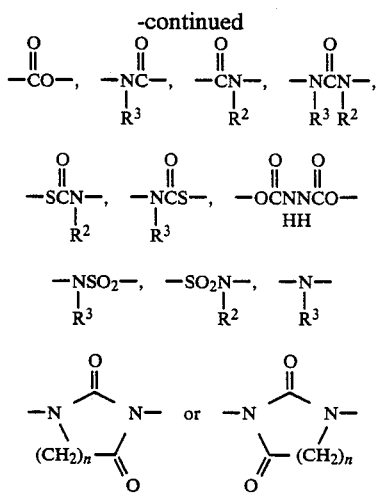

wherein n denotes 1 or 2, $R^8$ and $R^9$ each stand for hydrogen, a lower alkyl group, acyl group or aryl group, and $R^9$ may be combined with $R^{11}$ to form a ring.

Examples of the lower alkyl groups shown by $R^1$, $R^2$, $R^3$, $R^8$ or $R^9$ include straight-chain or branched alkyl groups having about 1 to about 6 carbon atoms, such as methyl, ethyl, propyl, butyl, isobutyl, sec-butyl, tert-butyl, pentyl, hexyl, etc. The lower alkyl groups may have unsaturated bond, and the unsaturated lower alkyl groups are exemplified by lower alkenyl groups whose carbon number ranges form about 2 to about 6, such as vinyl, allyl, 2-butenyl, 3-butenyl, etc.

Examples of the acyl group shown by R, $R^2$, $R^3$, $R^8$ or $R^9$ include lower alkanoyl groups, the carbon number of which ranges from about 2 to about 6, such as acetyl, propanoyl, butyryl, pyvaloyl, etc. and aromatic carbonyl groups (e.g. benzoyl, etc.).

Examples of the aryl group shown by $R^1$, $R^2$, $R^3$, $R^8$ or $R^9$ include aromatic monocyclic, dicyclic or tricyclic hydrocarbon residues, such as phenyl, 1-naphthyl, 2-naphthyl, phenanthryl, anthryl, etc., and aromatic monocyclic or dicyclic hetro-ring, such as thienyl, furyl, benzothienyl, benzofuranyl, etc. The aryl group may have 1 to 4 substituents (preferably 1 or 2) such as a halogeno group, a lower alkyl group, a lower alkoxy group, nitro group, cyano group, oxo group, hydroxyl group, amino group, a lower alkoxycarbonyl group, carbamoyl group, a lower alkylcarbamoyl group, etc. As the halogeno group, mention is made of fluoro, bromo, chloro, iodo, etc. As the lower alkyl group, mention is made of alkyl groups whose carbon number ranges from about 1 to about 6, and the lower alkyl groups may optionally have an unsaturated bond. As the lower alkyl group having an unsaturated bond, mention is made of lower alkenyl groups whose carbon number ranges from about 2 to about 6. Practical examples of the alkyl groups whose carbon number ranges from about 1 to about 6 and of the alkenyl groups whose carbon number ranges from about 2 to about 6 include groups similar to lower alkyl groups as the above-mentioned substituents at pyridinium ring. As the lower alkoxy group, mention is made of alkoxy groups whose carbon number ranges from about 1 to about 6. As the lower alkoxycarbonyl group, mention is made of alkoxycarbonyl groups, the carbon number of the alkoxy moiety of which ranges from about 1 to about 6. As the lower alkylcarbamoyl group, mention is made of N-alkylcarbamoyl groups, the carbon number of the alkyl moiety of which ranges from about 1 to about 6, and of N,N-dialkylcarbamoyl groups, the carbon number of each alkyl moiety of which ranges from about 1 to about 6. Practical examples of these groups include groups such as a lower alkoxy group, a lower alkoxycarbonyl group and a lower alkylcarbamoyl group used as the above-mentioned substituents at pyridinium ring. When U is a group of the formula

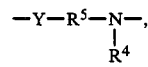

$R^2$ and $R^4$ may be combined to to form a ring. Specifically, as

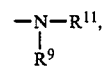

mention is made of groups shown by the following formulae:

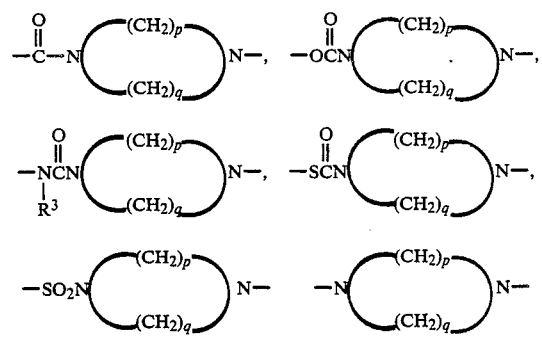

wherein p and q respectively stand for 2 or 3 $R^9$ and $R^{11}$ may be combined to form a ring. As the ring represented by the formula

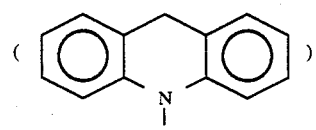

mention is made of, for example, a 3- to 8-membered monocyclic hetero-ring, such as 1-aziridinyl, 1-azetidinyl, piperidino, perhydro-1-azepinyl, perhydro-1-azocinyl, morpholino, thiomorpholino, 1-piperazinyl, 3-thiazolidinyl, etc., condensed bicyclic or cross-linked bicyclic hetero-ring, such as 1-indolyl, perhydro-1-indolyl, 2-isoindolyl, perhydro-2-isoindolyl, 1,2,3,4-tetrahydro-1-quinolyl, 1,2,3,4-tetrahydro-2-isoquinolyl, perhydro-1-quinolyl, perhydro-2-isoquinolyl, 3-azabicyclo[3,2,2]non-3-yl, etc., and condensed tricyclic hetero-ring such as 9-carbazolyl, 10-acridanyl ( [structure] )

10,11-dihydro-5H-5-dibenz[b,f]azepinyl, 5,6,11,12-tetrahydro-5-dibenz[b,f]azocinyl, 1,2,3,4-tetrahydro-9-carbazolyl, 10-phenoxazinyl, 10-phenothiazinyl, etc.

The above-mentioned hetro ring may have about one to about four (preferably one or two) substituents such as, among others, a lower alkyl group, a halogeno lower alkyl group, a hydroxy lower alkyl group, an acyloxy lower alkyl group, a lower alkoxy lower alkyl group, a lower alkoxy group, a halogeno lower alkoxy group, a lower alkoxy carbonyl-lower alkoxy group, a lower alkenyloxy group, aralkyloxy group, a lower alkoxy-lower alkoxy group, a lower alkoxycarbonyl group, carboxyl group, carbamoyl group, an N,N-di-lower alkylcarbamoyl group, an N-lower alkyl carbamoyl group, halogeno group, cyano group, nitro group, hydroxyl group, acyloxy group, amino group, a lower alkylsulfonylamino group, acylamino group, a lower alkoxycarbonylamino group, acyl group, mercapto group, a lower alkylthio group, a lower alkylsulfinyl group, a lower alkylsulfonyl group and oxo group. When the hetro ring has two or more substituents, the kinds of these substituents may be the same or different from one another.

Lower alkyl groups as the above-mentioned substituents are exemplified by alkyl groups whose carbon number ranges from 1 to about 6, such as methyl, ethyl, propyl, isopropyl, butyl, isobutyl, sec-butyl, tert-butyl, etc. As the halogeno lower alkyl group, mention is made of alkyl groups whose carbon number ranges from about 1 to about 6, which are substituted with 1 to 3 halogeno groups such as trifluoromethyl, fluoromethyl, chloromethyl, chloroethyl, fluoroethyl, etc. As the hydroxy lower alkyl group, mention is made of hydroxy alkyl groups whose carbon number ranges from about 1 to about 6, such as hydroxymethyl, hydroxyethyl, hydroxypropyl, hydroxybutyl, etc. As the acyloxy lower alkyl group, mention is made of alkyl groups whose carbon number ranges from about 1 to about 6, which are substituted with, for example, a lower alkanoyloxy group whose carbon number ranges from about 2 to about 6, or a benzoyloxy group such as acetoxyethyl, benzoyloxyethyl, etc. As the lower alkoxy-lower alkyl group, mention is made of alkyl groups whose carbon number ranges from about 1 to about 6, which are substituted with, for example, an alkoxy group whose carbon number ranges from about 1 to about 6 such as methoxyethyl, ethoxyethyl, propoxyethyl, butoxyethyl, methoxypropyl, methoxybutyl, ethoxypropyl, ethoxybutyl, etc. As the lower alkoxy group, mention is made of alkoxy groups whose carbon number ranges from about 1 to about 6 such as methoxy, ethoxy, propoxy, isopropoxy, butoxy, isobutoxy, sec-butoxy, tertbutoxy, etc. As the halogeno lower alkoxy group, mention is made of alkoxy groups whose carbon number ranges from about 1 to about 6, which are substituted with 1 to 3 halogeno groups such as chloroethoxy, fluoroethoxy, difluoroethoxy, trifluoroethoxy, chloropropoxy, chlorobutoxy, etc. As the lower alkoxy carbonyl-lower alkoxy group, mention is made of alkoxy groups whose carbon number ranges from about 1 to about 6, which are substituted with an alkoxycarbonyl group, the carbon number of the alkoxy moiety of which ranges from about 1 to about 6, such as methoxycarbonylmethoxy, ethoxycarbonylmethoxy, butoxycarbonylmethoxy, methoxycarbonylpropoxy, ethoxycarbonylethoxy, etc. Examples of the lower alkenyloxy group include alkenyloxy groups whose carbon number ranges from about 2 to about 6, such as vinyloxy, allyloxy, butenyloxy, etc. As the aralkyloxy group, mention is made of phenyl lower alkyloxy groups, the carbon number of the lower alkyl moiety of of which ranges from about 1 to about 6, such as benzyloxy, phenethyloxy, 3-phenylpropyloxy, α-methylphenethyloxy, α-methylbenzyloxy, α-ethylbenzyloxy, β-ethylphenethyloxy, β-methylphenethyloxy, etc. As the lower alkoxy-lower alkoxy group, mention is made of alkoxy groups whose carbon number ranges from about 1 to about 6, which are substituted with, for example, an alkoxy group whose carbon number ranges from 1 to about 6, such as ethoxymethoxy, methoxyethoxy, butoxyethoxy, ethoxypropoxy. Examples of the lower alkoxycarbonyl group include alkoxycarbonyl groups, the carbon number of the alkoxy moiety of which ranges from 1 to about 6, such as methoxycarbonyl, ethoxycarbonyl, propoxy carbonyl, butoxycarbonyl, etc. As the N,N-di-lower alkylcarbamoyl group, mention is made of N,N-dialkylcarbamoyl groups, the carbon number of each alkyl moiety of which ranges from about 1 to about 6, such as N,N-dimethylcarbamoyl, N,N-diethylcarbamoyl, N,N-dipropylcarbamoyl, N,N-dibutylcarbamoyl, N-ethyl-N-methylcarbamoyl, etc., and groups forming 5- or 6-membered ring structure(e.g. pyrrolidinylcarbonyl, piperidinocarbonyl) by combining dialkyl moieties together. As the N-lower alkylcarbamoyl group, mention is made of N-alkylcarbamoyl groups, the carbon number of the alkyl moiety of which ranges from about 1 to about 6, such as N-methylcarbamoyl, N-ethylcarbamoyl, N-propylcarbamoyl, N-butylcarbamoyl, etc. As the halogeno group, mention is made of halogeno groups such as chloro, fluoro, bromo and iodo. As the acyloxy group, mention is made of alkanoyloxy groups, the carbon number of which ranges from about 2 to about 6, such as acetoxy, propanoyloxy, butyryloxy, pivaloyloxy, etc., and benzoyloxy. As the lower alkylsulfonylamino group, mention is made of alkylsulfonylamino groups, the carbon number of which ranges from 1 to about 6, such as methanesulfonylamino, ethanesulfonylamino, etc. Examples of the acylamino group include alkanoylamino groups, whose carbon number ranges from about 2 to about 6, such as acetamido, propanoylamino, butyrylamino, pivaloylamino, etc., and benzamido group. As the alkoxycarbonylamino group, the carbon number of the alkoxy moiety of which ranges from about 1 to about 6, there can be used groups such as methoxycarbonylamino, ethoxycarbonylamino, propoxycarbonylamino, butoxycarbonylamino, etc. As the acyl group, mention is made of alkanoyl groups, the carbon number of which ranges from about 2 to about 6, such as acetyl, propanoyl, butyryl, pivaloyl, etc., and benzoyl group. As the lower alkylthio group, mention is made of alkylthio groups, the carbon number of which ranges from about 1 to about 6, such as methylthio, ethylthio, propylthio, butylthio, etc. As the lower alkylsulfinyl group, mention is made of alkylsulfinyl groups, the carbon number of which ranges from about 1 to about 6, such as methylsulfinyl, ethylsulfinyl, propylsulfinyl, butylsulfinyl, etc. As the lower alkylsulfonyl group, mention is made of alkylsulfonyl groups, the carbon number of which ranges from about 1 to about 6, such as methylsulfonyl, ethylsulfonyl, propylsulfonyl, butylsulfonyl, etc.

As the pyridinium ring

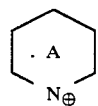

formed by condensation of an aromatic ring, mention is made of, for example, the quinolinium group and isoquinolinium group.

Examples of the counter anion shown by $W^{\ominus}$ include pharmacologically acceptable anions, for example, anion of an inorganic acid such as a chloride ion, bromide ion, iodide ion, sulfate ion, nitrate ion, phosphate ion, etc. and anion of an organic acid such as an acetate ion, tosylate ion, mesylate ion, etc.

Among the above-mentioned compounds, preferable ones are those rerpesentable by the following formula:

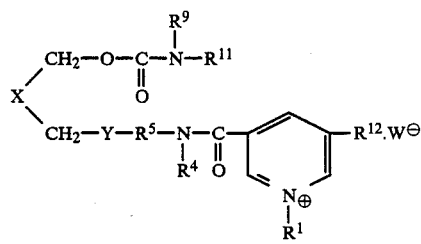

where $R^1$ stands for a lower alkyl, $R^4$ stands for a phenyl group optionally substituted with a halogeno group, $R^5$ stands for ethylene group or trimethylene group, $R^{11}$ stands for an alkyl group whose carbon number is 1 to 30, a cyclo-alkyl group whose carbon number is 3 to 8, phenyl group or naphthyl group, $R^{12}$ stands for a halogeno group, X stands for —$(CH_2)_m$— (wherein m denotes 0 or 1), $W^{\ominus}$ stands for a halogeno ion, Y stands for a group of the formula

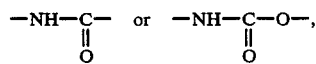

and $R^9$ stands for hydrogen or

stands for piperidino, morpholino or 1,2,3,4-tetrahydro-2-isoquinolyl when $R^9$ is bonded to $R^{11}$.

The compound (I) has, in some instances, an asymmetric carbon, and when two types of steric isomers, i.e. R-configuration and S-configuration, each of those isomers and a mixture of them are all included in the present invention.

The pyridinium compounds of the present invention can be synthesized by, for example, the processes shown below.

(A) A compound shown by the formula (III) $R^1$—$Q^1$ wherein $Q^1$ stands for a group which is readily substituted with a nitrogen atom (e.g. a halogeno group such as chloro, bromo, iodo, etc., toluenesulfonyloxy group, methanesulfonyloxy group, etc.) and $R^1$ is of the same meaning as defined above is allowed to react with a compound shown by the formula (II)

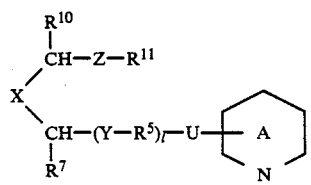

(II)

wherein

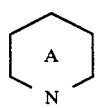

stands for an optionally substituted pyridine ring, and other symbols are of the same meaning as defined above.

Substituents at the pyridine ring shown by

are the same as those at the pyridinium ring shown by

(B) A compound represented by the formula (IV)

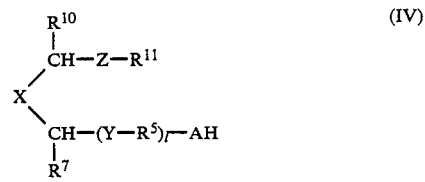

wherein A is —$NR^4$— or —O— and the other symbols are of the same meaning as defined above and a compound represented by the formula (V)

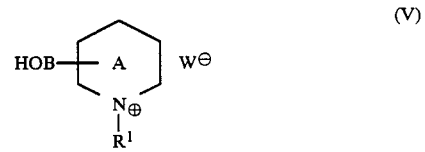

wherein B is —CO— or —$SO_2$— and the other symbols are of the same meaning as defined above are subjected to dehydrative condensation.

(C) A compound represented by the formula (VII)

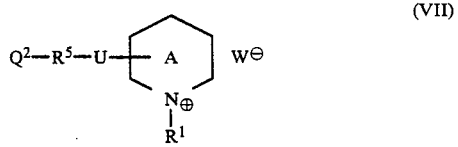

wherein $Q^2$ stands for OCN—,

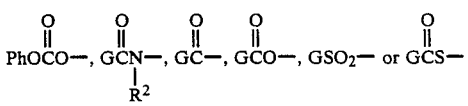

(wherein Ph stands for phenyl group and G stands for a halogeno group e.g. chloro), and other symbols are of the same meaning as defined above is allowed to react with a compound represented by the formula (VI)

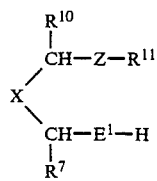
(VI)

wherein $E^1$ stands for —O—,

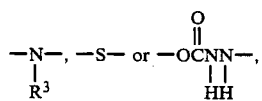

and other symbols are of the same meaning as defined above. [in the formula (I), the case where l is 1, and Y is

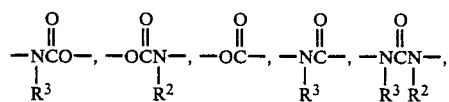

(D) A compound represented by the formula (IX)

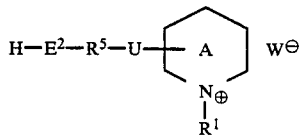
(IX)

wherein $E^2$ stands for —O—,

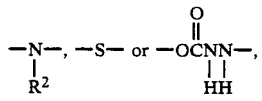

and other symbols are of the same meaning as defined above is allowed to react with a compound (VIII)

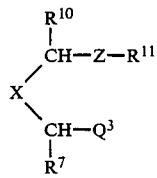
(VIII)

wherein $Q^3$ stands for —NCO

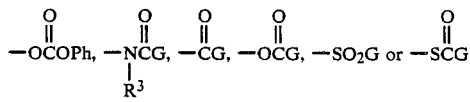

(wherein G stands for a halogeno group such as chloro), and other symbols are of the same meaning as defined above. [in the formula (I), the case l is 1, and Y is

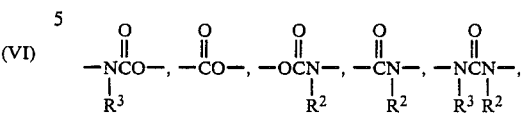

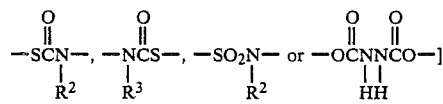

(E) A compound represented by the formula (XI), $Q^4$-$R^1$ wherein $Q^4$ stands for OCN—, PhOCO—, GCN—,

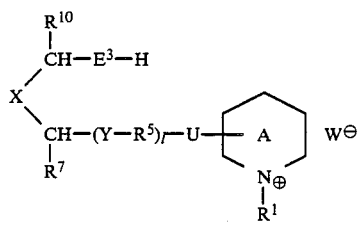

(wherein G stands for a halogeno group such as chloro), and $R^{11}$ is of the same meaning as defined above is allowed to react with a compound represented by the formula (X)

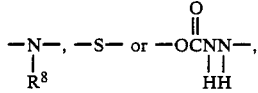
(X)

wherein $E^3$ stands for —O—,

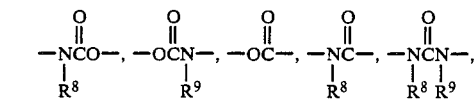

and other symbols are of the same meaning as defined above [in the formula (I), the case where Z stands for

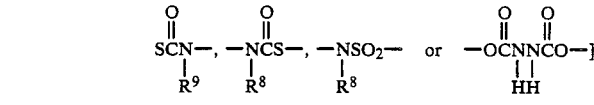

(F) A compound represented by the formula (XIII), H—$E^4$—$R^{11}$ wherein $E^4$ stands for the —O—,

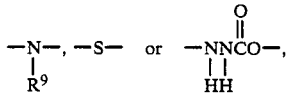

and R[11] is of the same meaning as defined above is allowed to react with a compound represented by the formula (XII)

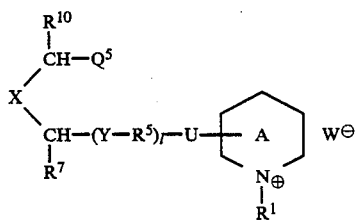 (XII)

wherein $Q^5$ stands for —NCO,

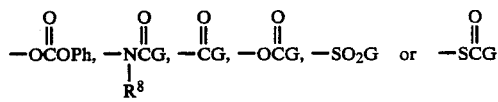

(wherein G stands for a halogeno group such as chloro), and other symbols are of the same meaning as defined above [in the formula (I), the case where Z is

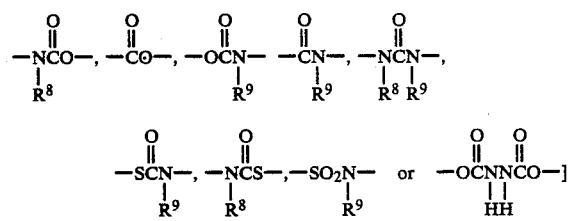

(G) A compound represented by the formula (XIV)

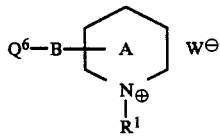 (XIV)

wherein $Q^6$ stands for a halogeno group (e.g., chloro, bromo), and other symbols are of the same meaning as defined above is allowed to react with a compound represented by the formula [IV].

The reaction between the compound (II) and the compound (III) in the process (A) can be conducted, using the compound (III) in an amount of from one equivalent to a large excess at temperatures ranging from 0° C. to +200° C. in the presence or absence of a solvent. As the solvent, mention is made of toluene, benzene, ether, dioxane, tetrahydrofuran, etc., and the compound (III) itself can be used as the solvent. The reaction may be carried out under heating in a sealed tube.

The dehydrative condensation of the compound (IV) with the compound (V) in the process (B) can be conducted by, for example, a conventional amido-linkage and ester-linkage forming reaction.

More specifically, the reaction can be conducted by singly using an amido-forming and ester-forming reagent, e.g. 1-ethoxycarbonyl-2-ethoxy-1,2-dihydroquinoline, dicyclohexylcarbodiimide, 1-cyclohexyl-3-(2-morpholinoethyl)carbodimide, meso-p-toluenesulfonate, N,N'-carbonyldimidazole, diphenyl phosphoric acid, diethyl cyanophosphate, 1-ethyl-3-(3-diethylaminopropyl)carbodiimide hydrochloride, etc., or by allowing a compound (V), after condensing with a phenol such as 2,4,5-trichlorophenol, pentachlorophenol, pentafluorophenol, 2-nitrophenol 4-nitrophenol or an N-hydroxy compound such as N-hydroxysuccinimide, 1-hydroxybenzotriazole, N-hydroxypiperidine, N-hydroxy-5-norbornene-2,3-dicarbodiimide, etc. in the presence of a catalyst such as dicyclohexyl carbodiimide to convert to an active ester, to react with a compound (IV); or by allowing a compound (V) to react with an acid chloride such as ethyl chlorocarbonate, isobutyl chlorocarbonate, benzyl chlorocarbonate, etc. to convert to a mixed acid anhydride, which is then allowed to react with a compound (IV).

This amido-linkage and ester-linkage forming reaction can be promoted by addition of organic base such as tertiary amines (e.g. triethylamine, pyridine, dimethylpyridine, N-methylpyridine) in the case of either reacting the compound (V) itself with the compound (IV), or reacting the active ester of the compound (V) or the mixed acid anhydride of the compound (V) with the compound (IV). This reaction is carried out at temperatures ranging from −30° C. to +50° C. in the presence or absence of a solvent (e.g. ether, toluene, benzene, chloroform, dichloromethane, dioxane, tetrahydrofuran). The reaction between the compound (VI) and the compound (VII) in the process (C) can be carried out at temperatures ranging from −10° C. to +150° C. in the absence or presence of a solvent (e.g. ether, toluene, benzene, chloroform, dichloromethane, dioxane, tetrahydrofuran, dimethylformamide). For accelerating the reaction, a tertiary amine (e.g. triethylamine, pyridine, dimethylaminopyridine, N-methylpiperidine) may be added to the reaction system. And, when $Q^2$ is —NCO, boron trifluoride ethyl ether ($BF_3.Et_2O$) may be added to the reaction system as the catalyst.

The reaction between the compound (VIII) and (IX) in the process (D), the reaction between the compound (X) and the compound (XII) in the process (E) and the reaction between the compound (XII) and the compound (XIII) in the process (F) are conducted under conditions similar to those for the reaction between the compound (VI) and the compound (VII) in the process (C).

The reaction between the compound (IV) and the compound (XIV) in the process (G) can be carried out at temperatures ranging from −20° C. to +150° C. in the absence or presence of a solvent (acetonitrile, dimethylformamide, dimethylacetamide, dimethylsulfoxide, tetrahydrofuran, benzene, toluene, ethyl acetate, chloroform, dichloromethane). In this case, for the purpose of accelerating the reaction rate, a base e.g. potassium carbonate, sodium hdyroxide, sodium hydrogencarbonate, pyridine, triethylamine, etc., can be allowed to co-exist in the reaction system.

The compound (II) can be prepared by, for example, (i) subjecting a compound (IV) and a compound represented by the formula,

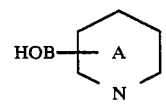 (XV)

wherein each symbol is of the same meaning as defined above to dehydrative condensation;

(ii) allowing a compound (IV) to react with a compound represented by the formula,

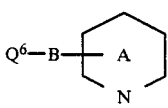

(XVI)

wherein each symbol is of the same meaning as defined above;

(iii) allowing a compound (VI) to react with a compound represented by the formula,

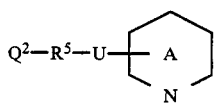

(XVII)

wherein each symbol is of the same meaning as defined above (iv) allowing a compound (VIII) to react with a compound represented by the formula,

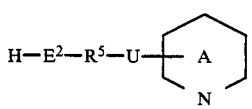

(XVIII)

wherein each symbol is of the same meaning as defined above; (v) allowing a compound represented by the formula,

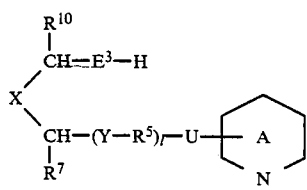

(XIX)

wherein each symbol is of the same meaning as defined above to react with a compound (XI), or (vi) allowing a compound represented by the formula,

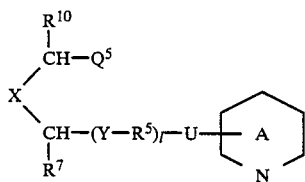

(XX)

wherein each symbol is of the same meaning as defined above to react with a compound (XIII).

The reaction between the compound (IV) and the compound (XV) is carried out in a manner as that for the reaction between the compound (IV) and the compound (V). The reaction between the compound (IV) and the compound (XVI) is carried out in a manner as that for the reaction between the compound (IV) and the compound (XIV). The reaction between the compound (VI) and the compound (XVII), the reaction between the compound (VIII) and the compound (XVIII), the reaction between the compound (XIX) and the compound (XI) and the reaction bewteen the compound (XX) and the compound (XIII) are carried out in a manner as that for the reaction between the compound (VI) and the compound (VII.

The compound (VI) can be obtained by, for example, the processes shown below.

(i)

$$\begin{array}{c} R^{10} \\ | \\ CH-E^3-H \\ X \\ \diagdown \\ CH-E^1-T^2 \\ | \\ R^7 \end{array} \xrightarrow{(XI)}$$

(XXI)

$$\begin{array}{c} R^{10} \\ | \\ CH-Z-R^{11} \\ X \\ \diagdown \\ CH-E^1-T^2 \\ | \\ R^7 \end{array} \xrightarrow{\text{removal of protecting group}} \text{(VI)}$$

(XXII)

(ii)

$$\begin{array}{c} R^{10} \\ | \\ CH-Q^5 \\ X \\ \diagdown \\ CH-E^1-T^2 \\ | \\ R^7 \end{array} \xrightarrow{(XIII)}$$

(XXIII)

$$\begin{array}{c} R^{10} \\ | \\ CH-Z-R^{11} \\ X \\ \diagdown \\ CH-E^1-T^2 \\ | \\ R^7 \end{array} \xrightarrow{\text{removal of protecting group}} \text{(VI)}$$

(XXII)

(iii)

$$\begin{array}{c} R^{10} \\ | \\ CH-OH \\ X \\ \diagdown \\ CH-E^1-T^2 \\ | \\ R^7 \end{array} \xrightarrow{G-R^{11} \ (XXV)}$$

(XXIV)

$$\begin{array}{c} R^{10} \\ | \\ CH-O-R^{11} \\ X \\ \diagdown \\ CH-E^1-T^2 \\ | \\ R^7 \end{array} \xrightarrow{\text{removal of protecting group}} \text{(VI)}$$

(XXVI)

in the formulae, $T^2$ stands for a protective group (e.g. a group protecting hydroxyl group and mercapto group, such as diphenylmethyl, trifluoroacetyl, 2-tetrahydropyranyl, trityl, benzyl, etc.; a group protecting amino group such as benzyloxycarbonyl, tert-butoxycarbonyl, trifluoroacetyl, trityl, benzyl, etc.), G stands for a halogeno group such as chloro, bromo, etc., and other symbols are of the same meaning as defined above.

The reaction between the compound (XXI) and the compound (XI), the reaction between the compound (XXIII) and the compound (XIII) and the reaction between the compound (XXIV) and the compound (XXV) are carried out under conditions like those for the reaction between the compound (VI) and the compound (VII) in the above-mentioned process (C).

The compound (IV) can obtained by, for example, the processes shown below.

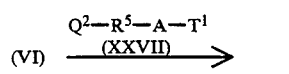

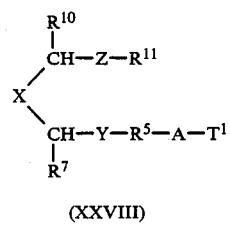

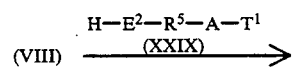

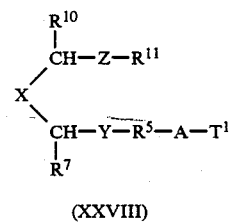

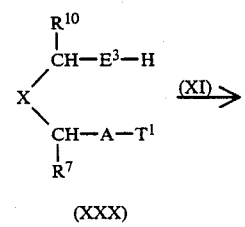

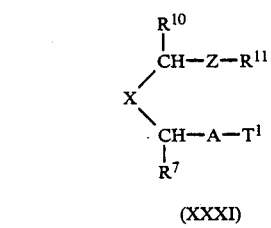

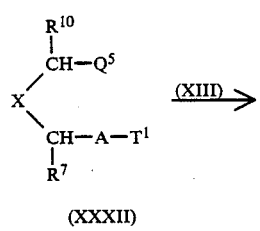

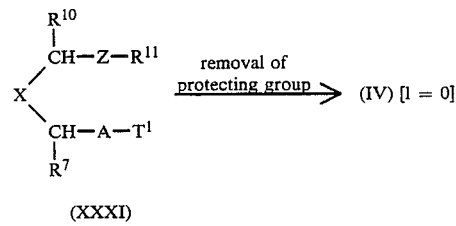

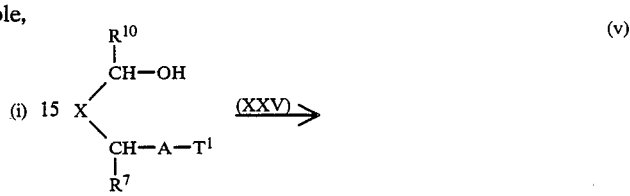

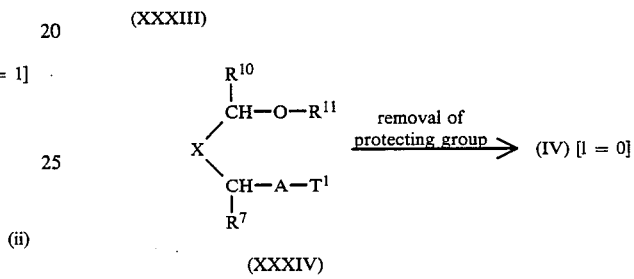

in the formulae, $T^1$ stands for a protecting group (an amino-protecting group, such as benzyloxycarbonyl, tert-butoxycarbonyl, trifluoroacetyl, trityl, benzyl, etc.), and other symbols are of the same meaning as defined above.

The reaction between the compounds (VI) and (XXVII), the reaction between the compounds (VI) and (XXVII), the reaction between the compounds (XXX) and (XI), the reaction between the compounds (XXXII) and (XIII), and the reaction between the compounds (XXXIII) and (XXV) are carried out under conditions of the reaction between the compounds (VI) and (VII) in the above-mentioned process (C).

The compound (IX) and the compound (XVIII) can be obtained by, for example, the processes shown below.

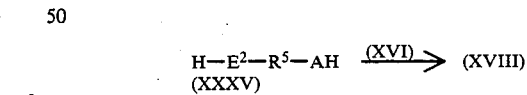

The reaction between the compounds (XXXV) and (XVI) is carried out under conditions like those for the reaction bewteen the compounds (IV) and (XIV) in the above-mentioned process (G), and the reaction between the compounds (XVIII) and (III) is carried out under conditions like those for the reaction bewteen the compounds (II) and (III) in the above-mentioned process (A).

The compounds (X) and (XIX) can be obtained by, for example, the process shown below.

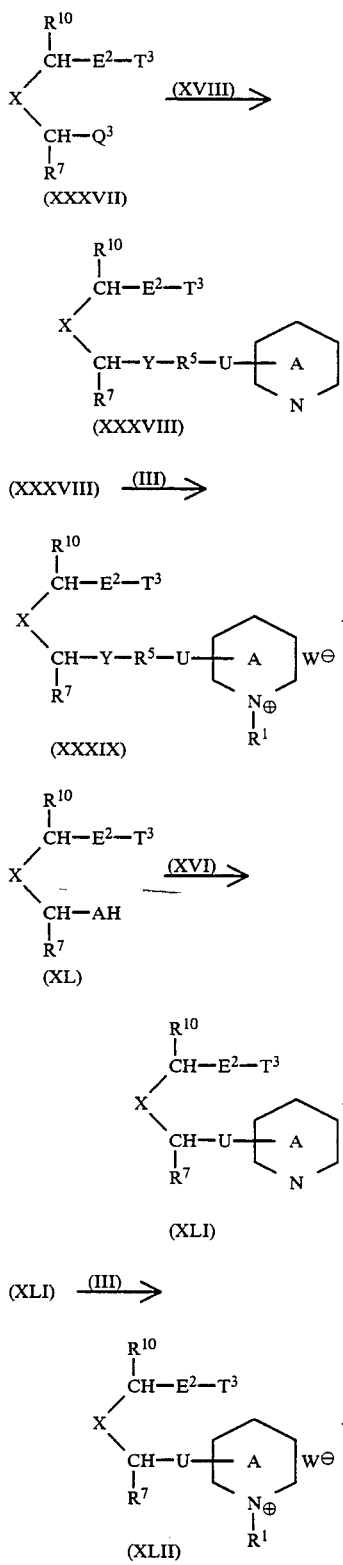

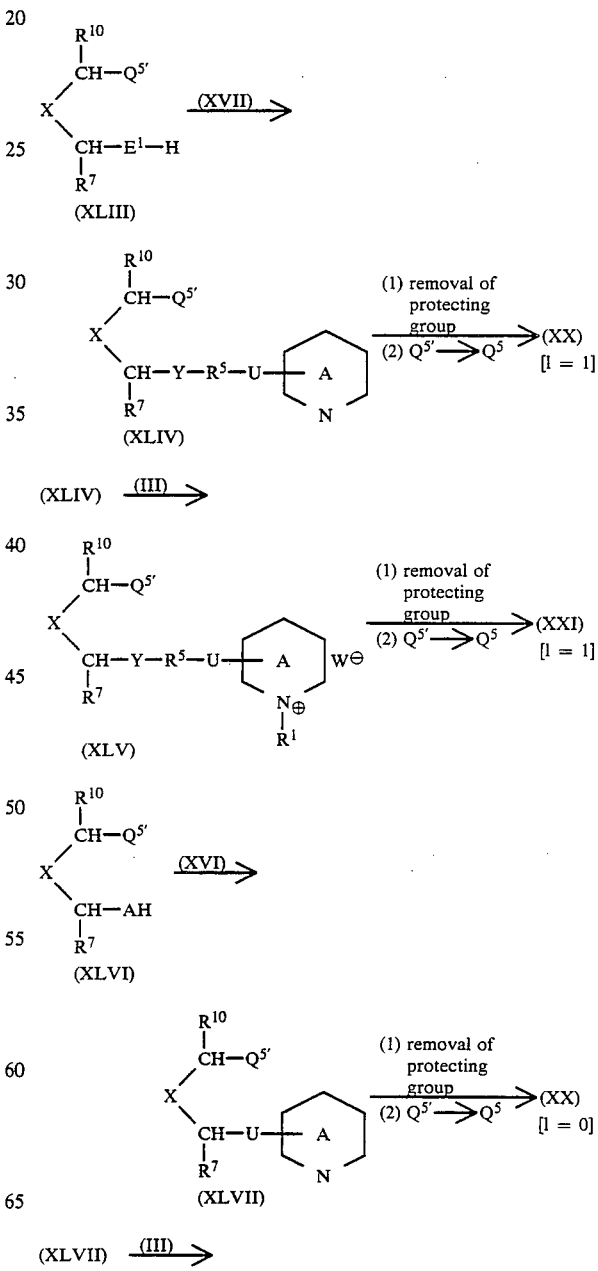

in the formulae, $T^3$ stands for a protecting group (e.g. a group protecting hydroxyl group and mercapto group, such as diphenylmethyl, trifluoroacetyl, 2-tetrahydropyranyl, trityl, benzyl, etc.; a group protecting amino group, such as benzyloxycarbonyl, tert-butoxycarbonyl, trifluoroacetyl, trityl, benzyl, etc.), and other symbols are of the same meaning as defined above.

The reaction between the compounds (XXXVII) and (XVII) is carried out under conditions like those for the reaction between the compounds (VI) and (VII) in the above-mentioned process (C), and the reaction between the compounds (XXXVIII) and (III) is carried out under conditions like those for the reaction between the compounds (II) and (III) in the above-mentioned process (A). The reaction between the compounds (XL) and (XVI) is carried out under conditions like those for the reaction between the compounds (IV) and (XIV) in the above-mentioned process (G), and the reaction between the compounds (XLI) and (III) is carried out under conditions like those for the reaction between the compounds (II) and (III).

The compounds (XII) and (XX) can be obtained by, for example, the processes shown below.

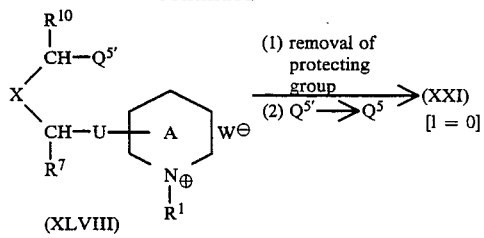

in the formulae, $Q^{5'}$ stands for a protected amino group (e.g. benzyloxycarbonylamino, tert-butoxycarbonylamino, trifluoroacetamido, tritylamino, benzylamino, phthalimido), a protected hydroxy group (e.g. diphenylmethloxy, trifluoroacetoxy, 2-tetrahydropyranyloxy, trityloxy, benzyloxy), a protected mercapto group (e.g. diphenylmethylthio, trifluoroacetylthio, 2-tetrahydropyranylthio, tritylthio, benzylthio), a protected carboxyl group (e.g. a lower ($C_{1-6}$)alkoxycarbonyl such as methoxycarbonyl, ethoxycarbonyl, tert-butoxycarbonyl, etc., benzyloxycarbonyl), and other symbols are of the same meaning as defined above.

The reaction between the compounds (XLIII) and (XVII) is carried out under conditions like these for the reaction between the compounds (VI) and (VII) in the above-mentioned process (C), the reaction between the compounds (XLIV) and (III) is carried out under conditions like those for the reaction between the compounds (II) and (III) in the above-mentioned process (A), and the reaction between the compounds (XLVI) and (XVI) is carried out under conditions like those for the reaction between the compounds (IV) and (XIV) in the above-mentioned process (G).

The reaction $Q^{5'} \rightarrow Q^5$, is carried out, after removing the protecting group, in the processes shown below.

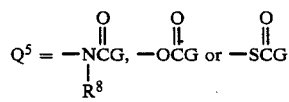

After removal of the protecting group, carbonyl halide such as phosgene is allowed to react with a compound (XLIV), (XLV), (XLVII) or (XLVIII) [$Q^{5'}$ stands for

—OH or —SH].

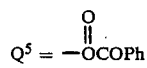

After removal of the protecting group, phenyl chlorocarbonate is allowed to react with a compound (XLIV), (XLV), (XLVII) or (XLVIII) [$Q^{5'}$ stands for —OH].

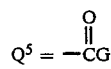

or —$SO_2G$

After the protecting group, phosphorus halogenate such as phosphorus trichloride, phosphorus pentachloride, etc. or thionyl halogenide such as thionyl chloride is allowed to react with a compound (XLIV), (XLV), (XLVII) or (XLVIII) [$Q^{5'}$ stands for —COOH or —$SO_3H$].

(iv) $Q^5$=—NCO

After removal of the protecting group, phosgene is allowed to react with a compound (XLIV), (XLV), (XLVII) or (XLVIII) [$Q^{5'}$ stands for —$NH_2$], then the reaction mixture is further heated, followed by subjecting to dehydrochlorination.

These reactions are all per se known ones and can be carried out in accordance with known conditions.

The above-mentioned reaction for removing the protecting group can be conducted by a per se known process. More specifically, benzyloxycarbonyl group, benzyl group, diphenyl methyl group can be removed by catalytic reduction (reaction temperatures, ranging from room temperature to $+100°$ C.) in a solvent (e.g. alcohol, acetic acid, water, tetrahydrofuran and a mixture thereof) in the presence of a catalyst (e.g. palladium carbon, platinum oxide, etc.). In the case of a mercapto group, when it becomes a catalyst poison, the removal can be carried out with the aid of metallic sodium in liquid ammonia.

In cases of trityl group, 2-tetrahydropyranyl group, tert-butoxycarbonyl group, the removal can be carried out in a solvent (e.g. water, alcohol, tetrahydrofuran, dioxane, etc.) in the presence of an acid (e.g. a mineral acid such as hydrochloric acid, phosphoric acid, sulfuric acid, etc., or an organic acid such as toluenesulfonic acid, methanesulfonic acid, acetic acid, etc.) at temperatures ranging from 0° C. to $+150°$ C. Trifluoroacetyl groups can be easily removed by processing with an alkali (e.g. aqueous solution of sodium hydroxide, sodium hydrogencarbonate).

A phthalimido group can be removed by allowing it to react with hydrazine hydrate in a solvent (e.g. methanol, ethanol).

Separation and purification of the compound (I) from the reaction mixture can be conducted in accordance with a conventional means (e.g. extraction, concentration, filtraiton, recrystallization, column chromatography, thin-layer chromatography).

Upon necessity, conversion into a desired $W^\ominus$ is possible by using ion-exchange resin.

The compound (I) exhibits excellent PAF antagonism and are useful as prophylactic and therapeutic agents of circulatory disturbances due to PAF, for example, thrombosis, apoplexy (e.g. cerebral hemorrhage, cerebral thrombosis), myocardial infarction, angina pectoris, venous thrombosis, nephritis (e.g. glomerular nephritis), diabetic nephritides, shock (e.g. endotoxin shock observed after grave infectious diseases or surgical operation, intravascular hemagglutination syndrome caused by endotoxin, anaphylactic shock, hemorrhagic shock); gastroenteric diseases caused by PAF (e.g. gastric ulcer); diseases associated with allergy and inflammation (e.g. bronchial asthma, psoriasis); pneumonia; rejection symptoms associated with increase in the amount of PAF produced in the case of internal organ transplantation; insufficiency of internal organ (e.g. heart, liver, kidney) in the case of internal organ operation etc. The compound (I) can be used also for the purpose of contraception of female mammals by inhibiting cytodieresis and/or implantation to uterus. The compound (I) is low in toxicity, and can therefore be administered orally or non-orally as it is in a form of powder or as a pharmaceutical composition in a suitable dosage form, to mammals (e.g. man, rabbit, dog, cat, rat, mouse and guinea pig). The dosage varies depending upon the subject to be administered, disease to be treated, conditions thereof and route of administration, and the compound (I) is used for prophylaxis or therapy of shock in a human adult, it is convenient to administer through intravenous injection usally in a single dose in the range of from about 0.001 to 1.0 mg/kg body weight, preferably from about 0.01 to 0.1 mg/kg body weight about once to five times a day, preferably about once to three times a day. And, the compound (I) can also be administered through drip injection in a single dose in the range of about from about 0.01 to about 0.1 mg/kg body weight/min. for about one hour, about once to five times a day, preferably once to three times a day. The dosages for other non-oral routes as well as the oral dosage may be selected referring to above-mentioned dose levels. When shock symptoms are very serious, dosage may be increased depending on the symptoms.

When the compound (I) is used orally for the prophylaxis or therapy of, for example, thrombosis, bronchial asthma, nephritis, etc. in a human adult, it is convenient to administer usually in a single dose in the range of from about 0.1 to about 30 mg/kg body weight, preferably in the range of from about 1 to about 10 mg/kg body weight, about once to five times a day, preferably from about once to three times. The dosages for other non-oral routes may be selected referring to the above-mentioned dose levels.

The pharmaceutical composition to be used for the above administration comprises an effective amount of the compound (I) and a pharmaceutically acceptable carrier or excipient, and the said composition is provided in a dosage form suitable for oral or non-oral administration.

The composition for oral administration includes, for example, solid or liquid dosage forms, and as their specific examples, there may be mentioned tablets (inclusive of sugar-coated tablets and film-coating tablets), pills, granules, powders, capsules (inclusive of soft capsules), syrups, emulsions, suspensions, etc. Such compositons can be prepared by per se known procedures and comprise carriers or excipients commonly used in the field of pharmaceutical preparation. Examples of the carriers and excipients for the preparation of tablets include lactose, starch, sugar and magnesium stearate, etc.

The compositions for non-oral administration include, for example, injections, supporitories, ointments, fomentations, paints. etc., and as examples of injectables, there may be mentioned dosage forms, such as injectable solutions for intravenous injections, for subcutaneous injection, for intracutaneous injection, for intramuscular injection and for drip injection. Such injectable solutions are prepared by per se known procedures, for example, by dissolving, suspending or emulsifying the compound (I) in a sterile aqueous or oily solution usually employed for injectable solutions. The aqueous solution for injection includes, for example, physiological saline solution, isotonic solution containing glucose and other adjuvants, and may be employed in combination with a suitable solubilizer, such as alcohols (e.g. ethanol), polyalcohols (e.g. propylene glycol, polyethylene glycol), and nonionic surface active agents [e.g. polysorbate 80, HCO-50(polyoxyethylene(50 mol.) adduct of hydrogenated castor oil)], etc. The oily solution includes, for example, sesame oil and soybean oil, and may be used in combination with such a solubilizer as benzyl benzoate, benzyl alcohol, etc. The injectable solution thus prepared is usually filled into suitable ampoules to be supplied as an injection. The suppositories for rectal administraiton are preapred by a per se known procedure, for example, by incorporating the compound (I) into a conventional base material for suppository use, followed by molding.

The above-mentioned compositions may contain any other active components, so long as they do not cause undesirable interactions by the incorporation with the compound (I). For example, to mammals suffering from infectious diseases, an antibiotic may be administered together with the compound (I) for preventing endotoxin-shock.

The pyridinium derivatives (I) of the present invention show excellent PAF antagonism even by oral administration. Therefore, the pyridinium derivatives (I) can be administered not only non-orally such as by injection, but also orally.

The following experimental examples will explain the effects of this invention in more detail.

EXPERIMENT EXAMPLE 1

Inhibitory action on platelet aggregation

[Test Method]

Blood was collected directly from the hearts of male rabbits using a syringe containing, as an anticoagulant, 3.15% citric acid (one part to 9 parts of blood). The blood was subjected to centrifuge at 800 rpm for ten minutes at room temperature to obtain platelet rich plasma (PRP). The remaining blood was further subjected to centrifuge at 3000 rpm for ten minnutes to separate platelet poor plasma (PPP) as the supernatant. PRP was diluted with PPP, and the number of platelets was adjusted to about 500,000/ $\mu$l. This PRP(250 $\mu$l) was stirred for two minutes at 37° C., and there was added a test sample, and the mixture was stirred for further two minutes, followed by addition of PAF of a given concentration. Platelet aggregation was examined by means of a platelet-agglutometer (manufactured by Rika Denki). Platelet aggregation preventing action of the test sample was determined based on the maximum percent light transmission (maximum percent. agglutination).

[Results]

As shown in Table 1.

TABLE 1

| Test Compound (Ex. No.) | Inhibitory Action on PAF-Induced Rabbit aggregation inhibitory action by PAF | | |
|---|---|---|---|
| | Concentration of test drug and inhibitory percentage (%) | | |
| | $3 \times 10^{-8}$M | $3 \times 10^{-7}$M | $3 \times 10^{-6}$M |
| 1 | 9 | 100 | 100 |
| 4 | 100 | 100 | 100 |
| 6 | 34 | 100 | 100 |
| 7 | 18 | 100 | 100 |
| 10 | | 91 | 100 |
| 15 | 22 | 100 | 100 |
| 19 | 42 | 100 | 100 |
| 22 | 11 | 100 | 100 |
| 25 | 18 | 100 | 100 |
| 27 | 3 | 100 | 100 |
| 44 | 27 | 100 | 100 |
| 52 | 27 | 100 | 100 |
| 77 | 51 | 100 | 100 |

TABLE 1-continued

Inhibitory Action on PAF-Induced Rabbit aggregation inhibitory action by PAF

| Test Compound (Ex. No.) | Concentration of test drug and inhibitory percentage (%) | | |
|---|---|---|---|
| | $3 \times 10^{-8}$M | $3 \times 10^{-7}$M | $3 \times 10^{-6}$M |
| 87 | 49 | 100 | 100 |
| 88 | 33 | 100 | 100 |
| 90 | 16 | 100 | 100 |
| 94 | 10 | 99 | 100 |
| 98 | 16 | 100 | 100 |
| 108 | 5 | 37 | 100 |
| 109 | 26 | 100 | 100 |

EXPERIMENT EXAMPLE 2

Inhibitory action on PAF-induced hypotension in rats.

[Test Method]

Sprague-Dawley male rats, each weighing about 250 g, were subjected to the experiment. The rats were cannulated on the side of femoral artery for measuring the blood pressure, and on the side of femoral vein for administering the drug. The blood pressure was measured through a pressure transducer and recorded. First, PAF (1 μg/kg) was administered intravenously (i.v.) to examine the extent of lowering of blood pressure. Then, the test samples were administered intravenously or orally. In the case of intravenous administration after 5 minutes, 1, 2, 4, 6 and 8 hours, and, in the case of oral administration, after 1, 2, 4, 5 and 8 hours, PAF was injected intravenously (1 μg/kg) to examine the lowering extent of blood pressure.

[Results]

The inhibitory action on PAF-induced hypotension (% inhibition) is indicated as the ratio of blood pressure-lowering degree (Δ mmHg) induced by PAF after administration of test samples relative to blood pressure-lowering degree (Δ mmHg) induced by PAF before administration of test samples. The results are shown in Table 2 and Table 3.

TABLE 2

Inhibitory Action on Lowering of Blood Pressure (i.v. administration)

| Test Compound (Ex.No.) | Dosage mg/kg | Inhibitory Rate (%) | | | | | |
|---|---|---|---|---|---|---|---|
| | | 5 min. | 1 hr. | 2 hr. | 4 hr. | 6 hr. | 8 hr. |
| 7 | 0.01 | 76 | 59 | 48 | 45 | 40 | 35 |
| | 0.03 | 100 | 84 | 81 | 68 | 57 | 51 |
| | 0.1 | 100 | 100 | 91 | 76 | 63 | 58 |
| 10 | 0.01 | 79 | 65 | 60 | 53 | 47 | 36 |
| | 0.03 | 100 | 97 | 84 | 65 | 55 | 47 |
| | 0.1 | 100 | 100 | 94 | 89 | 81 | 76 |
| 44 | 0.03 | 97 | 81 | 71 | 64 | 59 | 39 |
| 77 | 0.01 | 68 | 58 | 54 | 47 | 41 | |
| | 0.03 | 100 | 100 | 97 | 62 | 46 | 33 |
| 87 | 0.01 | 91 | 64 | 51 | 41 | 30 | 23 |
| 88 | 0.01 | 95 | 59 | 55 | 40 | 25 | 19 |
| 90 | 0.03 | 100 | 83 | 64 | 51 | 36 | 23 |
| 94 | 0.01 | 69 | 58 | 36 | 17 | 10 | 1 |
| | 0.03 | 100 | 94 | 86 | 70 | 63 | 52 |
| 108 | 0.1 | 100 | 100 | 97 | 75 | 58 | 45 |
| 109 | 0.1 | 100 | 100 | 97 | 71 | 50 | 46 |

TABLE 3

Inhibitory Action on Lowering of Blood Pressure (oral administration)

| Test Compound (Ex.No.) | Dosage mg/kg | Inhibitory Rate (%) | | | | |
|---|---|---|---|---|---|---|
| | | 1 hr. | 2 hr. | 4 hr. | 6 hr. | 8 hr. |
| 7 | 3 | 36 | 59 | 63 | 59 | 41 |
| | 10 | 100 | 97 | 92 | 84 | 78 |
| | 30 | 100 | 100 | 97 | 89 | 86 |
| 10 | 1 | 33 | 51 | 56 | 59 | 47 |
| | 3 | 79 | 83 | 87 | 83 | 81 |
| | 10 | 96 | 96 | 96 | 93 | 90 |
| 44 | 1 | 62 | 74 | 73 | 68 | 61 |
| | 3 | 77 | 84 | 97 | 94 | 92 |
| 52 | 1 | 30 | 47 | 37 | 51 | 31 |
| | 3 | 87 | 92 | 89 | 88 | 81 |
| | 10 | 92 | 95 | 98 | 96 | 95 |
| 77 | 1 | 56 | 64 | 72 | 66 | 59 |
| | 3 | 89 | 100 | 99 | 99 | 97 |
| 87 | 1 | 57 | 76 | 86 | 74 | 63 |
| | 3 | 100 | 97 | 99 | 93 | 88 |
| 88 | 1 | 70 | 75 | 73 | 61 | 58 |
| | 3 | 93 | 95 | 98 | 83 | 85 |
| 90 | 1 | 69 | 68 | 78 | 71 | 60 |
| | 3 | 96 | 99 | 94 | 87 | 81 |
| 94 | 1 | 27 | 34 | 50 | 50 | 40 |
| | 3 | 67 | 89 | 93 | 97 | 90 |
| 98 | 1 | 70 | 74 | 74 | 70 | 69 |
| | 3 | 87 | 91 | 93 | 93 | 89 |
| 108 | 1 | 64 | 61 | 55 | 51 | 42 |
| | 3 | 92 | 86 | 94 | 94 | 72 |
| 109 | 1 | 56 | 65 | 64 | 54 | 48 |
| | 3 | 95 | 97 | 97 | 92 | 80 |

EXPERIMENT EXAMPLE 3

Reversed Passive Arthus reaction

[Method]

Under ether anesthesia, the hair of the back of Sprague-Dawley male rats (7-week old, about 250 g body weight) was cut, and 0.5 ml of a 5% solution of gum arabia of a test compound relative to 100 g of the body weight of the animals was orally administered (one hour before injection of antigen). An antigen, egg albumin dissolved in physiological saline (5 mg/kg) was administered through the tail vein. Immediately, 0.1 ml each of a rabbit anti-egg albumin serum (containing 6 mg protein antibody/ml) was administered intracutaneously at one spot each of left- and right-hand sides of the back of rats. Three hours later, 1 ml of physiological saline containing 1% of Evans blue was given intravenously, and 30 minutes later, the skin of the animals was excised, and the area (mm$^2$) of blue spots was measured. The results were compared with those of the control group, and the inhibitory ratio was determined.

[Results]

In this experiment, the compound produced in Production Example 10 showed a preventive ratio of 57% by oral administration (6.25 mg/kg).

EXPERIMENT EXAMPLE 4

PAF inhibitory action in bronchoconstriction

Female and male Hartley guinea pigs weighing about 400 g were fixed on the dorsal position under anesthesia with an ethylcarbamate (1.5 g/kg, intraperitoneally). One leg of a cannula (4 legs) was inserted into the trachea, and two of the remaining three legs were connected to an artificial respirator (Harvard apparatus rodent respirator). The remaining one leg (side tube) was connected to a bronchospasm transducer 7020 (Ugobasile).

While the air volume per ventilation was adjusted to 5 to 7 ml and the air ventilation rate was controlled at 70 times/min., with a load pressure to the lung set at 10 cm H$_2$O, the overflown air volume was recorded on Rectigraph (Rectigraph-8S, San-ei Seiki Inc.) through a transducer. After 1 mg/kg of gallamine triethodide was given intravenously to the animals, histamine dihydrochloride (10 μg/kg) was applied intravenously to examine reaction of the animals. PAF(0.3 μg/kg) was administered intravenously, and, 30 sec. later, maximum bronchoconstriction was observed. Under these conditions, bronchoconstriction activity of the test samples was examined. The test sample was suspended in a 5% gum arabic solution, and given orally one hour before the administration of PAF. The compounds obtained in Production Examples 3 and 4 inhibited PAF-induced bronchoconstriction by oral administration (30 mg/kg). The respective inhibitions were 64.9% and 59.9%.

EXPERIMENT EXAMPLE 5

Acute Toxicity Test

[Method and Results]

Male Jcl-ICR mice (5 wk) were used in groups of five individuals. The animals of the respective groups were orally administered with the compounds (227), (236) and (303) respectively produced in Production Examples 87, 90 and 109 at the dose of 1000 mg/kg.

No death of mice was observed until after one week.

EXAMPLES

The following reference examples and production examples will serve to explain the present invention in more detail, but are not intended as limitation upon the scope of the invention.

REFERENCE EXAMPLE 1

2-(2-Naphthyloxy)ethanol

This compound was synthesized in accordance with the method disclosed in the literature reference[Bull. Chem. Soc. Japan, 46, 553(1973)], m.p.74° to 75° C.(72° to 74° C. in the literature reference).

In like manner, the following compounds were synthesized.

2-(1-Naphthyloxy)ethanol [m.p.41° to 42° C.]
2-[1-(4-Methoxy)naphthyloxy]ethanol [m.p.101° to 102° C.]
2-(3,4,5-Trimethoxyphenoxy)ethanol [m.p.40° to 42° C.]
2-(4-Fluorophenoxy)ethanol [oily product]

REFERENCE EXAMPLE 2

2-(1-naphthylcarbamoyloxy)ethanol

Ethylene glycol (3.0 g) was mixed with α-naphthyl isocyanate (8.5 g), and reaction was allowed to proceed at room temperature for 3 hours, then at 50° C. for 2 hours. The reaction mixture was poured into water, which was subjected to extraction with chloroform. The extract was concentrated and subjected to purification by means of a silica gel chromatography(silica gel 400 g, developing solvent:hexane-ethyl acetate, 1:2→1:3).

Recrystallization from ether afforded the desired compound (9.0 g), m.p.103° to 104° C.

Elemental Analysis for C$_{13}$H$_{13}$NO$_3$: Calcd.: C,67.52, H,5.67, N,6.06, Found: C,67.57, H,5.68, N,5.98.

IR(KBr)cm$^{-1}$: 3300,1720,1705,1530,1260,1240,

NMR(CDCl$_3$,60 MHz) δ: 2.96(1H,s), 3.7 to 4.1(2H,m), 4.2 to 4.6(2H,m), 7.2 to 8.1(7H,m),

REFERENCE EXAMPLE 3

2-(1-naphthyloxy)ethylamine

In anhydrous tetrahydrofuran (100 ml) were dissolved 2-(1-naphthyloxy)ethanol(3.76 g), triphenylphosphine(10.5 g), phthalimide(5.9 g) and diethyl azodicarboxylate(100 ml), and the solution was stirred at room temperature for one hour, followed by concentration. The concentrate was purified by subjecting to a silica gel chromatography(silica gel 250 g, developing solvent:Hexane:AcOEt=4:1→2:1) to obtain a phthaloyl compound(6.6 g). The phthaloyl compound was dissolved in methanol(60 ml), to which was added hydrazine hydrate(1.6 ml), and the mixture was heated for one hour under reflux. After completion of the reaction, the reaction mixture was concentrated. To the concentrate was added chloroform, and insolubles were deleted. The chloroform solution was concentrated to obtain the desired compound(2.2 g) as an oily product.

IR(neat)cm$^{-1}$: 1590, 1575, 1270, 1242, 1102.

NMR(CDCl$_3$,60 MHz) δ: 1.34(2H,broad s), 3.08(2H,t,J=5 Hz), 4.02(2H,t,J=5 Hz), 6.6 to 8.4(7H,m).

In a manner analogous to the above, the following compound was synthesized

2-[1-(4-methoxy)naphthyloxy]ethylamine, an oily product IR(neat)cm$^{-1}$: 3440,2910,1620,1582,1450,1382,1265,1095.

NMR(CDCl$_3$,60 MHz) δ: 1.55(2H, broad s), 3.02(2H, broad), 3.82(3H,s), 3.90(2H,t,J=6 Hz), 6.54(2H,s), 7.44(2H,m), 8.18(2H,m).

REFERENCE EXAMPLE 4

2-(1-Naphthylcarbamoyloxy)ethylamine

In dichloromethane(200 ml) were dissolved 2-aminoethanol (6.1 g) and di-tert-butyl dicarbonate(21.8 g), and the solution was stirred at room temperature overnight and concentrated to dryness. The concentrate was dissolved in dichloromethane(200 ml). To the solution was added α-naphthyl isocyanate(17 g), and the mixture was stirred at room temperature overnight. Insolubles were filtered off, and the filtrate was concentrated. The concentrate was dissolved in methanol(200 ml), to which was added methanolic hydrochloride(50 ml, containing 25 g of hydrogen chloride), and the mixture was stirred at room temperature for 2 hours. The reaction mixture was concentrated, and the concentrate was recrystallized from methanol to obtain the object compound as hydrochloride(26.2 g). This hydrochloride was dissolved in water and washed with dichloromethane. The aqueous layer was neutralized with an aqueous solution of sodium hydroxide, which was extracted with dichloromethane. The extract was dried over Glauber's salt, followed by concentration. Precipitating crystals were washed with petroleum ether to obtain the object compound, m.p.118° to 119° C.

The yield was 17.8 g.

Elemental Analysis for C$_{13}$H$_{14}$N$_2$O$_2$: Calcd.: C,67.81, H,6.13, N,12.17, Found: C,67.60, H,6.07, N,11.82.

IR(KBr)cm$^{-1}$: 2925, 1712, 1560, 1222.

NMR(CDCl$_3$,60 MHz) δ: 1.24(2H,broad s), 2.98(2H,t,J=5 Hz), 4.23(2H,t,J=5 Hz), 7.3 to 8.2(7H,m),

PRODUCTION EXAMPLE 1

Synthesis of 3-[N-[2-(2-methoxy-3-octadecylcarbamoyloxypropoxycarbonyl)]aminoethyl-N-methyl]carbamoyl-1-ethylpyridinium iodide(5)

(i) Synthesis of N-methyl-N-tert-butoxycarbonylaminoethanol(1)

In chloroform(50 ml) was dissolved N-methylethanolamine [2.81 ml(35 mmol.). To the solution was added tert-butyl S-(4,6-dimethylpyrimidin-2-yl)thiocarbonate[8.42 g(35 mmol.)], and the mixture was stirred at room temperature for 24 hours. The reaction mixture was concentrated under reduced pressure. To the concentrate was added ethyl acetate, and insolubles were filtered off, and the filtrate was concentrated under reduced pressure. The crude product thus obtained was purified by means of a column chromatography(silica gel:140 g; eluent:n-hexane/ethyl acetate=½) to obtain the object compound (1)[4.78 g(77.9%; yellow oily substance)].

TLC(Silica Gel: n-hexane/AcOEt=1/5)Rf=0.40.

NMR(90 MHz, CDCl$_3$) δ: 1.44(9H,s), 2.89(3H,s), 3.29(2H,t), 3.64(2H,t).

IR(Neat)cm$^{-1}$: 3400,2970,2925,1670,1480,1390,1362,1150.

(ii) Synthesis of N-methyl-N-tert-butoxycarbonylethylenediamine(2)

In anhydrous tetrahydrofuran(50 ml) were dissolved the compound(1) synthesized in (i)[1.402 g (8 mmol)], phthalimide[2.354 g (16 mmol.)] and triphenyl phosphine[4.197 g(16 mmol.)]. To the solution was added, under ice-cooling, diethyl diazacarboxylate[2.465 ml(16 mmol.)], and the mixture was stirred at room temperature for 3 hours. The reaction mixture was then concentrated under reduced pressure. The concentrate was purified by means of a column chromatography(silica gel:200 g; eluent:n-hexane/ethyl acetate=2/1) to obtain 2-(N-tert-butoxycarbonyl-N-methylamino)ethyl phthalimide(3.32 g).

NMR(90 MHz, CDCl$_3$) δ: 1.22(9H,s), 2.89(3H,s), 3.50(2H,t), 3.84(2H,t), 7.58 to 7.98(4H,m).

In methanol(60 ml) was dissolved this 2-(N-tert-butoxycarbonyl-N-methylamino)ethyl phthalimide(3.32 g). To the solution was added hydrazine hydrate(1.6 ml), and the mixture was refluxed for one hour. The reaction mixture was, after cooling, concentrated under reduced pressure. To the concentarate was added chloroform, then insolubles were filtered off. The filtrate was concentrated under reduced pressure. The crude product was purified by means of a column chromatography(silica gel:30 g; eluent:methanol/conc. ammonia water=100/1) to afford the object compound(2)[903 mg(64.8%, pale yellowish oily substance).

TLC(Silica Gel: MeOH/conc. NH$_4$OH=19/1) Rf=0.38.

NMR(90 MHz, CDCl$_3$) δ: 1.32(2H,br.s), 1.47(9H,s), 2.83(2H, br.t), 2.87(3H,s), 3.27(2H,t).

IR(Neat)cm$^{-1}$: 3350(br), 2980, 2920, 1680, 1480, 1398, 1370, 1160.

(iii) Synthesis of 3-[2-(N-tert-butoxycarbonyl-N-methyl)aminoethyl]carbamoyl-2-methyl-1-octadecylcarbamoyl glycerine(3)

To 2-methyl-1-octadecylcarbamoyl-3-phenoxycarbonyl glycerine[2.609 g(5 mmol.)] was added the compound(2) synthesized in (ii)[872 mg(5 mmol.)]. The mixture was heated at 90° C. for two hours. To the reaction mixture was added, after cooling, a 1N aqueous solution of sodium hydroxide. The mixture was subjected to extraction with chloroform. The organic layer was dried over anhydrous sodium sulfate, followed by distilling off the solvent under reduced pressure. The crude product was purified by means of a column chromatography (silica gel:90 g; eluent:n-hexane/ethyl acetate=1/1.5) to obtain the object compound(3)[2.68 g(89.1%, colorless syrup)].

TLC(Silica Gel; n-hexane/AcOEt=1/1.5) Rf=0.33.

NMR(90 MHz, CDCl$_3$) δ: 0.86(3H,m), 1.26(32H,s), 1.44(9H,s), 2.86(3H,s), 3.14(2H,q), 3.41(3H,s), 3.56(1H,quint), 4.14(4H,m), 4.81 (1H,br), 5.21(1H,br).

IR(Neat)cm$^{-1}$: 3315,2920,2845,1700,1530,1250,1155

(iv) Synthesis of 2-methyl-3-[2-(N-nicotinoyl-N-methyl)aminoethyl]carbamoyl-1-octadecylcarbamoyl glycerine(4) In methanol(10 ml) was dissolved the compound(3) synthesized in (iii)[2.596 g(4.31 mmol.)]. To the solution was added a 13% HCl/methanol solution, and the mixture was left standing at room temperature for one hour. The reaction mixture was concentrated under reduced pressure. To the hydrochloride thus obtained were added chloroform(40 ml), triethylamine [1.56 ml(11.19 mmol.)] and nicotinic acid chloride.hydrochloride[797 mg(4.47 mmol.)] under ice-cooling. The mixture was stirred at room temperature for one hour. The reaction mixture was washed with water, and the organic layer was dried over anhydrous sodium sulfate, followed by concentration under reduced pressure. The crude product thus obtained was purified by means of a column chromatography(silica gel:60 g; eluent:ethyl acetate/acetone=2/1) to afford the object compound(4)[2.613 g(100%, colorless solid)].

TLC(Silica Gel:AcOEt/acetone=2/1) Rf=0.25.

NMR(90 MHz,CDCl$_3$) δ: 0.89(3H,t),1.26(32H,s),3.06(3H,s),3.16 (2H,q),3.3 to 3.8(5H,m),3.43(3H,s), 4.16(4H,br.d),5.1 to 5.5(2H,br),7.37 (1H,m),7.77(1H,m),8.68(2H,m).

(v) Synthesis of 3-[N-[2-(2-methoxy-3-octadecylcarbamoyloxypropoxycarbonyl)]aminoethyl-N-methyl]carbamoyl-1-ethylpyridinium iodide(5)

To the compound(4) synthesized in (iv)[1.82 g(3 mmol.)] was added iodoethane(10 ml). The mixture was heated under reflux for 48 hours in nitrogen streams while shielding the light. The reaction mixture was, after cooling, concentrated under reduced pressure to obtain the object compound(5)[2.269 g (99.1%, pale yellow powder)].

TLC(Silica Gel;CHCl$_3$/MeOH=3/1) Rf=0.23.

NMR(90 MHz,CDCl$_3$) δ: 0.87(3H,t),1.26(32H,s),1.76(3H,t),3.13 (2H,q),3.16(3H,s),3.2 to 3.7(8H,m),4.16 (4H,m),4.90(2H,q),5.03(1H,br),6.40(1H, br),8.30(2H,m),8.98 to 9.61(2H,m).

IR(KBr)cm$^{-1}$: 3300,2900,2830,1700,1635,1520,1465,1240

PRODUCTION EXAMPLE 2

Synthesis of 3-[N-[2-(2-methoxy-3-octadecylcarbamoyloxypropoxycarbonyl)]aminoethyl-N-phenyl]carbamoyl-1-ethylpyridinium iodide(10)

(i) Synthesis of N-tert-butoxycarbonyl-N-phenylaminoethanol(6)

In chloroform(40 ml) was dissolved β-anilinoethanol[6.32 ml(50 mmol.)]. To the solution was added tert-butyl S-(4,6-dimethylpyrimidin-2-yl)thiocarbonate[13.10 g(60 mmol.)]. and the mixture was heated for two hours under reflux. The reaction mixture was cooled and washed with a 5% aqueous solution of potassium hydroxide. The organic layer was dried over anhydrous potassium carbonate, then the solvent was distilled off under reduced pressure. The crude product thus obtained was purified by means of a column chromatography (silica gel:180 g; eluent:n-hexane/ethyl acetate=2/1) to afford the object compound(6)[11.257 g(94.9%, colorless solid matter)].

TLC(Silica Gel;n-hexane/AcOEt=1/1) Rf=0.53.
NMR(90 MHz,CDCl$_3$) δ: 1.42(9H,s),2.79(1H,br),(3.78(4H,m), 7.26(5H,m).
IR(KBr)cm$^{-1}$: 3460,1668,1590,1395,1165.

(ii) Synthesis of N-tert-butoxycarbonyl-N-phenylethylenediamine(7)

In anhydrous tetrahydrofuran(100 ml) were dissolved the compound(6) synthesized in (i) [4.746 g (20 mmol.)], phthalimide (40 mmol.) and triphenyl phosphine[0.492 g(40 mmol.)]. To the solution was added, under ice-cooling, diazacarboxylate [6.165 ml(40 mmol.)]. The mixture was stirred at room temperature for 1.5 hour, and the reaction mixture was concentrated under reduced pressure. The concentrate was purified by means of a column chromatography(silica gel:250 g; eluent:n-hexane/ethyl acetate=3/1) to afford 2-(N-tert-butoxycarbonyl-N-phenylamino)ethyl phthalimide(8.235 g).

NMR(90 MHz, CDCl$_3$) δ: 1.30(9H,s), 3.94(4H,m), 7.26(5H,m), 7.76(4H,m).
IR(Neat)cm$^{-1}$: 1765, 1700, 1596, 1396.

This 2-(N-tert-butoxycarbonyl-N-phenyl)aminoethyl phthalimide(8.235 g) was dissolved in methanol(120 ml). To the solution was added hydrazine hydrate(4 ml), and the mixture was reflux for one hour. The reaction mixture was, after cooling, concentrated under reduced pressure. To the concentrate was added chloroform, and insolubles were filtered off. The filtrate was concentrated under reduced pressure to give a crude product, which was purified by means of a column chromatography(silica gel:100 g; eluent=methanol) to obtain the object compound(7)[3.816 g(80.7%,pale yellow oily product).

TLC(Silica Gel;MeOH) Rf=0.15.
NMR(90 MHz,CDCl$_3$) δ: 1.40(9H,s),2.83(2H,t),3.67(2H,t), 7.22(5H,m).
IR(Neat)cm$^{-1}$: 3450,2975,2920,1690,1598,1498,1390,1368,1160.

(ii) Synthesis of 3-[2-(N-tert-butoxycarbonyl-N-phenyl)aminoethyl]carbamoyl-2-methyl-1-octadecylcarbamoyl glycerine(8)

To 2-methyl-1-octadecylcarbamoyl-3-phenoxycarbonyl glycerine[8.347 g(16 mmol.)] was added the compound(7) synthesized in (ii) [3.781 g(16 mmol.)], and the mixture was heated at 90° C. for two hours. To the reaction mixture was cooled, to which was added a 5% aqueous solution of potassium hydroxide. The mixture was subjected to extraction with chloroform. The organic layer was dried over anhydrous potassium carbonate, then the solvent was distilled off under reduced pressure to leave a crude product, which was purified by means of a column chromatography(silica gel:250 g; n-hexane/ethyl acetate=1/1) to obtain the object compound(8)[10.396 g(97.9%, colorless syrup)].

TLC(Silica Gel;n-hexane/AcOEt=1/1) Rf=0.42.
NMR(90 MHz,CDCl$_3$) δ: 0.88(3H,t),1.24(32H,s),1.40(9H,s),3.14 (2H,q),3.37(2H,t),3.41(3H,s),3.54(1H, quint),3.76(2H,t),4.13(4H,m),4.77(1H,br), 5.20(1H,br),7.24(5H,m).

IR(Neat)cm$^{-}$:
3320,2910,2845,1700,1598,1520,1468,1395, 1365,1250,1150.

(iv) Synthesis of 3-[2-(N-nicotinoyl-N-phenyl)aminoethyl]carbamoyl-2-methyl-1-octadecylcarbamoyl glycerine(9)

In methanol(50 ml) was dissolved the compound(8) synthesized in (iii)[10.35 g(15.59 mmol.)]. To the solution was added a 13% HCl/methanol solution(20 ml), and the mixture was concentrated under reduced pressure. To the concentrate was added ether, and the mixture was subjected to filtration to obtain hydrochloride[8.71 g(93.1%, white powdery product)].

TLC(Silica Gel;CHCl$_3$/MeOH=49/1) Rf=0.32.

To this hydrochloride[1.20 g(2.0 mmol.)] were added, under ice-cooling, chloroform(20 ml), triethylamine[607 mg(6.0 mmol.)] and nicotinic acid chloride hydrochloride[427 mg (2.4 mmol.)]. The mixture was stirred at room temperature for 30 minutes. To the reaction mixture was added a 5% aqueous solution of potassium hydroxide and the mixture was subjected to extraction with chloroform. The organic layer was dried over anhydrous potassium carbonate, then the solvent was distilled off under reduced pressure to leave a crude product, which was subjected to purification by means of a column chromatography(silica gel:40 g; eluent:ethyl acetate) to obtain the object compound(9)[1.34 g(100%, colorless solid product)].

TLC(Silica Gel;AcOEt) Rf=0.30.
NMR(90 MHz, CDCl$_3$) δ: 0.86(3H,m),1.26(32H,s),3.14(2H,q), 3.43(3H,s),3.49(4H,m),4.03(2H,t), 4.14(4H,m),5.02(1H,br),5.43(1H,br), 6.9 to 7.3(6H,m),7.59(1H,m),8.46(2H,m).
IR(KBr)cm$^{-1}$: 3320,2905,2840,1700,1640,1590,1530,1250.

(v) Synthesis of 3-[N-[2-(2-methoxy-3-octadecylcarbamoyloxypropoxycarbonyl)]aminoethyl-N-phenyl]carbamoyl-1-ethylpyridinium iodide(10)

To the compound(9)[669 mg(1 mmol.)] synthesized in (iv) was added iodoethane(10 ml). The mixture was heated under reflux for 46 hours in nitrogen streams while shielding the light. The reaction mixture was cooled and concentrated under reduced pressure to obtain the object compound(10) [810 mg(98.2%, pale yellow powdery product)].

TLC(Silica Gel;CHC$_3$/MeOH=5/1) Rf=0.15.
NMR(90 MHz,CDCl$_3$) δ: 0.86(3H,t),1.25(32H,s),1.44(3H,t), 3.12(2H,q),3.40(3H,s),3.55(3H,m), 3.8 to 4.2(6H,m),4.82(2H,q),5.00 (1H,br),6.18(1H,br),7.1 to 7.5(5H,m), 7.98(1H,br.t),8.32(1H,br.d),9.35(2H,m).
IR(KBr)cm$^{-1}$: 3300,2905,2840,1700,1650,1590,1520,1250.

PRODUCTION EXAMPLE 3

Synthesis of 5-bromo-3-[N-[2-(2-methoxy-3-octadecylcarbamoyloxyproxycarbonyl)]aminoethyl-N-phenyl]carbamoyl-1-ethyl pyridinium iodide(12)

(i) Synthesis of 3-[2-[N-(5-bromonicotinoyl)-N-phenyl]aminoethyl]carbamoyl-2-methyl-1-octadecylcarbamoyl glycerine (11)

To the hydrochloride[1.20 g(2 mmol.)] synthesized in Production Example 2-(iv) were added chloroform(15 ml), triethylamine[1.67 ml(12 mmol)] and 5-bromonicotinic acid chloride.hydrochloride[771 mg(3 mmol)]

under ice-cooling. The mixture was stirred at room temperature for one hour. To the reaction mixture was added a 5% aqueous solution of sodium hydrogen carbonate and the mixture was subjected to extraction with chloroform. The organic layer was dried over anhydrous potassium carbonate, then the solvent was distilled off under reduced pressure to leave a crude product, which was subjected to purification by means of a column chromatography(silica gel:60 g; eluent:n-hexane/ethyl acetate=½) to obtain the object compound(11)[1.323 g(88.5%, colorless solid product)].

TLC(Silica Gel;n-hexane/AcOEt=½) Rf=0.34.
NMR(90 MHz,CDCl$_3$) δ: 0.87(3H,m),1.26(32H,s),3.13(2H,q),3.42 (3H,s),3.49(3H,m),4.06(2H,t),4.13(4H,m), 4.95(1H,br),5.35(1H,br),7.0 to 7.4(5H, m), 7.81(1H,m),8.32(1H,d),8.49(1H,d).

IR(KBr)cm$^{-1}$: 3290,2900,2840,1685,1640,1595,1540,1255.

(ii) Synthesis of 5-bromo-3-[N-[2-(2-methoxy-3-octadecylcarbamoyloxy propoxycarbonyl)]aminoethyl-N-phenyl]carbamoyl-1-ethyl pyrimidium iodide(12)

To the compound(11) synthesized in (i)[748 mg(1 mmol.)] was added iodoethane(8 ml). The mixture was heated under reflux for 36 hours in nitrogen streams while shielding the light and then was cooled and concentrated under reduced pressure to obtain the object compound(12)[885 mg(97.9%, pale yellow powdery product)].

TLC(Silica Gel;CHC$_3$/MeOH=3/1) Rf=0.47.
NMR(90 MHz,CDCl$_3$) δ: 0.85(3H,m),1.25(32H,s),1.43(3H,t), 3.12(2H,q),3.2 to 3.7(3H,m),3.39(3H,s), 3.8 to 4.2(6H,m),4.85(2H,q),4.6 to 5.0 (1H,br),6.22(1H,br),7.2 to 7.6(5H,m), 8.38(1H,br),9.37(1H,br),9.55(1H,br).

IR(KBr)cm$^{-1}$: 3390,2900,2850,1700,1645,1520,1220.

PRODUCTION EXAMPLE 4

Synthesis of 5-bromo-3-[N [2-[2-(2-dodecyloxyethoxy)ethoxycarbonyl]]aminoethyl-N-phenyl]carbamoyl-1-ethyl pyridinium iodide(15)

(i) Synthesis of N-tert-butoxycarbonyl-N-phenyl-N'-[2-(2-dodecyloxyethoxy)ethoxycarbonyl]ethylenediamine(13)

In methylene chloride(10 ml) were dissolved 2-(2-dodecyloxyethoxy)ethanol[823 mg(3 mmol.)] and pyridine[475 mg (6.0 mmol.)]. To the solution was added, under ice-cooling, phenyl chlorocarbonate[517 mg(3.3 mmol.)], then the mixture was stirred for one hour at room temperature. To the reaction mixture was added 1N HCl, which was subjected to extraction with chloroform. The organic layer was dried over anhydrous sodium sulfate, then the solvent was distilled off under reduced pressure to leave a crude carbonate(1.90 g).

To this crude carbonate was added the compound(6) synthesized in Production Example 2-(ii). The mixture was heated at 90° C. for two hours. After cooling, the resulting crude product was purified by means of a column chromatography (silica gel:65 g; eluent:n-hexane/ethyl acetate-2/1) to obtain the object compound(13)[1.266 g(78.6%, colorless oily product)].

TLC(Silica Gel;n-hexane/AcOEt=2/1) Rf=0.22.
NMR(90 MHz,CDCl$_3$) δ: 0.87(3H,t),1.27(20H,s),1.43(9H,s), 3.23 to 3.93(12H,m),4.20(2H,t), 5.17(1H,br),7.30(5H,m).

IR(Neat)cm$^{-1}$: 3330,2910,2850,1700,1598,1255,1150.

Synthesis of 5-bromo-3-[N-[2-[2-(2-dodecyloxyethoxy)ethoxycarbonyl]]aminoethyl-N-phenyl]carbamoyl pyridine(14)

The compound(13) synthesized in (i)[1.02 g(1.9 mmol.)] was dissolved in chloroform/methanol(1/1)(20 ml), to which was added 13% HCl/methanol solution(5 ml). The mixture was then left standing for one hour at room temperature. The solvent was then distilled off under reduced pressure to obtain hydrochloride[792 mg(88.1%)].

To this hydrochloride[473 mg(1.0 mmol.)] were added chloroform(15 ml) and triethylamine[607 mg(6 mmol.)]. To the mixture was added, under ice-cooling, 5-bromonicotinic acid chloride.hydrochloride[360 mg(1.4 mmol.)], followed by stirring at room temperature for 30 minutes. To the reaction mixture was added a 1N aqueous solution of sodium hydroxide, followed by extraction with chloroform. The organic layer was dried over anhydrous potassium carbonate, then the solvent was distilled off under reduced pressure to leave a crude product, which was purified by means of a column chromatography (silica gel:30 g; eluent:n-hexane/ethyl acetate=1/1.5) to obtain the object compound(14)[620 mg(100%,white powdery product)].

TLC(Silica Gel;n-hexane/AcOEt=1/1.5) Rf=0.31.
NMR(90 MHz,CDCl$_3$) δ: 0.86(3H,t),1.27(20H,s),3.36 to 3.70 (10H,m),4.07(2H,t),4.21(2H,t),5.33 (1H,br),7.0 to 7.4(5H,m),7.83(1H,t), 8.33(1H,d),8.51(1H,d).

IR(Neat)cm$^{-1}$: 3320,2920,2845,1720,1650,1595,1495,1250,1108.

(iii) Synthesis of 5-bromo-3-[N-[2-[2-(2-dodecyloxyethoxy)ethoxycarbonyl]]aminoethyl-N-phenyl]carbamoyl-1-ethylpyridinium iodide(15)

To the compound(14) synthesized in (ii) 620 mg(1 mmol.)] was added iodoethane(10 ml), and the mixture was heated under reflux for 60 hours in nitrogen streams while shielding the light. The reaction mixture was cooled and concentrated under reduced pressure to obtain the object compound(15)[723 mg (93.1%,pale yellow powdery product)].

TLC(Silica Gel;CHC$_3$/MeOH=6/1) Rf=0.37.
NMR 90 MHz,CDCl$_3$) δ: 0.86(3H,t),1.26(20H,s),1.43(3H,m), 3.33 to 3.68(8H,m),3.9 to 4.2(4H,m), 4.87(2H,q),6.02(1H,br),7.41(5H,m), 8.37(1H,br),9.36(1H,br),9.55(1H,br).

IR(KBr)cm$^{-1}$: 3260,2910,2840,1700,1650,1590,1250.

PRODUCTION EXAMPLE 5

Synthesis of 3-[N-[2-[2-(2-dodecyloxyethoxy)ethoxycarbonyl]-]aminoethyl-N-phenyl]carbamoyl-1-ethyl pyridinium iodide (17)

(i) Synthesis of 3-[N-[2-[2-(2-dodecyloxyethoxy)ethoxycarbonyl]]aminoethyl-N-phenyl]carbamoyl pyridine(16)

To the hydrochloride synthesized in Production Example 4-(ii)[237 mg(0.5 mmol.)] were added chloroform(10 ml) and triethylamine[303 mg(3 mmol.)]. To the mixture was added, under ice-cooling, nicotinic acid chloride.hydrochloride [125 mg(0.7 mmol.)], and the resultant was stirred at room temperature for 30 minutes. To the reaction mixture was added a 1N aqueous solution of sodium hydroxide, followed by extraction with chloroform. The organic layer was dried over anhydrous potassium carbonate, then the solvent was distilled off under reduced pressure to leave a crude product, which was purified by means of a column chromatography(silica gel:13 g; eluent:ethyl acetate) to obtain the object compound (16)[270 mg(100%, colorless solid product)].

TLC(Silica Gel;AcOEt) Rf=0.23.

NMR(90 MHz,CDCl$_3$) δ: 0.87(3H,t),1.27(20,s),3.37 to 3.70 (10H,m),4.09(2H,t),4.20(2H,t),5.38 (1H,br),7.00 to 7.30(5H,m),7.57(1H,t), 7.66(1H,t),8.50(2H,br).

IR(KBr)cm$^{-1}$: 3320,2915,2845,1690,1643,1595,1540,1495,1270.

(ii) Synthesis of 3-[N-[2-[2-(2-dodecyloxyethoxy)ethoxycarbonyl]]aminoethyl-N-phenyl]carbamoyl-1-ethylpyridinium iodide (17)

To the compound(16) synthesized in (i)[270 mg(0.5 mmol.) was added iodoethane(5 ml) and it was heated under reflux for 60 hours in nitrogen streams while shielding the light. The reaction mixture was was cooled and concentrated under reduced pressure to obtain the object compound(17)[334 mg (95.7%, pale yellow resinous product)].

TLC(Silica Gel;CHC$_3$/MeOH=3/1) Rf=0.25.

NMR(90 MHz), CDCl$_3$) δ: 0.87(3H,t),1.27(20H,s),1.43(3H,t), 3.33 to 3.67(10H,m),3.9 to 4.2(4H,m), 4.80(2H,q),6.03(1H,br),7.18 to 7.53 (5H,m),8.00(1H,br t),8.33(1H,br d), 9.31(2H,br d).

IR(Neat)cm$^{-1}$: 3275(br),2920,2840,1700,1640,1585,1490, 1450,1400,1245,1110.

PRODUCTION EXAMPLE 6

Synthesis of 5-bromo-3-[N-[2-[2-(1-naphthyloxy)ethyl]carbamoyloxy]ethyl-N-phenyl]carbamoyl-1-ethylpyridinium iodide(20)

(i) Synthesis of 5-bromo-3-[N-(2-hydroxyethyl)-N-phenyl]carbamoylpyridine(18)

In chloroform(100 ml) were dissolved 2-anilinoethanol [2.058 g(15 mmol.)] and triethylamine[10.45 ml(75 mmol.)], to which was added, under ice-cooling, 5-bromonicotinic acid chloride hydrochloride[4.24 g(16.5 mmol.)], followed by stirring at room temperature for one hour. The reaction mixture was washed with a 1N aqueous solution of sodium hydroxide. The organic layer was dried over anhydrous potassium carbonate, followed by distilling off the solvent under reduced pressure to leave a crude product. The crude product was purified by means of a column chromatography (silica gel:100g; eluent:n-hexane/ethyl acetate=¼) to obtain the object compound(18)[3.427 g(71.1%,colorless solid product)].

TLC(Silica Gel; AcOEt/acetone(5/1)]: Rf=0.33.

NMR(90 MHz,CDCl$_3$) δ: 3.16(1H,br t),3.86(2H,br t),4.11(2H,t), 7.27(5H,m),7.86(1H,m),8.37(1H,d), 8.53(1H,d).

IR(KBr)cm$^{-1}$: 3440,1640,1590,1400,1295,1080.

(ii) Synthesis of 5-bromo-3-[N-[2-[2-(1-naphthyloxy)ethyl]carbamoyloxy]ethyl-N-phenyl]carbamoylpyridine(19)

In methylene chloride(10 ml) were dissolved the alcohol compound(18) synthesized in (i)[707 mg(2.2 mmol.)] and pyridine 348 mg(4.4 mmol.)]. To the solution was added, under ice-cooling, phenyl chlorocarbonate[413 mg(2.64 mmol.)], followed by stirring at room temperature for 30 minutes. The reaction mixture was washed with a 5% aqueous solution of sodium hydrogen carbonate, and the organic layer was dried over anhydrous sodium sulfate. The solvent was then distilled off under reduced pressure to leave a crude carbonate compound (1.229 g).

To this crude compound was added 2-naphthyloxy ethylamine [374 mg(2 mmol.)] and the mixture was heated at 82° C. for 1.5 hour. The reaction mixture was cooled to obtain a crude product, which was purified by means of a column chromatography(silica gel:60g; eluent:hexane/ethyl acetate=1/1.5) to obtain the object compound(19)[836 mg(78.2%, colorless solid product)].

TLC(Silica Gel; n-hexane/AcOEt(½)]: Rf=0.31.

NMR(90 MHz,CDCl$_3$) δ: 3.65(2H,m),4.13(4H,m),4.38(2H,t), 5.15(1H,br),6.75(1H,dd),6.88 to 7.62 (9H,m),7.78(2H,m),8.28(1H,d),8.48(1H,d).

IR(film)cm$^{-1}$: 3290,1720,1630,1598,1399,1240,1108.

(iii) Synthesis of 5-bromo-3-[N-[2-[2-(1-naphthyloxy)ethyl]carbamoyloxy]ethyl-N-phenyl]carbamoyl-1-ethylpyridinium iodide(20)

To the compound(19) synthesized in (ii)[303 mg(0.567 mmol.)] was added iodoethane(10 ml) and it was heated for 72 hours under reflux in nitrogen streams while shielding the light. The reaction mixture was cooled and concentrated under reduced pressure to give a crude product, which was washed with ether to obtain the object compound(20)[391 mg(100%, pale yellow powdery product)].

TLC[Silica Gel; CHCl$_3$/MeOH(3/1)]: Rf=0.30.

NMR(90 MHz,CDCl$_3$) δ: 1.29(3H,t),3.65(2H,m),4.18(6H,m),4.75 (2H,q),6.29(1H,br),6.76(1H,dd),7.0 to 7.7(9H,m),7.74(1H,m),8.19(2H,m),9.18 (1H,br s),9.27(1H,br s).

IR(KBr)cm$^{-1}$: 3400(br),1700,1650,1590,1400,1260,1240,1102.

PRODUCTION EXAMPLE 7

Synthesis of 5-bromo-3-[N-[2-[2-(1-naphthyloxy)ethyl]carbamoyloxy]ethyl-N-phenyl]carbamoyl-1-propylpyridinium iodide(21)

To the compound(19)[1.306 g(2.44 mmol.)] synthesized in Production Example 6-(ii) was added 1-iodopropane(30 ml), and the mixture was treated under reflux for 68 hours in nitrogen streams while shielding the light. The reaction mixture was cooled and then concentrated under reduced pressure to give a crude product, which was purified by means of a column chromatography(silica gel:50 g; eluent:chloroform/methanol=6/1) to obtain the object compound(21)[1.313 g(76.3%, pale yellow powdery product).

TLC[Silica Gel; CHCl$_3$/MeOH(3/1)]: Rf=0.37.

NMR(90 MHz,CDCl$_3$) δ: 0.66(3H,t),1.67(2H,m),3.66(2H,m), 4.20(6H,m),4.74(2H,br t),6.34(1H,m), 6.77(1H,dd),6.9 to 7.7(9H,m),7.75(1H,m), 8.24(2H,m),9.21(1H,br s),9.27(1H,br s).

IR(KBr)cm$^{-1}$: 3400,1710,1660,1590,1400,1270,1242,1103.

PRODUCTION EXAMPLE 8

Synthesis of 5-bromo-3-[N-[2-[2-(1-naphthyloxy)ethyl]carbamoyloxy]ethyl-N-phenyl]carbamoyl-1-propylpyridinium chloride(22)

In 70% methanol/water(75 ml) was dissolved the compound (21) synthesized in Production Example 7[1.057 g(1.5 mmol.)]. The solution was treated with IRA-410(Cl−)[75 ml: eluent; 70% methanol/water] to afford the object compound(22)[919 mg (100%,pale yellow powdery product).

TLC[Silica Gel; CHCl$_3$/MeOH(4/1)]: Rf=0.20.
NMR(90 MHz,CDCl$_3$) δ: 0.62(3H,t),1.69(2H,m),3.68(2H,m),4.22 (6H,m),4.81(2H,br t),6.79(1H,dd), 6.9 to 7.6(9H,m),7.76(1H,m),8.26(2H,m), 9.52(1H,br s),9.66(1H,br s).

IR(KBr)cm$^{-1}$: 3400,1700,1650,1589,1398,1260,1240,1100.

PRODUCTION EXAMPLE 9

Synthesis of 5-bromo-3-[N-[2-[2-(1-naphthylcarbamoyloxy)ethyl]carbamoyloxy]ethyl-N-phenyl]carbamoyl-1-propylpyridinium iodide(24)

(i) Synthesis of 5-bromo-3-[N-[2-[2-(1-naphthylcarbamoyloxy)ethyl]carbamoyloxy]ethyl-N-phenyl]carbamoyl pyridine(23)

In methylene chloride(30 ml) were dissolved the alcohol compound(18) synthesized in Production Example 6-(i)[1.132 g (3.53 mmol.)] and pyridine[557 mg(7.05 mmol.)]. To the solution was added, under ice-cooling, phenyl chlorocarbonate [662 mg(4.23 mmol.)], and the mixture was stirred at room temperature for 10 minutes. The reaction mixture was washed with a 5% aqueous solution of sodium hydrogen carbonate, and the organic layer was dried over anhydrous sodium sulfate, then the solvent was distilled off under reduced pressure to obtain a crude carbonate compound(2.02 g).

To this crude carbonate compound was added 2-naphthylcarbamoyloxyethylamine[812 mg(3.53 mmol.)], and the mixture was heated at 95° C. for two hours. The reaction mixture was cooled, and the resulting crude product was purified by means of a column chromatography(silica gel:60 g; eluent:hexane/ethyl acetate=1/2) to obtain the object compound(23)[1.484 g (72.9%, colorless solid product)].

TLC[Silica Gel; n-hexane/AcOEt(1/2)]: Rf=0.23.

NMR(900 MHz, CDCl$_3$) δ: 3.45(2H,m), 4.00 to 4.50(6H,m), 5.13 (1H,m), 6.9 to 8.0(13H,m), 8.30(1H,m), 8.43(1H,m).

IR(KBr)cm$^{-1}$: 3300,1710,1635,1590,1530,1490,1215.
(ii) Synthesis of 5-bromo-3-[N-[2-[2-(1-naphthylcarbamoyloxy)ethyl]carbamoyloxy]ethyl-N-phenyl]carbamoyl-1-propylpyridinium iodide(24)

To the compound(23) synthesized in (i)[1.355 g(2.35 mmol.)] was added 1-iodopropane(30 ml), and the mixture was heated under reflux for 68 hours in nitrogen stream while shielding the light. The reaction mixture was cooled and concentrated under reduced pressure to give a crude product, which was purified by means of a column chromatography(silica gel:50 g; eluent:-chloroform/methanol=6/1) to afford the object compound (24)[1.204 g(68.6%, pale yellow powdery product)].

TLC[Silica Gel; CHCl$_3$/MeOH(4/1)]: Rf=0.29.
NMR(90 MHz, CDCl$_3$) δ: 0.57(3H,m),1.58(2H,m),3.49(2H,m),4.16 (6H,m),4.52(2H,br t),6.71(1H,m),6.97 to 7.91(11H,m),8.14(2H,m),8.98(1H,br s), 9.35(1H,br s).

IR(KBr)cm$^{-1}$: 3260,1710,1655,1595,1525,1492,1220.

PRODUCTION EXAMPLE 10

Synthesis of 5-bromo-3-[N-[2-[2-(1-naphthylcarbamoyloxy)ethyl]carbamoyloxy]ethyl-N-phenyl]carbamoyl-1-propylpyridinium chloride(25).

In 70% methanol/water(60 ml) was dissolved the compound (24) synthesized in Production Example 9[972 mg(1.3 mmol.)]. The solution was treated with IRA-410(Cl−)[60 ml: eluent; 70% methanol/water] to give the compound(25)[852 mg(100%, pale yellow powdery product).

TLC[Silica Gel;CHCl$_3$MeOH(4/1)]: Rf=0.17.
NMR(90 MHz,CDCl$_3$) δ: 0.51(3H,t),1.56(2H,m),3.52(2H,m),4.20 (6H,m),4.58(2H,m),7.07(1H,m),7.0 to 7.9(10H,m),8.17(2H,m),8.84(1H,br s), 9.10(1H,br s), 9.77(1H,br s).

IR(KBr)cm$^{-1}$: 3380,1700,1650,1588,1520,1490,1260,1220.

PRODUCTION EXAMPLE 11

Synthesis of 5-bromo-3-[N-[2-[2-(1-naphthyloxy)ethoxycarbonylamino]ethyl]-N-phenyl]carbamoyl-1-propylpyridinium chloride(29)

(i) Synthesis of N-phenyl-N'-[2-(1-naphthyloxy)ethoxycarbonyl]ethylenediamine(26)

To 2-(1-naphthyloxy)ethanol[1.70 g(9.00 mmol.)] and pyridine[1.46 ml(18.0 mmol.)] dissolved in dichloromethane(30 ml) was added dropwise, under ice-cooling while stirring, phenyl chloroformate[1.24 ml(9.90 mmol.)], then the mixture was stirred for 30 minutes at room temperature. The reaction mixture was washed with a 5% solution of sodium hydrogencarbonate and was then dried, followed by distilling off the solvent. To this residue was added N-phenylethylenediamine [1.31 ml(10.0 mmol.)], and the mixture was heated at 70° C. for 30 minutes. The resultant was cooled and subjected to a silica gel column chromatography eluting with hexane-ethyl acetate(2:1) to afford the compound(26)[3.04 g(96.1%)] as yellow powder.

IR(Neat)cm$^{-1}$: 3360(br),3050,1700(br),1600.

NMR(90 MHz,CDCl$_3$) δ: 2.90 to 3.54(4H,m),4.02 to 4.34(2H,m), 4.34 to 4.65(2H,m),5.18(1H,t,r t), 6.30 to 6.88(4H,m),6.88 to 7.62(6H,m), 7.62 to 7.92(1H,m),8.15 to 8.42(1H,m).

(ii) Synthesis of 5-bromo-3-[N-[2-[2-(1-naphthyloxy)ethoxycarbonylamino]ethyl]-N-phenyl]carbamoylpyridine(27)

To a solution of the compound(26) synthesized in (i)[2.83 g (8.10 mmol.)] and triethylamine[5.98 ml(42.9 mmol.)] in chloroform(47 ml) was added, under stirring and ice-cooling, 5-bromonicotinic acid chloride hydrochloride[2.76 g(10.7 mmol.)]. The mixture was stirred at room temperature for 30 minutes. The reaction mixture was washed with a 1N aqueous solution of sodium hydroxide and dried, then the solvent was distilled off under reduced pressure. The residue was subjected to a silica gel column chromatography eluting with hexaneethyl acetate(2:1) to obtain the compound(27) [3.93 g(90.9%)] as a colorless oily product.

IR(Neat)cm$^{-1}$: 3310(br),3040,1710(br),1640(br),1590.

NMR(90 MHz,CDCl$_3$) δ: 3.44(2H,q,J=6 Hz),4.03(2H,t,J=6 Hz), 4.25(2H,t,J=6 Hz),4.52(2H,t,J=6 Hz), 5.39(1H,m),6.75(1H,dd,J=2,6 Hz),6.75 to 7.64(9H,m), 7.64 to 7.95(2H,m), 8.12 to 8.42(2H,m), 8.42 to 8.60 (1H,d,J=2 Hz).

(iii) Synthesis of 5-bromo-3-[N-[2-[2-(1-naphthyloxy)ethoxycarbonylamino]ethyl]-N-phenyl]carbamoyl-1-propylpyridinium iodide(28)

A solution of the compound(27) synthesized in (ii) [3.13 g (3.99 mmol.)] in n-propyl iodide(30 ml) was stirred at 110° C. for 40 hours. Resulting precipitates were washed with ether, followed by drying to afford the compound(28)[2.85 g(quant.)] as a yellow powdery product.

IR(KBr)cm$^{-1}$: 3400(br),3040,1700(br),1650(br),1590.
NMR(90 MHz,CDCl$_3$) δ: 0.67(3H,m),1.70(2H,m),3.53(2H,m),4.02 (2H,m),4.27(2H,m),4.49(2H,m),4.68(2H,m), 6.30(1H,m),6.77(1H,m),6.91 to 7.60 (9H,m), 7.60 to 7.90(1H,m),8.05 to 8.47 (2H,m),9.34(1H,br s),9.40(1H,br s).

(iv) Synthesis of 5-bromo-3-[N-[2-[2-(1-naphthyloxy)ethoxycarbonylamino]ethyl]-N-phenyl]carbamoyl-1-propylpyridinium chloride(29)

In a mixture solution of methanol-water(7:3)(20 ml) was dissolved the compound(28) synthesized in (iii)[704 mg(1.00 mmol.)], and the solution was processed with anion exchange resin(IRA-410[Cl$^-$]). The eluate was concentrated under reduced pressure to obtain the compound(29)[473 mg(77.2%)] as yellow powder.

IR(KBr)cm$^{-1}$: 3400(br),3040,1710(br),1650(br),1590.
NMR(90 —MHZ,CDCl$_3$) δ: 0.70(3H,t,J=7 Hz),1.77(2H,q,J=7 Hz),3.54 (2H,m),4.01(2H,m),4.30(2H,t,J=5 Hz), 4.53(2H,t,J=5 Hz),4.69(2H,t,J=7 Hz), 6.82(1H,dd,J=2,6 Hz),6.97 to 7.94 (10H,m),8.50 to 8.34(1H,m),8.52(1H, br s),9.60(1H,br s),9.78(1H,br s).

PRODUCTION EXAMPLE 12

Synthesis of 5-bromo-1-hexyl-3-[N-[2-[2-(1-naphthyloxy)ethoxycarbonylamino]ethyl]-N-phenyl]carbamoylpyridinium iodide(30)

A solution of the compound(27) synthesized in Production Example 11-(ii) [302 mg(0.57 mmol.)] in hexyl iodide(5 ml) was stirred for two days at 110° C. Resulting precipitates were washed with ether, followed by drying to afford the compound (30)[416 mg(98.6%)] as yellow powder.

IR(KBr)cm$^{-1}$: 3400(br),3050,1710(br),1650(br),1590.
NMR(90 MHz,CDCl$_3$) δ: 0.70 to 0.98(3H,m),1.18(6H,m),1.57 (2H,m),3.48(2H,m),4.02(2H,m),4.25(2H,m), 4.48(2H,m),4.65(2H,m),6.12(1H,m),6.77 (1H,dd,J=2.7 Hz),6.95 to 7.62(9H,m), 7.62 to 7.90(1H,m),8.10 to 8.35(1H,m), 8.42(1H,br s),9.05 to 9.40(2H,m).

PRODUCTION EXAMPLE 13

Synthesis of 5-bromo-1-isopentyl-3-[N-[2-[2-(1-naphthyloxy)ethoxycarbonylamino]ethyl]-N-phenyl]carbamoylpyridinium iodide (31)

A solution of the compound(27) synthesized in Production Example 11-(ii)[327 mg(0.61 mmol.)] in isoamyl iodide(5 ml) was heated under stirring for two days at 110° C. Resulting precipitates were washed with ether, followed by drying to afford the compound(31)[460 mg(quant.)] as yellow powder.

IR(KBr)cm$^{-1}$: 3400(br),1700(br),1650(br),1590.

NMR(90 MHz,CDCl$_3$) δ: 0.63 to 1.20(6H,m),1.20 to 2.00(3H,m), 3.50(2H,m),4.04(2H,m),4.24(2H,m),4.50 (2H,m),4.61(2H,m),6.05(1H,m),6.76(1H, dd,J=2,6 Hz),6.97 to 7.64(9H,m),7.64 to 7.90(1H,m),8.07 to 8.30(1H,m),8.37 (1H,br s),9.08(1H,br s),9.17(1H,br s).

PRODUCTION EXAMPLE 14

Synthesis of 5-bromo-1-isopropyl-3-[N-[2-[2-(1-naphthyloxy)ethoxycarbonyl aminoethyl]-N-phenyl]carbamoylpyridinium iodide(32)

A solution of the compound(27) synthesized in Production Example 11-(ii) [335 mg(0.63 mmol.)] in isopropyl iodide(5 ml) was stirred for two days at 110° C. Resulting precipitates were washed with ether, followed by drying to afford the compound(32)[423 mg(95.3%)] as yellow powder.

IR(KBr)cm$^{-1}$: 3400(br),1700(br),1650(br),1590.

NMR(90 MHz,CDCl$_3$) δ: 1.42(6H,d,J=6 Hz),2.80 to 3.53(1H,m), 3.90(2H,m),4.02 to 4.56(6H,m),4.13 (2H,m),6.96(1H,dd,J=2,6 Hz),7.06 to 7.68(9H,m),7.68 to 8.04(2H,m),8.04 to 8.33(1H,m),8.62 to 8.88(1H,m), 9.08(1H,br s),9.45(1H,br s).

PRODUCTION EXAMPLE 15

Synthesis of 5-bromo-1-ethyl-3-[N-ethyl-N-[2-[2-(1-naphthyloxy)ethyl]carbamoyloxy]ethyl]carbamoylpyridinium iodide(35)

(i) Synthesis of 5-bromo-3-[N-(2-hydroxyethyl)-N-ethyl]carbamoylpyridine(33)

To a solution of N-ethylaminoethanol[1.34 g(15.0 mmol.)] and triethylamine[10.5 m((75 mmol.)] in chloroform(70 ml) was added, under stirring and ice-cooling, 5-bromonicotinic acid chloride hydrochloride[4.24 g(16.5 mmol.)]. The mixture was stirred at room temperature for one hour. The reaction mixture was washed with a 1N aqueous solution of sodium hydroxide, which was then dried. The solvent was distilled off under reduced pressure. The residue was subjected to a silica gel column chromatography, followed by elution with hexane-acetone(6:1) to obtain the compound(33)[3.28 g(79.9%)] as a yellow oily product.

IR(Neat)cm$^{-1}$: 3350(br),3040,1620(br).

NMR(90 MHz,CDCl$_3$) δ: 1.18(3H,t,J=7 Hz),3.00 to 4.10(6H,m), 7.94(1H,t,J=2 Hz),8.61(1H,d,J=2 Hz), 8.73(1H,d,J=2 Hz).

(ii) Synthesis of 5-bromo-3-[N-ethyl-N-[2-[2-(1-naphthyloxy)ethyl]carbamoyloxy]ethyl]carbamoylpyridine(34)

To a solution of the compound(33) synthesized in (i)[683 mg (2.50 mmol.)] and pyridine[0.40 ml(5.0 mmol.)] in dichloromethane(10 ml) was added dropwise, under stirring with ice-cooling, phenyl chloroformate[0.35 ml(2.75 mmol.), and the mixture was stirred for 30 minutes at room temperature. The reaction mixture was washed with a 5% aqueous solution of sodium hydrogencarbonate and then dried, followed by distilling off the solvent. To the residue was added 2-(1-naphthyloxy)ethylamine[468 mg(2.50 mmol.)], and the mixture was heated at 80° C. for 1.5 hour. The reaction mixture was cooled and subjected to a silica gel column chromatography. The column was eluted with hexane-ethyl acetate(1:3) to give the compound(34)[890 mg(73.2%)] as colorless powder.

IR(KBr)cm$^{-1}$: 3300,3040,1710(br),1630(br),1590.

NMR(90 MHz,CDCl$_3$) δ: 1.09(3H,t,J=6 Hz),3.33(2H,m),3.68(2H,t, J=5 Hz),3.72(2H,q,J=5 Hz),4.22(4H,t,J=5 Hz), 5.27(1H,m),6.77(1H,dd,J=2.7 Hz),7.16 to 7.65(4H,m),7.65 to 7.95(2H,m),8.03 to 8.36(1H,m),8.54(1H,d,J=2 Hz),8.70(1H,d, J=2 Hz).

(iii) Synthesis of 5-bromo-1-ethyl-3-[N-ethyl-N-[2-[2-(1-naphthyloxy)ethyl]carbamoyloxy]ethyl]carbamoylpyridinium iodide(35)

A solution of the compound(34) synthesized in (ii)[292 mg (0.60 mmol.)] was stirred for two days at 110° C. Resulting precipitates were washed with ether and then dried to obtain the compound(35)[393 mg(quant.)] as yellow powder IR(KBr)cm$^{-1}$: 3400(br) 3040,1700(br),1640(br),1590.

NMR(90 MHz,DMSO-d$_6$) δ: 1.14(3H,m),1.54(3H,m),3.00 to 3.84 (6H,m),4.16(4H,t,J=6 Hz),4.60(2H,q, J=6 Hz),6.93(1H,dd,J=2.7 Hz),7.27 to 7.70(4H,m),7.70 to 7.79(1H,m),8.10 to 8.37(1H,m),8.84 to 9.07(1H,m), 9.32(1H,br s),9.58(1H,br s).

PRODUCTION EXAMPLE 16

Synthesis of 5-bromo-3-[N-ethyl-N-[2-[2-(1-naphthyloxy)ethyl]carbamoyloxy]ethyl]carbamoyl-1-propylpyridinium iodide (36)

A solution of the compound(34) synthesized in Production Example 15-(ii)[292 mg(0.60 mmol)] in propyl iodide(5 ml) was heated under stirring for two days at 110° C. Resulting precipitates were washed with ether and dried to obtain the compound(36)[407 mg(quant.)] as yellow powder.

IR(KBr)cm$^{-1}$: 3400(br),3040, 1710(br),1640(br),1590.

NMR(90 MHz,DMSO-d$_6$) δ: 0.68 to 1.33(6H,m),1.56 to 2.24(2H, m),3.00 to 3.85(6H,m),4.16(4H,t,J=6 Hz), 4.53(2H,t,J=6 Hz),6.92(1H,dd,J=2.7 Hz), 7.23 to 7.70(4H,m),7.70 to 7.97(1H,m), 8.10 to 8.37(1H,m),8.80 to 9.07(1H,m), 9.33(1H,br s),9.60(1H,br s).

PRODUCTION EXAMPLE 17

Synthesis of 5-bromo-1-ethyl-3-[N-[2-[2-(1-naphthyloxy)ethyl]carbamoyloxy]ethyl-N-propyl]carbamoylpyridinium iodide (39)

(i) Synthesis of 5-bromo-3-[N-(2-hydroxyethyl)-N-propyl]carbamoylpyridine(37)

To a solution of N-n-propylaminoethanol[1.55 g(15.0 mmol.)] and triethylamine[10.5 ml(75 mmol.)] in chloroform(70 ml) was added, under stirring and ice-cooling, 5-bromonicotinic acid chloride hydrochloride[4.24 g(16.5 mmol.)]. The mixture was stirred for one hour at room temperature. The reaction mixture was washed with a 1N aqueous solution of sodium hydroxide and then dried, followed by distilling off the solvent under reduced pressure. The residue was subjected to a silica gel column chromatography, eluting with hexane-acetone(6:1), to obtain the compound(37)[3.32 g(77.1%)] as a yellow oily product.

IR(Neat)cm$^{-1}$: 3350(br),3040,1610(br).

NMR(90 MHz,CDCl$_3$) δ: 0.82(3H,m),1.62(2H,q,J=7 Hz),2.95 to 4.05 (6H,m),7.93(1H,t,J=2 Hz),8.59(1H,d,J=2 Hz),8.73(1H,d,J=2 Hz).

(ii) Synthesis of 5-bromo-3-[N-[2-[2-(1-naphthyloxy)ethyl]carbamoyloxy]ethyl-N-propyl]carbamoylpyridine(38)

To a solution of the compound(37) synthesized in i)[718 mg (2.50 mmol.)] and pyridine[0.40 ml(5.0 mmol.)] in dichloromethane(10 ml) was added dropwise, under ice-cooling and stirring, phenyl chloroformate[0.35 ml(2.75 mmol.)]. The mixture was stirred for 30 minutes at room temperature. The reaction mixture was washed with a 5% aqueous solution of sodium hydrogencarbonate, which was then dried, followed by distilling off the solvent. To the residue was added 2-(1-naphthyloxy)ethylamine[468 mg(2.50 mmol.)], and the mixture was heated at 80° C. for 1.5 hour. The reaction mixture was cooled and subjected to a silica gel column chromatography, eluting with hexane-ethyl acetate(1:3), to afford the compound(38)[763 mg (61.0%)] as colorless powder.

IR(Neat)cm$^{-1}$: 3300(br),3040,1710(br),1630(br),1590.

NMR(90 MHz,CDCl$_3$) δ: 0.45(3H,m),1.52(2H,m),3.23(2H,m),3.68 (2H,t,J=6 Hz),2.71(2H,t,J=6 Hz),4.22(4H,t,J=6 Hz),5.38(1H,br t, J=6 Hz),6.78(1H,dd,J=2.7 Hz),7.14 to 7.63(4H,m),7.63 to 7.96 (2H,m),8.06 to 8.37(1H,m),8.58(1H,d,J=2 Hz),8.70(1H,d,J=2 Hz).

(iii) Synthesis of 5-bromo-1-ethyl-3-[N-[2-[2-(1-naphthyloxy)ethyl]carbamoyloxy]ethyl-N-propyl]carbamoylpyridinium iodide(39)

A solution of the compound(38) synthesized in (ii)[247 mg (0.49 mmol.)] in ethyl iodide(5 ml) was stirred at 110° C. for two days. Resulting precipitates were washed with ether, followed by drying to obtain the compound(39)[324 mg(quant.) as yellow powder.

IR(KBr)cm$^{-1}$: 3400(br),3040,1710(br),1630(br),1590.

NMR(90 MHz,DMSO-d$_6$) δ: 0.47 to 1.23(3H,m),1.23 to 1.86(5H,m), 2.93 to 3.86(6H,m),4.17(4H,m),4.63(2H,m),6.80 to 7.06(1H, m),7.20 to 7.70(4H,m),7.70 to 7.86(1H,m),8.12 to 8.43(1H, m),8.73 to 9.10(1H,m),9.35(1H,br,s),9.62(1H,br s).

PRODUCTION EXAMPLE 18

Synthesis of 5-bromo-3-[N-[2-[2-(1-naphthyloxy)ethyl]carbamoyloxy]ethyl-N-propyl]carbamoyl-1-propylpyridinium iodide(40)

A solution of the compound(38) synthesized in the Production Example 17-(ii)[203 mg(0.41 mmol.)] in propyl iodide(5 ml) was stirred for two days at 110° C. Resulting precipitates were washed with ether, followed by drying to obtain the compound (40)[264 mg(quant.)] as yellow powder.

IR(KBr)cm$^{-1}$: 3400(br),3040,1710(br),1640(br),1590.

NMR(90 MHz,DMSO-d$_6$) δ: 0.60 to 1.24(6H,m),1.53(4H,m),3.00 to 3.90(6H,m),4.18(4H,m),4.63(2H,m),6.82 to 7.10(1H,m),7.37 to 7.72(4H,m),7.72 to 8.01(1H,m),8.12 to 8.46(1H,m),8.78 to 9.10(1H,m),9.35(1H,br s),9.62(1H,br s).

PRODUCTION EXAMPLE 19

Synthesis of
5-bromo-1-ethyl-3-[N-butyl-N-[2-[2-(1-naphthyloxy)ethyl]carbamoyloxy]ethyl]carbamoylpyridinium iodide(43)

(i) Synthesis of 5-bromo-3-[N-butyl-N-(2-hydroxyethyl)]carbamoylpyridine(41)

To a solution of N-n-butylaminoethanol[1.76 g(15.0 mmol.)] and triethylamine[10.5 ml(75 mmol.)] in chloroform(70 ml) was added, under ice-cooling and stirring, 5-bromonicotinic acid chloride hydrochloride[4.24 g(16.5 mmol.)], and the mixture was stirred for one hour at room temperature. The reaction mixture was washed with a 1N aqueous solution of sodium hydroxide, which was then dried, followed by distilling off the solvent under reduced pressure. The residue was subjected to a silica gel column chromatography, eluting with hexane-acetone(7:1) to obtain the compound(41)[4.04 g(89.4%)] as a yellow oily product.

IR(Neat cm$^{-1}$: 3350(br),3040,1610(br).

NMR(90 MHz,CDCl$_3$) δ: 0.87(3H,m),1.02 to 1.82(4H,m),2.75 to 4.03(6H,m),7.93(1H,t,J=2 Hz),8.60(1H,d,J=2 Hz),8.73(1H,d, J=2 Hz).

(ii) Synthesis of 5-bromo-3-[N-butyl-N-[2-[2-(1-naphthyloxy)ethyl]carbamoyloxy]ethyl]carbamoylpyridine(42)

To a solution of the compound(41) synthesized in (i)[753 mg (2.50 mmol.)] and pyridine[0.40 ml(5.0 mmol.)] in dichloromethane(10 ml) was added dropwise, under stirring and ice-cooling, phenyl chloroformate[0.35 ml(2.75 mmol.)], and the mixture was stirred for 30 minutes at room temperature. The reaction mixture was washed with a 5% aqueous solution of sodium hydrogencarbonate and then dried, followed by distilling off the solvent. To the residue was added 2-(1-naphthyloxy)ethylamine[468 mg(2.50 mmol.)], and the mixture was heated for 1.5 hour at 80° C. The reaction mixture was cooled and subjected to a silica gel column chromatography, eluting with hexane-ethyl acetate(1:3), to afford the compound (42)[961 mg(74.7%)] as a colorless oily product.

IR(Neat)cm$^{-1}$: 3300(br),3040,1710(br),1630(br),1590.

NMR(90 MHz,CDCl$_3$) δ: 0.77(3H,m),1.47(4H,m),3.22(2H,m),3.66 (2H,t,J=5 Hz),3.68(2H,q,J=5 Hz),4.18(4H,t,J=5 Hz),5.46(1H, br t,J=6 Hz),6.74(1H,dd,J=2,7 Hz),7.04 to 7.61(4H,m),7.61 to 7.96(2H,m),8.03 to 8.37(1H,m),8.56(1H,br s),8.70(1H,br s)

(iii) Synthesis of 5-bromo-1-ethyl-3-[N-butyl-N-[2-[2-(1-naphthyloxy)ethyl]carbamoyloxy]ethyl]carbamoylpyridinium iodide(43)

A solution of the compound(42) synthesized in (ii)[295 mg (0.57 mmol)] in ethyl iodide(5 ml) was stirred for two days at 110° C. Resulting precipitates were washed with ether, followed by drying to give the compound(43)[346 mg(90.5%)] as yellow powder.

IR(KBr)cm$^{-1}$: 3400(br),3040,1710(br),1640(br),1590.

NMR(90 MHz,DMSO-d$_6$) δ: 0.53 to 1.21(5H,m),1.21 to 2.15(4H,m), 2.90 to 3.84(6H,m),4.17(4H,m),4.56(2H,m),6.76 to 7.1(1H,m), 7.13 to 7.68(4H,m),7.68 to 8.06(1H,m),8.06 to 8.42(1H,m), 8.82 to 9.10(1H,m),9.35(1H,br s),9.62(1H,br s).

PRODUCTION EXAMPLE 20

Synthesis of
5-bromo-3-[N-butyl-N-[2-[2-(1-naphthyloxy)ethyl]carbamoyloxy]ethyl]carbamoyl-1-propylpyridinium iodide (44)

A solution of the compound(42) synthesized in Production Example 19-(ii) [295 mg(0.57 mmol.)] in propyl iodide (5 ml was stirred for two days at 110° C. Resulting precipitates were washed with ether, followed by drying to obtain the compound(44)[325 mg(quant.)] as yellow powder.

IR(KBr)cm$^{-1}$: 3400(br),3040,1710(br),1640(br),1590.

NMR(90 MHz,DMSO-d$_6$) δ: 0.54 to 1.15(5H,m),1.15 to 1.70(2H,m), 1.70 to 2.20(2H,m),2.96 to 3.83(6H,m),4.16(4H,m),4.56(2H,m), 6.78 to 7.15(1H,m),7.20 to 7.69(4H,m),7.69 to 8.00(1H,m), 8.79 to 9.10(1H,m),9.34(1H,br s),9.61(1H,br s).

PRODUCTION EXAMPLE 21

Synthesis of
5-bromo-3-[N-(4-fluorophenyl)-N-[2-[2-(1-naphthylcarbamoyloxy)ethyl]carbamoyloxy]ethyl]carbamoyl-1-propylpyridinium chloride(48)

(i) Synthesis of 5-bromo-3-[N-(4-fluorophenyl)-N-(2-hydroxyethyl)]carbamoylpyridine(45)

To a solution of N-(4-fluorophenyl)aminoethanol[621 mg (4.00 mmol.)] and triethylamine[2.79 ml(20.0 mmol.)] in chloroform(20 ml) was added, under ice-cooling and stirring, 5-bromonicotinic acid chloride hydrochloride[1.13 g(4.40 mmol.)], and the mixture was stirred for one hour at room temperature. The reaction mixture was washed with a 1N aqueous solution of sodium hydroxide and then dried, followed by distilling off the solvent under reduced pressure. The residue was subjected to a silica gel column chromatography, eluting with hexane-ethyl acetate(1:3), to obtain the compound(45)[649 mg(47.8%)] as pale yellow prisms.

IR(KBr)cm$^{-1}$: 3400(br),3050,1620(br).

NMR(90 MHz,CDCl$_3$) δ: 3.82(2H,t,J=5 Hz),4.25(2H,t,J=5 Hz),6.76 to 7.36(4H,m),7.86(1H,t,J=2 Hz),8.34(1H,d,J=2 Hz),8.53(1H,d, J=2 Hz).

(ii) Synthesis of 5-bromo-3-[N-(4-fluorophenyl)-N-[2-[2-(1-naphthylcarbamoyloxy)ethyl]carbamoyloxy]ethyl]carbamoylpyridine(46)

To a solution of the compound(45) synthesized in (i)[591 mg (1.74 mmol.)] and pyridine[0.28 m((3.48 mmol.)] in dichloromethane(5 ml) was added dropwise, under ice-cooling while stirring, phenyl chloroformate[0.24 m((1.91 mmol.)], and the mixture was stirred for 30 minutes at room temperature. The reaction mixture was washed with a 5% aqueous solution of sodium hydrogencarbonate then dried, followed by distilling off the solvent. To the residue was added 2-(1-naphthylcarbamoyloxy)ethylamine[401 mg(1.74 mmol.)], and the mixture was heated for one hour at 80° C., which was subjected, after cooling, to a silica gel column chromatography, eluting with hexane-ethyl acetate(1:2), to thereby obtain the compound(46) [727 mg(70.2%)] as a colorless oily product.

IR(KBr)cm$^{-1}$: 3300(br),3050,1720(br),1640(br),1590.

NMR(90 MHz,CDCl$_3$) δ: 3.46(2H,q,J=5 Hz),4.10(2H,t,J=5 Hz),4.29 (2H,t,J=5 Hz),4.35(2H,t,J=5 Hz),5.24(1H,br t,J=5 Hz),6.76 to 7.23(4H,m),7.23 to 7.67(4H,m),7.67 to 8.00(4H,m),8.33(1H, br s),8.48(1H,d,J=2 Hz).

(iii) Synthesis of 5-bromo-3-[N-(4-fluorophenyl)-N-[2-[2-(1-naphthylcarbamoyloxy)ethyl]carbamoyloxy]ethyl]carbamoyl-1-propylpyridinium iodide(47)

A solution of the compound(46)[624 mg(1.05 mmol.)] synthesized in (ii) in propyl iodide(10 ml) was stirred for two days at 110° C. Resulting precipitates were washed with ether and dried to obtain the compound(47)[861 mg(quant.)] as yellow powder.

IR(KBr)cm$^{-1}$: 3400(br),3040,1710(br),1650(br),1590.
NMR(90 MHz,CDCl$_3$) δ: 0.70(3H,t,J=7 Hz),1.73(2H,m),3.40(2H,m), 4.23(6H,m),4.58(2H,br t,J=7 Hz),6.70 to 7.23(3H,m),7.23 to 7.96(7H,m),7.96 to 8.30(1H,m),8.38(1H,br s),8.55(1H,br s),9.25(1H,br s),9.43(1H,br s).

(iv) Synthesis of 5-bromo-3-[N-(4-fluorophenyl)-N-[2-[2-(1-naphthylcarbamoyloxy)ethyl]carbamoyloxy]ethyl]carbamoyl- 1-propylpyridinium chloride(48)

A solution of the compound(47) synthesized in (iii)[630 mg (0.82 mmol.)] in a mixture solution of methanol-water(7:3) (16 ml) was allowed to pass through anion exchange resin (IRA-410[Cl$^-$])(16 ml). The eluate thus obtained was concentrated under reduced pressure to afford the compound(48) [397 mg(75.8%)] as yellow powder.

IR(KBr)cm$^{-1}$: 3350(br),1710(br),1650(br),1600.
NMR(90 MHz,DMSO-d$_6$) δ: 0.66(3H,t,J=7 Hz),1.76(2H,m),3.33(2H,m), 4.14(6H,m),4.53(2H,m),6.80 to 8.34(11H,m),8.74(1H,br s), 9.39(1H,br s),9.52(2H,br s).

PRODUCTION EXAMPLE 22

Synthesis of 5-bromo-3-[N-(4-chlorophenyl)-N-[2-[2-(1-naphthylcarbamoyloxy)ethyl]carbamoyloxy]ethyl]carbamoyl-1-propylpyridinium chloride(52)

(i) Synthesis of 5-bromo-3-[N-(4-chlorophenyl)-N-(2-hydroxyethyl)]carbamoylpyridine(49)

To a solution of N-(4-chlorophenyl)aminoethanol[687 mg (4.00 mmol.)] and triethylamine[2.79 ml(20.0 mmol.)] in chloroform(20 ml) was added, under ice-cooling with stirring, 5-bromonicotinic acid chloride hydrochloride[1.13 g(4.40 mmol.)], and the mixture was stirred for one hour at room temperature. The reaction mixture, was washed with a 1N aqueous solution of sodium hydroxide, then dried, followed by distilling off the solvent under reduced pressure. The residue was subjected to a silica gel column chromatography, eluting with hexane-ethyl acetate (1:3) to obtain the compound(99)[608 mg(45.3%)] as pale yellow prisms.

IR(KBr)cm$^{-1}$: 3400(br),3050,1620(br).
NMR(90 MHz,CDCl$_3$) δ: 3.85(2H,t,J=5 Hz),4.07(2H,t,J=5 Hz),7.10 (2H,d,J=9 Hz),7.27(2H,d,J=9 Hz),7.89(1H,t,J=2 Hz),8.30(1H,d,J=2 Hz),8.53(1H,d,J=2 Hz).

(ii) Synthesis of 5-bromo-3-[N-(4-chlorophenyl)-N-[2-[2-(1-naphthylcarbamoyloxy)ethyl]carbamoyloxy]ethyl]carbamoylpyridine(50)

To a solution of the compound(49) synthesized in (i)[150 mg (0.45 mmol.)] and pyridine[0.07 ml(0.90 mmol.)] in dichloromethane(2 ml) was added dropwise, under ice-cooling while stirring, phenyl chloroformate[0.06 ml(0.49 mmol.)]. The mixture was stirred for 30 minutes at room temperature. The reaction mixture was washed with a 5% aqueous solution of sodium hydrogencarbonate and then dried, followed by distilling off the solvent. To the residue was added 2-(1-naphthylcarbamoyloxy)ethylamine[104 mg(0.45 mmol.)], and the mixture was heated at 80° C. for one hour. The reaction mixture was cooled and subjected to a silica gel column chromatography, eluting with hexane-ethyl acetate(1:2), to obtain the compound (50)[171 mg(62.8%)] as a colorless oily product.

IR(KBr)cm$^{-1}$: 3300(br),3050,1710(br),1650(br),1590.
NMR(90 MHz,CDCl$_3$) δ: 3.48(2H,q,J=5 Hz),4.10(2H,t,J=5 Hz),4.30 (2H,t,J=5 Hz),4.35(2H,t,J=5 Hz),5.10(1H,m),7.03(2H,d,J=9 Hz), 7.22(2H,d,J=9 Hz),7.33 to 7.70(4H,m),7.70 to 8.03(4H,m), 8.32(1H,br s),8.51(1H,d,J=2 Hz).

(ii) Synthesis of 5-bromo-3-[N-(4-chlorophenyl)-N-[2-[2-(1-naphthylcarbamoyloxy)ethyl]carbamoyloxy]ethyl]carbamoyl1-propylpyridinium iodide(51)

A solution of the compound(50) synthesized in (ii)[131 mg (0.21 mmol.)] in propyl iodide(5 ml) was stirred for two days at 110° C. Resulting precipitates were washed with ether and then dried to obtain the compound(51)[150 mg(91.4%)] as yellow powder.

IR(KBr)cm$^{-1}$: 3400(br),3050,1720(br),1660(br),1590.
NMR(90 MHz, CDCl$_3$) δ: 0.70(3H,t,J=7 Hz),1.73(2H,m),3.50(2H,m), 4.28(6H,m),4.60(2H,br t,J=7 Hz),6.90(1H,m),7.13 to 8.13 (10H,m),8.13 to 8.35(1H,m),8.52(1H,br s),8.68(1H,br s), 9.38(2H,br s).

(iv) Synthesis of 5-bromo-3-[N-(4-chlorophenyl)-N-[2-[2-(1-naphthylcarbamoyloxy)ethyl]carbamoyloxy]ethyl]carbamoyl-1-propylpyridinium chloride(52)

A solution of the compound(51) synthesized in ii)[50 mg (0.06 mmol.)] in a mixture of methanol-water(7:3) was allowed to pass through anion exchange resin(IRA-410[Cl$^-$])(2 ml).

The eluate thus obtained was concentrated under reduced pressure to afford the compound(52)[30 mg(72.4%)] as yellow powder.

IR(KBr)cm$^{-1}$: 3370(br),1710(br),1650(br),1600.
NMR(90 MHz,CDCl$_3$) δ: 0.50(3H,t,J=7 Hz),1.52(2H,m),3.50(2H,m), 4.10(2H,m),4.26(4H,m),4.53(2H,m),7.00 to 8.00(10H,m), 8.23(2H,m),8.66(1H,m),8.80(1H,m),10.80(1H,br s).

PRODUCTION EXAMPLE 23

Synthesis of 5-bromo-3-[N-(4-chlorophenyl)-N-[2-[2-(1-naphthyloxy)ethyl]carbamoyloxy]ethyl]carbamoyl-1-propylpyridinium chloride(55)

(i) Synthesis of 5-bromo-3-[N-(4-chlorophenyl)-N-[2-[2-(1-naphthyloxy)ethyl]carbamoyloxy]ethyl]carbamoylpyridine(53)

To a solution of the compound(49) synthesized in Production Example 22-(i)[150 mg(0.45 mmol.)] and pyridine[0.07 ml(0.90 mmol)] in dichloromethane(2 ml was added dropwise, under ice-cooling while stirring, phenyl chloroformate[0.06 ml 0.49 mmol.)]. The mixture was stirred for 30 minutes at room temperature. The reaction mixture was washed with a 5% aqueous solution of sodium hydrogencarbonate, then dried, followed by distilling off the solvent. To the residue was added 2-(1-naphthyloxy)ethylamine[84 mg(0.45 mmol.)], and the mixture was heated for one hour at 80° C. The reaction mixture was cooled and subjected to a silica gel column chromatography, eluting with hexane-ethyl acetate(1:2), to obtain the compound (53)[212 mg(83.7%)] as a pale yellow oily product.

IR(KBr)cm$^{-1}$: 3300(br),3030,1710(br),1640(br),1580.
NMR(90 MHz,CDCl$_3$) δ: 3.66(2H,q,J=5 Hz),4.12(2H,t,J=5 Hz),4.18 (2H,t,J=5 Hz),4.40(2H,t,J=5 Hz),5.16(1H,m),6.80(1H,dd,J=2.7

Hz),6.98(2H,d,J=9 Hz),7.15(2H,d,J=9 Hz),7.25 to 7.62(4H,m), 7.67 to 7.93(4H,m),8.08 to 8.39(2H,m),8.54(1H,d,J=2 Hz).

(ii) Synthesis of 5-bromo-3-[N-(4-chlorophenyl)-N-[2-[2-(1-naphthyloxy)ethyl]carbamoyloxy]ethyl]carbamoyl-1-propylpyridinium iodide(54)

A solution of the compound(53) synthesized in (i)[181 mg (0.32 mmol.) in propyl iodide(5 ml) was stirred for two days at 110° C. Resulting precipitates were washed with ether and dried to obtain the compound(54)[240 mg(quant.)] as yellow powder.

IR(KBr)cm$^{-1}$: 3450(br),3040,1710(br),1660(br),1590.
NMR(90 MHz,CDCl$_3$) δ: 0.72(3H,t,J=7 Hz),1.77(2H,m),3.60(2H,m), 4.17(2H,m),4.23(4H,m),4.75(2H,br t,J=7 Hz),6.38(1H,m), 6.79(1H,dd,J=2,7 Hz),7.00 to 7.60(8H,m),7.63 to 7.87(1H,m), 8.30(1H,m),8.34(1H,br s),9.14(1H,br s),9.29(2H,br s).

(iii) Synthesis of 5-bromo-3-[N-(4-chlorophenyl)-N-[2-[2-(1-naphthyloxy)ethyl]carbamoyloxy]ethyl]carbamoyl-1-propylpyridinium chloride(55)

The compound 54) synthesized in )[132 mg(0.18 :mmol.)] was dissolved in a mixture of methanol-water(7:3)(2 ml). The solution was allowed to pass through anion exchange resin (IRA-410[Cl$^-$])(4 ml). The eluate was concentrated under reduced pressure to obtain the compound(55)[83 mg(71.2%)] as yellow powder.

IR(KBr)cm$^{-1}$: 3350(br),1700(br),1650(br),1590
NMR(90 MHz,CDCl$_3$) δ: 0.65(3H,t,J=7 Hz),1.67(2H,m),3.72(2H,m), 4.10(2H,m),4.24(4H,m),4.78(2H,m),6.83(1H,m),6.96 to 7.63 (9H,m),7.63 to 7.99(1H,m),8.30(2H,m),9.23(1H,m),9.76(2H,m).

PRODUCTION EXAMPLE 24

Synthesis of 5-bromo-3-[N-(4-bromophenyl)-N-[2-[2-(1-naphthylcarbamoyloxy)ethyl]carbamoyloxy]ethyl]carbamoyl-1propylpyridinium chloride(59)

(i) Synthesis of 5-bromo-3-[N-(4-bromophenyl)-N-(2-hydroxyethyl)]carbamoylpyridine(56)

To a solution of N-(4-bromophenyl)aminoethanol[864 mg(4.00 mmol.)] and triethylamine[2.79 ml(20.0 mmol.)] in chloroform (20 ml) was added, under ice-cooling while stirring, to 5-bromonicotinic acid chloride hydrochloride[1.13 g(4.40 mmol.)], and the mixture was stirred for one hour at room temperature. The reaction mixture was washed with 1N aqueous solution of sodium hydroxide and then dried, followed by distilling off the solvent under reduced pressure. The residue was subjected to a silica gel column chromatography, eluting with hexane-ethyl acetate(1:3), to obtain the compound(56) [650 mg (40.6%)] as pale yellow prisms.

IR(KBr)cm$^{-1}$: 3400,3050,1620(br).
NMR(90 MHz,CDCl$_3$) 67 : 3.85(2H,t,J=5 Hz),4.07(2H,t,J=5 Hz),7.02 (2H,d,J=9 Hz),7.42(2H,d,J=9 Hz),7.87(1H,t,J=2 Hz),8.30(1H,d,J=2 Hz),8.54(1H,d,J=2 Hz).

(ii) Synthesis of 5-bromo-3-[N-(4-bromophenyl)-N-[2-[2-(1-naphthylcarbamoyloxy)ethyl)]carbamoyloxy]ethyl]carbamoylpyridine(57)

To a solution of the compound(56) synthesized in (i) [298 mg (0.74 mmol.)] and pyridine[0.12 ml (1.48 mmol.)] in dichloromethane (5 ml) was added dropwise, under ice-cooling while stirring, phenyl chloroformate[0.10 ml(0.80 mmol.)], and the mixture was stirred for 30 minutes at room temperature. The reaction mixture was washed with a 5% aqueous solution of sodium hydrogencarbonate and then dried, followed by distilling off the solvent. To the residue was added 2-(1-naphthylcarbamoyloxy)ethylamine [170 mg(0.74 mmol.)], and the mixture was heated for one hour at 80° C. The reaction mixture was, after cooling, subjected to a silica gel column chromatography, eluting with hexane-ethyl acetate (1:2), to obtain the compound (57)[409 mg(84.2%)] as a colorless oily product.

IR(KBr)cm$^{-1}$: 3350(br), 1710 (br),1640(br)
NMR(90 MHz,CDCl$_3$) δ: 3.46(2H,q,J=5 Hz),4.10(2H,t,J=5 Hz),4.29(2H,t,J=5 Hz),4.34(2H,t,J=5 Hz),5.18(1H,m),7.97(2H,d,J=9 Hz), 7.36(2H,d,J=9 Hz),7.15 to 8.03(10H,m),8.28(1H,d,J=2 Hz), 8.50(1H,d,J=2 Hz).

(iii) Synthesis of 5-bromo-3-[N-(4-bromophenyl)-N-[2-[2-(1-naphthylcarbamoyloxy)ethyl]carbamoyloxy]ethyl]carbamoyl-1-propylpyridinium iodide(58)

A solution of the compound(57) synthesized in (ii) [335 mg (0.51 mmol.)] in propyl iodide(5 ml) was stirred for two days at 110° C. Resulting precipitates were washed with ether and then dried to obtain the compound(58)[434 mg(quant.)] as yellow powder.

IR(KBr)cm$^{-1}$: 3350(br),3040,710, 1650, 1590.
NMR(90 MHz,CDCl$_3$) δ: 0.70(3H,t,J=7 Hz), 1.75(2H,m),3.47(2H,m), 4.24(6H,m),4.56(2H,m),6.90(1H,m),7.20 to 7.95(10H,m), 7.97 to 8.30(1H,m),8.58(1H,br s),8.78(1H,br s),9.38(1H,br s),9.40(1H,br s).

(iv) Synthesis of 5-bromo-3-[N-(4-bromophenyl)-N-[2-[2-(1-naphthylcarbamoyloxy)ethyl]carbamoyloxy]ethyl]carbamoyl-1-propylpyridinium chloride(59)

The compound(58) synthesized in (iii) [264 mg(0.32 mmol.)] was dissolved in a mixture of methanol-water(7:3)(6 ml). The solution was allowed to pass through anion exchange resin (IRA-410[Cl$^-$1])(6 ml). The eluate was concentrated under reduced pressure to obtain the compound(59)[152 mg(64.7%)] as yellow powder.

IR(KBr)cm$^{-1}$:3350(br),3040,1710(br),1650(br),1600.
NMR(90 MHz,DMSO-d$_6$) δ: 0.63(3H,t,J=7 Hz),1.74(2H,m),2.94 to 3.66(2H,m),4.14(6H,m),4.50(2H,br t,J=6 Hz),6.90 to 8.32(11H, m),8.84(1H,br s),9.34(1H,m),9.60(1H,br s).

PRODUCTION EXAMPLE 25

Synthesis of 5-bromo-3-[N-(4-iodophenyl)-N-[2-[2-(1-naphthylcarbamoyloxy)ethyl]carbamoyloxy]ethyl]carbamoyl-1-propylpyridinium chloride(63)

(i) Synthesis of 5-bromo-3-[N-(2-hydroxyethyl)-N-(4-iodophenyl)]carbamoylpyridine(60)

To a solution of N-(4-iodophenyl)aminoethanol[.1.05 g(4.00 mmol.)] and triethylamine[2.79 ml(20.0 mmol.)] in chloroform (20 ml) was added, under ice-cooling while stirring, 5-bromonicotinic acid chloride hydrochloride[1.13 g(4.40 mmol.)], and the mixture was stirred for one hour at room temperature. The reaction mixture was washed with a 1N aqueous solution of sodium hydroxide and then dried, followed by distilling off the solvent under reduced pressure. The residue was subjected to a silica gel column chromatography, eluting with hexane-ethyl acetate(1:3), to obtain the compound(60) [589 mg(33.0%)] as colorless prisms.

IR(KBr)cm$^{-1}$:3310(br),3040,1630(br),1590.

NMR(90 MHz,CDCl₃) δ: 3.81(2H,t,J=5 Hz),4.07(2H,t,J=5 Hz),6.90 (2H,d,J=9 Hz),7.62(2H,t,J=9 Hz),7.88(1H,t,J=2 Hz),8.30(1H,d,J=2 Hz),8.57(1H,d,J=2 Hz).

(ii) Synthesis of 5-bromo-3-[N-(4-iodophenyl)-N-[2-[2-(1-naphthylcarbamoyloxy)ethyl]carbamoyloxy]ethyl]-carbamoylpyridine(61)

To a solution of the compound(60) synthesized in (i) [310 mg (0.69 mmol.)] and pyridine[0.11 ml(1.38 mmol.)] in dichloromethane (5 ml) was added dropwise, under ice-cooling while stirring, phenyl chloroformate[0.10 ml(0.80 mmol.)], and the mixture was stirred for 30 minutes at room temperature. The reaction mixture was washed with a 5% aqueous solution of sodium hydrogencarbonate and then dried, followed by distilling off the solvent. To the residue was added 2-(1-naphthylcarbamoyloxy)ethylamine [159 mg(0.69 mmol.)], and the mixture was heated for one hour at 80° C. The reaction mixture was cooled and subjected to a silica gel column chromatography, eluting with hexane-ethyl acetate(1:2), to afford the compound (61) [324 mg(66.8%)] as a colorless oily product.

IR(KBr)cm⁻¹:3300(br),3040,1710(br),1640(br), 1590.
NMR(90 MHz,CDCl₃) δ: 3.48(2H,q,J=5 Hz),4.10(2H,t,J=5 Hz),4.30(2H,t,J=5 Hz),4.34(2H,t,J=5 Hz),5.17(1H,m),6.84(2H,d,J=9 Hz), 7.30 to 7.69(6H,m),7.69 to 8.03(4H,m),8.30(1H,br s),8.5(1H,d,J=2 Hz).

(iii) Synthesis of 5-bromo-3-[N-(4-iodophenyl)-N-[2-[2-(1-naphthylcarbamoyloxy)ethyl]carbamoyloxy]ethyl]-carbamoyl-1-propylpyridinium iodide(62)

A solution of the compound(61) synthesized in (ii) [263 mg (0.37 mmol.)] in propyl iodide(5 ml) was stirred for two days at 110° C. Resulting precipitates were washed with ether and then dried to obtain the compound(62) [318 mg(quant.)] as yellow powder.

IR(KBr)cm⁻¹:3250(br),3040, 1710(br), 1650(br), 1590.
NMR(90 MHz,CDCl₃) δ: 0.68(3H,t,J=7 Hz), 1.73(2H,m),3.47(2H,m), 4.24(6H,m),4.58(2H,m),6.84(1H,m),7.03 to 7.94(10H,m), 8.15(1H,m),8.54(2H,m),9.34(2H,m).

(iv) Synthesis of 5-bromo-3-[N-(4-iodophenyl)-N-[2-[2-(1-naphthylcarbamoyloxy)ethyl]carbamoyloxy]ethyl]-carbamoyl-1-propylpyridinium chloride(63)

The compound(62) synthesized in (ii) [156 mg(0.18 mmol.)] was dissolved in a mixture solvent, methanol-water(7:3)(4 ml). The solution was allowed to pass through anion exchange resin (IRA-410[Cl⁻])(4 ml), and the eluate was concentrated under reduced pressure to obtain the compound(63)[83 mg(59.0%)] as yellow powder.

IR(KBr)cm⁻¹:3370(br),3040, 1700(br), 1650(br), 1600.
NMR(90 MHz,CDCl₃) δ: 0.50(3H,t,J=7 Hz), 1.53(2H,m),3.50(2H,m), 4.05(2H,m),4.22(4H,m),4.55(2H,m),6.83 to 8.00(10H,m),8.20(1H,m),8.30(1H,m),8.78(1H,m),8.90(1H,m),9.85(1H,m).

PRODUCTION EXAMPLE 26

Synthesis of 5-bromo-3-[N-(p-tolyl)-N-[2-[2-(1-naphthylcarbamoyloxy)ethyl]carbamoyloxy]ethyl]carbamoyl-1-propylpyridinium chloride(67)

(i) Synthesis of 5-bromo-3-[N-(2-hydroxyethyl)-N-(p-tolyl)]-carbamoylpyridine(64)

To a solution of N-(p-tolyl)aminoethanol[605 mg(4.00 mmol.)] and triethylamine[2.79 ml(20.0 mmol.)]in chloroform(20 ml) was added, under ice-cooling while stirring, 5-bromonicotinic acid chloride hydrochloride[1.13 g(4.40 mmol.)], and the mixture was stirred for one hour at room temperature. The reaction mixture was washed with 1N aqueous solution of sodium hydroxide and then dried, followed by distilling off the solvent under reduced pressure. The residue was subjected to a silica gel column chromatography, eluting with hexane-ethyl acetate(1:3) to obtain the compound(64)[686 mg(51.2%)] as pale yellow needles.

IR (Neat)cm⁻¹: 3450,3040,1640(br).
NMR(90 MHz,CDCl₃) δ: 2.29(3H,s),3.83(2H,t,J=5 Hz),4.10(2H,t, J=5 Hz),7.00(2H,d,J=9 Hz),7.08(2H,d,J=9 Hz),8.87(1H,t,2 Hz), 8.32(1H,d,J=2 Hz),8.50(1H,d,J=2 Hz).

(ii) Synthesis of 5-bromo-3-[N-(p-tolyl)-N-[2-[2-(1-naphthylcarbamoyloxy)ethyl]carbamoyoxy]ethyl]carbamoylpyridine(65)

To a solution of the compound(64)[630 mg(1.88 mmol.)] synthesized in (i) and pyridine[0.26 ml(3.76 mmol.)] in dichloromethane(5 ml) was added dropwise, under ice-cooling while stirring, phenyl chloroformate[0.30 ml(2.07 mmol.)], and the mixture was stirred for 30 minutes at room temperature. The reaction mixture was washed with a 5% aqueous solution of sodium hydrogencarbonate and then dried, followed by distilling off the solvent. To the residue was added 2-(1-naphthylcarbamoyloxy)ethylamine[433 mg(1.88 mmol.)], and the mixture was heated for one hour at 80° C. The reaction mixture was cooled and subjected to a silica gel column chromatography, eluting with hexane-ethyl acetate(1:2), to obtain the compound(65)[777 mg(69.9%)] as a colorless oily product.

IR(Neat)cm⁻¹:3300(br),3040,1710(br),1640(br).
NMR(90 MHz, CDCl₃) δ: 2.24(3H,s),3.45(2H,q,J=5 Hz),4.10 (2H,t, J=5 Hz),4.28(2H,t,J=5 Hz),4.34(2H,t,J=5 Hz),5.34(1H,m),6.98 (2H,d,J=9 Hz),7.02(2H,d,J=9 Hz),7.30 to 7.70(4H,m),7.70 to 8.03(4H,m),8.32(1H,br s),8.45(1H,d,J=2 Hz).

(iii) Synthesis of 5-bromo-3-[N-(p-tolyl)-N-[2-[2-(1-naphthylcarbamoyloxy)ethyl]carbamoyloxy]ethyl]carbamoyl-1-propylpyridinium iodide(66)

A solution of the compound(65) synthesized in ii)[689 mg (1.16 mmol.)] in propyl iodide(10 ml) was stirred for two days at 110° C. Resulting precipitates were washed with ether and dried to obtain the compound(66)[885 mg(quant.)] as yellow powder.

IR(Neat)cm⁻¹:3400(br),3040,1700(br),1650(br), 1600.
NMR(90 MHz,CDCl₃) δ: 0.56(3H,t,J=7 Hz),1.58(2H,m),2.20(3H,br s), 3.49(2H,m),4.22(6H,m),4.56(2H,br t,J=7 Hz),6.73(1H,m), 6.87 to 7.92(10H,m),7.92 to 8.45(3H,m),9.08(2H,m),9.34(2H,m).

(iv) Synthesis of 5-bromo-3-[N-(p-tolyl)-N-[2-[2-(1-naphthylcarbamoyloxy)ethyl]carbamoyloxy]ethyl]carbamoyl-1-propylpyridinium chloride(67)

The compound(66) synthesized in (iii)[800 mg(1.05 mmol.)], was dissolved in a mixture of methanol-water(7:3)(20 ml). The solution was allowed to pass through anion exchange resin (IRA-410[Cl⁻])(20 ml), and the eluate was concentrated under reduced pressure to obtain the compound(67)[583 mg(82.8%)] as yellow powder.

IR(Neat)cm⁻¹:3370(br),3040, 1710(br), 1650(br), 1600.

NMR(90 MHz,CDCl₃) δ: 0.58(3H,t,J=7 Hz),1.66(2H,m),2.20(3H,br s), 2.85 to 3.78(2H,m),4.12(6H,m),4.50(2H,m),6.70 to 8.34 (11H,m),8.80(1H,m),9.30(1H,m),9.58(2H,m).

PRODUCTION EXAMPLE 27

Synthesis of 5-bromo-3-[N-[2-[2-(1-naphthylcarbamoyloxy)ethyl]-carbamoyloxy]ethyl-N-(3,4,5-trimethoxyphenyl)]carbamoyl-1-propylpyridinium chloride(71)

(i) Synthesis of 5-bromo-3-[N-(2-hydroxyethyl)-N-(3,4,5-trimethoxyphenyl)]carbamoylpyridine(68)

To a solution of N-(3,4,5-trimethoxyphenyl)aminoethanol [909 mg(4.00 mmol.)] and triethylamine[2.79 ml(20.0 mmol.)] in chloroform(20 ml) was added, under ice-cooling while stirring, 5-bromonicotinic acid chloride hydrochloride[1.13 g (4.40 mmol.)], and the mixture was stirred for one hour at room temperature. The reaction mixture was washed with 1N aqueous solution of sodium hydroxide and then dried, followed by distilling off the solvent under reduced pressure. The residue was subjected to a silica gel column chromatography, eluting with hexane-ethyl acetate(1:3), to obtain the compound(68)[656 mg(39.9%)] as colorless prisms.

IR(Neat)cm⁻¹:3350(br),3050,1640,1590 .
NMR(90 MHz,CDCl₃) δ: 3.74(6H,s),3.80(3H,s),3.85(2H,t,J=5 Hz), 4.09(2H,t,J=5 Hz),6.38(2H,s),7.92(1H,t,J=2 Hz),8.47(1H,br s), 8.58(1H,br s).

(ii) Synthesis of 5-bromo-3-[N-[2-[2-(1-naphthylcarbamoyloxy)ethyl]carbamoyloxy]ethyl-N-(3,4,5-trimethoxyphenyl)]carbamoylpyridine(69)

To a solution of the compound(68) synthesized in (i)[313 mg (0.76 mmol.)] and pyridine[0.12 ml(1.52 mmol.)] in dichloromethane(2.5 ml) was added dropwise, under ice-cooling while stirring, phenyl chloroformate[0.10 ml(0.80 mmol.)], and the mixture was stirred for 30 minutes at room temperature. The reaction mixture was washed with a 5% aqueous solution of sodium hydrogencarbonate and then dried, followed by distilling off the solvent. To the residue was added 2-(1-naphthylcarbamoyloxy)ethylamine[175 mg(0.76 mmol.)], and the mixture was heated for one hour at 80° C. The reaction mixture was, after cooling, subjecting to a silica gel column chromatography, eluting with hexane-ethyl acetate(1:2), to afford the compound(69)[323 mg(63.7%)] as a colorless oily product.

IR(Neat)cm⁻¹:3300(br),3050,1720(br), 1650(br), 1590.
NMR(90 MHz,CDCl₃) δ: 3.43(2H,q,J=5 Hz),3.70(6H,s),3.74(3H,s), 4.19(2H,t,J=5 Hz),4.24(2H,t,J=5 Hz),4.40(2H,t,J=5 Hz),5.09(1H,m),6.35(2H,s),7.30 to 7.77(4H,m),7.77 to 8.10(4H,m), 8.44(1H,br s),8.52(1H,br s).

(iii) Synthesis of 5-bromo-3-[N-[2-[2-(1-naphthylcarbamoyloxy)ethyl]carbamoyloxy]ethyl-N-(3,4,5-trimethoxyphenyl)]carbamoyl-1-propylpyridinium iodide(70)

A solution of the compound(69) synthesized in (ii) [226 mg (0.34 mmol.)] in propyl iodide(5 ml) was stirred for two days at 110° C. Resulting precipitates were washed with ether and then dried to obtain the compound(70)[270 mg(quant.)] as yellow powder.

IR(Neat)cm⁻¹:3350(br),3040,1710(br), 1650(br), 1590.
NMR(90 MHz,CDCl₃) δ: 0.64(3H,t,J=7 Hz),1.65(2H,m),3.50(2H,m), 3.73(3H,s),3.80(6H,s),4.25(6H,m),4.52(2H,br t,J=7 Hz),6.74(2H,s),6.82(1H,m),7.24 to 7.90(6H,m),7.95 to 8.30(2H,m), 8.47(1H,br s),8.67(1H,br s),9.75(1H,br s).

(iv) Synthesis of 5-bromo-3-[N-[2-[2-(1-naphthylcarbamoyloxy)ethyl]carbamoyloxy]ethyl-N-(3,4,5-trimethoxyphenyl)]carbamoyl-1-propylpyridinium chloride(71)

The compound(70) synthesized in (iii) [115 mg(0.14 mmol.)] was dissolved in a mixture of methanol-water(7:3)(4 ml), and the solution was allowed to pass through anion exchange resin (IRA-410[Cl⁻])(4 ml). The eluate was concentrated under reduced pressure to obtain the compound(71)[62 mg(60.5%)] as yellow powder.

IR(Neat)cm⁻¹:3380(br),3040,1710(br), 1650(br), 1590.
NMR(90 MHz,CDCl₃) δ: 0.62(3H,t,J=7 Hz), 1.75(2H,m),3.34(2H,m), 3.59(3H,s),3.73(6H,s),4.16(6H,m),4.54(2H,br t,J=7 Hz),6.83 (2H,s),7.32 to 7.85(5H,m),7.85 to 8.03(1H,m),8.03 to 8.27(1H,m),8.98(1H,br s),9.52(1H,br s),9.67(2H,s).

PRODUCTION EXAMPLE 28

Synthesis of 5-bromo-3-[N-[2-[2-(1-naphthylcarbamoyloxy)ethoxy]-carbonylamino]ethyl-N-phenyl]carbamoyl-1-propylpyridinium iodide(74)

(i) Synthesis of N-[2-[2-(1-naphthylcarbamoyloxy)ethoxycarbonylamino]ethyl]aniline(72)

In dichloromethane(24 ml) was dissolved 2-(1-naphthylcarbamoyloxy)ethanol (1.85 g, 8 mmol.). To the solution was added pyridine(2.2 g, 28 mmol.), to which was added dropwise phenyl chloroformate(2.19 g, 14 mmol.). The mixture was stirred for two hours at room temperature. To the reaction mixture were added ice-water(22 ml) and sodium hydrogencarbonate (1.28 g), which was stirred for 30 minutes at room temperature. The organic layer was separated, and the aqueous layer was subjected to extraction with dichloromethane(20 ml). The dichloromethane layers were combined and dried over anhydrous sodium sulfate, followed by concentration to dryness under reduced pressure. To the residue was added N-phenylethylenediamine(1.09 g, 8 mmol.), and the mixture was stirred for 16 hours at 65° C., followed by purification by means of a silica gel column chromatography(silica gel 20 g, developing solvent n-hexane-ethyl acetate(2:1)). The product was recrystallized from ethyl acetate-n-hexane(1:2) to afford the object product as colorless needles, m.p. 107° to 108° C. The yield was 2.32 g.

Elemental Analysis for $C_{22}H_{23}N_3O_4$: Calcd.: C,67.16, H,5.89, N,10.68, Found: C,67.23, H,5.92 N, 10.75.

(ii) Synthesis of 5-bromo-3-[N-[2-[2-(1-naphthylcarbamoyloxy)ethoxy]carbonylamino]ethyl-N-phenyl]carbamoylpyridine(73)

The compound obtained in (i)(2.32 g, 5.9 mmol.) was dissolved in dichloromethane(12 ml). To the solution was added triethylamine(2.38 g, 23.6 mmol.), to which was added, under ice-cooling, 5-bromonicotinic acid chloride hydrochloride (2.28 g, 8.87 mmol.) in limited amounts. The reaction mixture was stirred for one hour at room temperature, to which were added water(20 ml) and dichloromethane(20 ml). To the mixture was further added sodium hydrogencarbonate(1.5 g), which was stirred vigorously for one hour, followed by separating the dichloromethane layer. The dichloromethane layer was dried over anhydrous sodium sulfate, and concentrated to dryness under reduced pressure. The residue was purified by means of a silica gel column chromatography(silica gel 20 g, developing solvent n-hexane-ethyl acetate-chloroform (1:1:1)) to obtain the object compound(73)(colorless resinous substance). The yield was 3.29 g.

NMR(60 MHz,CDCl$_3$) δ: 3.53(2H,br.t),4.10 (2H,t), 4.27 (1H,br.s), 4.38(4H,s),5.53(1H,br.s),6.9 to 8.6(12H,m),8.73(1H,br.s), 8.92(1H,br.s).

(iii) Synthesis of 5-bromo-3-[N-[2-[2-(1-naphthylcarbamoyloxy)ethoxy]carbonylamino]ethyl-N-phenyl]carbamoyl-1-propylpyridinium iodide(74)

The compound obtained in (ii)(1.0 g, 1.73 mmol.) was dissolved in n-propyliodide(5 ml), and the solution was stirred for 74 hours at 110° C. The reaction mixture was concentrated, and the concentrate was purified by means of a silica gel column chromatography(silica gel 20 g, developing solvent CHCl$_3$,CHCl$_3$-MeOH(9:1) to obtain the object compound(74)(1.0 g) as a yellow resinous product.

TLC,silica gel, CHCl$_3$-MeOH-H$_2$O(65:25:4) Rf=0.49

IR(film)cm$^{-1}$:3250,3025,2950,2920,1700,1650,1590,1520,1490, 1440,1400,1350,1250,1220,1150,1105,1080,780,740,705.

NMR(60 MHz,CDCl$_3$) δ: 0.65(3H,t), 1.77(2H,m),3.57(2H,br.s),4.10 (2H,br.s),4.40(4H,s),4.40 to 5.2(3H,m),6.40(1H,br.s),7.0 to 8.0(12H,m),8.20(1H,s),9.12(1H,s),9.27(1H,s).

PRODUCTION EXAMPLE 29

Synthesis of
5-bromo-3-[N-[2-(2-phenoxyethoxy)carbonylamino]ethyl-N-phenyl]carbamoyl-1-propyl-pyridinium iodide (77)

(i) Synthesis of N-[2-[2-(phenoxyethoxy)carbonylamino]ethyl]aniline(75)

In dichloromethane(45 ml) was dissolved 2-phenoxyethanol (2.07 g,15 mmol.), to which was added pyridine(4.15 g). To the mixture was added dropwise, under ice-cooling, phenyl chloroformate(4.11 g, 26.3 mmol.), and the mixture was stirred for two hours at room temperature. To the reaction mixture were added ice water(40 ml) and sodium hydrogencarbonate (4.2 g), which was stirred for one hour at room temperature. The dichloromethane layer was separated and dried over anhydrous sodium sulfate, followed by concentration to dryness under reduced pressure. To the concentrate was added N-phenylethylenediamine(2.04 g,15 mmol.), and the mixture was stirred for two days at 65° C. The reaction mixture was concentrated, and the concentrate was purified by means of a silica gel column chromatography(silica gel 30 g, developing solvent AcOEt:n-hexane(1:3)), followed by recrystallization from n-hexane-AcOEt to obtain the object compound(75)(3.2 g).

IR(KBr)cm$^{-1}$: 3350,3015,2925,2860,1700,1600,1500,1460,1320, 1240,1175,1150,1090,1050,1000,925,890,760,700.

NMR(60 MHz,CDCl$_3$) δ: 3.28(5H,br.s),4.10(2H,m),4.40(2H,m), 6.4 to 7.5(10H),5.10(1H,—NH—).

(ii) Synthesis of 5-bromo-3-[N-phenyl-N-[2-(2-phenoxyethoxy)carbonylamino]ethyl]carbamoylpyridine(76)

The compound obtained in (i)(2.8 g,9.3 mmol.) was dissolved in dichloromethane(20 ml), to which was added triethylamine (5.6 g, 56 mmol.). To the mixture was added, under ice-cooling, 5-bromonicotinic acid chloride hydrochloride(3.6 g, 14 mmol.) in limited amounts. The mixture was stirred for one hour at room temperature. To the reaction mixture were added dichloromethane(20 ml) and water(40 ml), to which was further added sodium hydrogencarbonate(2.24 g). The mixture was stirred for 30 minutes at room temperature, then the dichloromethane layer was separated and dried over anhydrous sodium sulfate, which was purified by means of a silica gel column chromatography(silica gel 30 g, developing solvent AcOEt-CHCl$_3$- n-hexane(1:1:2) to obtain the object compound(76) as a colorless oily product(4.2 g).

TLC,silica gel, AcOEt-n-hexane(1:1) Rf=0.37.

IR(film)cm$^{-1}$:
3300,3040,2920,1710,1635,1590,1520,1490,1440, 1390,1290,1240,1150,1100,1050,1020,920,895,700,660.

NMR(60 MHz,CDCl$_3$) δ: 3.54(2H,m),4.15(4H,m),4.38(2H,m),5.37 (1H,br.s),6.70 to 7.60(10H), 7.75(1H,s),8.23(1H,s),8.47(1H,s).

(iii) Synthesis of 5-bromo-3-[N-phenyl-N-[2-(2-phenoxyethoxy)-carbonylamino]ethyl]carbamoyl-1-propyl-pyridinium iodide(77)

The compound obtained in (ii) (1.0 g) was dissolved in n-propyl iodide(5 ml), and the solution was stirred for 72 hours at 65° C. The reaction mixture was concentrated to dryness, and the concentrate was purified by means of a silica gel column chromatography(silica gel 20 g, developing solvent CHCl$_3$→CHCl$_3$-MeOH(9:1)) to obtain the object compound(77) (1.45 g) as a yellow solid product.

TLC,silica gel, CHCl$_3$—MeOH—H$_2$O(65:25:4) Rf=0.58.

IR(film)cm$^{-1}$: 3250,3000,2950,1700,1650,1590,15 1450, 1400,1230,1150,1080,1050,920,740,700.

NMR(60 MHz,CDCl$_3$) δ: 0.75(3H,t,J=7 Hz), 1.80(2H,m),3.58(2H,br.s), 4.12(4H,m),4.33(2H,m),4.75(2H,t,J=7 Hz),6.20(1H,br.s),6.6 to 7.7(10H,m),8.37(1H,s),9.27(1H,s),9.41 (1H,s).

Elemental Analysis for C$_{29}$H$_{35}$N$_3$O$_7$BrI.H$_2$O : Calcd. C,45.68, H,4.89, N,5.51, Found C,45.81, H,4.72, N,5.44.

PRODUCTION EXAMPLE 30

Synthesis of
5-bromo-3-[N-phenyl-N-[2-[2-(4-fluorophenoxy)ethoxy]carbonylamino]ethyl]carbamoyl-1-propylpyridinium iodide (80)

(i) Synthesis of N-[2-[2-(4-fluorophenoxy)ethoxy]carbonylamino]ethylaniline(78)

In dichloromethane (40 ml) was dissolved 2-(4-fluorophenoxy)ethanol (2.03 g, 13 mmol.), to which was added pyridine(3.6 g, 45.5 mmol.). To the mixture was added dropwise, under ice-cooling, phenyl chloroformate(3.56 g,22.8 mmol.), which was stirred for two hours at room temperature. To the reaction mixture were added ice-water(40 ml) and sodium hydrogencarbonate(3.6 g, 45 mmol.), and the mixture was stirred for 30 minutes at room temperature. The dichloromethane layer was separated, dried over anhydrous sodium sulfate and concentrated under reduced pressure. To the concentrate was added N-phenylethylenediamine(1.77 g, 13 mmol.), and reaction was allowed to proceed for 72 hours at 65° C. The reaction mixture was concentrated and purified by means of a silica gel column chromatography(silica gel 30 g, developing solvent AcOEt-CHCl₃-n-hexane(1:1:1)) to obtain the object compound (78)(3.78 g) as colorless crystals, m.p.71° C.

NMR(60 MHz,CDCl₃) δ: 0.33(4H,br.s),3.90(1H,br.s),4.10 (2H,m), 4.43(2H,m),5.13(1H,br.,s),6.4 to 7.5(9H,m).

(ii) Synthesis of 5-bromo-3-[N-phenyl-N-[2-[2-(4-fluorophenoxy)ethoxy]carbonylamino]ethyl]carbamoylpyridine(79)

The compound obtained in (i)(0.78 g, 2.45 mmol.) was dissolved in dichloromethane(10 ml), to which was added triethylamine(0.99 g, 9.8 mmol.). To the mixture was added, under ice-cooling, 5-bromonicotinic acid chloride hydrochloride (0.94 g, 3.7 mmol.), which was stirred for one hour at room temperature. To the reaction mixture were added chloroform (15 ml), water(15 ml) and sodium hydrogencarbonate(1.176 g, 45 mmol.), which was stirred vigorously for 30 minutes at room temperature. To the reaction mixture was further added dichloromethane(15 ml), then the dichloromethane layer was separated, dried over anhydrous sodium sulfate and then concentrated to dryness. The concentrate was purified by means of a silica gel column chromatography(silica gel 20 g, developing solvent AcOEt-CHCl₃-n-hexane(1:1:1)) to obtain the object compound(79)(1.1 g) as colorless crystals, m.p. 100° to 101° C.

IR(KBr)cm⁻¹: 3350,3050,2950,2800,1720,1635,1590,1500,1455, 1440,1415,1390,1350,1305,1280,1245,1220,1210,1150,1100, 1060,1020,980,920,895,870,830,765,750,740,700.

NMR(60 MHz,CDCl₃) δ: 3.55(3H,t,J=6 Hz),4.12 (4H,m),4.42(2H,t, J=5 Hz),5.37(1H,br.s),6.7 to 7.5(9H,m),7.77(1H,s),8.25 (1H,s),8.47(1H,s).

(iii) Synthesis of 5-bromo-3-[N-phenyl-N-[2-[2-(4-fluorophenoxy)ethoxy]carbonylamino]ethyl]carbamoyl-1-propylpyridinium iodide(80)

The compound obtained in (ii) (1.1 g, 2.2 mmol.) was dissolved in a mixture solvent of toluene(2 ml) and n-propyliodide(5 ml), and the solution was stirred for 64 hours at 110° C. The reaction mixture was concentrated to dryness under reduced pressure. The concentrate was purified by means of a silica gel column chromatography(silica gel 20 g, developing solvent CHCl₃→CHCl₃:MeOH(9:1)) to obtain the object compound(80) (yellow solid matter)(1.3 g).

TLC,silica gel, CHCl₃—MeOH—H₂O(65:25:4) Rf=0.56.

IR(film)cm⁻¹: 3250,3050,2950,2860,1700,1650,1590,1500,1455, 1440,1400,1280,1250,1205,1100,1050,920,835,770,750,705.

NMR(60 MHz,CDCl₃) δ: 0.73(3H,t,J=8 Hz), 1.82(2H,m),3.60(2H,br.s), 4.12(4H,m),4.32(2H,br.s),4.80(2H,m),6.80 to 7.70(5H,m), 6.10(1H,br.s),8.30(1H,s),9.23(1H,s),9.37(1H,s),

Elemental Analysis for C₂₀H₂₃N₃O₄BrFI.0.5H₂O: Calcd. C,45.83, H,4.29, N,6.17, Found C,46.05, H,4.18, N,6.17.

PRODUCTION EXAMPLE 31

Synthesis of 5-bromo-3-[N-phenyl-N-[2-[2-(3,4,5-trimethoxyphenoxy]ethoxy]carbonylamino]ethyl]carbamoyl-1-propylpyridinium iodide(83)

(i) Synthesis of N-[2-[2-(3,4,5-trimethoxyphenoxy)ethoxy]carbonylamino]ethylaniline(81)

In dichloromethane(24 ml) was dissolved 2-(3,4,5-trimethoxyphenoxy)ethanol(2.0 g, 8 mmol.). To the solution was added pyridine(2.2 g, 28 mmol.). To the mixture was added dropwise, under ice-cooling, phenyl chloroformate(2.19 g, 14 mmol.), which was stirred for two hours at room temperature. To the reaction mixture were added dichloromethane(20 ml), ice-water (20 ml) and sodium hydrogencarbonate(4.0 g, 50 mmol.), followed by stirring for 30 minutes at room temperature. The resultant was left standing, then the dichloromethane layer was separated, dried over anhydrous sodium sulfate and concentrated to dryness under reduced pressure. To the concentrate was added N-phenylethylenediamine(1.09 g, 8 mmol.), and the mixture was heated for 16 hours at 65° C., which was then subjected to purification by means of a silica gel column chromatography(silica gel 40 g, developing solvent AcOEt- n-hexane(1:3) AcOEt-n-hexane-CHCl₃(1:1:1)) to obtain the object compound(81)(2.45 g) as colorless crystals,m.p.96.5° C.

IR(KBr)cm⁻¹: 3350,2910,2850,2800,1700,1600,1500,1445,1415, 1260,1220,1070,1050,1000,800,780,745,700.

NMR(60 MHz,CDCl₃) δ: 3.37(4H,br.s),3.78(3H,s),3.82(6H,s), 4.17(2H,m),4.42(2H,m),5.05(1H,br.s),6.17(2H,s),6.3 to 7.5(5H,m)

Synthesis of 5-bromo-3-[N-phenyl-N-[2-[2-(3,4,5-trimethoxyphenoxy)ethoxy]carbonylamino]ethyl]carbamoylpyridine (82)

The compound obtained in (i)(1.02 g, 2.6 mmol.) was dissolved in dichloromethane(12 ml), to which was added triethylamine(1.05 g, 10 mmol.). To the mixture was added, under ice-cooling, 5-bromonicotinic acid chloride hydrochloride (1.00 g), and the resultant was stirred for two hours at room temperature. To the reaction mixture were added dichloromethane(12 ml), water(24 ml) and sodium hydrogencarbonate (960 mg), and the mixture was stirred for 30 minutes at room temperature, then left standing, followed by separating the dichloromethane layer and drying over anhydrous sodium sulfate. The resultant was concentrated to dryness under reduced pressure, and the concentrate was purified by means of a silica gel column chromatography(silica gel 20 g, developing solvent AcOEt-n-hexane-CHCl₃(1:1:1)) to obtain the object compound(82) as a colorless resinous product(1.46 g).

IR(film)cm⁻¹: 3330,3050,2930,2820,1710,1640,1590,1500,1450, 1420,1390,1230,1195,1125,1080,1050,1010,895,780,750,740, 700.

NMR(60 MHz,CDCl₃) δ: 3.48(2H,m),3.83(9H,s),4.12(4H,m),4.40 (2H,m),5.43(1H,br.s),6.07(2H,s),7.30(5H,m),7.72(1H,s), 8.22(1H,s),8.40(1H,s)

(iii) Synthesis of 5-bromo-3-[N-phenyl-N-[2-[-(3,4,5-trimethoxyphenoxy)ethoxy]carbonylamino]ethyl]carbamoyl-1-propylpyridinium iodide(83)

The compound obtained in (ii)(1.46 g) was dissolved in a mixture solvent of toluene(2 ml) and n-propyliodide(5 ml), and the solution was stirred for 54 hours at 110° C. The reaction mixture was concentrated to dryness under reduced pressure. The concentrate was purified by means of a silica gel column chromatography(silica gel 28 g, developing solvent CHCl₃→CHCl₃-MeOH(9:1)) to obtain the object compound(83) (1.64 g) as a yellow solid product.

IR(film)cm$^{-1}$:
3250,3030,2950,1710,1655,1590,1455,1420,1400, 1280,1230,1200,1130,1005,780,740,700.

NMR(60 MHz,CDCl$_3$) δ: 0.73(3H,t,J=6.5 Hz),1.87 (2H,m),3.57(2H, br.s),3.77(3H,s),3.83(6H,s),4.12(4H,m),4.32(2H,m),4.83 (2H,t,J=6 Hz),5.77(1H,br.s),6.18 (2H,s),7.37(5H,m),8.42 (1H,s),9.35(1H,s),9.43(1H,s).

PRODUCTION EXAMPLE 32

Synthesis of
5-bromo-3-[N-benzyl-N-[2-[2-(1-naphyloxy)ethyl]car-bamoyloxy]ethyl]carbamoyl-1-ethylpyridinium iodide (86)

(i) Synthesis of 5-bromo-3-[N-benzyl-N-(2-hydroxyethyl)]carbamoylpyridine(84)

In chloroform(100 ml) were dissolved 2-(benzylamino)ethanol [2.268g(15 mmol.)] and triethylamine [10.45 ml(75 mmol.)]. To the solution was added, under ice-cooling, 5bromonicotinic acid chloride hydrochloride [4.24 g(16.5 mmol.)]. The mixture was then stirred for one hour at room temperature. The reaction mixture was washed with a 5% aqueous solution of sodium hydroxide, and the organic layer was dried over anhydrous potassium carbonate, then the solvent was distilled off under reduced pressure. The crude product thus obtained was purified by means of a column chromatography(silica gel: 150 g; eluent:ethyl acetate) to obtain the object compound (84)[4.13 g(82.4%,colorless syrup)].

TLC(Silica Gel;AcOEt): Rf=0.44.
NMR(90 MHz,CDCl$_3$) δ: 3.73(4H,m),4.67(2H,br),7.35(5H,m), 7.96(1H,br s),8.66(1H,m),8.69(1H,d).
IR(Neat)cm$^{-1}$: 3360,1625,1580,1410,1260,1070.

(ii) Synthesis of 5-bromo-3-[N-benzyl-N-[2-[2-(1-naphthyloxy)ethyl]carbamoyloxy]ethyl]carbamoyl-pyridine(85)

In methylene chloride(20 ml) were dissolved the alcohol compound(84) synthesized in (i) [1.01 g(3 mmol.)] and pyridine [475 mg(6 mmol.)]. To the solution was added, under icecooling, phenyl chlorocarbonate [564 mg(3.6 mmol.)], and the mixture was stirred for 30 minutes at room temperature. The reaction mixture was washed with a 5% aqueous solution of sodium hydrogencarbonate, and the organic layer was dried over anhydrous sodium sulfate, then the solvent was distilled off under reduced pressure to obtain a crude carbonate compound(1.61 g).

To this crude carbonate compound was added 2-(1-naphthyloxy)ethylamine [562 mg(3 mmol.)], and the mixture was heated for one hour at 80° C. The reaction mixture was cooled and the resulting crude product was purified by means of a column chromatography(silica gel:60 g; eluent:hexane/ethyl acetate=½) to obtain the object compound(85)[1.00 g(61.0%, colorless syrup)].

TLC[Silica Gel;n-hexane/AcOEt(½)]: Rf=0.4.
NMR(90 MHz,CDCl$_3$) δ: 3.69(4H,m),4.20(4H,m),4.59(2H,br s), 5.31(1H,br),6.78(1H,dd),6.9 to 7.6(9H,m),7.78(1H,m), 7.88(1H,t),8.24(1H,m),8.58(1H,d),8.68(1H,d).
IR(Neat)cm$^{-1}$: 3300,1710,1620,1578,1505,1400,1230,1100.

(iii) Synthesis of 5-bromo-3-[N-benzyl-N-[2-[2-(1-naphthyloxy)ethyl]carbamoyloxy]ethyl]carbamoyl-1-ethylpyridinium iodide(86)

To the compound(85) synthesized in (ii) [219 mg(0.4 mmol.) was added iodoethane(10 ml), and the mixture was heated under reflux for 72 hours in nitrogen streams while shielding the light. The reaction mixture was, after cooling, concentrated under reduced pressure to give a crude product, followed by washing with ether to obtain the object compound (86) [281 mg(99.7%,pale yellow powder)].

TLC[Silica Gel;CHCl$_3$/MeOH(3/1)]: Rf=0.28.
NMR(90 MHz,CDCl$_3$) δ: 1.46(3H,t),3.67(4H,m),4.21(4H,m),4.69 (2H,s),4.85(2H,q),6.75(1H,dd),6.9 to 7.7(9H,m),7.75(1H,m), 8.0 to 8.6(2H,m),9.30(2H,m)
IR(KBr)cm$^{-1}$: 3400(br),1705,1640,1575,1450,1270,1255,1240,1100.

PRODUCTION EXAMPLE 33

Synthesis of
5-bromo-3-[N-benzyl-N-[2-[2-(1-naphthyloxy)ethyl]-carbamoyloxy]ethyl]carbamoyl-1-propylpyridinium iodide (87)

To the compound(85) synthesized in Production Example 32-ii) [437 mg(0.8 mmol.)] was added 1-iodopropane(20 ml), and the mixture was heated under reflux for 72 hours in nitrogen streams while shielding the light. The reaction mixture was, after cooling, concentrated under reduced pressure to obtain a crude product, which was washed with ether to afford the object compound(87)[575 mg(100%,pale yellow powder)]
TLC[Silica Gel;CHCl$_3$/MeOH(3/1)]: Rf=0.35.
NMR(90 MHz,CDCl$_3$) δ: 0.87(3H,m),1.87(2H,m),3.70(4H,m),4.21 (4H,m),4.71 (2H,br s),4.80(2H,m),6.28(1H,br),6.77(1H,dd), 6.9 to 7.6(9H,m),7.75(1H,m),8.1 to 8.7(2H,m),9.37(2H,m).
IR(KBr)cm$^{-1}$: 3420,1710,1648,1580,1460,1275,1248,1108 .

PRODUCTION EXAMPLE 34

Synthesis of
5-bromo-3-[N-methyl-N-[2-[2-(1-naphthyloxy)ethyl]-carbamoyloxy]ethyl]carbamoyl-1-ethylpyridinium iodide (90)

(i) Synthesis of 5-bromo-3-[N-(2-hydroxyethyl)-N-methyl]carbamoylpyridine (88)

In chloroform(100 ml) were dissolved N-methyl ethanolamine [1.127 g(15 mmol.)] and triethylamine [10.45 ml(75 mmol.)]. To the solution was added, under ice-cooling, 5-bromonicotinic acid chloride hydrochloride[4.24 g(16.5 mmol.). The mixture was then stirred for one hour at room temperature. The reaction mixture was washed with a 5% aqueous solution of sodium hydroxide, and the organic layer was dried over anhydrous potassium carbonate, then the solvent was distilled off under reduced pressure. The crude product thus obtained was purified by means of a column chromatography(silica gel: 100 g; eluent:ethyl acetate/acetone=3/1) to obtain the object compound(88)[3.19(82.0%,pale yellow oily product)].

TLC(Silica Gel;AcOEt/acetone(3/l)) : Rf=0.25.
NMR(90 MHz,CDCl$_3$) δ: 3.08(3H,s),3.30(1H,s),3.73(4H,m),7.96 (1H,t),8.60(1H,d),8.68(1H,m).
IR(Neat)cm$^{-1}$: 3330,1620,1400,1070,750.

(ii) Synthesis of 5-bromo-3-[N-[2-[2-(1-naphthyloxy)ethyl]carbamoyloxy]ethyl]carbamoylpyridine(89)

In methylene chloride(15 ml) were dissolved the alcohol compound(88) synthesized in (i) [712 mg(2.75 mmol.)] and pyridine[435 mg(5.5 mmol.)]. To the solution was added, under ice-cooling, phenyl chlorocarbonate [517 mg(3.3 mmol.)], and the mixture was stirred for 10 minutes at room temperature. The reaction mixture was washed with a 5% aqueous solution of sodium hydrogencarbonate. The organic layer was dried over anhydrous sodium sulfate, then the solvent was distilled off under reduced pressure to obtain a crude carbonate compound(1.30 g).

To this crude carbonate compound was added 2-(1-naphthyloxy)ethylamine [468 mg(2.5 mmol.)], and the mixture was heated for one hour at 85° C. Thus-obtained crude product, after cooling, was purified by means of a column chromatography (silica gel:60 g; eluent:hexane/ethyl acetate=¼) to afford the object compound(89)[929 mg(78.7%,colorless powder)].

TLC[Silica Gel;n-hexane/AcOEt(¼)]: Rf=0.17.

NMR(90 MHz,CDCl$_3$) δ: 3.00(3H,br s),3.70(4H,m),4.20(4H,t), 5.41(1H,br),6.77(1H,dd),7.1 to 7.6(9H,m),7.77(1H,m), 7.88(1H,t),8.23(1H,m),8.57(1H,d),8.68(1H,d),

IR(Neat)cm$^{-1}$: 3275,1700,1610,1395,1240,1100.

(iii) Synthesis of 5-bromo-3-[N-methyl-N-[2-[2-(1-naphthyloxy)ethyl]carbamoyloxy]ethyl]carbamoyl-1-ethylpyridinium iodide(90)

To the compound(89) synthesized in (ii) [242 mg(0.512 mmol)] was added iodoethane(10 ml), and the mixture was heated under reflux for 60 hours in nitrogen streams while shielding the light. The reaction mixture was, after cooling, concentrated under reduced pressure to give a crude product, which was washed with ether to obtain the object compound(90) [319 mg (99.2%,pale yellow powder).

TLC[Silica Gel;CHCl$_3$/MeOH(3/1)]: Rf=0.19.

NMR(90 MHz,CDCl$_3$) δ: 1.59(3H,m),3.10(3H,br s),3.66(4H,m), 4.19(4H,m),4.89(2H,m),6.19(1H,br),6.75(1H,dd),7.1 to 7.5(4H,m),7.75(1H,m),8.23(1H,m),8.48(1H,br s),9.33(2H,br s).

IR(KBr)cm$^{-1}$: 3405(br), 1700,1638,1576,1400,1270,1238,1100.

PRODUCTION EXAMPLE 35

Synthesis of 5-bromo-3-[N-methyl-N-[2-[2-(1-naphthyloxy)ethyl]-carbamoyloxy]ethyl]carbamoyl-1-propylpyridinium iodide (91)

To the compound(89) synthesized in Production Example 34-ii) [467 mg(0.989 mmol.)] was added 1-iodopropane(20 ml), and the mixture was heated under reflux for 60 hours in nitrogen streams while shielding the light. The reaction mixture was, after cooling, concentrated under reduced pressure to give a crude product, which was washed with ether to obtain the compound(91)[631 mg(99.3%,pale yellow powder)]

TLC[Silica Gel;CHCl$_3$/MeOH(3/1)]: Rf=0.25.

NMR(90 MHz,CDCl$_3$) δ: 0.95(3H,m),1.98(2H,m),3.12 (3H,br s),3.67 (4H,m),4.19(4H,m),4.84(2H,m),6.17 (1H,br),6.75(1H,dd),7.2 to 7.6(4H,m),7.72(1H,m),8.23(1H,m),8.50(2H,br s),9.37(2H,br s).

IR(KBr)cm$^{-1}$: 3400(br),1700,1640,1575,1455,1400,1270,1240,1100.

PRODUCTION EXAMPLE 36

Synthesis of 5-bromo-3-[4-[2-(1-naphthyloxy)ethoxycarbonyl]-1-piperazinyl]carbonyl-1-ethylpyridinium iodide(95)

(i) Synthesis of N-benzyl-N'-[2-(1-naphthyloxy)ethoxycarbonyl]piperazine(92)

In methylene chloride(20 ml) were dissolved 2-(1-naphthyloxy)ethanol [941 mg(5 mmol.)] and pyridine [791 mg(10 mmol.)]. To the solution was added, under ice-cooling, phenyl chlorocarbonate[861 mg(5.5 mmol.)], and the mixture was stirred for 30 minutes at room temperature. The reaction mixture was washed with a 5% aqueous solution of sodium hydrogencarbonate. The organic layer was dried over anhydrous sodium sulfate, then the solvent was distilled off under reduced pressure to obtain a crude carbonate compound(1.818 g).

To this crude carbonate compound was added N-benzylpiperazine [1.043 ml(6 mmol.)], and the mixture was heated for one hour at 90° C. The crude product thus obtained was, after cooling, purified by means of a column chromatography(silica gel:80 g; eluent:hexane/ethyl acetate=1/1) to afford the object compound(92)[1.935 g(99.1%,colorless resinous substance].

TLC[Silica Gel;n-hexane/AcOEt(1/1)]: Rf=0.28.

NMR(90 MHz,CDCl$_3$) δ: 2.33(4H,t),3.43(6H,m),4.30(2H,m),4.56 (2H,m),6.79(1H,dd),7.1 to 7.5(9H,m),7.78(2H,m),8.28(1H,d).

IR(film)cm$^{-1}$: 1695,1592,1578,1430,1270,1230,1130,1102,1003.

(ii) Synthesis of N-[2-(1-naphthyloxy)ethoxycarbonyl]-piperazine(93)

The compound(92) synthesized in (i) [1.81 g(4.64 mmol.)] was dissolved in a mixture of ethanol(10 ml) and a 90% aqueous solution of acetic acid(50 ml). To the solution was added 10%Pd/C(900 mg), which was subjected to catalytic reduction for 6.5 hours. The catalyst was filtered off, and the filtrate was concentrated under reduced pressure. The concentrate was dissolved in chloroform, and the solution was washed with a 5% aqueous solution of sodium hydroxide. The organic layer was dried over anhydrous potassium carbonate, then the solvent was distilled off under reduced pressure to leave a crude product, which was purified by means of a column chromatography(silica gel:50 g; eluent:chloroform/methanol=10/1) to give the object compound(93) [1.32 g(94.8%,colorless oily product).

TLC[Silica Gel;CHCl$_3$/MeOH(3/1)]: Rf=0.41.

NMR(90 MHz,CDCl$_3$) δ: 1.72(1H,br s),2.74(4H,t),3.43(4H,t), 4.32(2H,m),4.58(2H,m),6.81(1H,dd),7.35 to 7.56(4H,m), 7.79(1H,m),8.29(1H,m),

IR(film)cm$^{-1}$: 1695,1579,1418,1272,1238,1135,1105.

(ii) Synthesis of N-[2-(1-naphthyloxy)ethoxycarbonyl]-N'-(5-bromonicotinoyl)piperazine(94)

In chloroform(30 ml) were dissolved the compound(95) synthesized in (ii) [601 mg(2 mmol.)] and triethylamine[607 mg (6 mmol.)]. To the solution was added, under ice-cooling, 5-bromonicotinic acid chloride hydrochloride[617 mg(2.4 mmol.)], then the mixture was stirred for 30 minutes at room temperature. The reaction mixture was washed with a 5% aqueous solution of sodium hydroxide. The organic layer was dried over anhydrous potassium carbonate, then the solvent was distilled off under reduced pressure. The crude product thus obtained was purified by means of a column chromatography(silica gel:50 g; eluent:ethyl acetate) to afford the object compound(94)[717 mg(74.0%,colorless resinous product).

TLC(Silica Gel;AcOEt): Rf=0.44.

NMR(90 MHz,CDCl3) δ: 3.50(8H,br s),4.39(2H,m),4.61(2H,m), 6.82(1H,dd),7.36 to 7.59(4H,m),7.80(1H,m),7.88(1H,m), 8.28(1H,m),8.53(1H,d),8.75(1H,d).

IR(film)cm$^{-1}$:
1700,1630,1590,1575,1460,1410,1232,1102,1008.

(iv) Synthesis of 5-bromo-3-[4-[2-(1-naphthyloxy)ethoxycarbonyl]-1-piperazinyl]carbonyl-1-ethylpyridinium iodide(95)

To the compound(94) synthesized in (iii) [242 mg(0.5 mmol.)] was added iodoethane(10 ml), and the mixture was heated under reflux for 48 hours in nitrogen streams while shielding the light. The reaction mixture was, after cooling, concentrated under reduced pressure to give a crude product, which was washed with ether to afford the object compound(95)[281 mg (87.8%,pale yellow powder)].

TLC[Silica Gel;CHCl3/MeOH(3/1)]: Rf=0.30.

NMR(90 MHz,CDCl3) δ: 1.71 (3H,t),3.63(8H,s),4.40(2H,m),4.60 (2H,m),4.83(2H,q),6.86(1H,dd),7.37 to 7.57(4H,m),7.82 (1H,m),8.26(1H,m),8.58(1H,br s),9.28(1H,br S),9.37(1H,br s).

IR(KBr)cm$^{-1}$:
3400(br),1680,1630,1612,1570,1465,1425,1248, 1225,1105,775.

PRODUCTION EXAMPLE 37

Synthesis of 5-bromo-3-[4-[2-(1-naphthyloxy)ethoxycarbonyl]-1-piperazinyl]carbonyl-1-propylpyridinium iodide(96)

To the compound(94) synthesized in Production Example 36-(iii) [400 mg(0.826 mmol.)] was added 1-iodopropane(15 ml). The mixture was heated under reflux for 48 hours in nitrogen streams while shielding the light. The reaction mixture was, after cooling, concentrated under reduced pressure to give a crude product. The crude product was washed with ether to afford the object product(96) [527 mg(97.5%,pale yellow powder)].

TLC[Silica Gel;CHCl3/MeOH(3/1)]: Rf=0.43.

NMR(90 MHz,CDCl3) δ: 1.02(3H,t),2.07(2H,q),3.63(8H,br s),4.37 (2H,m),4.57(2H,m),4.77(2H,t),6.82(1H,dd),7.2 to 7.7(4H,m), 7.80(4H,m),8.25(1H,m),8.50(1H,br s),9.27(1H,br s),9.35 (1H,br s).

IR(KBr)cm$^{-1}$: 3410,1690,1640,1577,1430,1270,1230.

PRODUCTION EXAMPLE 38

Synthesis of 1-ethyl-3-[N-[2-(1-naphthyloxy)ethoxycarbonylamino]ethyl-N-phenyl]carbamoylquinolinium iodide(98)

(i) Synthesis of 3-[N-[2-(1-naphthyloxy)ethoxycarbonylamino]-ethyl-N-phenyl]carbamoylquinoline(97)

In chloroform(25 ml) were dissolved the compound synthesized in Production Example 11-(i)[526 mg(1.5 mmol.)] and triethylamine[607 mg(6 mmol.)]. To the solution was added, under icecooling, quinoline carboxylic acid chloride hydrochloride [513 mg(2.25 mmol.)], and the mixture was stirred for 30 minutes at room temperature. The reaction mixture was washed with a 5% aqueous solution of sodium hydroxide, and the organic layer was dried over anhydrous potassium carbonate, then the solvent was distilled off under reduced pressure to leave a crude product, which was purified by means of a column chromatography(silica gel:40 g; eluent:n-hexane/ethyl acetate=≃) to obtain the object compound(97) [482 mg(63.6%, color less powder).

TLC[Silica Gel;n-hexane/AcOEt(≃)]: Rf=0.23.

NMR(90 MHz,CDCl3) δ: 3.51 (2H,q),4.14 (2H,t),4.27 (2H,t),4.54 (2H,t),5.57(1H,br),6.77(1H,dd),6.8 to 8.1(14H,m),8.14 (1H,d),8.29(1H,m),8.70(1H,d).

IR(film)cm$^{-1}$: 3300,1700,1620 .

(ii) Synthesis of 1-ethyl-3-[N-[2-(1-naphthyloxy)ethoxycarbonylamino]ethyl-N-phenyl]carbamoyl-quinolinium iodide(98)

To the compound(97) synthesized in (i) [200 mg(0.4 mmol.)] was added iodoethane(10 ml), and the mixture was heated under reflux for 46 hours in nitrogen streams while shielding the light. The reaction mixture was cooled and then concentrated under reduced pressure to give a crude product, which was washed with ether to afford the object compound(98) [259 mg (97.9%, pale yellow powder)].

TLC[Silica Gel;CHCl3/MeOH(3/1)]: Rf=0.40.

NMR(90 MHz,CDCl3) δ: 1.40 (3H,t),3.55(2H,m),4.17 (4H,m),4.46(2H,br t), 5.00(2H,q),6.54(1H,m),6.70(1H,dd),6.8 to 8.3(15H,m),8.70 (1H,br s),9.88(1H,br s).

IR(KBr)cm$^{-1}$:
3410(br),1710,1645,1590,1418,1398,1240.

PRODUCTION EXAMPLE 39

Synthesis of 3-[N-[2-(1-naphthyloxy)ethoxycarbonylamino]-ethyl-N-phenyl]carbamoyl-1-propyl-quinolinium iodide(99)

To the compound(97) synthesized in Production Example 38-(ii) [245 mg(0.485 mmol.)] was added 1-iodopropane(15 ml), and the mixture was heated under reflux for 46 hours in nitrogen streams while shielding the light. The reaction mixture was cooled and then concentrated under reduced pressure to give a crude product, which was washed with ethyl acetate and ether to obtain the object compound(99) [304 mg(92.8%,pale yellow powder)].

TLC[Silica Gel;CHCl3/MeOH(3/1)]: Rf=0.40.

NMR(90 MHz,CDCl3) δ: 0.71 (3H,t), 1.77 (2H,q), 3.54 (2H,m), 4.18 (4H,m),4.44(2H,m),4.95(2H,t),6.53(1H,m),6.72(1H,m),- 6.9 to 8.3(15H,m),8.79(1H,br s),9.90(1H,br s),

IR(KBr)cm$^{-1}$:
3380,1700,1648,1590,1520,1490,1398,1240,780.

PRODUCTION EXAMPLE 40

Synthesis of 3-[N-[2-(butylcarbamoyloxy)ethyl]-N-phenyl]-carbamoyl-1-ethylpyridinium iodide(102)

(i) Synthesis of 3-[N-(2-hydroxyethyl)-N-phenyl]carbamoylpyridine(100)

In methylene chloride(20 ml) were dissolved 2-anilinoethanol[2.784 g(20 mmol.)] and triethylamine [5.575 ml(40 mmol.)]. To the solution was added, under ice-cooling, nicotinic acid chloride hydrochloride[3.56 g(20 mmol.)], and the mixture was stirred for three hours at room temperature. The reaction mixture was washed with a 1N aqueous solution of sodium hydroxide, and the organic layer was dried over anhdyrous potassium carbonate, followed by distilling off the solvent under reduced pressure. The crude product thus obtained was purified by means of a column chromatography(silica gel:180 g;eluent:ethyl acetate/acetone=5/1) to obtain the object compound(100)[4.84 g(100%,colorless oily product)].

TLC(Silica Gel;AcOEt): Rf=0.14.

NMR(90 MHz,CDCl$_3$) δ: 3.50(1H,br s),3.81(2H,t),4.07(2H,t), 7.01 to 7.39(6H,m),7.60(1H,d t),8.43(1H,dd),8.5l(1H,d).

IR(KBr)cm$^{-1}$: 3350,1635,1590,1490.

(ii) Synthesis of 3-[N-[2-(butylcarbamoyloxy)ethyl]-N-phenyl]carbamoylpyridine(101)

To the alcohol compound(100) synthesized in (i) [969 mg (4 mmol.)] was added butylisocyanate [4.5 ml(40 mmol.)]. The mixture was then heated under reflux for 16 hours. The reaction mixture was cooled and concentrated under reduced pressure to give a crude product, followed by subjecting the crude product to purification by means of a column chromatography(silica gel:40 g; eluent:ethyl acetate) to obtain the object compound(101)[1.172 g(85.8%,colorless oily product)].

TLC(Silica Gel;AcOEt): Rf=0.37.

NMR(90 MHz,CDCl$_3$) δ: 0.88(3H,t),1.36(4H,m),3.08(2H,m),4.18(2H,d), 4.33(2H,d),4.66(1H,br),6.9 to 7.3(6H,m),7.58(1H,d t), 8.44(1H,dd),8.48(1H,d).

IR(film)cm$^{-1}$: 3300,2950,2910,2850,1705,1630,1520,1390,1250.

(ii) Synthesis of 3-[N-[2-(butylcarbamoyloxy)ethyl]-N-phenyl]-carbamoyl-1-ethylpyridinium iodide(102)

To the compound(10l) synthesized in (ii) [683 mg(2 mmol.)] was added iodoethane(10 ml), and the mixture was heated under reflux for 72 hours in nitrogen streams while shielding the light. The reaction mixture was cooled and concentrated under reduced pressure to obtain the object compound(102) [915 mg (92.0%,pale yellow powder)].

TLC[Silica Gel;CHCl$_3$/MeOH(3/1)]: Rf=0.22.

NMR(90 MHz,CDCl$_3$) δ: 0.88(3H,m),1.48(7H,m),3.10 (2H,m),4.21 (4H,m),4.90(2H,q),5.72(1H,br),7.39(5H,m),8.00(1H,br t), 8.32(1H,br d),9.38(2H,m).

IR(KBr)cm$^{-1}$: 3270,1700,1650,1590,1490,1250.

PRODUCTION EXAMPLE 41

Synthesis of 3-[N-[2-(octadecylcarbamoyloxy)ethyl]-N-phenyl]carbamoyl-1-ethylpyridinium iodide(104)

(i) Synthesis of 3-[N-[2-(octadecylcarbamoyloxy)ethyl]-N-phenyl]carbamoylpyridine(103)

To the alcohol compound(100) synthesized in Production Example 40-(i)[485 mg(2 mmol.)] were added octadecylisocyanate [1.4 ml(4 mmol.)] and toluene(3 ml), and the mixture was heated under reflux for 17 hours at 92° C. To the reaction mixture was added, after cooling, water, followed by extraction with chloroform. The organic layer was dried over anhydrous potassium carbonate, then the solvent was distilled off under reduced pressure. The crude product thus obtained was subjected to purification by means of a column chromatography(silica gel:50 g; eluent:ethyl acetate) to obtain the object compound(103) [728 mg(67.7%,colorless solid matter)].

TLC(Silica Gel;AcOEt): Rf=0.50.

NMR(90 MHz,CDCl$_3$) δ: 0.86(3H,t),1.27(32H,s),3.08(2H,m),4.20 (2H,d),4.34(2H,d),4.62(1H,br),6.9 to 7.3(6H,m),7.61(1H, d t),8.49(2H,m)

IR(KBr)cm$^{-1}$: 3350,2910,2840,1684,1638,1590,1510,1240.

(ii) Synthesis of 3-[N-[2-(octadecylcarbamoyloxy)ethyl]-N-phenyl]carbamoyl-1-ethylpyridinium iodide(104)

To the compound(103) synthesized in (i) [538 mg(1 mmol.)] was added iodoethane(8 ml), and the mixture was heated under reflux for 72 hours in nitrogen streams while shielding the light. The reaction mixture was cooled and concentrated under reduced pressure to obtain the object compound (104) [694 mg (100%,pale yellow powder)].

TLC[Silica Gel;CHCl$_3$/MeOH(3/1)]: Rf=0.43.

NMR(90 MHz, CDCl$_3$) δ: 0.88(3H,m), 1.24(32H,m), 1.45(3H,t), 3.10 (2H,m), 4.19(4H,m), 4.87(2H,q), 5.60(1H,br), 7.34(5H,m), 7.95 (1H,br t), 8.25(1H,br d), 9.31(2H,m).

IR(KBr)cm$^{-1}$: 2910,2840,1698,1650,1590,1490,1250

PRODUCTION EXAMPLE 42

Synthesis of 5-bromo-3-[N-[2-(1-naphthylcarbamoyloxy)ethyl]-N-phenyl]carbamoyl-1-propyl-pyridinium chloride(106)

(i) Synthesis of 5-bromo-3-[N-[2-(1-naphthylcarbamoyloxy)ethyl]-N-phenyl]carbamoylpyridine(105)

To the alcohol compound(18) synthesized in Production Example 6-(i) [642 mg(2 mmol.)] were added 1-naphthylisocyanate [0.344 ml(2.4 mmol.)] and pyridine(5 ml), and the mixture was stirred for one hour at room temperature. The reaction mixture was concentrated under reduced pressure. The crude product thus obtained was purified by means of a column chromatography(silica gel:30 g;eluent:hexane/ethyl acetate=1/1.5) to obtain the object compound(105) [981 mg(100%, colorless resinous product)].

TLC(Silica Gel;hexane/AcOEt=1/1.5): Rf=0.38.

NMR(90 MHz,CDCl$_3$) δ: 4.23(2H,t),4.50(2H,t),6.8 to 8.0(14H,m), 8.27(1H,d),8.47(1H,d) .

IR(film)cm$^{-1}$: 3250,1700,1640

(ii) Synthesis of 5-bromo-3-[N-[2-(1-naphthylcarbamoyloxy)ethyl]-N-phenyl]carbamoyl-1-propyl-pyridinium chloride(106)

To the compound(105) synthesized in (i) [736 mg(1.5 mmol)] was added 1-iodopropane (15 ml), and the mixture was heated under reflux for 48 hours in nitrogen streams while shielding the light. The reaction mixture was cooled and concentrated under reduced pressure. The concentrate was treated with IRA-410(Cl$^-$) [60 ml; eluent:70% methanol/water], followed by purification by means of a column chromatography(silica gel: 30 g; eluent:chloroform/methanol=6/1) to obtain the object compound(90)[593 mg(69.5%,pale yellow powder)].

TLC[Silica Gel;CHCl$_3$/MeOH(3/1)]: Rf=0.29.

NMR(90 MHz,CDCl$_3$)δ: 0.51(3H,t), 1.54(2H,m), 4.14(2H,m), 4.39 (2H,m), 4.63(2H,m), 6.9 to 7.9(10H,m),8.21(2H,m),9.30(1H, br s), 9.61(2H,br s).

IR(KBr)cm$^{-1}$: 3380,1705,1655,1590,1490,1400,1222 .

PRODUCTION EXAMPLE 43

Synthesis of 5-bromo-3-[N-(2-naphthyl)-N-[2-[2-(1-naphthylcarbamoyloxy)ethyl]carbamoyloxy]ethyl]carbamoyl-1-propylpyridinium chloride(110)

(i) Synthesis of 5-bromo-3-[N-(2-hydroxyethyl)-N-(2-naphthyl)]carbamoylpyridine(107)

To a solution of N-(2-naphthyl)aminoethanol [780 mg(4.17 mmol.)] and triethylamine [2.91 ml(20.9 mmol.)] in chloroform (20 ml) was added, under ice-cooling and stirring, 5-bromonicotinic acid chloride hydrochloride [1.18 g(4.58 mmol.)], and the mixture was stirred for 30 minutes at room temperature. The reaction mixture was washed with a 1N aqueous solution of sodium hydroxide, which was dried, followed by distilling off the solvent under reduced pressure. The residue was subjected to a silica gel column chromatography, eluting with hexaneethyl acetate(1:2), to afford the compound(107) [608 mg(39.3%)] as colorless powder.

IR(KBr)cm$^{-1}$: 3420(br),3050, 1640(br),1600.

NMR(90 MHz,CDCl$_3$) δ: 3.83(2H,t,J=5 Hz),4.16(2H,t,J=5 Hz), 7.00 to 8.06(7H,m),7.97(1H,t,J=2 Hz),8.37(1H,d,J=2 Hz), 8.43(1H,d,J=2 Hz).

(ii) Synthesis of 5-bromo-3-[N-(2-naphthyl)-N-[2-[2-(1-naphthylcarbamoyloxy)ethyl]carbamoyloxy]ethyl]carbamoylpyridine(108)

To a solution of the compound(107) synthesized in (i) [394 mg (1.11 mmol.)] and pyridine [0.54 ml (6.66 mmol.)] in chloroform (10 ml) was added dropwise, under ice-cooling and stirring, phenyl chloroformate [0.42 m (3.33 mmol.)], and the mixture was stirred for 30 minutes at room temperature. The reaction mixture was washed with a 5% aqueous solution of sodium hydrogencarbonate and dried, followed by distilling off the solvent. To the residue was added 2-(1-naphthylcarbamoyloxy)ethylamine [767 mg(3.33 mmol.)], and the mixture was heated for one hour at 120° C. The reaction mixture was cooled and subjected to a silica gel column chromatography, eluting with hexane-ethyl acetate(1:2) to afford the compound(108)[484 mg(69.5%)] as a colorless oily product.

IR(KBr)cm$^{-1}$: 3330(br),3050, 1717(br),1650(br),1600.

NMR(90 MHz,CDCl$_3$) δ: 3.41(2H,m),3.96 to 4.55(6H,m),5.43(1H,m), 7.05 to 8.05(15H,m),8.31(1H,d,J=2 Hz),8.36(1H,d,J=2 Hz).

(iii) Synthesis of 5-bromo-3-[N-(2-naphthyl)-N-[2-[2-(1-naphthylcarbamoyloxy)ethyl]carbamoyloxy]ethyl]carbamoyl-1-propylpyridinium iodide(109)

A solution of the compound(108) synthesized in (ii) [390 mg (0.62 mmol.)] in propyl iodide(5 ml) was stirred for two days at 110° C. Resulting precipitates were washed with ether and dried to obtain the compound (109) [523 mg(quant.)] as yellow powder.

IR(KBr)cm$^{-1}$: 3420(br), 3270(br), 3050, 1720(br), 1660(br), 1600.

NMR(90 MHz, CDCl$_3$)δ: 1.28(3H,m),1.75(2H,br s),3.52(2H,m),4.00 to 4.64(8H,m),6.83(1H,m),7.05 to 8.40(15H,m),6.67(1H,br s), 9.53(1H,br s).

(iv) Synthesis of 5-bromo-3-[N-(2-naphthyl)-N-[2-[2-(1-naphthylcarbamoyloxy)ethyl]carbamoyl]ethyl]carbamoyl-1-propylpyridinium chloride(110)

The compound (109) [412 mg(0.52 mmol.)] synthesized in (iii) was dissolved in a mixture(20 ml) of methanol-water(7:3). The solution was allowed to pass through anion exchange resin (IRA-410[Cl$^-$]) (20 ml). The eluate was concentrated under reduced pressure to obtain the compound (110) [322 mg (88.3%)] as yellow powder.

IR(KBr)cm$^{-1}$: 3240(br), 3050, 1710(br), 1630(br), 1600.

NMR(90MHz,DMSO-d$_6$): 1.27(3H,m),2.86(2H,m),3.50(2H,m),4.17 (6H,m),4.41(2H,m),7.10 to 8.47(14H,m),8.93(1H,br s), 9.80(1H,br s).

PRODUCTION EXAMPLE 44

Synthesis of 5-bromo-3-[N-(3-chlorophenyl)-N-[2-[2-(1-naphthylcarbamoyloxy)ethyl]carbamoyloxy]ethyl]carbamoyl-1-propylpyridinium chloride(114)

(i) Synthesis of 2-[N-(3-chlorophenyl)-N-(tert-butoxycarbonyl)]aminoethanol(111)

To a solution of 3-chloroanilinoethanol[943 mg(5.49 mmol.)] in dichloromethane(10 ml) was added di-tert-butyl dicarbonate [1.20 g(5.49 mol.)], and the mixture was stirred for two days at room temperature. The solvent was distilled off under reduced pressure, and the residue was subjected to a silica gel column chromatogrpahy, eluting with hexane-ethyl acetate (1:1), to afford the compound(111) [803 mg(53.8%)] as a pale yellow oily prodcut.

IR(Neat)cm$^{-1}$: 3400(br),1690(br),1590.

NMR(90 MHz,CDCl$_3$)δ: 1.44(9H,s),3.78(4H,br s),7.41 to 7.64(4H,m).

(ii) Synthesis of 5-bromo-3-[N-(3-chlorophenyl)-N-[2-[2-(1-naphthylcarbamoyloxy)ethyl]carbamoyloxy]ethyl]carbamoylpyridine(112)

To a solution of the compound(111) synthesized in i) [740 mg (2.72 mmol.)] and pyridine [0.88 ml(10.9 mmol.)] in chloroform (10 ml) was added dropwise, under ice-cooling while stirring, phenyl chloroformate [0.76 ml(6.00 mmol.)], and the mixture was stirred for five minutes at room temperature. The reaction mixture was washed with a 5% aqueous solution of hydrogencarbonate and then dried, and the solvent was distilled off. To the residue was added 2-(1-naphthylcarbamoyloxy)ethylamine [689 mg(3.00 mmol.)], and the mixture was heated for one hour at 80° C. The reaction mixture was, after cooling, subjected to a silica gel column chromatography, eluting with hexane-ethyl acetate(1:1), to obtain a pale yellow oily product(1.14 g).

To a solution of the above-mentioned crude product [1.12 g (2.12 mmol.)] in methanol(5 ml) was added 14M methanol solution of hydrogen chloride(5 ml), and the mixture was stirred for three hours at room temperature. The reaction mixture was made alkaline with a saturated aqueous solution of sodium hydrogencarbonate, which was subjected to extraction with chloroform. The organic layer was separated and dried, then the solvent was distilled off under reduced pressure to obtain a yellow oily product(908 mg).

To a solution of the above-mentioned compound [900 mg(2.10 mmol.)] and triethylamine [2.19 ml(15.8 mmol.)] in chloroform (10 ml) was added, under ice-cooling while stirring, 5-bromonicotinic acid chloride hydrochloride [0.89 g(3.47 mmol.)], and the mixture was stirred for 20 minutes at room temperature. The reaction mixture was washed with a saturated aqueous solution of sodium hydrogencarbonate and then dried, and the solvent was distilled off under reduced pressure.

The residue was subjected to a silica gel column chromatography, eluting with hexane-ethyl acetate(1:1), to obtain the compound (112) [562 mg(29.0% based on 111)] as a pale yellow oily product.

IR(KBr)cm$^{-1}$: 3230,3200,3100,1700,1670(br).

NMR(90MHz,CDCl$_3$)δ: 3.46(2H,q,J=5 Hz),3.87 to 4.50(6H,m),5.17 (1H,br t,J=5 Hz), 6.80 to 8.03(12H,m),8.34(1H,br s),8.50 (1H,d,J=2 Hz).

(iii) Synthesis of 5-bromo-3- [N-(3-chlorophenyl)-N- [2-[2-(1-naphthylcarbamoyloxy)ethyl]carbamoyloxy]ethyl]carbamoyl-1-propylpyridinium iodide(113)

A solution of the compound(112) synthesized in (ii) [520 mg (0.85 mmol.)] in propyl iodide(5 ml) was stirred for two days at 110° C. Resulting precipitates were washed with ether and dried to obtain the compound(113) [526 mg(79.2%)] as yellow powder.

IR(KBr)cm$^{-1}$: 3320(br),3060,1720(br),1650(br),1590.

NMR(90 MHz,CDCl$_3$)δ: 0.64(3H,t,J=7 Hz),1.65(2H,m),3.53(2H,m), 4.23(6H,m),4.59(2H,br t,J=7 Hz),6.73(1H,m),7.10 to 7.95 (12H,m),8.04(1H,br s),8.25(1H,br s),9.62(1H,br s).

(iv) Synthesis of 5-bromo-3- [N-(3-chlorophenyl)-N- [2-[2-(1-naphthylcarbamoyloxy)ethyl]carbamoyloxy]ethyl]carbamoyl-1-propylpyridinium chloride(114)

The compound(113) synthesized in (iii) [439 mg(0.56 mmol.)] was dissolved in a mixture solution(10 ml) of methanol-water (7:3), which was allowed to pass through anion exchange resin (IRA-410[Cl$^-$]) (20 ml). The eluate was concentrated under reduced pressure to obtain the compound(114) [308 mg(72.4%)] as yellow powder.

IR(KBr)cm$^{-1}$: 3270(br),1710(br),1660(br),1590.

NMR(90 MHz,CDCl$_3$)δ: 0.50(3H,t,J=7 Hz),0.58(2H,m),3.47(2H,m), 4.15(2H,m),4.57(4H,br t,J=7 Hz),6.96 to 7.76(11H,m),8.20 (2H,m),8.76(1H,br s),9.05(1H,br s),9.85(1H,br s).

PRODUCTION EXAMPLE 45

Synthesis of 5-bromo-3- [N-[2-(1-naphthylcarbamoyloxy)ethyl]-carbamoylmethyl-N-phenyl]carbamoyl-1-propylpyridinium chloride (119)

(i) Synthesis of N-chloroacetyl-2-(1-naphthylcarbamoyloxy)ethylamine(115)

To a solution of 2-(1-naphthylcarbamoyloxy)ethylamine [1.15 g (5.00 mmol.)] and triethylamine [1.39 ml(10.0 mmol.)] in chloroform (15 ml) was added dropwise, under ice-cooling while stirring, chloroacetyl chloride [0.44 ml(5.50 mmol.)]. The mixture was stirred for 30 minutes under ice-cooling. The reaction mixture was washed with a saturated aqueous solution of sodium hydrogen carbonate and water, successively and then dried, followed by distilling off the solvent. Crystals thus obtained were washed with hexane-ethyl acetate(1:2) to afford the compound(115) [1.40 g(91.3%)] as a yellow oily product.

IR(KBr)cm$^{-1}$: 3320(br),3050,1710(br),1590.

NMR(90 MHz,CDCl$_3$)δ: 3.61(2H,q,J=6 Hz),4.02(2H,s),4.34(2H,t, J=5 Hz),7.05(1H,m),7.23 to 8.12(7H,m).

(ii) Synthesis of N-(N-phenylglycyl)-2-(1-naphthylcarbamoyloxy)ethylamine(116)

A solution of the compound(115) synthesized in i) [307 mg (1.00 mmol.)] and aniline [0.18 ml(2.00 mmol.)] in toluene(2 ml) was heated under reflux for 24 hours. The reaction mixture was, after cooling, diluted with ethyl acetate and washed with a 1N sodium hydroxide solution and dried, and then the solvent was distilled off. The residue was subjected to a silica gel column chromatography, eluting with hexane-ethyl acetate(1:2), to obtain the compound(116) [151 mg(41.5%)] as a brown oily product.

IR(Neat)cm$^{-1}$: 3370(br),3050,1720(br),1660(br),1590.

NMR(90 MHz,CDCl$_3$)δ: 3.54(2H,q,J=6 Hz),3.67(2H,br s),4.20(2H, t,J=6 Hz),4.73(1H,m),6.20 to 8.10(12H,m).

(iii) Synthesis of 5-bromo-3- [N- [2-(1-naphthylcarbamoyloxy)ethyl]carbamoylmethyl-N-phenyl]carbamoylpyridine(117)

To a solution of the compound(116) synthesized in (ii) [266 mg(0.73 mmol.) and triethylamine [0.20 ml(1.46 mmol.)] in chloroform(7 ml) was added, under ice-cooling while stirring, 5-bromonicotinic acid chloride hydrochloride [208 mg(0.81 mmol.)], and the mixture was stirred for 30 minutes at room temperature. The reaction mixture was washed with a saturated aqueous solution of sodium hydrogencarbonate, which was dried, and then the solvent was distilled off under reduced pressure. The residue was subjected to a silica gel column chromatography, eluting with hexane-ethyl acetate(1:3), to obtain the compound(117) [329 mg(82.1%)] as a pale yellow oily product.

IR(KBr)cm$^{-1}$: 3310(br),3050,1720(br),1650(br),1590.

NMR(90 MHz,CDCl$_3$) 3.63(2H,q,J=6 Hz),4.34(2H,t,J=6 Hz),4.48 (2H,s),7.10(5H,s-like),7.21 to 8.04(8H,m),8.28(1H,d,J=2 Hz), 8.45(1H,d,J=2 Hz).

(iv) Synthesis of 5-bromo-3- [N- [2-(1-naphthylcarbamoyloxy)ethyl]carbamoylmethyl-N-phenyl] carbamoyl-1-propylpyridinium iodide(118)

A solution of the compound(117) synthesized in (iii) [297 mg (0.54 mmol.)] in propyl iodide(5 ml) was stirred for two days at 110° C. Resulting precipitates were subjected to a silica gel column chromatography, eluting with chloroform-methanol (10:1→5:1), to obtain the compound(118) [213 mg(54.8%)] as yellow powder.

IR(KBr)cm$^{-1}$: 3250(br),3040,1720(br),1660(br),1590.

NMR(90 MHz,CDCl$_3$)δ: 0.65(3H,t,J=7 Hz),1.60(2H,m),3.60(2H,m), 4.00 to 4.50(4H,m),4.60(2H,br,s),6.86 to 8.17(12H,m), 8.40(1H,br s),8.90(1H,br s),9.08(1H,br s).

(v) Synthesis of 5-bromo-3- [N- [2-(1-naphthylcarbamoyloxy)ethyl]carbamoylmethyl-N-phenyl]carbamoyl-1-propylpyridinium chloride(119)

The compound(118) synthesized in (iv) [163 mg(0.23 mmol.)] was dissolved in a mixture of methanol-water(7:3)(20 ml). The solution was allowed to pass through anion exchange resin (IRA-410[Cl$^-$])(20 ml), and the eluate was concentrated under reduced pressure to obtain the compound(119) [103 mg(62.4%)] as yellow powder.

IR(KBr)cm$^{-1}$: 3220(br),3050,1720(br),1660(br),1590.

NMR(90 MHz,CDCl$_3$)δ: 0.59(3H,t,J=7 Hz),1.60(2H,m),3.64(2H,m), 4.00 to 4.64(4H,m),4.64(2H,br s),6.84 to 8.25(12H,m), 8.40(1H,br s),9.14(2H,br s).

PRODUCTION EXAMPLE 46

Synthesis of 5-bromo-3- [N- [3-[2-(1-naphthylcarbamoyloxy)ethyl]carbamoyl]propyl-N-phenyl]carbamoyl-1-propylpyridinium chloride(123)

(i) Synthesis of N-(4-chlorobutyryl)-2-(1-naphthylcarbamoyloxy)ethylamine(120)

To a solution 2-(1-naphthylcarbamoyloxy)ethylamine [1.15 g (5.00 mmol.)] and triethylamine [1.39 ml(10.0 mmol.)] in chloroform(15 ml) was added dropwise, under ice-cooling while stirring, 4-chlorobutyryl chloride [0.62 ml(5.50 mmol.)]. The mixture was stirred for 30 minutes under ice-cooling. The reaction mixture was washed with a saturated aqueous solution of sodium hydrogencarbonate and water, successively, which was dried, followed by distilling off the solvent. Resultant crystals were washed with ether to obtain the compound(120) [1.38 g(82.4%)] as pale brown crystals.

IR(KBr)cm$^{-1}$: 3290(br),3070,1700(br),1650(br),1600.
NMR(90 MHz,CDCl$_3$)δ: 1.80 to 2.50(4H,m),3.34 to 3.70(4H,m),4.27 (2H,t,J=6 Hz),6.07(1H,m),7.18(1H,m),7.20 to 8.07(7H,m).

(ii) Synthesis of N-(4-anilinobutyryl)2-(1-naphthylcarbamoyloxy)ethylamine(121)

A solution of the compound(120) synthesized in i) [992 mg (2.96 mmol.)] and aniline [0.54 ml(5.93 mmol.)] in toluene (6 ml) was heated udner reflux for five hours. The reaction mixture was, after cooling, diluted with ethyl acetate and washed with a 1N aqueous solution of sodium hydroxide, followed by drying and distilling off the solvent. The residue was subjected to a silica gel column chromatography, eluting with ethyl acetate, to obtain the compound(121) [407 mg(35.1%)] as a brown oily product.

IR(KBr)cm$^{-1}$: 3300(br),3070,1710(br),1650(br),1600.
NMR(90 MHz,CDCl$_3$)δ: 1.85(2H,quint.J=7 Hz),2.20(2H,t,J=7 Hz), 3.07(2H,t,J=7 Hz),3.49(2H,q,J=7 Hz),4.24(2H,t,J=7 Hz), 6.08(1H,m),6.34 to 8.10(13H,m).

(iii) Synthesis of 5-bromo-3- [N- [3- 2-(1-naphthylcarbamoyloxy)ethyl]carbamoyl]propyl-N-phenyl]carbamoylpyridine (122)

To a solution of the compound(121) synthesized in (ii) [346 mg(0.88 mmol.)] and triethylamine [0.25 ml(1.77 mmol.)] in chlorofrom(6 ml) was added, under ice-cooling while stirring, 5-bromonicotinic acid chloride hydrochloride [250 mg (0.97 mmol.)], and the mixture was stirred for 30 minutes at room temperature. The reaction mixture was washed with a 1N aqueous solution of sodium hydroxide, followed by drying and distilling off the solvent under reduced pressure. The residue was subjected to a silica gel column chromatography, eluting with ethyl acetate-methanol(10:1) to obtain the compound(122) [260 mg(75.5%)] as a pale yellow oily product.

IR(KNr)cm$^{-1}$: 3290(br),3050,1730(br),1640(br),1590.
NMR(90 MHz,CDCl$_3$) 1.90(2H,quint.J=7 Hz),2.39(2H,t,J=7 Hz), 3.62(2H,q,J=6 Hz),3.95(2H,t,J=7 Hz),4.35(2H,t,J=6 Hz), 6.65 to 8.02(17H,m).

(iv) Synthesis of 5-bromo-3- [N- [3- [2-(1-naphthylcarbamoyloxy)ethyl]carbamoyl]propyl-N-phenyl]carbamoyl-1-propylpyridinium chloride(123)

A solution of the compound(122) synthesized in (iii) [220 mg (0.38 mmol.)] in propyl iodide(8 ml) was stirred for two days at 110° C. Resulting precipitates were washed with ether to obtain a crude iodide compound (300 mg) as yellow powder.

The crude compound [300 mg(0.40 mmol.)] was dissolved in a mixture of methanol-water(7:3)(20 ml). The solution was allowed to pass through anion exchange resin(IRA-410[Cl$^-$]) (20 ml), and the eluate was concentrated under reduced pressure to obtain the compound(123) [160 mg(56.5% based on 122)] as yellow powder.

IR(KBr)cm$^{-1}$:
3390(br),3240(br),3050,1720(br),1650(br),1590.

NMR(90 MHz,CDCl$_3$)δ: 0.50(3H,t,J=7 Hz),1.55(2H,m),1.87(2H,m), 2.20 to 3.12(2H,m),3.56(2H,m),3.89(2H,m),4.26(2H,m), 6.85 to 8.68(14H,m),8.93(1H,br s),8.98(1H,br s),9.94 (1H,br s).

PRODUCTION EXAMPLE 47

Synthesis of 5-bromo-3-[N-[2-(1-naphthylcarbamoyloxy)-ethoxy]ethyl]-N-phenyl]carbamoyl-1-propylpyridinium chloride (127)

(i) Synthesis of 2-(2-anilinoethoxy)ethanol(124)

A solution of 2-(2-chloroethoxy)ethanol [1.25 g(10.0 mmol.)] and aniline [1.82 ml(20.0 mmol.)] in toluene(10 ml) was heated for 25 hours under reflux. The reaction mixture was, after cooling, washed with a saturated aqueous solution of sodium hydrogencarbonate, which was dried, and then the solvent was distilled off. The residue was subjected to a silica gel column chromatography, eluting with hexane-ethyl acetate(1:3), to obtain the compound(124) [809 mg(44.6%)] as a brown oily product.

IR(Neat)cm$^{-1}$: 3370(br),3050,1600.
NMR(90 MHz,CDCl$_3$)δ: 3.27(2H,t,J=5 Hz),3.67(2H,t,J=5 Hz),6.62 (2H,d,J=8 Hz),6.67(1H,t,J=8 Hz),7.17(2H,t,J=8 Hz).

(ii) Synthesis of 5-bromo-3- [N- [2-(2-hydroxyethoxy)ethyl]N-phenyl]carbamoylpyridine(125)

To a solution of the compound(124) synthesized in (i) [511 mg (2.82 mmol.)] and triethylamine [0.79 ml(5.64 mmol.)]in chloroform (14 ml) was added, under ice-cooling while stirring, 5-bromonicotinic acid chloride hydrochloride [797 mg(3.10 mmol.)], and the mixture was stirred for 30 minutes at room temperature. The reaction mixture was washed with a 1N aqueous solution of sodium hydroxide and dried, and the solvent was distilled off under reduced pressure. The residue was subjected to a silica gel column chromatography, eluting with ethyl acetate-methanol(10:1) to obtain the compound(125) [700 mg(68.0%)] as a pale brown oily product.

IR(Neat)cm$^{-1}$: 3430(br),3060,1650(br),1590.
NMR(90 MHz,CDCl$_3$)δ: 3.48 to 3.90(6H,m),4.12(2H,t,J=6 Hz), 7.00 to 7.44(5H,m),7.82(1H,t,J=2 Hz),8.31(1H,d,J=2 Hz), 8.48(1H,d,J=2 Hz).

(iii) Synthesis of 4-bromo-3-[N-[2-[2-(1-naphthylcarbamoyloxy)ethoxy]ethyl]-N-phenyl]carbamoylpyridine(126)

To a solution of the compound(125) synthesized in (ii) [670 mg(1.83 mmol.)] in pyridine(4 ml) was added dropwise 1-naphthyl isocyanate [0.29 ml(2.02 mmol.)], and the mixture was stirred for one hour at room temperature. The solvent was distilled off, and the residue was subjected to a silica gel column chromatography, eluting with hexane-ethyl acetate (1:1) to obtain the compound(126) [485 mg(49.6%)] as a colorless oily product.

IR(Neat)cm$^{-1}$:
3300(br),3050,1730(br),1650(br),1600.
NMR(90 MHz,CDCl$_3$)δ: 3.77(4H,m),4.08(2H,t,J=6 Hz),4.37(2H,t, J=6 Hz),6.92 to 8.12(13H,m),8.47(2H,m).

(iv) Synthesis of 5-bromo-3- [N- [2- [2-(1-naphthylcarbamoyloxy)ethoxy]ethyl]-N-phenyl]carbamoyl-1-propylpyridinium chloride(127)

A solution of the compound(126) synthesized in (iii) [430 mg (0.80 mmol.)] in propyl iodide(8 ml) was stirred for two days at 110° C. Resulting precipitates were washed with ether to give a crude iodide compound(586 mg) as brown powder.

The above-mentioned crude product was dissolved in a mixture of methanol-water(7:3)(20 ml), and the solution was allowed to pass through anion exchange resin-(IRA-410[Cl⁻]) (20 ml). The eluate was concentrated under reduced pressure. The concentrate was subjected to a silica gel column chromatography, eluting with methanol-chloroform(1:10), to afford the compound(127) [210 mg(42.6% based on 125)] as yellow powder.

IR(KBr)cm⁻¹: 3410(br),3050,1720(br),1650(br),1590.
NMR(90 MHz,CDCl₃) 0.48(3H,m),1.47(2H,m),3.70(4H,m),4.05 (2H,m), 4.32(2H,m),4.59(2H,m),6.72 to 8.33(12H,m),8.47(1H,br s),9.21(2H,br s),9.90(1H,br).

PRODUCTION EXAMPLE 48

Synthesis of 5-bromo-3- [N- [2- [2-[2-(1-naphthylcarbamoyloxy)ethoxy]ethoxy]ethyl]-N-phenyl]carbamoyl-1-propylpyridinium chloride(131)

(i) Synthesis of 2- [2-(2-anilinoethoxy)ethoxy]ethanol(128)

A solution of 2- [2-(2-chloroethoxy)ethoxy]ethanol [1.69 g (10.0 mmol.)] and aniline [1.82 ml(20.0 mmol.)] in toluene(10 ml) was heated under reflux for 25 hours. The reaction mixture was, after cooling, washed with a saturated aqueous solution of sodium hydrogencarbonate and dried, followed by distilling off the solvent. The residue was subjected to a silica gel column chromatography, eluting with hexane-ethyl acetate(1:3), to obtain the compound(128) [1.34 g(59.5%)] as a brown oily product.

IR(Neat)cm⁻¹: 3390(br),3050,1600.
NMR(90 MHz,CDCl₃)δ: 3.27(2H,t,J=6 Hz),3.66(10H,m),6.64(2H,d, J=8 Hz),6.68(1H,t,J=8 Hz),7.15(1H,t,J=8 Hz).

(ii) Synthesis of 5-bromo-3- [N- [2- [2-(2-hydroxyethoxy)ethoxy]-ethyl]-N-phenyl]carbamoylpyridine(129)

To a solution of the compound(128) synthesized in (i) [1.14 g (5.06 mmol.)] and triethylamine [1.41 ml(10.1 mmol.)] in chloroform(25 ml) was added, under ice-cooling while stirring, 5-bromonicotinic acid chloride hydrochloride [1.43 g(5.57 mmol.)], and the mixture was stirred for 30 minutes at room temperature. The reaction mixture was washed with a 1N aqueous solution of sodium hydroxide and dried, and then the solvent was distilled off under reduced pressure. The residue was subjected to a silica gel column chromatography, eluting with elute acetate-methanol(10:1), to obtain the compound(129) [915 mg(44.2%)] as a brown oily product.

IR(Neat)cm⁻¹: 3440(br),3060,1650(br),1590.
NMR(90 MHz,CDCl₃)δ: 3.64(8H,s),3.75(2H,t,J=6 Hz),4.10(2H,t, J=6 Hz),7.22(5H,m),7.85(1H,t,J=2 Hz),8.37(1H,br s),8.50 (1H,d,J=2 Hz).

(iii) Synthesis of 5-bromo-3- [N- [2- [2- [2-(1-naphthylcarbamoyloxy)ethoxy]ethoxy]ethyl]-N-phenyl]carbamoylpyridine(130)

To a solution of the compound(129) synthesized in (ii) [880 mg(2.15 mmol.)] in pyridine(4 ml) was added dropwise 1-naphthyl isocyanate [0.34 ml(2.37 mmol.)], and the mixture was stirred for one hour at room temperature. The solvent was then distilled off, and the residue was subjected to a silica gel column chromatography, eluting with hexane-ethyl acetate(1:1) to obtain the compound(130) [871 mg(70.0%)] as a colorless oily product.

IR(Neat)cm⁻¹: 3290(br),3050,1730(br),1650(br),1600.
NMR(90 MHz,CDCl₃)δ: 3.63(4H,s),3.73(4H,t,J=5 Hz),4.03(2H,t, J=5 Hz),4.35(2H,t,J=5 Hz),7.18(5H,br s),7.25 to 8.07(9H,m), 8.37(2H,br s).

(iv) Synthesis of 5-bromo-3- [N- [2- [2- [2-(1-naphthylcarbamoyloxy)ethoxy]ethoxy]ethyl]-N-phenyl]carbamoyl-1-propylpyridinium chloride(131)

A solution of the compound(130) synthesized in (iii) [840 mg (1.45 mmol.)] in propyl iodide(15 ml) was stirred for two days at 110° C. Resulting precipitates were washed with ether to obtain a crude iodide product(1.86 g) as brown powder.

The above-mentioned crude product was dissolved in a mixture of methanol-water(7:3)(20 ml), and the solution was allowed to pass throught anion exchange resin-(IRA-410[Cl⁻]) (20 ml). The eluate was concentrated under reduced pressure, and the concentrate was subjected to a silica gel column chromatography, eluting with methanol-chloroform(1:10) to give the compound(131) [430 mg(45.1% based on 130)] as yellow powder.

IR(KBr)cm⁻¹: 3390(br),3050,1720(br),1650(br),1590.
NMR(90 MHz,CDCl₃)δ: 0.63(3H,m),1.62(2H,m),3.64(8H,m),4.24 (2H,m),4.36(2H,m),4.72(2H,m),6.95 to 8.50(13H,m),9.20 (1H,m),9.92(1H,m).

PRODUCTION EXAMPLE 49

Synthesis of 5-bromo-3- [N- [2-[2-(phenylcarbamoyloxy)ethyl]carbamoyloxy]ethyl-N-phenyl]carbamoyl-1-propylpyridinium chloride(134)

(i) Synthesis of 5-bromo-3- [N- [2-(2-hydroxyethyl)carbamoyloxy]ethyl-N-phenyl]carbamoylpyridine(132)

In methylene chloride(20 ml) were dissolved the alcohol compound(18) synthesized in Production Example 6-(i) [1.927 g (6 mmol.)] and pyridine [949 mg(12 mmol.)]. To the solution was added, under ice-cooling, phenyl chlorocarbonate [1.127 g (7.2 mmol.)], and the mixture was stirred for 10 minutes at room temperature. The reaction mixture was washed with a 5% aqueous solution of sodium hydrogencarbonate, and the organic layer was dried over anhydrous sodium sulfate, then the solvent was distilled off under reduced pressure to give a crude carbonate compound(2.945 g).

To this crude carbonate compound was added ethanolamine [513 mg(8.4 mmol.)], and the mixture was heated for two hours at 90° C., which was then cooled. Thus-obtained crude product was purified by means of a column chromatography(silica gel: 90 g; eluent:ethyl acetate/acetone=5/1) to obtain the object compound(132) [2.45 g(100%, colorless resinous substance)].

TLC [Silica Gel;AcOEt/acetone(5/1)]: Rf=0.36.
NMR(90 MHz,CDCl₃)δ: 3.28(2H,m),3.63(2H,m),4.16(2H,m),4.33 (2H,m),5.47(1H,m),7.0 to 7.4(5H,m),7.82(1H,t),8.34(1H,d), 8.50(1H,d).

IR(film)cm⁻¹: 3300,1700,1635,1590,1491,1390,1252.

(ii) Synthesis of 5-bromo-3- [N- [2- 2-(phenylcarbamoyloxy)ethyl]carbamoyloxy]ethyl]-N-phenyl]carbamoylpyridine(133) In pyridine(5 ml) was dissolved the alcohol compound(132) synthesized in (i) [612 mg(1.5 mmol.)]. To the solution was added phenyl isocyanate [214 mg(1.8 mmol.)], and the mixture was stirred for 1.5 hour at room temperature. The reaction mixture was concentrated under reduced pressure, and the resultant crude product was purified by means of a column chromatography(silica gel:30 g; eluent:hexane/ethyl acetate=½) to obtain the object compound(133) [714 mg(90.3%,white powder)].

TLC(Silica Gel;hexane/AcOEt(½): Rf=0.31.

NMR(90 MHz,CDCl₃)δ: 3.42(2H,m),4.0 to 4.4(6H,m),5.30(1H,br), 6.9 to 7.6(11H,m),7.80(1H,t),8.34(1H,d),8.50(1H,d)

IR(KBr)cm⁻¹: 3290,1710,1630,1590,1530,1445,1220.

(ii) Synthesis of 5-bromo-3- [N- [2- [2-(phenylcarbamoyloxy)ethyl]carbamoyloxy]ethyl-N-phenyl]carbamoyl-1-propylpyridinium chloride(134)

To the compound(133) synthesized in (ii) [527 mg(1 mmol.)] was added 1-iodopropane(20 ml). The mixture was heated under reflux for 48 hours in nitrogen streams while shielding the the light. The reaction mixture was, after cooling, concentrated under reduced pressure. Thus-obtained crude product was dissolved in 70% methanol/water(60 ml), and the solution was processed with IRA-410(Cl⁻) [60 ml:eluent; 70% methanol/water], followed by purification by means of a column chromatography(silica gel;20 g; eluent:chloroform/methanol=6/1) to obtain the object compound(134) [531 mg(87.6%,pale yellow powder).

TLC [Silica Gel;CHCl₃/MeOH(3/1)]: Rf=0.23.

NMR(90 MHz,CDCl₃)δ: 0.66(3H,t),1.76(2H,m),3.44(2H,m),4.16 (6H,br s),4.84(2H,br t),6.8 to 7.5(12H,m),8.26(1H,br s), 9.02(1H,br s),9.28(1H,br s),9.75(1H,br s).

IR(KBr)cm⁻¹: 3350,1710,1650,1525,1220.

PRODUCTION EXAMPLE 50

Synthesis of 5-bromo-3- [N- [2- [2-(4-fluorophenylcarbamoyloxy)ethyl]carbamoyloxy]ethyl-N-phenyl]carbamoyl-1-propylpyridinium chloride(136)

(i) Synthesis of 5-bromo-3- [N- [2- [2-(4-fluorophenylcarbamoyloxy)ethyl]carbamoyloxy]ethyl-N-phenyl]-carbamoylpyridine (135)

In pyridine(5 ml) was dissolved the compound(132) synthesized in Production Example 49-(i) [612 mg(1.5 mmol.)], to which was added 4-fluorophenylisocyanate [247 mg(1.8 mmol.)], followed by stirring for 1.5 hour at room temperature. The reaction mixture was concentrated under reduced pressure. The crude product thus obtained was purified by means of a column chromatography (silica gel:30 g; eluent:hexane/ethyl acetate=½) to obtain the object compound(135)[692 mg(84.6%, white powder)].

TLC [Silica Gel;hexane/AcOEt(½)]: Rf=0.28.

NMR(90 MHz,CDCl₃)δ: 3.43(2H,br q),4.0 to 4.4(6H,m),5.32(1H,m), 6.8 to 7.4(9H,m),7.63(1H,br),7.80(1H,t),8.35(1H,d),8.50 (1H,d).

IR(KBr)cm⁻¹: 3300,1710,1637,1590,1505,1410,1300,1210.

(ii) Synthesis of 5-bromo-3- [N- [2- [2-(4-fluorophenylcarbamoyloxy)ethyl]carbamoyloxy]ethyl-N-phenyl]-carbamoyl-1-propylpyridinium chloride(136)

To the compound(135) synthesized in (i) [545 mg(1 mmol.)] was added 1-iodopropane(20 ml), and the mixture was heated under reflux for 48 hours in nitrogen streams while shielding the light. The reaction mixture was, after cooling, concentrated under reduced pressure. The crude prodcut thus obtained was dissolved in 70% methanol/water(60 ml), and the solution was processed with IRA-410(Cl⁻) [60 ml: eluent;70% methanol/water], followed by purification by means of a column chromatography(silica gel:20 g; eluent:chloroform/methanol=6/1) to obtain the object compound(136) [575 mg(92.2%,pale yellow powder)].

TLC [Silica Gel;CHCl₃/MeOH(3/1)]: Rf=0.24.

NMR(90 MHz,CDCl₃)δ: 0.70(3H,t),1.78(2H,m),3.46(2H,m),4.18 (6H,br s),4.89(2H,t),6.89(2H,m),7.1 to 7.6(9H,m),8.25 (1H,br s),9.15(1H,br s),9.21(1H,br s),9.83(1H,br s).

IR(KBr)cm⁻¹: 3350(br),1700,1650,1610,1595,1502,1404,1210.

PRODUCTION EXAMPLE 51

Synthesis of 5-bromo-3- [N- [2- [2-(cyclohexylcarbamoyloxy)ethyl]carbamoyloxy]ethyl-N-phenyl]carbamoyl-1-propylpyridinium chloride(138)

(i) Synthesis of 5-bromo-3-[N-[2-[2-(cyclohexylcarbamoyloxy)ethyl]carbamoyloxy]ethyl-N-phenyl]carbamoylpyridine(137) The compound(132) synthesized in Production Example 49-(i) [612 mg(1.5 mmol.)] was dissolved in pyridine(5 m0, to which was added cyclohexylisocyanate [225 mg(1.8 mmol.)], and the mixture was stirred for 5 hours at 80° to 100° C. The reaction mixture was concentrated under reduced pressure. The crude product thus obtained was purified by means of a column chromatography(silica gel:30 g; eluent:hexane/ethyl acetate=½) to obtain the object product(137) [722 mg(90.2%, colorless resinous substance)].

TLC [Silica Gel;hexane/AcOEt(½)]: Rf=0.25.

NMR(90 MHz,CDCl₃)δ: 0.6 to 1.9(10H,m),3.27(3H,m),3.6 to 4.4 (6H,m),4.77(1H,m),5.02(1H,br),6.8 to 7.3(5H,m),7.70(1H,t), 8.20(1H,d),8.38(1H,d).

IR(KBr)cm⁻¹: 3300,2915,2840,1680,1635,1500,1396,1230.

(ii) Synthesis of 5-bromo-3- [N- [2- [2-(cyclohexylcarbamoyloxy)ethyl]carbamoyloxy]ethyl-N-phenyl]carbamoyl-1-propylpyridinium chloride(138)

To the compound(137) synthesized in (i) [533 mg(1 mmol.)] was added 1-iodopropane(20 ml), and the mixture was heated under reflux for 48 hours in nitrogen streams while shielding the light. The reaction mixture was, after cooling, concentrated under reduced pressure to leave a crude product, which was dissolved in 70% methanol/water(60 ml). The solution was processed with IRA-410(Cl⁻) [60 ml:eluent; 70% methanol/water], followed by purification by means of a column chromatography (silica gel:20 g; eluent:chloroform/methanol=6/1) to obtain the object compound(138) [441 mg(72.1%, pale yellow powder)].

TLC [Silica Gel;CHCl₃/MeOH(3/1)]: Rf=0.32.

NMR(90 MHz,CDCl₃)δ: 0.77(3H,t),0.9 to 2.2(12H,m),3.38(3H,m), 4.16(6H,m),4.98(2H,t),5.49(1H,br),7.06(1H,m),7.36(5H,m), 8.33(1H,br s),9.68(1H,br s),9.76(1H,br s).

IR(KBr)cm⁻¹: 3400,1700,1650,1590,1520,1230.

PRODUCTION EXAMPLE 52

Synthesis of 5-bromo-3-[N-2-[3-(1-naphthylcarbamoyloxy)propyl] carbamoyloxy]ethyl-N-phenyl]carbamoyl-1-propyl pyridinium chloride(141)

(i) Synthesis of 5-bromo-3- [N- [2-(3-hydroxypropyl)-carbamoyloxy]ethyl-N-phenyl]carbamoylpyridine(139)

The alcohol compound(18) synthesized in Production Example 6-(i) [964 mg(3 mmol.)] and pyridine [475 mg(6 mmol.)] were dissolved in methylene chloride(10 ml). To the solution was added, under ice-cooling, phenyl chlorocarbonate [564 mg(3.6 mmol.)], and the mixture was stirred for 10 minutes at room temperature. The reaction mixture was washed with a 5% aqueous solution of sodium hydrogencarbonate. The organic layer was dried over anhydrous sodium sulfate, then the solvent was distilled off under reduced pressure to obtain a crude carbonate compound(1.473 g).

To this crude carbonate compound was added 3-amino-1-propanol [315 mg(4.2 mmol.)], and the mixture was heated for two hours at 90° C., which was then cooled. The crude product thus obtained was purified by means of a column chromatography (silica gel:45 g; eluent:ethyl acetate/acetone=5/1) to obtain the object compound(139) [1.236 g(97.6%, colorless solid substance)].

TLC [Silica Gel;AcOEt/acetone(5/1)]: Rf=0.33.
NMR(90 MHz,CDCl$_3$)δ: 1.67(2H,quint),2.85(1H,br),3.27(2H,q), 3.65(2H,q),4.14(2H,m),4.36(2H,m),5.22(1H,br),7.0 to 7.4 (5H,m),7.83(1H,t),8.33(1H,d),8.52(1H,d).
IR(film)cm$^{-1}$:
3325,1700,1640,1591,1490,1392,1300,1252.

(ii) Synthesis of 5-bromo-3- [N- [2- [3-(1-naphthylcarbamoyloxy)propyl]carbamoyloxy]ethyl-N-phenyl]carbamoylpyridine(140)

The alcohol compound(139) synthesized in (i) [422 mg(1 mmol.)] was dissolved in pyridine(5 ml), to which was added 1-naphthylisocyanate [0.172 ml(1.2 mmol.)], and the mixture was stirred for 10 hours at room temperature. The reaction mixture was concentrated under reduced pressure. The crude product thus obtained was purified by means of a column chromatography (silica gel:25 g; eluent:hexane/ethyl acetate=⅓) to obtain the object compound(140) [420 mg(71.0%, white powder)].

TLC [Silica Gel;hexane/AcOEt(⅓)]: Rf=0.42.
NMR(90 MHz,CDCl$_3$)δ: 1.83(2H,quint),3.23(2H,q),3.94 to 4.4 (6H,m),5.17(1H,br t),6.9 to 8.0(15H,m),8.30(1H,d),8.43 (1H,d).
IR(KBr)cm$^{-1}$:
3280,1708,1638,1590,1530,1488,1258,1210.

(iii) Synthesis of 5-bromo-3- [N- [2- [3-(1-naphthylcarbamoyloxy)propyl]carbamoyloxy]ethyl-N-phenylcarbamoyl-1-propyl pyridinium chloride(141)

To the compound(140) synthesized in (ii) [350 mg(0.592 mmol.)] was added 1-iodopropane(15 ml), and the mixture was heated under reflux for 48 hours in nitrogen streams under shielding the light. The reaction mixture was cooled and then concentrated under reduced pressure. The crude product thus obtained was dissolved in 70% methanol/water(30 ml). The solution was processed with IRA-410(C-) [30 ml: eluent;70% methanol/water], which was purified by means of a column chromatography (silica gel:20 g; eluent:-chloroform/methanol=6/1) to obtain the object compound(141) [356 mg(86.0%, pale yellow powder)].

TLC [Silica Gel;CHCl$_3$/MeOH(3/1)]: Rf=0.31
NMR(90 MHz,CDCl$_3$)δ: 0.57(3H,t),1.58(2H,m),1.95(2H,m),3.32 (2H,m),3.9 to 4.4(6H,m),4.67(2H,m),7.0 to 8.2(15H,m), 9.28(1H,br s),9.73(1H,br s).
IR(KBr)cm$^{-1}$:
3300,1698,1655,1585,1520,1490,1250,1220.

PRODUCTION EXAMPLE 53

Synthesis of 5-bromo-3- [N- [2- [4-(1-naphthylcarbamoyloxy)butyl]carbamoyloxy]ethyl-N-phenyl]carbamoyl-1-propylpyridinium chloride(144)

(i) Synthesis of 5-bromo-3- [N- [2-(4-hydroxybutyl)carbamoyloxy]ethyl-N-phenyl]carbamoylpyridine(142)

In methylene chloride(10 ml) were dissolved the alcohol compound(18) synthesized in Production Example 6-(i) [964 mg (3 mmol.)] and pyridine [475 mg(6 mmol.)]. To the solution was added, under ice-cooling, phenyl chlorocarbonate [564 mg (3.6 mmol.)]. The mixture was stirred for 10 minutes at room temperature. The reaction mixture was washed with a 5% aqueous solution of sodium hydrogencarbonate, and the organic layer was dried over anhydrous sodium sulfate, followed by distillation under reduced pressure to obtain a crude carbonate(1.473 g).

To this crude carbonate compound was added 4-amino-1-butanol [374 mg(4.2 mmol.)], and the mixture was heated for two hours at 90° C., followed by cooling. The crude product thus obtained was purified by means of a column chromatography (silica gel:45 g; eluent:ethyl acetate/acetone=5/1) to obtain the object(142) [869 mg(66.4%, colorless resinous substance).

TLC [Silica Gel;AcOEt/acetone(5/1)]: Rf=0.34.
NMR(90 MHz,CDCl$_3$)δ: 1.54(4H,m),2.55(1H,br),3.14(2H,m),3.61 (2H,m),4.15(2H,m),4.34(2H,m),5.15(1H,br),7.0 to 7.4(5H,m), 7.81(1H,t),8.31(1H,d),8.50(1H,d).
IR(film)cm$^{-1}$:
3300,1698,1638,1590,1490,1390,1299,1250.

(ii) Synthesis of 5-bromo-3- [N- [2- [4-(1-naphthylcarbam,oyloxy)butyl]carbamoyloxy]ethyl-N-phenyl]carbamoylpyridine(143)

The alcohol compound(142) synthesized in (i) [436 mg(1 mmol.)] was dissolved in pyridine(5 ml), to which was added 1-naphthylisocyanate [0.172 ml(1.2 mmol.)], followed by stirring for 10 hours at room temperature. The reaction mixture was concentrated under reduced pressure. The crude compound thus obtained was purified by means of a column chromatography (silica gel:25 g; eluent:hexane/ethyl acetate=⅓) to give the object compound(143) [391 mg(64.6%, white powder)].

TLC [Silica Gel;hexane/AcOEt(⅓)]: Rf=0.43.
NMR(90 MHz,CDCl$_3$)δ: 1.62(4H,m),3.15(2H,m),3.9 to 4.4(6H,m), 4.92(1H,br t),6.9 to 8.0(15H,m),8.32(1H,br s),8.42(1H,br s).
IR(KBr)cm$^{-1}$:
3290,1705,1635,1590,1525,1490,1250,1220.

(ii) Synthesis of 5-bromo-3- [N- [2- [4-(1-naphthylcarbamoyloxy)butyl]carbamoyloxy]ethyl-N-phenyl]carbamoyl-1-propylpyridinium chloride(144)

To the compound(143) synthesized in (ii) [321 mg(0.530 mmol.)] was added 1-iodopropane(15 ml), and the mixture was heated under reflux for 48 hours in nitrogen streams while shielding the light. The reaction mixture was cooled and concentrated under reduced pressure to leave a crude product, which was dissolved in 70% methanol/water(30 ml). The solution was processed with IRA-410(Cl-) [30 ml: eluent;70% methanol/water], which was subjected to purification by means of a column chromatography(silica gel:15 g; eluent:chloroform/methanol=10/1) to obtain the object compound(144) [60 mg(16.6%, pale yellow powder)].

TLC [Silica Gel;CHCl₃/MeOH(3/1)]: Rf=0.31.
NMR (90 MHz,CDCl₃)δ: 0.64(3H,m),1.73(4H,m),2.23(2H,m),3.24 (2H,m),4.20(6H,m),4.70(2H,m), 7.0 to 8.1(14H,m),8.14 (1H,br s),9.21(1H,br s), 9.67(1H,br s).
IR(KBr)cm⁻¹: 3475,1700,1645,1590,1530,1490,1255,1222.

PRODUCTION EXAMPLE 54

Synthesis of 5-bromo-3- [N- [2-[5-(1-naphthylcarbamoyloxy)pentyl]carbamoyloxy]ethyl-N-phenyl]carbamoyl-1-propylpyridinium chloride(147)

(i) Synthesis of 5-bromo-3- [N- [2-(5-hydroxypentyl)-carbamoyloxy]ethyl-N-phenyl]carbamoylpyridine(145)

In methylene chloride(10 ml) were dissolved the alcohol compound(18) synthesized in Production Example 6-(i) [964 mg (3 mmol.)] and pyridine [475 mg(6 mmol.)]. To the solution was added, under ice-cooling, phenyl chlorocarbonate [564 mg (3.6 mmol.)], and the mixture was stirred for 10 minutes at room temperature. The reaction mixture was washed with a 5% aqueous solution of sodium hydrogencarbonate. The organic layer was dried over anhydrous sodium sulfate, then the solvent was distilled off under reduced pressure to leave a crude carbonate compound(1.473 g).

To this crude carbonate compound was added 5-amino-1-pentanol [433 mg(4.2 mmol.)], which was heated for two hours at 90° C. The reaction mixture was cooled, and the crude product thus obtained was purified by means of a column chromatography(silica gel:45 g; eluent:ethyl acetate/acetone=5/1) to obtain the object compound(145) [1.16 g(85.9%, colorless resinous substance)].

TLC [Silica Gel;AcOEt/acetone(5/1)]: Rf=0.49.
NMR(90 MHz,CDCl₃)δ: 1.43(6H,m),2.44(1H,br),3.11(2H,m),3.57 (2H,m),4.14(2H,m),4.33(2H,m),5.02(1H,br),7.0 to 7.4(5H, m),7.77(1H,t),8.29(1H,d),8.47(1H,d).
IR(film)cm⁻¹: 3300,2925,2850,1700,1638,1592,1492,1390,1300, 1250.

(ii) Synthesis of 5-bromo-3- [N- [2- [5-(1-naphthylcarbamoyloxy)pentyl]carbamoyloxy]ethyl-N-phenyl]carbamoylpyridine(146) In pyridine(5 ml) was dissolved the alcohol compound(145) [450 mg(1 mmol.)], to which was added 1-naphthylisocyanate [0.172 ml(1.2 mmol.)], and the mixture was stirred for ten hours at room temperature. The reaciton mixture was concentrated under reduced pressure. The crude product thus obtained was purified by means of a column chromatography(silica gel:25 g; eluent:hexane/ethyl acetate=⅓) to obtain the object compound(146) [476 mg(76.8%, white powder).

TLC [Silica Gel;hexane/AcOEt(⅓)]: Rf=0.44.
NMR(90 MHz,CDCl₃)δ: 1.1 to 1.8(6H,m),3.10(2H,m),3.9 to 4.4 (6H,m),4.86(1H,br t),6.9 to 6.9(15H,m),8.30(1H,d),8.46 (1H,d).
IR(KBr)cm⁻¹: 3290,1700,1630,1590,1530,1515,1490,1250,1220.

(iii) Synthesis of 5-bromo-3- [N- [2- [5-(1-naphthylcarbamoyloxy)pentyl]carbamoyloxy]ethyl-N-phenyl]carbamoyl-1-propylpyridinium chloride(147)

To the compound(146) synthesized in (ii) [356 mg(0.575 mmol)] was added 1-iodopropane(15 ml), and the mixture was heated under reflux for 48 hours in nitrogen streams while shielding the light. The reaction mixture was cooled and concentrated under reduced pressure to give a crude product, which was dissolved in 70% methanol/water(30 ml). The solution was processed with IRA-410(Cl⁻) [30 ml: eluent;70% methanol/water], which was purified by means of a column chromatography(silica gel:15 g; eluent:-chloroform/methanol=6/1) to obtain the object compound(147) [163 mg(40.6%, pale yellow powder)].

TLC [Silica Gel;CHCl₃/MeOH(3/1)]: Rf=0.35.
NMR(90 MHz,CDCl₃)δ: 0.63(3H,t),1.60(6H,m),2.23(2H,m),3.22 (2H,m),4.14(6H,m),4.68(2H,br t),6.9 to 8.0(14H,m),8.10 (1H,br s),9.18(1H,br s),9.71(1H,br s).
IR(KBr)cm⁻¹: 3300,1696,1652,1585,1520,1490,1252,1220.

PRODUCTION EXAMPLE 55

Synthesis of 5-bromo-3- [N- [2- [2-[2-(1-naphthylcarbamoyloxy)ethoxy]ethyl]carbamoyloxy]ethyl-N-phenyl]carbamoyl-1-propyl-pyridinium chloride(150)

(i) Synthesis of 5-bromo-3- [N- [2- [2-(2-hydroxyethoxy)ethyl]carbamoyloxy]ethyl-N-phenyl]carbamoylpyridine(148)

In methylene chloride(10 ml) were dissolved the alcohol compound(18) synthesized in Production Example 6-(i) [964 mg (3 mmol.)] and pyridine [475 mg(6 mmol.)]. To the solution was added, under ice-cooling, phenyl chlorocarbonate [564 mg (3.6 mmol.)], and the mixture was stirred for 10 minutes at room temperature. The reaction mixture was washed with a 5% aqueous solution of sodium hydrogencarbonate. The organic layer was dried over anhydrous sodium sulfate, then the solvent was distilled off under reduced pressure to obtain a crude carbonate compound(1.473 g).

To this crude carbonate compound was added 2-(2-aminoethoxy)ethanol [442 mg(4.2 mmol.)], and the mixture was heated for two hours at 90° C. The reaction mixture was cooled, and the crude product thus obtained was purified by means of a column chromatography(silica gel:45 g; eluent:ethyl acetate/acetone=5/1) to obtain the object compound(148) [1.36 g(100%, colorless resinous substance).

TLC [Silica Gel;AcOEt/acetone(5/1)]: Rf=0.29.
NMR(90 MHz,CDCl₃)δ: 3.0 to 3.8(8H,m),4.14(2H,m),4.33(2H,m), 5.53(1H,br t),7.0 to 7.4(5H,m),7.78(1H,t),8.30(1H,d), 8.47(1H,d).
IR(film)cm⁻¹: 3325,1700,1630,1590,1530,1490,1384,1300,1258, 1120,1065.

(ii) Synthesis of 5-bromo-3- [N- [2- [2- [2-(1-naphthylcarbamoyloxy)ethoxy]ethyl]carbamoyloxy]ethyl-N-phenyl]carbamoylpyridine(149)

The alcohol compound(148) synthesized in (i) [452 mg(1 mmol.)] was dissolved in pyridine(5 ml), to which was added 1-naphthylisocyanate [0.172 ml(1.2 mmol.)], and the mixture was stirred for 10 hours at room temperature. The reaction mixture was concentrated under reduced pressure to give a crude product, which was purified by means of a column chromatography(silica gel:25 g; eluent:hexane/ethyl acetate=⅓) to obtain the object compound(149) [420 mg(67.6%), white powder].

TLC [Silica Gel;hexane/AcOEt(⅓)]: Rf=0.27.
NMR(90 MHz,CDCl₃)δ: 3.4 to 3.7(6H,m),3.9 to 4.4(6H,m),5.27 (1H,br t), 6.9 to 8.0(15H,m),8.33(1H,d),8.46(1H,d).
IR(KBr)cm⁻¹: 3280,1715,1635,1590,1530,1489,1390,1298,1252, 1220,1100.

(iii) Synthesis of 5-bromo-3- [N- [2- [2- [2-(1-naphthylcarbamoyloxy)ethoxy]ethyl]carbamoyloxy]ethyl-N-phenyl]carbamoyl-1-propylpyridinium chloride(150)

To the compound(149) synthesized in (ii) [350 mg(0.563 mmol.)] was added 1-iodopropane(15 ml), and the mixture was heated under reflux for 48 hours in nitrogen streams while shielding the light. The reaction mixture was cooled and concentrated under reduced pressure to leave a crude product, which was dissolved in 70% methanol/water(30 ml). The solution was processed with IRA-410(Cl−) [30 ml:eluent;70% methanol/water], followed by purification by means of a column chromatography (silica gel:20 g; eluent:chloroform/methanol=6/1) to obtain the object compound(150) [355 mg(90.1%, pale yellow powder)].

TLC [Silica Gel;CHCl,/MeOH(3/1)]: Rf=0.35.

NMR(90 MHz,CDCl$_3$)δ: 0.57(3H,t),1.61(2H,m),3.2 to 3.8(6H,m), 3.9 to 4.4(6H,m),4.64(2H,br t),7.0 to 8.2(4H,m),8.31(1H, br s),9.28(1H,br s),9.57(1H,br s).

IR(KBr)cm$^{-1}$:
3320,1700,1650,1538,1520,1490,1255,1225.

PRODUCTION EXAMPLE 56

Synthesis of 5-chloro-3- [N- [2-[2-(1-naphthyloxy)ethyl]carbamoyloxy]ethyl-N-phenyl]carbamoyl-1-propylpyridinium iodide(153)

(i) Synthesis of 5-chloro-3- [N-(2-hydroxyethyl)-N-phenyl]carbamoylpyridine(151)

In chloroform(10 ml) were dissolved 2-anilinoethanol [412 mg (3 mmol.) and triethylamine [2.09 ml(15 mmol.)]. To the solution was added, under ice-cooling, 5-chloronicotinic acid chloride hydrochloride [637 mg(3 mmol.)]. The mixture was then stirred for one hour at room temperature. The reaction mixture was washed with a 1N aqueous solution of sodium hydroxide. The organic layer was dried over anhydrous potassium carbonate, then the solvent was distilled off under reduced pressure. The crude product thus obtained was purified by means of a column chromatography(silica gel:3.3 g; eluent: n-hexane/ethyl acetate=1/5) to obtain the object compound (151) [670 mg(80.7%, pale yellow oily product)].

TLC [Silica Gel;hexane/AcOEt(⅓)]: Rf=0.27.
NMR(90 MHz,CDCl$_3$)δ:
3.02(1H,br),3.81(2H,t),4.10(2H,t),7.0 to 7.3(5H,m),7.67(1H,t),8.28(1H,.d),8.37(1H,d).

IR(film)cm$^{-1}$:
3370,1630,1590,1390,1300,1280,1075,1022,770,752.

(ii) Synthesis of 5-chloro-3- [N- [2- [2-(1-naphthyloxy)ethyl]carbamoyloxy]ethyl-N-phenyl]carbamoylpyridine(152)

In methylene chloride(10 ml) were dissolved the alcohol compound(151) synthesized in (i) [415 mg(1.5 mmol.)] and pyridine [237 mg(3 mmol.)]. To the solution was added, under icecooling, phenyl chlorocarbonate [305 mg(1.95 mmol.)]. The mixture was then stirred for 15 minutes at room temperature. The reaction mixture was washed with a 5% aqueous solution of sodium hydrogencarbonate, and the organic layer was dried over anhydrous sodium sulfate, followed by distilling off the solvent under reduced pressure to obtain a crude carbonate compound(722 mg).

To this crude carbonate compound was added 2-(1-naphthyloxy)ethylamine [309 mg(1.65 mmol.)], and the mixture was heated for two hours at 90° C., which was then cooled. The crude product thus obtained was purified by means of a column chromatography(silica gel:30 g; eluent:hexane/ethyl acetate=1/1.5) to obtain the object compound(152) [534 mg(72.7%, colorless solid substance).

TLC [Silica Gel;n-hexane/AcOEt(1/1.5)]: Rf=0.28.
NMR(90 MHz,CDCl$_3$)δ:
3.64(2H,m),4.13(4H,m),4.38(2H,t),5.16 (1H,br),6.74(1H,dd),6.8 to 7.6(9H,m),7.78(1H,m),8.18 (1H,m),8.21(1H,d),8.35(1H,d).

IR(film)cm$^{-}$:
3275,1710,1620,1588,1575,1530,1490,1390,1298, 1270,1230,1100.

(iii) Synthesis of 5-chloro-3- [N- [2- [2-(1-naphthyloxy)ethyl]carbamoyloxy]ethyl-N-phenyl]carbamoyl-1-propylpyridinium iodide(153)

To the compound(152) synthesized in (ii) [490 mg(1 mmol.)] was added iodopropane(20 ml), and the mixture was heated under reflux for 48 hours in nitrogen streams while shielding the light. The reaction mixture was cooled and then concentrated under reduced pressure to give a crude product, which was purified by means of a column chromatography(silica gel:23 g; eluent:chloroform/methanol=6/1) to obtain the object compound(153) [573 mg(86.8%, pale yellow powder)].

TLC [Silica Gel;CHCl$_3$:/MeOH(3/1)]: Rf=0.37.
NMR(90 MHz,CDCl$_3$)δ:
0.67(3H,t),1.63(2H,m),3.67(2H,m),4.17 (6H,m),4.72(2H,t),6.36(1H,br),6.77(1H,dd),6.9 to 7.5(9H, m),7.75(1H,m),8.09(1H,br s),8.27(1H,m),9.21(2H,br s).

IR(KBr)cm$^{-1}$:
3250(br),1705,1652,1588,1490,1395,1270,1254, 1240, 1100,780.

PRODUCTION EXAMPLE 57

Synthesis of 5-chloro-3- [N- [2-[2-(1-naphthyloxy)ethyl]carbamoyloxy]ethyl-N-phenyl]carbamoyl-1-propylpyridinium chloride(154)

The compound(153) synthesized in Production Example 56-(iii) [396 mg(0.6 mmol.)] was dissolved in 70% methanol/water(30 ml). The solution was processed with IRA-410(Cl−) [30 ml: eluent: 70% methanol/water] to obtain the object compound(154) [341 mg (100%, pale yellow powder)].

TLC [Silica Gel;CHCl$_3$/MeOH(3/1)]: Rf=0.33.
NMR(90 MHz,CDCl$_3$)δ:
0.63(3H,t),1.64(2H,m),3.67(2H,m),4.23 (6H,m),4.83(2H,br t),6.80(1H,dd),6.9 to 7.6(9H,m),7.76 (1H,m),8.07(1H,br),8.26(1H,m),9.51(1H,br s),9.68(1H,br s).

IR(KBr)cm$^{-1}$:
3400,1700,1652,1590,1575,1490,1400,1260,1240, 1100.

PRODUCTION EXAMPLE 58

Synthesis of 5-iodo-3-[N-[2-[2-(l-naphthyloxy)ethyl]carbamoyloxy]ethyl-N-phenyl]carbamoyl-1-propylpyridinium iodide(157)

(i) Synthesis of 5-iodo-3-[N-(2-hydroxyethyl)-N-phenyl]carbamoylpyridine(155)

In chloroform(10 ml) were dissolved 2-anilinoethanol[412 mg(3 mmol.)] and triethylamine[2.09 ml(15 mmol.)]. To the solution was added, under ice-cooling, 5-iodonicotinic acid chloride hydrochloride[912 mg(3 mmol.)], and the mixture was stirred for one hour at room temperature. The reaction mixture was washed with a 1N aqueous solution of sodium hydroxide, and the aqueous layer was dried over anhydrous potassium carbonate, then the solvent was distilled off under reduced pressure. The crude product thus obtained was purified by means of a column chromatography(silica gel:50 g; eluent:n-hexane/ethyl acetate=¼) to obtain the object compound(155 )[841 mg(76.1%, colorless solid). TLC[Silica Gel;hexane/AcOEt(½)]: Rf=0.31. NMR(90 MHz,CDCl₃)δ: 3.12(1H,br),3.82(2H,m),4.09(2H,t),7.0 to 7.4(5H,m),8.01(1H,t),8.32(1H,d),8.62(1H,d). IR(KBr)cm¹: 3340,1628,1581,1565,1485,1430,1400,1290,1088, 1075,744.

(ii) Synthesis of 5-iodo-3-[N-[2-[2-(1-naphthyloxy)ethyl]-carbamoyloxy]ethyl-N-phenyl]carbamoylpyridine(156)

In methylene chloride(10 ml) were dissolved the alcohol compound(155) synthesized in i)[552 mg(1.5 mmol.)] and pyridine[237 mg(3 mmol.)]. To the solution was added, under ice-cooling, phenyl chlorocarbonate[305 mg(1.95 mmol.)], and the mixture was stirred for 15 minutes at room temperature. The reaction mixture was washed with a 5% aqueous solution of sodium hydrogencarbonate, and the organic layer was dried over anhydrous sodium sulfate, followed by distilling off the solvent under reduced pressure to obtain a crude carbonate compound(951 mg).

To this crude carbonate compound was added 2-(1-naphthyloxy)ethylamine[309 mg(1.65 mmol.)], which was heated for two hours at 90° C., followed by cooling. The crude product thus obtained was purified by means of a column chromatography(silica gel: 35 g; eluent:hexane/ethyl acetate=1/1.5) to obtain the object compound(156)[661mg(75.8%, colorless solid)].

TLC[Silica Gel;n-hexane/AcOEt(1/1.5)]: Rf=0.35. NMR(90 MHz,CDCl₃)δ: 3.63(2H,m),4.13(4H,m),4.37(2H,t),5.13 (1H,br),6.74(1H,dd),6.8 to 7.5(9H,m),7.77(1H,m),7.93(1H,t), 8.17(1H,d),8.27(1H,d),8.60(1H,d).

IR(KBr)cm⁻¹:3275,1712,1622,1590,1530,1488,1390,- 1298,1268, 1230,1100.

(iii) Synthesis of 5-iodo-3-[N-[2-[2-(1-naphthyloxy)ethyl]-carbamoyloxy]ethyl-N-phenyl]carbamoyl-1-propylpyridinium iodide(157)

To the compound(156) synthesized in (ii) [581 mg(1 mmol.)]was added iodopropane(20 ml), and the mixture was heated under reflux for 48 hours in nitrogen streams while shielding the light. The reaction mixture was, after cooling, concentrated under reduced pressure to obtain a crude product, which was purified by means of a column chromatography(silica gel:25 g; eluent:-chloroform/methanol=6/1) to obtain the object compound(157)[700 mg(93.2%, pale yellow powder)].

TLC[Silica Gel;CHCl₃/MeOH(3/1)]: Rf=0.39. NMR(90 MHz,CDCl₃)δ: 0.66(3H,t),1.65(2H,m),3.66(2H,m),4.17 (6H,m),4.68(2H,m),6.17(1H,br),6.77(1H,dd),6.9 to 7.5(9H, m),7.77(1H,m),8.26(1H,m),8.41(1H,br s),8.97(1H,br s),9.33 (1H,br s).

IR(KBr)cm⁻¹: 3400(br),1700, 1650, 1584, 1484, 1390, 1265, 1238, 1100,775.

PRODUCTION EXAMPLE 59

Synthesis of 5-iodo-3-[N-[2-[2-(1-naphthyloxy)ethyl]-carbamoyloxy]ethyl-N-phenyl]carbamoyl-1-propylpyridinium chloride(158)

The compound(157) synthesized in Production Example 58-(iii) [451 mg(0.6 mmol.)] was dissolved in 70% methanol/water (30 ml), and the solution was processed with IRA-410(Cl⁻) [30 ml: eluent;70% methanol/water] to obtain the object compound(158)[396 mg(100%, pale yellow powder)].

TLC[Silica Gel;CHCl₃/MeOH(3/1)]: Rf=0.30. NMR(90 MHz,CDCl₃)δ: 0.63(3H,t),1.63(2H,m),3.68(2H,m),4.24 (6H,m),4.77(2H,m),6.80(1H,dd),6.9 to 7.5(9H,m),7.77(1H, m),8.27(1H,m),8.35(1H,br s),9.47(2H,m).

IR(KBr)cm⁻¹: 3375,1700,1646,1590,1575,1490,1398,1265,1240, 1102.

PRODUCTION EXAMPLE 60

Synthesis of 3-[N-[2-[2-(l-naphthyloxy)ethyl]-carbamoyloxy]ethyl-N-phenyl]carbamoyl-5-nitro-1-propylpyridinium iodide(161)

(i) Synthesis of 3-[N-(2-hydroxyethyl)-N-phenyl]carbamoy-5-nitropyridine(159)

In chloroform(10 ml) were dissolved 2-anilinoethanol [412 mg(3 mmol.)] and triethylamine[2.09 ml(15 mmol.)]. To the solution was added, under ice-cooling, 5-nitronicotinic acid chloride hydrochloride[669 mg(3 mmol.)]. The mixture was stirred for one hour at room temperature. The reaction mixture was washed with a 1N aqueous solution of sodium hydroxide. The organic layer was dried over anhdyrous sodium carbonate, followed by distilling off the solvent under reduced pressure to give a crude product. The crude product was purified by means of a column chromatography(silica gel: 35 g; eluent:n-hexane/ethyl acetate=¼) to obtain the object compound(159)[570 mg(66.1%, colorless resinous substance)].

TLC[Silica Gel;hexane/AcOEt(½)]: Rf=0.28. NMR(90MHz, CDCl₃)δ: 2.81(1H,br t),3.89(2H,m),4.16(2H,t),7.30 (5H,m),8.43(1H,t),8.77(1H,d),9.27(1H,d)

IR(KBr)cm⁻¹: 3380,1632,1590,1568,1530,1490,1460,1390,1352, 1298,1280,1080,1016,760,735

(II) Synthesis of 3-[N-[2-[2-(l-naphthyloxy)ethyl]carbamoyloxy]ethyl-N-phenyl]carbamoyl-5-nitropyridine(160)

In methylene chloride(10 ml) were dissolved the alcohol compound(159) synthesized in (i)[431 mg(1.5 ml) and pyridine [237 mg(3 mmol.)]. To the solution was added, under ice-cooling, phenyl chlorocarbonate[305 mg(1.95 mmol.)], and the mixture was stirred for 15 minutes at room temperature. The reaction mixture was washed with a 5% aqueous solution of sodium hydrogencarbonate, then the organic layer was dried over anhydrous sodium sulfate, followed by distilling off the solvent under reduced pressure to obtain a crude carbonate compound(791 mg).

To this crude carbonate compound was added 2-(1-naphthyloxy)ethylamine[309 mg(1.65 mmol.)], and the mixture was heated for two hours at 90° C. The reaction mixture was cooled, and the resulting crude product was purified by means of a column chromatography(-silica gel:35 g; eluent:hexane/ethyl acetate=1/1.5) to obtain the object compound(160)[620 mg(82.6%, pale yellow powder)].

TLC[Silica Gel;n-hexane/AcOEt(1/1.5)]: Rf=0.29. NMR(90 MHz),CDCl₃)δ: 3.65(2H,m),4.17(4H,m),4.42(2H,t),5.25 (1H,br),,6.75(1H,dd),7.11(5H,br s),7.2 to 7.6(4H,m),7.79

(1H,m),8.20(1H,m),8.30(1H,br s),8.70(1H,br s),9.20(1H,br s).

IR(KBr)cm$^{-1}$:
3300,1712,1630,1599,1582,1568,1520,1400,1355, 1300,1270,1232,1100,800,770.

(ii) Synthesis of 3-[N-[2-[2-(l-naphthyloxy)ethyl]carbamoyloxy]ethyl-N-phenyl]carbamoyl-5-nitro-1-propylpyridinium iodide (161)

To the compound(160) synthesized in (ii)[501 mg(1 mmol.)] was added iodopropane(20 ml). The mixture was heated under reflux for 48 hours in nitrogen streams while shielding the light. The reaction mixture was, after cooling, concentrated under reduced pressure to give a crude product, which was purified by means of a column chromatography(silica gel:15 g; eluent:-chloroform/methanol=6/1) to obtain the object compound (161)[45 mg(6.7%, pale yellow powder)].

TLC[Silica Gel;CHCl$_3$/MeOH(3/1)]: Rf=0.36.
NMR(90 MHz,CDCl$_3$+CD$_3$OD)δ: 0.75(3H,),2.05(2H,m),3.60(2H,m), 3.8 to 4.8(8H,m),6.77(1H,m),7.0 to 7.9(10,m),8.0 to 8.3 (2H,m),9.59(2H,m).

IR(KBr)cm$^{-1}$:
3380(br),1700,1660,1599,1572,1500,1435,1390, 1265,1235,1100,758.

PRODUCTION EXAMPLE 61

Synthesis of
5-bromo-3-[N-[2-[2-[l-(4-methoxy)naphthyloxy]ethyl]-carbamoyloxy]ethyl-N-phenyl]carbamoyl-1-propyl-pyridinium iodide(163)

(i) Synthesis of 5-bromo-3-[N-[2-[2-[l-(4-methoxy)naphthyloxy]ethyl]carbamoyloxy]ethyl-N-phenyl]carbamoylpyridine (162)

In methylene chloride(10 ml) were dissolved the alcohol compound(18) synthesized in Production Example 6-(i)[482 mg (1.5 mmol.)] and pyridine[237 mg(3 mmol.)]. To the solution was added, under ice-cooling, phenyl chlorocarbonate[305 mg (1.95 mmol.)], and the mixture was stirred for 15 minutes at room temperature. The reaction mixture was washed with a 5% aqueous solution of sodium hydrogencarbonate. The organic layer was dried over anhydrous sodium sulfate, then the solvent was distilled under reduced pressure to obtain a crude carbonate compound(792 mg).

To this crude carbonate compound was added 2-[1-(4-methoxy)naphthyloxy]ethylamine[326 mg(1.5 mmol.)], and the mixture was heated for two hours at 90° C., which was then cooled. The resulting crude product was purified by means of a column chromatography(silica gel:30 g; eluent:hexane/ethyl acetate=½) to obtain the object compound(162)[553 mg(65.3%, colorless powder)].

TLC[Silica Gel;n-hexane/AcOEt(½)]: Rf=0.36.
NMR(90 MHz,CDCl$_3$)δ: 3.61(2H,m),3.94(3H,s),4.08(2H,t),4.15 (2H,t),4.38(2H,t),5.18(1H,m),6.64(2H,s),7.08(5H,m),7.- 49 (2H,m),7.76(1H,t),8.15(2H,m),8.27(1H,br s),8.46(1H,br s).

IR(KBr)cm$^{-1}$:
3270,1710,1630,1590,1455,1395,1380,1300,1270, 1234,1100,770.

(ii) Synthesis of 5-bromo-3-[N-[2-[2-[l-(4-methoxy)-naphthyloxy]ethyl]carbamoyloxy ethyl-N-phenyl]carbamoyl-1-propylpyridinium iodide(163)

To the compound(162) synthesized in (i)[452 mg(0.8 mmol.)]was added iodopropane(15 ml), and the mixture was heated for 72 hours under reflux in nitrogen streams while shielding the light. The reaction mixture was cooled and concentrated under reduced pressure to give a crude product, which was purified by means of a column chromatography (silica gel: 20 g; eluent:-chloroform/methanol=6/1) to obtain the object compound(163)[519 mg(88.2%, pale yellow powder).

TLC[Silica Gel;CHCl$_3$/MeOH(3/1)]: Rf=0.35.
NMR(90 MHz,CDCl$_3$)δ: 0.67(3H,t),1.66(2H,m),3.63(2H,m),3.94 (3H,s),4.17(6H,m),4.76(2H,m),6.30(1H,m),6.70(2H,s),6- .9 to 7.6(7H,m),8.20(2H,m),8.29(1H,br s),9.25(1H,br s), 9.35(1H,br s).

IR(KBr)cm$^{-1}$:
3250,1705,1650,1588,1520,1490,1460,1380,1275, 1240,1152,1100.

PRODUCTION EXAMPLE 62

Synthesis of
5-bromo-3-[N-[2-[2-(l-naphthyloxy)ethoxycarbohy-drazino]carbonyloxyethyl]-N-phenyl]carbamoyl-1-propylpyridinium iodide(166)

(i) Synthesis of 2-(1-naphthyloxy)ethoxycarbohy-drazine(164)

In methanol(10 ml) was dissolved a crude carbonate(697 mg) synthesized in a manner similar to that of Production Example 11-(i) from 2-(1-naphthyloxy)e-thanol[376 mg(2 mmol.)], phenyl chlorocarbonate[0.276 ml(2.2 mmol)] and pyridine[0.324 ml (4 mmol.)]. To the solution was added hydrazine hydrate [0.194 ml(4 mmol.)], and the mixture was stirred for 1.5 hour at room temperature. The reaction mixture was concentrated under reduced pressure, and the concentrate was recrystallized from methanol to afford the object compound(164)[440 mg(89.3%, colorless powder)].

TLC(Silica Gel;hexane/AcOEt=½): Rf=0.32.
NMR(90 MHz,CDCl$_3$+CD$_3$OD)δ: 4.30(2H,m),4.59(2H,m),6.80(1H,dd), 7.44(4H,m),7.78(1H,m),8.27(1H,m).

IR(KBr)cm$^{-1}$:
3300,3225,1710,1642,1580,1520,1395,1290,1265, 1244,1180,1102,1070,798,778.

(ii) Synthesis of 5-bromo-3-[N-[2-[2-(l-naphthyloxy)e-thoxycarbohydrazino]carbonyloxyethyl]-N-phenyl]-carbamoylpyridine(165)

In methylene chloride(10 ml) were dissolved the alcohol compound(18)[321 mg(1 mmol.)] synthesized in Production Example 6-(i) and pyridine[158 mg(2 mmol.)]. To the solution was added, under ice-cooling, phenyl chlorocarbonate[188 mg(1.2 mmol.)], and the mixture was stirred for 10 minutes at room temperature. The reaction mixture was washed with a 5% aqueous solution of sodium hydrogencarbonate. The organic layer was dried over anhydrous sodium sulfate, then the solvent was distilled off under reduced pressure to obtain a crude carbonate compound(528 mg).

To this crude carbonate compound was added the compound (164)[246 mg(1 mmol.)] synthesized in (i), and the mixture was heated for 30 hours at 90° C., which was then cooled. The crude product thus obtained was purified by means of a column chromatography(silica gel:30 g; eluent:hexane/ethyl acetate=½) to obtain the object compound(165)[277 mg(38.3%, colorless powder)].

TLC[Silica Gel;hexane/AcOEt(½)]: Rf=0.48.
NMR(90 MHz,CDCl$_3$)δ: 3.8 to 4.5(6H,m),4.60(2H,m),6.73(1H,dd), 6.8 to 7.5(9H,m),7.77(2H,m),8.25(2H,m),8.43(1H,d).

IR(KBr)cm$^{-1}$:
3240,1722,1640,1590,1490,1398,1212,1105,1072, 780.

(iii) Synthesis of 5-bromo-3-[N-[2-[2-(l-naphthyloxy)ethoxycarbohydrazino]carbonyloxyethyl]-N-phenyl]-carbamoyl-lpropylpyridinium iodide(166)

To the compound(165) synthesized in (ii)[200 mg(0.337 mmol.)]was added 1-iodopropane(7 ml), and the mixture was heated for 72 hours under reflux in nitrogen streams while shielding the light and then cooled. The reaction mixture was concentrated under reduced pressure, and the concentrate was purified by means of a column chromatography(silica gel:15 g; eluent:chloroform/methanol=6/1) to obtain the object compound (166)[240 mg(93.3%, pale yellow powder).

TLC[Silica Gel;CHCl$_3$/MeOH(3/1)]: Rf=0.24.

NMR(90MHz,CDCl$_3$)δ: 0.64(3H,t),1.74(2H,m),3.8 to 4.6(8H,m), 7.00(1H,dd),7.1to 7.6(8H,m),7.87(1H,m),8.18(1H,m),8.72 (1H,br s),9.07(1H,br s),9.2 to 9.5(2H,m).

IR(KBr)cm$^{-1}$:
3390,1722,1652,1590,1490,1452,1398,1270,1218, 1102,1088,778.

PRODUCTION EXAMPLE 63

Synthesis of
3-[N-[2-(2-methoxy-3-octadecylcarbamoyloxypropoxycar)]aminoethyl]carbamoyl-1-ethylpyridinium iodide(168)

(i) Synthesis of 3-[N-[2-(2-methoxy-3-octadecylcarbamoyloxypropoxycarbonyl)]aminoethyl]carbamoyl-pyridine(167)

In chloroform(15 ml) were dissolved 3-(2-aminoethyl)carbamoyl-2-methyl-1-octadecylcarbamoylglycerine[488 mg(1 mmol.)] and triethylamine[0.279 ml(2 mmol.)]. To the solution was added, under ice-cooling, nicotinic acid chloride hydrochloride[214 mg(1.2 mmol.)], and the mixture was stirred for one hour at room temperature. The reaction mixture was washed with a 1N aqueous solution of sodium hydroxide, and the organic layer was dried over anhydrous potassium hydroxide, then the solvent was distilled off under reduced pressure. The crude product thus obtained was purified by means of a column chromatography(silica gel:20 g; eluent:chloroform/methanol=30/1), followed by recrystallization from acetone to afford the object compound(167)[465 mg(78.4%, colorless powder).

TLC[Silica Gel;CHCl$_3$/MeOH(10/1)]: Rf=0.35.

NMR(90MHz,CDCl$_3$)δ:
0.87(3H,m),1.26(32H,s),3.12(2H,m),3.40 (3H,s)3.2 to 3.8(5H,m),4.15(4H,m),5.25(1H,br),5.74(1H,br), 7.35(1H,m),7.71(1H,br),8.20(1H,m),8.67(1H,m),9.04(1H,br)

IR(KBr)cm$^{-1}$:
3310,2910,2845,1689,1640,1590,1540,1470,1335,1260.

(ii) Synthesis of 3-[N-[2-(2-methoxy-3-octadecylcarbamoyloxypropoxycarbonyl)]aminoethyl]carbamoyl-1-ethylpyridinium iodide(168)

To the compound(167) synthesized in i)[593 mg(1 mmol.)] was added iodoethane(10 ml), and the mixture was heated for 72 hours under reflux in nitrogen streams while shielding the light and then cooled. The reaction mixture was concentrated under reduced pressure to give a crude product, which was recrystallized from acetone to obtain the object compound (168)[745 mg(99.5%, pale yellow powder)].

TLC[Silica Gel;CHCl$_3$/MeOH/H$_2$O(65/25/4)]: Rf=0.28.

NMR(90 MHz,CDCl$_3$)δ:
0.86(3H,m),1.25(32H,s),1.76(3H,t),3.11 (2H,m),3.41(3H,s),3.2 to 3.8(5H,m),4.15(4H,m),5.00(3H,m), 6.04(1H,br),8.20(1H,m),8.70(1H,m),9.09(1H,m),9.27(1H,m), 9.93(1H,m).

IR(KBr)cm$^{-1}$: 3310,2910,1845,1690,1650,1540,1280.

PRODUCTION EXAMPLE 64

Synthesis of
4-[N.[2-(2-methoxy-3-octadecylcarbamoyloxypropoxycarbonyl)]aminoethyl]carbamoyl-1-ethylpyridinium iodide(170)

(i) Synthesis of 4-[N-[2-(2-methoxy-3-octadecylcarbamoyloxypropoxycarbonyl)]aminoethyl]carbonyl-pyridine(169)

In chloroform(15 ml) were dissolved 3-(2-aminoethyl)carbamoyl-2-methyl-1-octadecylcarbamoylglycerine[488 mg(1 mmol.)] and triethylamine[0.279 ml(2 mmol.)]. To the solution was added, under ice-cooling, isonicotinic acid chloride hydrochloride[214 mg(1.2 mmol.)], and the mixture was stirred for one hour at room temperature. The reaction mixture was washed with a 1N aqueous solution of sodium hydroxide. The organic layer was dried over anhydrous potassium carbonate, then the solvent was distilled off under reduced pressure. The crude product thus obtained was purified by means of a column chromatography(silica gel:20 g; eluent:chloroform/methanol=19/1) to obtain the object compound(169)[547 mg(92.3%, colorless powder).

TLC[Silica Gel;CHCl$_3$/MeOH(10/1)]: Rf=0.35.

NMR(90 MHz,CDCl$_3$)δ:
0.87(3H,t),1.26(32H,s),3.11(2H,q),3.38 (3H,s),3.3 to 3.6(5H,m).4.11 (4H,m),4.97(1H,br),5.64(1H,br), 7.67(3H,m),8.69(2H,d).

IR(KBr)cm$^{-1}$::3300,2910,2840,1690,1640,1598,1540,-1460,1338,1260.

(ii) Synthesis of 4-[N-[2-(2-methoxy-3-octadecylcarbamoyloxypropoxycarbonyl)]aminoethyl]carbamoyl-1-ethylpyridinium iodide(170)

To the compound(169) synthesized in (i)[474 mg(0.8 mmol.)] was added iodoethane(5 ml),and the mixture was heated under reflux for 72 hours at room temperature in nitrogen streams while shielding the light. The reaction mixture was cooled and then concentrated under reduced pressure. The crude product thus obtained was recrystallized from ethyl acetate to obtain the object compound(170)[564 mg(94.2%, pale yellow powder)].

TLC[Silica Gel;CHCl$_3$/MeOH(3/1)]: Rf=0.23.

NMR(90 MHz,CDCl$_3$)δ:
0.84(3H,t),1.26(32H,s),3.12(2H,q),3.40 (3H,s),3.3 to 3.7(5H,m),4.13(4H,m),4.95(2H,q),5.24(1H,t), 6.13(1H,br),8.66(2H,d),8.83(1H,br),9.31(2H,d).

IR(KBr)cm$^{-1}$: 3320,2910,2845,1685,1530,1470,1272.

PRODUCTION EXAMPLE 65

Synthesis of
2-[N-[2-(2-methoxy-3-octadecylcarbamoyloxypropoxycarbonyl)]aminoethyl]carbamoyl-1-ethylpyridinium iodide(172)

(i) Synthesis of 2-[N-[2-(2-methoxy-3-octadecylcarbamoyloxypropoxycarbonyl)]aminoethyl]carbamoyl-pyridine(171)

In chloroform(15 ml) were dissolved 3-(2-aminoethyl)carbamoyl-2-methyl-1-octadecylcarbamoylglycerine[488 mg(1 mmol.)] and triethylamine[0.279 ml(2 mmol.)]. To the solution was added, under ice-cooling, picolinoylchloride hydrochloride [214 mg(1.2 mmol.)], and the mixture was stirred for one hour at room temperature. The reaction mixture was washed with a 1N aqueous solution of sodium hydroxide. The organic layer was dried over anhydrous potassium carbonate, then the solvent was distilled off under reduced pressure. The crude product thus obtained was purified by means of a column chromatography (silica gel:20 g; eluent:chloroform/methanol=30/1), followed by recrystallization from acetone to obtain the object compound(171) [Silica Gel;CHCl$_3$/MeOH(10/1)]: Rf=0.45.

NMR(90 MHz,CDCl$_3$)$\delta$: 0.87(3H,t),1.24(32H,s),3.14 (3H,s),3.3 to 3.7(5H,m),4.14(4H,m),4.83(1H,br),5.40(1H,br), 7.40(1H,m),7.81(1H,dt),8.14(1H,d),8.31(1H,br),8.53(1H,dd)

IR(KBr)cm$^1$: 3325,2910,2845,1692,1649,1530,1260.

(ii) Synthesis of 2-[N-[2-(2-methoxy-3-octadecylcarbamoyloxypropoxycarbonyl)]aminoethyl]carbamoyl-1-ethylpyridinium iodide(172)

To the compound(171) synthesized in (i)[356 mg(0.6 mmol.)] was added iodoethane(5 ml), and the mixture was heated for 72 hours under reflux in nitrogen streams while shielding the light and then cooled. The reaction mixture was concentrated under reduced pressure to give a crude product which was purified by means of a column chromatography(silica gel:12 g; eluent:chloroform/methanol=8/1). From the earlier eluate was recovered the starting material(171)[127 mg], and from the latter eluate was obtained the object compound(172) (92 mg, 31.8% based on the recovery of the starting material, pale yellow powder).

TLC[Silica Gel;CHCl$_3$/MeOH(3/1)]: Rf=0.23.
NMR(90 MHz,CDCl$_3$)$\delta$: 0.87(3H,t),1.27(32H,S),1.71(3H,t),3.13 (2H,q),3.43(3H,s),3.3 to 3.7(5H,m),4.16(4H,m),4.79(2H,q), 5.06(1H,t),6.00(1H,br),8.23(2H,m),8.65(1H,br t),9.10(1H, br), 9.23(1H,m).

IR(KBr)cm$^{-1}$: 3310,2910,2845,1690,1665,1610,1540,1260.

PRODUCTION EXAMPLE 66

Synthesis of 6-chloro-3-[N-[2-(2-methoxy-3-octadecylcarbamoyloxypropoxycarbonyl)]aminoethyl]carbamoyl-1-ethylpyridinium iodide(174)

(i) Synthesis of 6-chloro-3-[N-[2-(2-methoxy-3-octadecylcarbamoyloxypropoxycarbonyl)]aminoethyl]carbamoylpyridine(173)

To the hydrochloride synthesized in Production Example 2-(iv) [1.20 g(2 mmol.)] were added, under ice-cooling, chloroform (15 ml), triethylamine[1.67 ml(12 mmol.)] and 6-chloronicotinic acid chloride hydrochloride[850 mg(4 mmol.)]. The mixture was stirred for two hours at room temperature. The reaction mixture was washed with a 1N aqueous solution of sodium hydroxide. The organic layer was dried over anhydrous potassium carbonate, and the solvent was distilled off under reduced pressure. The crude product thus obtained was purified by means of a column chromatography(silica gel:54 g; eluent: hexane/ethyl acetate=$\frac{1}{2}$) to obtain the object compound(173) [374 mg(26.6%, colorless powder)].

TLC[Silica Gel;hexane/AcOEt($\frac{1}{2}$)]: Rf=0.24.
NMR(90 MHz,CDCl$_3$)$\delta$: 0.86(3H,t),1.25(32H,s),3.14(2H,q),3.41 (3H,s),3.3 to 3.6(3H,m),3.9 to 4.2(6H,m),4.94(1H,br), 5.37(1H,br),7.12(1H,m),7.27(5H,m),7.57(1H,dd),8.26(1H,d).

IR(KBr)cm$^{-1}$: 3300,2905,2845,1690,1645,1535,1395,1260.

(ii) Synthesis of 6-chloro-3-[N-[2-(2-methoxy-3-octadecylcarbamoyloxypropoxycarbonyl)]aminoethyl]carbamoyl-1ethylpyridinium iodide(174)

To the compound(173) synthesized in (i)[340 mg(0.483 mmol.)]was added iodoethane(5 ml). The mixture was heated for 108 hours under reflux in nitrogen streams while shielding the light, which was then cooled. The reaction mixture was concentrated under reduced pressure, and the resulting crude product was purified by means of a column chromatography (silica gel:15 g; eluent:chloroform/methanol=5/1) to obtain the object compound(174)[23 mg(5.4%, pale yellow powder)].

TLC[Silica Gel;CHCl$_3$/MeOH(3/1)]: Rf=0.36
NMR(90MHZ,CDCl$_3$)$\delta$: 0.88(3H,m),1.27(32H,s),1.63(3H,m),3.13 (2H,m),3.43(3H,s),3.3 to 3.6(3H,m),4.1l(6H,m),4.82(3H,m), 5.78(1H,br),7.35(5H,m),7.78(1H,m),8.18(1H,m),9.08(1H,m).

IR(KBr)cm$^{-1}$: 3270,2900,2840,1700,1650,1590,1520,1255.

PRODUCTION EXAMPLE 67

Synthesis of 2-chloro-3-[N-[2-(2-methoxy-3-octadecylcarbamoyloxypropoxycarbonyl)]aminoethyl]carbamoyl-1-ethylpyridinium iodide(176)

(i) Synthesis of 2-chloro-3-[N-[2-(2-methoxy-3-octadecylcarbamoyloxypropoxycarbonyl)]aminoethyl]carbamoylpyridine (175)

To the hydrochloride synthesized in Production Example 2-(iv)[1.20 g(2 mmol.)] were added chloroform(15 ml), triethylamine[1.67 ml(12 mmol.)] and 2-chloronicotinic acid chloride hydrochloride[850 mg(4 mmol.)] under ice-cooling. The mixture was stirred for two hours at room temperature. The reaction mixture was washed with a 1N aqueous solution of sodium hydroxide. The organic layer was dried over anhydrous potassium carbonate, then the solvent was distilled off. The crude product thus obtained was purified by means of a column chromatography(silica gel:60 g; eluent:hexane/ ethyl acetate=$\frac{1}{2}$) to obtain the object compound(175)[1.132 g(80.5%, colorless powder)].

TLC[Silica Gel; hexane/AcOEt($\frac{1}{2}$)]: Rf=0.29.
NMR(90 MHz,CDCl$_3$)$\delta$: 0.85(3H,t),1.24(32H,s),3.12(2H,q),3.41(3H,s),3.51(3H,m),3.9 to 4.2(6H,m),4.84(1H,br),5.37(1H, br),7.02(1H,dd),7.18(5H,s),7.47(1H,dd),8.19(1H,dd)

IR(KBr)cm$^{-1}$: 3310,2910,2845,1710,1640,1540,1225
(ii) Synthesis of 2-chloro-3-[N-[2-(2-methoxy-3-octadecylcarbamoyloxypropoxycarbonyl)]aminoethyl]carbamoyl-1ethylpyridinium iodide(176)

To the compound(175) synthesized in i)[703 mg(1 mmol.)] was added iodoethane(10 ml), and the mixture was heated for 72 hours under reflux in nitrogen streams while shielding the light. The reaction mixture was, after cooling, concentrated under reduced pressure. The crude product thus obtained was purified by means of a column chromatography (silica gel:20 g; eluent:-chloroform/methanol=15/1) to obtain the object product(176)[60 mg(6.98%, pale yellow powder)].

TLC[Silica Gel;CHCl$_3$/MeOH(3/1)]: Rf=0.33.

NMR(90 MHz,CDCl$_3$)δ: 0.87(3H,m),1.25(32H,s),1.87(3H,m), 3.12(2H,q),3.33(3H,s),3.43(3H,m),3.8 to 4.3(6H,m),4.83 (3H,m),7.40(5H,m),8.33(1H,m),8.8 to 9.2(2H,m).

IR(KBr)cm$^{-1}$: 3355,2905,2840,1710,1660,1580,1490,1450,1410, 1235.

PRODUCTION EXAMPLE 68

5-Bromo-3-[N-[2-[(2-butylcarbamoyloxy-2-phenyl)ethyl]carbamoyloxy]ethyl-N-phenyl]carbamoyl-1-propylpyridinium chloride (179)

(i) Synthesis of 5-bromo-3-[N-[2-[(2-hydroxy-2-phenyl)ethyl]carbamoyloxy]ethyl-N-phenyl]carbamoylpyridine (177)

In methylene chloride(20 m%) were dissolved the alcohol compound(18) synthesized in Production Example 6-(i)[1.606 g (5 mmol.)] and pyridine[0.809 ml(10 mmol.)]. To the solution was added phenyl chlorocarbonate[0.753 ml(6 mmol.)] under ice-cooling, and the mixture was stirred for 10 minutes at room temperature The reaction mixture was washed with a 5% aqueous solution of sodium hydrogencarbonate. The organic layer was dried over anhydrous sodium sulfate, then the solvent was distilled off under reduced pressure to leave a crude carbonate compound (2.64 g). To this crude compound was added 2-amino-1-phenylethanol[823 mg(6 nunol.)], and the mixture was heated at 90° C. for two hours. The reaction mixture was cooled, and a crude product then obtained was purified by means of a column chromatography(silica gel: 100 g; eluent:hexane/ethyl acetate=⅓) to obtain the desired compound (177)[2.044 g(84%, colorless resinous substance].

TLC(Silica Gel; n-hexane/AcOEt=⅓): Rf=0.32.

NMR(90 MHz, CDCl$_3$)δ2.98 to 3.8(3H m) 3.9 to 4.4(4H m) 4.78(1H,m), 5.38(1H,m), 6.98 to 7.50(10H,m), 7.77(1H,t), 8.27(1H,d), 8.43(1H,d).

IR(Neat) cm$^{-1}$: 3340, 3050, 1700, 1630, 1590, 1490, 1390

(ii) Synthesis of 5-bromo-3-[N-[2-[(2-butylcarbamoyloxy-2-phenyl)ethyl]carbamoyloxy]ethyl-N-phenyl]carbamoylpyridine (178)

In methylene chloride(5 m%) were dissolved the alcohol compound(177) synthesized in (i)[484 mg(1 mmol.)] and pyridine [0.162 ml(2 mmol.)]. To the solution was added, under ice-cooling, phenyl chlorocarbonate[0.276 ml(2.2 mmol.)], then the mixture was stirred for 30 minutes at room temperature. The reaction mixture was washed with a 5% aqueous solution of sodium hydrogencarbonate. The organic layer was dried over anhydrous sodium sulfate, then the solvent was distilled off under reduced pressure to leave a crude carbonate compound(1.126 g).

To this crude carbonate compound was added n-butylamine [0.297 ml(3 mmol.)], and the mixture was heated for 1.5 hour under reflux. The reaction mixture was cooled, and a crude product thus obtained was purified by means of a column chromatography(silica gel: 30 g; eluent:hexane/ethyl acetate=1/1.5) to obtain the desired compound(178)[583 mg (100%, colorless resinous substance)].

TLC(Silica Gel; n-hexane/AcOEt=1/1.5): Rf=0.36.

NMR(90 MHz, CDCl$_3$)δ0.90(3H,m), 1.40(4H,m), 3.14(2H,q), 3.50(2H,m), 4.00 to 4.47(4H,m), 4.70(1H,br), 5.13(1H,br), 5.70(1H,t), 6.98 to 7.4(10H,m), 7.80(1H,t), 8.30(1H,d), 8.47 (1H,d).

IR(Neat) cm$^{-1}$: 3300, 2920, 2850, 1690, 1630, 1505, 1240

(iii) Synthesis of 5-bromo-3-[N-[2-[(2-butylcarbamoyloxy-2-phenyl)ethyl]carbamoyloxy]ethyl-N-phenyl]carbamoyl-1-propylpyridinium chloride(179)

To the compound(178) synthesized in (ii) [542 mg(0.93 mmol.)] was added 1-iodopropane(15 ml), and the mixture was heated for 72 hours, while shielding light, in nitrogen streams under reflux. The reaction mixture was, after cooling, concentrated under reduced pressure. The crude product thus obtained was dissolved in 70% methanol/water(30 ml), which was processed with IRA-410(Cl$^-$)[30 ml], then subjected further to a column chromatography(silica gel: 15 g ; eluent: chloroform/methanol=10/1) to obtain the desired compound[229 mg (37.2%, pale yellow powder)].

TLC(Silica Gel; CHCl$_3$/MeOH=5/1): Rf=0.16.

NMR(90 MHz, CDCl$_3$)δ0.73(3H,m), 0.86(3H,t), 1.1 to 1.9 (8H,m), 3.08(2H,m), 3.48(2H,m), 3.8 to 4.4(4H,m), 4.70(1H,br), 4.93(2H,m), 5.70(1H,t), 6.90(1H,br), 7.30(10H,m), 8.30(1H,br s), 9.68(2H,br s).

IR(KBr) cm$^{-1}$: 3400,2920,1700,1650,1530,1490,1420,1240.

PRODUCTION EXAMPLE 69

5-Bromo-3-[N-[2-[(2-acetoxy-2-phenyl)ethyl]carbamoyloxy]-ethyl-N-phenyl]carbamoyl-1-propyl-pyridinium chloride (181)

(i) Synthesis of 5-bromo-3-[N-[2-[(2-acetoxy-2-phenyl)ethyl]carbamoyloxy]ethyl-N-phenyl]carbamoylpyridine (180)

In chloroform(5 ml) were dissolved the alcohol compound (177) synthesized in Production Example 68-(i)[484 mg(1 mmol.)]and triethylamine[0.836 ml(6 mmol.)]. To the solution was added, under ice-cooling, acetyl chloride[0.17 m (2.4 mmol.)], and the mixture was stirred at room temperature for 24 hours. The reaction mixture was washed with a 5% aqueous solution of sodium hydrogencarbonate. The organic layer was dried over anhydrous sodium sulfate, then the solvent was distilled off under reduced pressure. The crude product thus obtained was purified by means of a column chromatography(silica gel: 20 g; eluent:hexane/ethyl acetate=1/1.5) to obtain the desired compound(180)[306 mg(58.1%, pale yellow resinous substance)].

TLC(Silica Gel; n-hexane/AcOEt=⅓): Rf=0.44

NMR(90 MHz, CDCl$_3$)δ2.06(3H,s), 3.47(2H,m), 4.25(4H,m), 4.93(1H,m), 5.78(1H,t), 6.97 to 7.4(10H,m), 7.77(1H,t), 8.27 (1H,d), 8.47(1H,d).

IR(Neat) cm$^{-1}$: 3300, 1710, 1695, 1630, 1590, 1490, 1375, 1240, 1150, 1030.

(ii) Synthesis of 5-bromo-3-[N-[2-[(2-acetoxy-2-phenyl)ethyl]carbamoyloxy]ethyl-N-phenyl]carbamoyl-1-propylpyridinium chloride(181)

To the compound(180) synthesized in i)[276 mg(0.524 mmol.)] was added 1-iodopropane(10 m%), and the mixture was heated in nitrogen streams, while shielding light, for 48 hours under reflux. The reaction mixture was, after cooling, concentrated under reduced pressure, and the crude product thus obtained was dissolved in 70% methanol/water(30 ml). The solution was processed with IRA-410(C$^-$)[30 ml] and further purified by means of a column chromatography(silica gel: 15 g ; eluent:chloroform/methanol=6/1Σ3/1) to obtain the desired product (181)[214 mg(67.5%, pale yellow powder)].

TLC(Silica Gel;CHCl3/MeOH=3/1): Rf=0.28.

NMR(90 MHz,CDCl3)δ0.73(3H,m), 1.76(2H,m), 2.12(3H,s), 3.50(2H,br t), 4.20(4H,m), 4.94(2H,br t), 5.90(1H,t), 6.87 (1H,br), 7.37(10H,m), 8.33(1H,s), 9.73(2H,m).

IR(KBr) cm$^{-1}$: 3360, 2965, 1720, 1655, 1595, 1492, 1233.

PRODUCTION EXAMPLE 70

5-Bromo-3-[N-[2-[1-(2-acetoxy)propyl]carbamoyloxy]ethyl-N-phenyl]carbamoyl-1-propylpyridinium chloride (184)

(i) Synthesis of 5-bromo-3-[N-[2-[1-(2-hydroxy)propyl]carbamoyloxy]ethyl-N-phenyl]carbamoylpyridine (182)

In methylene chloride(20 ml) were dissolved the alcohol compound(18) synthesized in Production Example 6-i)[1.606 g (5 mmol.)] and pyridine[0.809 ml(10 mmol.)]. To the solution was added, under ice-cooling, phenyl chlorocarbonate[0.753 ml (6 mmol.)], and the mixture was stirred for 10 minutes at room temperature. The reaction mixture was washed with a 5% aqueous solution of sodium hydrogen carbonate. The organic layer was dried over anhydrous sodium sulfate, then the solvent was distilled off under reduced pressure to leave a crude carbonate compound(2.64 g)

To this crude carbonate compound was added 1-amino-2-propanol [451 mg(6 mmol.)] and the mixture was heated at 90° C. for two hours. The reaction mixture was cooled, and the crude product thus obtained was purified by means of a column chromatography (silica gel: 100 g; eluent: ethyl acetate) to obtain the desired compound(182)[1.816 g(86%, colorless resinous substance TLC(Silica Gel; AcOEt): Rf=0.24.

NMR(90 MHz, CDCl3)δ1.12(3H,d), 3.0 to 3.9(3H,m), 4.0 to 4.6 (4H,m), 5.13(1H,br d), 7.02 to 7.4(5H,m), 7.80(1H,t), 8.30 (1H,d), 8.48(1H,d).

IR(Neat) cm$^{-1}$: 3300, 2970, 1700, 1649, 1590, 1520, 1491, 1385, 1256.

(ii) Synthesis of 5-bromo-3-[N-[2-[1-(2-acetoxy)propyl]carbamoyloxy]ethyl-N-phenyl]carbamoylpyridine (183)

In chloroform (5 ml) were dissolved the alcohol compound(182) synthesized in (i)[422 mg(1 mmol.)] and triethylamine[0.836 ml(6 mmol.)]. To the solution was added, under ice-cooling, acetyl chloride[0.17 ml(2.4 mmol.)], and the mixture was stirred at room temperature for 24 hours. The reaction mixture was washed with a 5% aqueous solution of sodium hydrogencarbonate, and the organic layer was dried over anhydrous sodium sulfate, followed by distilling off the solvent under reduced pressure. The crude product thus obtained was purified by means of a column chromatography(silica gel : 20 g; eluent:hexane/ethyl acetate=1/1.5) to obtain the object compound(183)[356 mg(77.0%, colorless resinous substance)]. TLC(Silica Gel; n-hexane/AcOEt=½): Rf=0.38.

NMR(90 MHz, CDCl3)δ1.13(3H,d), 2.07(3H,s), 3.6 to 4.5 (6H,m), 4.85(1H,m), 7.00 to 7.4(5H,m), 7.83(1H,t), 8.33(1H,d), 8.47(1H,d).

IR(Neat) cm$^{-1}$: 3300, 1710, 1640, 1590, 1520, 1490, 1375, 1230, 1078.

(iii) Synthesis of 5-bromo-3-[N-[2-[1-(2-acetoxy)propyl]carbamoyloxy]ethyl-N-phenyl]carbamoyl-1-propyl-pyridinium chloride (184)

To the compound(183) synthesized in (i)[325 mg(0.77 mmol.)]was added 1-iodo propane(15 ml), and the mixture was heated under reflux for 48 hours in nitrogen streams while shielding light. The reaction mixture was cooled and concentrated under reduced pressure. The crude product thus obtained was dissolved in 70% methanol/water(30 ml), and the solution was processed with IRA-410(C$^-$)[30 ml], which was further purified by means of a column chromatography(silica gel: 15 g; eluent: chloroform/methanol=6/1) to obtain the object compound (184)[311 mg(74.4%, pale yellow powder)].

TLC(Silica Gel; CHCl3/MeOH=3/1): Rf=0.24.

NMR(90 MHz, CDCl3)δ0.76(3H,t), 1.22(3H,d), 1.83(2H,m), 2.06(3H,s), 3.7 to 4.3(6H,m), 4.97(2H,br t), 6.78(1H,br), 7.40(5H,m), 8.36(1H,br s), 9.77(2H,br s).

IR(KBr) cm$^{-1}$: 3400, 2945, 1710, 1658, 1595, 1532, 1492, 1400, 1230, 1078, 1040.

PRODUCTION EXAMPLE 71

5-Bromo-3-[N-[2-[(2-piperidinocarbonyloxy)ethyl]carbamoyloxy]ethyl-N-phenyl]carbamoyl-1-propyl-pyridinium chloride (186)

(i) Synthesis of 5-bromo-3-[N-[2-[(2-piperidinonocarbonyloxy)ethyl]carbamoyloxy]ethyl-N-phenyl]carbamoylpyridine (185)

In methylene chloride(10 ml) were dissolved the alcohol compound(132) synthesized in Production Example 49-i)[816 mg (2 mmol.)] and pyridine[0.324 ml(4.0 mmol.)]. To the solution was added, under ice-cooling, phenyl chlorocarbonate[301 ml (2.4 mmol.)], and the mixture was stirred at room temperature for 10 minutes. The reaction mixture was washed with a 5% aqueous solution of sodium hydrogencarbonate, then the organic layer was dried over anhydrous sodium sulfate, followed by distilling off the solvent under reduced pressure to obtain a crude carbonate compound(1.159 g).

To this crude carbonate compound was added piperidine[396 ml (4 mmol.)], and the mixture was heated at 50° C. for 4 hours. The reaction mixture was cooled, then the crude product thus obtained was purified by means of a column chromatography (silica gel: 50 g; eluent: hexane/ethyl acetate=⅓→ethyl acetate) to obtain the object compound(185)[1.00 g (96.2%, colorless resinous substance)].

TLC(Silica Gel;n-hexane/AcOEt=⅓): Rf=0.26.

NMR(90 MHz, CDCl3)δ1.57(6H,m), 3.40(6H,m), 3.9 to 4.4 (6H,m), 5.14(1H,m), 7.0 to 7.4(5H,m), 7.81(1H,t), 8.31(1H,d), 8.51(1H,d).

IR(Neat) cm$^{-1}$: 3300, 2925, 1680, 1640, 1588, 1520, 1490, 1430, 1380, 1228, 1150, 1093, 1020

(ii) Synthesis of 5-bromo-3-[N-[2-[(2-piperidinocarbonyloxy)ethyl]carbamoyloxy]ethyl-N-phenyl]carbamoyl-1-propylpyridinium chloride(186)

To the compound(185) synthesized in i)[975 mg(1.877 mmol.)] was added 1-iodopropane(20 ml), and the mixture was heated under reflux for 48 hours in nitrogen streams while shielding light. The reaction mixture was cooled, then concentrated under reduced pressure. The crude product thus obtained was dissolved in 70% methanol/water(30 ml). The solution was processed with IRA-410(Cl$^-$)[100 ml], which was further purified by column chromatography(silica gel : 30 g; eluent: chloroform/methanol=6/1) to obtain the object compound[869 mg(77.4%, pale yellow powder)].

TLC(Silica Gel;CHCl$_3$/MeOH=3/1): Rf=0.27.

NMR(90 MHz, CDCl$_3$)δ0.74(3H,t), 1.53(6H,br s), 1.83(2H,m), 3.37(6H,m), 4.17(6H,m), 4.96(2H,t), 6.93(1H,m), 7.35(5H,m), 8.36(1H,br s), 9.70(1H,br s), 9.84(1H,br s).

IR(KBr) cm$^{-1}$: 3380, 3225, 2930, 1690, 1650, 1598, 1535, 1495, 1430, 1258, 1230, 1150.

PRODUCTION EXAMPLE 72

5-Bromo-3-[N-[2-[(2-hexylcarbamoyloxy)ethyl]carbamoyloxy]ethyl-N-phenyl]carbamoyl-1-propyl-pyridinium chloride (188)

(i) Synthesis of 5-bromo-3-[N-[2-[(2-hexylcarbamoyloxy)ethyl]carbamoyloxy]ethyl-N-phenyl]carbamoylpyridine (187)

In methylene chloride(10 ml) were dissolved the alcohol compound(132) synthesized in Production Example 49-i)[816 mg (2 mmol.)] and pyridine[0.324 ml(4.0 mmol.)]. To the solution was added, under ice-cooling, phenyl chlorocarbonate[0.301 ml (2.4 mmol.)], and the mixture was stirred at room temperature for 10 minutes. The reaction mixture was washed with a 5% aqueous solution of sodium hydrogen carbonate. The organic layer was dried over anhydrous sodium sulfate, then the solvent was distilled off under reduced pressure to obtain a crude carbonate compound(1.159 g).

To this crude carbonate compound was added n-hexylamine [317 ml(2.4 mmol.)], and the mixture was heated at 90° C. for two hours. The reaction mixture was cooled, and the crude product thus obtained was purified by means of a column chromatography(silica gel: 25 g; eluent: hexane/ethyl acetate=½) to obtain the object compound(187)[933 mg(87.1%, pale yellow oily substance)].

TLC(Silica Gel; n-hexane/AcOEt=½): Rf=0.26.

NMR(90 MHz, CDCl$_3$) 0.87(3H,t), 1.30(8H,m), 3.13(2H,q), 3.35(2H, br q), 3.9 to 4.5(6H, m), 5.07(2H, m), 7.00 to 7.4 (5H, m), 7.80(1H, t), 8.30(1H, d), 8.49(1H, d).

IR(Neat) cm$^{-1}$: 3330, 2955, 2935, 1720, 1650, 1598, 1530, 1498, 1390, 1300, 1248, 1150, 1104, 1022, 750.

(ii) Synthesis of 5-bromo-3-[N-[2-[(2-hexylcarbamoyloxy)ethyl]carbamoyloxy]ethyl-N-phenyl]carbamoyl-1-propylpyridinium chloride (188)

To the compound(187) synthesized in i)[803 mg(1.50 mmol.)] was added 1-iodopropane(20 ml), and the mixture was heated under reflux for 60 hours in nitrogen streams while shielding light. The reaction mixture was cooled, then concentrated under reduced pressure. The crude product thus obtained was dissolved in 70% methanol/water(50 ml), and the solution was processed with IRA-410(C$^-$)[70 ml], followed by purification by means of a column chromatography(silica gel: 30 g; eluent: chloroform/methanol=6/1) to obtain the object compound (188) 608 mg(66.0%, pale yellow powder)].

TLC(Silica Gel ; CHCl$_3$/MeOH=3/1): Rf=0.40

NMR(90 MHz, CDCl$_3$)δ0.75(3H,t), 0.85(3H,t), 1.25(8H, br s), 1.83(2H, m), 3.10(2H, q), 3.37(2H, m), 4.13(6H, m), 4.95(2H, t), 5.72(1H, br), 7.08(1H, br), 7.34(5H, m), 8.32(1H, br s), 9.72(2H, br s).

IR(KBr) cm$^{-1}$: 3340, 2930, 1709, 1656, 1594, 1530, 1494, 458, 1404, 1247.

PRODUCTION EXAMPLE 73

5-Bromo-3-[N-[2-[(2-dodecylcarbamoyloxy)ethyl]carbamoyloxy]-ethyl-N-phenyl]carbamoyl-1-propyl-pyridinium chloride (190)

(i) Synthesis of 5-bromo-3-[N-[2-[(2-dodecylcarbamoyloxy)ethyl]carbamoyloxy]ethyl-N-phenyl]carbamoylpyridine (189)

In methylene chloride(10 mmol.) were dissolved the alcohol compound(132) synthesized in Production Example 49-(i)[816 mg (2 mmol.)] and pyridine[0.324 ml(4.0 mmol.)]. To the solution was added, under ice-cooling, phenyl chlorocarbonate[0.301 ml (2.4 mmol.)], and the mixture was stirred at room temperature for 10 minutes. The reaction mixture was washed with a 5% aqueous solution of sodium hydrogencarbonate. The organic layer was dried over anhydrous sodium sulfate, then the solvent was distilled off under reduced pressure to obtain a crude carbonate compound(1.159 g).

To this crude carbonate compound was added 1-aminododecane [445 mg(2.4 mmol.)], and the mixture was heated at 90° C. for two hours. The reaction mixture was cooled, and the crude product thus obtained was purified by means of a column chromatography(silica gel: 40 g; eluent: hexane/ethyl acetate=½) to obtain the object compound(189)[1.17 g(94.4%, white waxy product)].

TLC(Silica Gel; n-hexane/AcOEt=½): Rf=0.50

NMR(90 MHz, CDCl$_3$)δ0.87(3H,t), 1.28(20H,m), 3.13(2H,q), 3.25(2H,q), 3.9 to 4.5(6H,m), 4.9 to 5.3(2H,br), 7.03 to 7.5 (5H,m), 7.82(1H,m), 8.34(1H,m), 8.53(1H,m).

IR(KBr) cm$^{-1}$: 3350, 2922, 2852, 1694, 1655, 1597, 1523, 1303, 1264.

(ii) Synthesis of 5-bromo-3-[N-[2-[(2-dodecylcarbamoyloxy)ethyl]carbamoyloxy]ethyl-N-phenyl]carbamoyl-1-propylpyridinium chloride (190)

To the compound(189) synthesized in i)[929 mg(1.50 mmol.)] was added 1-iodopropane(20 ml), and the mixture was heated under reflux for 60 hours in nitrogen streams while shielding light. The reaction mixture was cooled, then concentrated under reduced pressure. The crude product thus obtained was dissolved in 70% methanol/water(50 ml). The solution was processed with IRA-410(C$^-$)[70 ml], which was further subjected to purification by means of a column chromatography(silica gel: 30 g; eluent: chloroform/methanol=6/1) to obtain the object compound (190)[533 mg(50.9%, pale yellow powder)].

TLC(Silica Gel; CHCl$_3$/MeOH=3/1): Rf=0.41.

NMR(90 MHz, CDCl$_3$)δ0.76(3H,t), 0.87(3H,t), 1.28(20H,s), 1.84g(2H,m), 3.11(2H,q), 3.38(2H,br q), 4.14(6H,m), 4.97(2H,t), 5.68(1H,br), 7.09(1H,br), 7.34(5H,m), 8.31(1H,br s), 9.68(1H, br s), 9.74(1H,br s).

IR(KBr) cm$^{-1}$: 3342, 2926, 2856, 1708, 1657, 1594, 1532, 494, 1458, 1405, 1249.

PRODUCTION EXAMPLE 74

5-Bromo-3-[N-[2-[2-(4-phenylbutylcarbamoyloxy)ethyl]carbamoyloxy]ethyl-N-phenyl]carbamoyl-1-propylpyridinium chloride (192)

(i) Synthesis of 5-bromo-3-[N-[2-[2-(4-phenylbutylcarbamoyloxy)ethyl]carbamoyloxy]ethyl-N-phenyl]carbamoylpyridine(191)

In methylene chloride(10 ml) were dissolved the alcohol compound(132) synthesized in Production Example 49-(i)[816 mg (2 mmol.)] and pyridine[0.324 ml(4.0 mmol.)]. To the solution was added, under ice-cooling, phenyl chlorocarbonate [0.301 ml(2.4 mmol.)], and the mixture was stirred at room temperature for 10 minutes. The reaction mixture was washed with a 5% aqueous solution of sodium hydrogencarbonate. The organic layer was dried over anhydrous sodium sulfate, then the solvent was distilled off under reduced pressure to leave a crude carbonate compound[1.159 g].

To this crude carbonate compound was added 4-phenylbutylamine[387 ml(2.4 mmol.)], and the mixture was heated at 90° C. for two hours. The reaction mixture was cooled, and the crude product thus obtained was purified by means of a column chromatography(silica gel: 50 g; eluent: hexane/ethyl acetate=½) to obtain the object compound(191)[1.035 g(88.7%, colorless oily product)].

TLC(Silica Gel; n-hexane/AcOEt=½): Rf=0.36

NMR(90 MHz,CDCl$_3$)δ1.3 to 1.8(4H,m), 2.62(2H,t), 3.16 (2H,t), 3.16(2H,q), 3.36(2H,q), 3.9 to 4.6(6H,m), 5.13(2H,br), 7.0 to 7.5(10H,m), 7.82(1H,m), 8.33(1H,m), 8.52(1H,m)

IR(Neat) cm$^{-1}$: 3350, 2950, 1720, 1650, 1600, 1530, 1498, 460, 1396, 1302, 1250, 1150, 1102.

(ii) Synthesis of 5-bromo-3-[N-[2-[2-(4-phenylbutylcarbamoyloxy)ethyl]carbamoyloxy]ethyl-N-phenyl]carbamoyl-1-propylpyridinium chloride (192)

To the compound(191) synthesized in (i)[875 mg(1.5 mmol.)] was added 1-iodopropane(20 ml), and the mixture was heated under reflux for 60 hours in nitrogen streams while shielding light. The reaction mixture was cooled and concentrated under reduced pressure. The crude product thus obtained was dissolved in 70% methanol/water(50 ml). The solution was processed with IRA-410(C$^-$)[100 ml] and further subjected to a column chromatography(silica gel: 30 g; eluent: chloroform/methanol=6/1) to obtain the object compound(192)[690 mg (69.5%, pale yellow powder)].

TLC(Silica Gel; CHCl$_3$/MeOH=3/1): Rf=0.35.

NMR(90 MHz, CDCl$_3$)δ0.73(3H,t), 1.3 to 2.0(6H,m), 2.59 (2H,t), 3.13(2H,q), 3.36(2H,m), 4.10(6H,m), 4.93(2H,t), 5.80 (1H,br), 6.9 to 7.5(10H,m), 8.30(1H,br s), 9.60(1H, br s), 9.75(1H,br s).

IR(KBr) cm$^{-1}$: 3358, 2938, 1710, 1657, 1593, 1529, 1494, 1246.

PRODUCTION EXAMPLE 75

5-Bromo-3-[N-[2-[2-(4-hexylphenylcarbamoyloxy)ethyl]carbamoyloxy]ethyl-N-phenyl]carbamoyl-1-propylpyridinium chloride (194)

(i) Synthesis of 5-bromo-3-[N-[2-[2-(4-hexylphenylcarbamoyloxy)ethyl]carbamoyloxy]ethyl-N-phenyl]carbamoylpyridine(193)

In methylene chloride(10 ml) were dissolved the alcohol compound(132) synthesized in Production Example 49-(i)[816 mg (2 mmol.)] and pyridine[0.324 ml(4.0 mmol.)]. To the solution was added, under ice-cooling, phenyl chlorocarbonate[0.301 ml (2.4 mmol.)]. The mixture was stirred for 10 minutes at room temperature. The reaction mixture was washed with a 5% aqueous solution of sodium hydrogencarbonate. The organic layer was dried over anhydrous sodium sulfate, then the solvent was distilled off under reduced pressure to leave a crude carbonate compound[1.159 g].

To this crude carbonate compound was added 4-hexylaniline [514 ml (2.4 mmol.)], and the mixture was heated at 90° C. for two hours and at 110° C. for 12 further hours. The reaction mixture was, after cooling, purified by means of a column chromatography(silica gel: 35 g; eluent: hexane/ethyl acetate=½) to obtain the object compound(193)[901 mg (73.7%, pale yellow oily substance)].

TLC(Silica Gel;n-hexane/AcOEt=½): Rf=0.40

NMR(90 MHz, CDCl$_3$)δ0.87(3H,t), 1.0 to 1.7(8H,m), 2.55 (8H,m), 2.55(2H,t), 3.45(2H,m), 3.9 to 4.4(6H,m), 5.15(1H,br), 6.9 to 7.5(9H,m), 7.82(1H,m), 8.33(1H,m), 8.52(1H,m).

IR(Neat) cm$^{-1}$: 3290, 2920, 1710, 1630, 1590, 1510, 1490, 1390, 1230.

(ii) Synthesis of 5-bromo-3-[N-[2-[2-(4-hexylphenylcarbamoyloxy)ethyl]carbamoyloxy]ethyl-N-phenyl]carbamoyl-1-propylpyridinium chloride(194)

To the compound(193) synthesized in (i)[734 mg(1.20 mmol.)] was added 1-iodopropane(20 ml), and the mixture was heated under reflux for 60 hours in nitrogen streams while shielding light. The reaction mixture was, after cooling, concentrated under reduced pressure. The crude product thus obtained was dissolved in 70% methanol/water(50 ml). The solution was processed with IRA-410(C$^-$)[70 ml] and purified by means of a column chromatography(silica gel: 30 g; eluent: chloroform/methanol=6/1) to obtain the object compound(194) [372 mg(44.9%, pale yellow powder)].

TLC(Silica Gel; CHCl$_3$/MeOH=3/1): Rf=0.43.

NMR(90 MHz, CDCl$_3$)δ0.70(3H,t), 0.87(3H,t), 1.0 to 1.9 (10H,m), 2.52(2H,t), 3.43(2H,m), 4.19(6H,br s), 4.89(2H,br t), 6.9 to 7.5(10H,m), 8.33(1H,br s), 8.77(1H,m), 9.43(1H,br s), 9.80(1H,br s).

IR(KBr)cm$^{-1}$: 3246, 3044, 2958, 2928, 1714, 1656, 1617, 1595, 1536, 1494, 1414, 1312, 1224.

PRODUCTION EXAMPLE 76

5-Bromo-3-[N-[2-[(2-morpholinocarbonyloxy)ethyl]carbamoyloxy]ethyl-N-phenyl]carbamoyl-1-propylpyridinium chloride (196)

(i) Synthesis of 5-bromo-3-[N-[2-[(2-morpholinocarbonyloxy)ethyl]carbamoyloxy]ethyl-N-phenyl]carbamoyl pyridine(195)

In methylene chloride(10 ml) were dissolved the alcohol compound(132) synthesized in Production Example 49-i)[816 mg (2 mmol.)] and pyridine[0.324 ml(4.0 mmol.)]. To the solution was added, under ice-cooling, phenyl chlorocarbonate[0.301 ml (2.4 mmol.)], and the mixture was stirred at room temperature for 10 minutes. The reaction mixture was washed with a 5% aqueous solution of sodium hydrogencarbonate, and the organic layer was dried over anhydrous sodium sulfate. The solvent was then distilled off to leave a crude carbonate compound [1.159 g].

To this crude carbonate compound was added morpholine [209 ml(2.4 mmol.)], and the mixture was heated at 90° C. for two hours. The reaction mixture was cooled and the crude product thus obtained was purified by means of a column chromatography(silica gel: 30 g; eluent: ethyl acetate) to obtain the object compound(195)[946 mg(90.7%, colorless oily substance)].

TLC(Silica Gel;AcOEt): Rf=0.34.

NMR(90 MHz, CDCl$_3$) δ6 3.1 to 3.7(10H,m), 3.9 to 4.5(6H,m), 5.10(1H,br), 7.03 to 7.4(5H,m), 7.83(1H,t), 8.34(1H,d), 8.54 (1H,d).

IR(Neat) cm$^{-1}$: 3330, 2955, 2855, 1700, 1650, 1598, 1530, 1492, 1430, 1382, 1240, 1118.

(ii) Synthesis of 5-bromo-3-[N-[2-[(2-morpholinocarbonyloxy)ethyl]carbamoyloxy]ethyl-N-phenyl]carbamoyl-1-propylpyridinium chloride(196)

To the compound(195) synthesized in (i)[782 mg(1.5 mmol.)]was added 1-iodopropane(20 ml), and the mixture was heated under reflux for 60 hours in nitrogen streams while shielding light. The reaction mixture was cooled, and then concentrated under reduced pressure to leave a crude product, which was dissolved in 70% methanol/water(50 ml). The solution was processed with IRA-410(Cl−)[70 ml]and then further subjected to purification by means of a column chromatography (silica gel: 30 g; eluent: chloroform/methanol=6/1) to obtain the object compound(196)[765 mg(85.0%, pale yellow powder)].

TLC(Silica Gel ; CHCl$_3$:/MeOH=3/1): Rf=0.23.

NMR(90 MHz, CDCl$_3$) δ0.77(3H,t), 1.84(2H,m), 3.1 to 3.8 (10H,m), 4.21(6H,br s), 4.97(2H,m), 7.1 to 7.5(5H,m), 8.42 (1H,br s), 9.76(1H,br s), 9.84(1H,br s).

IR(KBr) cm$^{-1}$: 3246, 2958, 2928, 1714, 1656, 1617, 1595, 1536, 1494, 1414, 1312, 1224.

PRODUCTION EXAMPLE 77

5-Bromo-3-[N-[2-[[2-(1,2,3,4-tetrahydroisoquinolyl)carbonyloxy]ethyl]carbamoyloxy]ethyl-N-phenyl]carbamoyl-1-propylpyridinium chloride (198)

(i) Synthesis of 5-bromo-3-[N-[2-[[2-(1,2,3,4-tetrahydroisoquinolyl)carbonyloxy]ethyl]carbamoyloxy]ethyl-N-phenyl]carbamoylpyridine (197)

In methylene chloride(10 ml) were dissolved the alcohol compound(132) synthesized in Production Example 49-i)[816 mg (2 mmol.)]and pyridine[0.324 ml(4.0 mmol.)]. To the solution was added, under ice-cooling, phenyl chlorocarbonate[0.301 ml (2.4 mmol.)], and the mixture was stirred at room temperature for 10 minutes. The reaction mixture was washed with a 5% aqueous solution of sodium hydrogencarbonate. The organic layer was dried over anhydrous sodium sulfate, followed by distilling off the solvent to obtain a crude carbonate compound (1.159 g).

To this crude carbonate compound was added 1,2,3,4-tetrahydro-isoquinoline [300 ml(2.4 mmol.)], and the mixture was heated at 90° C. for two hours. The reaction mixture was cooled, and the crude product was purified by means of a column chromatography (silica gel: 30 g; eluent: hexane/ethyl acetate=½) to obtain the object compound(197)[993 mg(87.5%, colorless resinous substance)].

TLC(Silica Gel; n-hexane/AcOEt=½): Rf=0.23.

NMR(90 MHz, CDCl$_3$) δ2.82(2H,t), 3.40(2H,m), 3.66(2H,t), 4.0 to 4.5(6H,m), 4.58(2H,s), 5.16(1H,m), 6.99 to 7.5(9H,m), 7.79(1H,m), 8.30(1H,m), 8.49(1H,m)

IR(Neat) cm$^{-1}$: 3350, 1705, 1652, 1599, 1498, 1435, 1390, 1300, 1230.

(ii) Synthesis of 5-bromo-3-[N-[2-[[2-(1,2,3,4-tetrahydroisoquinolyl)carbonyloxy]ethyl]carbamoyloxy]ethyl-N-phenyl]-carbamoyl-1-propylpyridinium chloride (198)

To the compound(197) synthesized in (i)[851 mg(1.50 mmol.)] was added 1-iodopropane(20 ml), and the mixture was heated under reflux for 60 hours in nitrogen streams while shielding light. The reaction mixture was cooled and concentrated under reduced pressure. The crude product thus obtained was dissolved in 70% methanol/water(50 ml). The solution was processed with IRA-410(Cl$^{-1}$) [70 ml], followed by purification by means of a column chromatography(silica gel: 30 g; eluent: chloroform/methanol=6/1) to obtain the object compound(198)[656 mg(67.7%, pale yellow powder)].

TLC(Silica Gel; CHCl$_3$/MeOH=3/1): Rf=0.40.

NMR(90 MHz, CDCl$_3$) δ0.72(3H,t), 1.79(2H,m), 2.80(2H,t), 3.46(2H,m), 3.64(2H,t), 3.9 to 4.4(6H,m), 4.58(2H,s), 4.91 (2H,m), 6.9 to 7.5(10H,m), 8.34(1H,m), 9.67(2H,m).

IR(KBr) cm$^{-1}$: 3380, 2960, 1701, 1659. 1592, 1495, 1430, 1230.

PRODUCTION EXAMPLE 78

5-Bromo-3-[N-[2-[2-(4-hexyloxyphenylcarbamoyloxy)ethyl]carbamoyloxy]ethyl-N-phenyl]carbamoyl-1-propylpyridinium chloride (200)

(i) Synthesis of 5-bromo-3-[N-[2-[2-(4-hexyloxyphenylcarbamoyloxy)ethyl]carbamoyloxy]ethyl-N-phenyl]-carbamoylpyridine(199)

In methylene chloride(10 ml) were dissolved the alcohol compound(132) synthesized in Production Example 49-i)[816 mg (2 mmol.)] and pyridine[0.324 ml(4.0 mmol.)]. To the solution was added, under ice-cooling, phenyl chlorocarbonate[0.301 ml (2.4 mmol.)], and the mixture was stirred at room temperature for 10 minutes. The reaction mixture was washed with a 5% aqueous solution of sodium hydrogencarbonate, and the organic layer was dried over anhydrous sodium sulfate. The solvent was then distilled off under reduced pressure to obtain a crude carbonate compound[1.159 g].

To this crude carbonate compound was added 4-hexyloxyaniline [464 mg(2.4 mmol.)], and the mixture was heated at 100° C. for 18 hours. The reaction mixture was cooled, and the crude product thus obtained was purified by means of a column chromatography(silica gel: 15 g; eluent: hexane/ethyl acetate=1/2.5) to obtain the object compound(199)[430 mg(34.3%, pale yellow oily substance)].

TLC(Silica Gel; n-hexane/AcOEt=1/2.5): Rf=0.39.

NMR(90 MHz, CDCl$_3$) δ0.89(3H,t), 1.1 to 1.9(8H,m), 3.43 (2H,m), 3.90(2H,t), 4.0 to 4.4(6H,m), 5.20(1H,m), 6.82(1H,d), 7.24(9H,m), 7.81(1H,m), 8.34(1H,m), 8.52(1H,d).

IR(Neat) cm−3280, 2920, 1680, 1640, 1588, 1490, 1380

(ii) Synthesis of 5-bromo-3-[N-[2-[2-(4-hexyloxyphenylcarbamoyloxy)ethyl]carbamoyloxy]ethyl-N-phenyl]-carbamoyl-1propylpyridinium chloride (200)

To the compound(199) synthesized in (i)[377 mg(0.60 mmol.)] was added iodopropane(15 ml), and the mixture was heated under reflux for 68 hours in nitrogen streams while shielding light. The reaction mixture was cooled and concentrated under reduced pressure. The crude product thus obtained was dissolved in 70% methanol/water(50 ml), and the solution was processed with IRA-410(Cl−) [60 ml], followed by purification by means of a column chromatography(silica gel: 20 g; eluent: chloroform/methanol=6/1) to obtain the object compound(200)[204 mg(48.2%, pale yellow powder)].

TLC(Silica Gel; CHCl$_3$:/MeOH=3/1): Rf=0.32.

NMR(90 MHz, CDC$_3$) δ0.70(3H,t), 0.09(3H,t), 1.1 to 1.9 (10H,m), 3.43(2H,m), 3.88(2H,t), 4.19(6H,m), 4.87(2H,br t), 6.76(1H,d), 7.0 to 7.5(9H,m), 8.30(1H,br s), 8.72(1H,br s), 9.35(1H,br s), 9.80(1H,br s).

IR(KBr) cm$^{-1}$: 3250, 2932, 1715, 1657, 1595, 1536, 1513, 1219.

PRODUCTION EXAMPLE 79

5-Bromo-3-[N-[2-[3-(1-naphthylcarbamoyloxy)prop-2-yl]carbamoyloxy]ethyl-N-phenyl]carbamoyl-1-propyl-pyridinium chloride (203)

(i) Synthesis of 5-bromo-3-[N-[2-[3-(1-hydroxy)prop-2-yl]1 carbamoyloxy]ethyl-N-phenyl]carbamoylpyridine (201)

In methylene chloride(10 ml) were dissolved the alcohol compound(18) synthesized in Production Example 6-i)[606 mg (2 mmol.)] and pyridine[0.324 ml(4 mmol.)]. To the solution was added, under ice-cooling, phenyl chlorocarbonate[0.301 ml(2.4 mmol.), and the mixture was stirred at room temperature for 10 minutes. The reaction mixture was washed with a 5% aqueous solution of sodium hydrogencarbonate. The organic layer was dried over anhydrous sodium sulfate, and the solvent was then distilled off under reduced pressure to obtain a crude carbonate compound(1.056 g). To this crude product was added DL-2-amino-1-propanol[223 ml(2.8 mmol.)], and the mixture was heated at 90° C. for two hours. The reaction mixture was cooled, and the crude product thus obtained was purified by means of a column chromatography(silica gel: 30 g; eluent: ethyl acetate/acetone=7/1) to obtain the object compound(201)[811 mg(96%, colorless resinous substance)].

TLC(Silica Gel; AcOEt/acetone=6/1): Rf=0.43.
NMR(90 MHz, CDCl$_3$) $\delta$1.14(3H,d), 3.1 to 4.0(4H,m), 4.0 to 4.5(4H,m), 5.17(1H,d), 7.00 to 7.4(5H,m), 7.77(1H,t), 8.29(1H,d), 8.47(1H,d).
IR(Neat) cm$^{-1}$: 3320, 3050, 2960, 1702, 1640, 1590, 1490

(ii) Synthesis of 5-bromo-3-[N-[2-[3-(1-naphthylcarbamoyloxy)prop-2-yl]carbamoyloxy]ethyl-N-phenyl]-carbamoylpyridine (202)

In pyridine(10 ml) was dissolved the alcohol compound (201) synthesized in (i)[633 mg(1.5 mmol.)]. To the solution was added 1-naphthyl isocyanate[0.258 ml(1.8 mmol.)], and the mixture was stirred at room temperature for 20 hours. The reaction mixture was concentrated under reduced pressure. The crude product thus obtained was purified by means of a column chromatography(silica gel: 25 g; eluent: hexane/ethyl acetate=½) to obtain the object compound(202) [407 mg(45.9%, colorless resinous substance)].

TLC(Silica Gel; n-hexane/AcOEt=½): Rf=0.38
NMR (90 MHz, CDCl$_3$) $\delta$1.15(3H,d), 3.8 to 4.6(7H,m), 5.05 (1H,br d), 6.95 to 8.0(14H,m), 8.28(1H,d), 8.41(1H,d), 8.61 (1H,m).

(ii) Synthesis of 5-bromo-3-[N-[2-[3-(1-naphthylcarbamoyloxy)prop-2-yl]carbamoyloxy]ethyl-N-phenyl]-carbamoyl-1-propyl pyridinium chloride (203)

To the compound(202) synthesized in (ii)[355 mg(0.6 mmol.)] was added 1-iodopropane (15 ml), and the mixture was heated under reflux for 53 hours in nitrogen streams while shielding light. The reaction mixture was cooled and concentrated under reduced pressure. The crude product thus obtained was dissolved in 70% methanol/water(50 ml), and the solution was processed with IRA-410(Cl$^-$)[50 ml], followed by further purification by means of a column chromatography(silica gel: 20 g; eluent: chloroform/methanol=8/1) to obtain the object compound(203) [247 mg(61.4%, pale yellow powder)].

TLC(Silica Gel; CHCl$_3$/MeOH=3/1): Rf=0.35
NMR(90 MHz, CDCl$_3$) $\delta$0.50(3H,t), 1.27(3H,d), 1.55(2H,m), 3.5 to 4.8(9H,m), 6.8 to 7.6(10H,m), 7.73(2H,m), 8.06(1H,br s), 8.17(1H,m), 8.77(1H,br s), 8.99(1H,br s), 9.81(1H,br s).

IR(KBr) cm$^{-1}$: 3402, 2972, 1712, 1656, 1594, 1541, 1495, 1224.

PRODUCTION EXAMPLE 80

5-Bromo-3-[N-[2-[N'-methyl-N'-(2-$\alpha$-naphthylcarbamoyloxyethyl)]carbamoyloxy]ethyl-N-phenyl]carbamoyl-1-propylpyridinium chloride (206)

(i) Synthesis of 5-bromo-3-[N-[2-[N'-(2-hydroxyethyl)-N'-methyl]carbamoyloxy]ethyl-N-phenyl]carbamoylpyridine(204)

In methylene chloride(10 m() were dissolved the alcohol compound(18) synthesized in Production Example 6-i[606 mg (2 mmol.)] and pyridine[0.324 m((4 mmol.)]. To the solution was added, under ice-cooling, phenyl chlorocarbonate[0.301 ml (2.4 mmol)] and the mixture was stirred at room temperature for 10 minutes. The reaction mixture was washed with a 5% aqueous solution of sodium hydrogencarbonate. The organic layer was dried over anhydrous sodium sulfate, then the solvent was distilled off under reduced pressure to leave a crude carbonate compound(1.056 g).

To this crude carbonate compound was added N-methylethanol amine[225 ml(2.8 mmol.)], and the mixture was heated at 90° C. for two hours. The reaction mixture was cooled, and the resulting crude product was purified by means of a column chromatography(silica gel: 30 g; eluent: ethyl acetate/acetone=5/1) to obtain the object compound(204)[758 mg(89.8%, colorless resinous substance)].

TLC(Silica Gel; AcOEt/acetone=5/1): Rf=0.37.
NMR(90 MHz, CDCl$_3$) $\delta$2.87(3H,s), 3.35(2H,br t), 3.69 (2H,br t), 4.23(4H,m), 7.23(5H,m), 7.77(1H,t), 8.29(1H,d), 8.47(1H,d).
IR(Neat) cm$^{-1}$: 3440, 3050, 2940, 1700, 1645, 1592, 1550, 1492, 1394, 1300, 1210, 1150.

(ii) Synthesis of 5-bromo-3-[N-[2-[N'-methyl-N'-(2-naphthylcarbamoyloxyethyl)]carbamoyloxy]ethyl-N-phenyl]carbamoylpyridine (205)

In pyridine(10 ml) was dissolved the alcohol compound (204) synthesized in (i)[633 mg(1.5 mmol.)]. To the solution was added 1-naphthyl isocyanate[0.258 ml(1.8 mmol.)], and the mixture was stirred at room temperature for 20 hours. The reaction mixture was concentrated under reduced pressure, and the resulting crude product was purified by means of a column chromatography(silica gel: 25 g; eluent: hexane/ethyl acetate=½) to obtain the object compound(205)[465 mg (52.4%, colorless resinous substance)].

TLC(Silica Gel; n-hexane/AcOEt=½): Rf=0.28
NMR(90 MHz, CDCl$_3$) $\delta$2.84(3H,br d), 3.51(2H,m), 4.26(6H,m), 6.94 to 8.0(14H,m), 8.27(1H,m), 8.44(1H,m).

(ii) Synthesis of 5-bromo-3-[N-[2-[N-methyl-N'-(2-naphthylcarbamoyloxyethyl)]carbamoyloxy]ethyl-N-phenyl]carbamoyl-1-propylpyridinium chloride (206)

To the compound(205) synthesized in (ii) [355 mg(0.6 mmol.)] was added 1-iodopropane(15 ml). The mixture was heated under reflux for 53 hours in nitrogen streams while shielding light. The reaction mixture was cooled and concentrated under reduced pressure. The crude product thus obtained was dissolved in 70% methanol/water(50 ml). The solution was processed with IRA-410(Cl$^-$)[50 ml] and then further purified by means of a column chromatography(silica gel: 20 g; eluent: chloroform/methanol=6/1) to obtain the object compound (206)[335 mg(83.3%, pale yellow powder)].

TLC(Silica Gel; CHCl$_3$:/MeOH=3/1): Rf=0.40.

NMR(90 MHz, CDC$_3$) δ0.58(3H,t), 1.59(2H,m), 2.80(3H,br), 3.49(2H,m), 4.26(6H,m), 4.68(2H,m), 7.0 to 8.1(13H,m), 8.20 (1H,m), 9.16(1H,m), 9.81(1H,m).

IR(KBr) cm$^-$: 3416, 2966, 1699, 1655, 1595, 1541, 1494, 1402, 1224, 1171.

PRODUCTION EXAMPLE 81

5-Bromo-3-[N-[2-[N'-benzyl-N'-(2-α-naphthylcarbamoyloxyethyl)]carbamoyloxy]ethyl-N-phenyl]-carbmoyl-1-propylpyridinium chloride (209)

(i) Synthesis of 5-bromo-3-[N-[2-[N'-benzyl-N'-(2-hydroxyethyl)]carbamoyloxy]ethyl-N-phenyl]carbamoylpyridine (207)

In methylene chloride(10 ml) were dissolved the alcohol compound(18) synthesized in Production Example 6-i)[606 mg (2 mmol.)] and pyridine[0.324 ml(4 mmol.)]. To the solution was added, under ice-cooling, phenyl chlorocarbonate[0.301 ml (2.4 mmol.)], and the mixture was stirred at room temperature for 10 minutes. The reaction mixture was washed with a 5% aqueous solution of sodium hydrogencarbonate. The organic layer was dried over anhydrous sodium sulfate, followed by distilling off the solvent under reduced pressure to obtain a crude carbonate compound(1.056 g).

To this crude carbonate compound was added N-benzylethanolamine[398 ml(2.8 mmol.)], and the mixture was heated at 90° C. for two hours. The reaction mixture was cooled, and the resulting crude product was purified by means of a column chromatography(silica gel: 30 g; eluent: hexane/ethyl acetate=1/5) to obtain the object compound(207)[752 mg (75.1%, colorless resinous substance)].

TLC(Silica Gel; hexane/AcOEt=1/5): Rf=0.32

NMR(90 MHz, CDCl$_3$) δ3.70(4H,br), 4.0 to 4.8(6H,m), 6.8 to 7.4(7H,m), 7.72(1H,m), 7.95(1H,m), 8.25(1H,m), 8.45(1H,d), 8.67(2H,m).

IR(Neat) cm$^{-1}$: 3360, 2920, 1675, 1620, 1410, 1290, 1230, 1060.

(ii) Synthesis of 5-bromo-3-[N-[2-[N'-benzyl-N'-(2-α-naphthylcarbamoyloxyethyl)]carbamoyloxy]ethyl-N-phenyl]carbamoylpyridine (208)

In pyridine(7 ml) was dissolved the alcohol compound(207) synthesized in (i)[500 mg(1.0 mmol.)]. To the solution was added 1-naphthyl isocyanate[0.172 ml(1.2 mmol.)], and the mixture was stirred at room temperature for 20 hours. The reaction mixture was concentrated under reduced pressure, and the resulting crude product was purified by means of a column chromatography(silica gel: 25 g; eluent: hexane/ethyl acetate=1/1) to obtain the object compound(208)[219 mg (32.8%, colorless resinous substance)].

TLC(Silica Gel; n-hexane/AcOEt=1/1.5): Rf=0.39

NMR(90 MHz, CDC$_3$) 3.45(2H,m), 3.9 to 4.6(8H,m), 6.8 to 7.9(19H,m), 8.23(1H,m), 8.42(1H,m).

(ii) Synthesis of 5-bromo-3-[N-[2-[N'-benzyl-N'-(2-α-naphthylcarbamoyloxyethyl)]carbamoyloxy]ethyl-N-phenyl]carbamoyl-1-propylpyridinium chloride (209)

To the compound(208) synthesized in (ii) [200 mg(0.3 mmol.)] was added 1-iodopropane(15 ml), and the mixture was heated under reflux for 53 hours in nitrogen streams while shielding light. The reaction mixture was cooled and concentrated under reduced pressure. The crude product thus obtained was dissolved in 70% methanol/water(50 ml). The solution was processed with IRA-410(Cl$^-$)[50 ml], which was further purified by means with a column chromatography(silica gel: 20 g; eluent: chloroform/methanol=6/1) to obtain the object compound (209)[180 mg(80.4%, pale yellow powder)].

TLC(Silica Gel; CHCl$_3$/MeOH=6/1): Rf=0.23.

NMR(90 MHz, CDC$_3$) δ0.54(3H,t), 1.54(2H,m), 3.42(2H,m), 3.9 to 4.9(8H,m), 6.9 to 8.0(15H,m), 8.20(1H,m), 8.91(1H,m), 9.12(1H,br s), 9.86(2H,m).

IR(KBr) cm$^{-1}$: 3418, 2966, 1702, 1657, 1594, 1540, 1495, 1266.

PRODUCTION EXAMPLE 82

5-Bromo-3-[N-[2-[N'-(2-α-naphthylcarbamoyloxyethyl)-N'-phenyl]carbamoyloxy]ethyl-N-phenyl]carbamoyl-1-propylpyridinium chloride (212)

(i) Synthesis of 5-bromo-3-[N-[2-[N'-(2-hydroxyethyl)-N'-phenyl]carbamoyloxy]ethyl-N-phenyl]carbamoylpyridine (210)

In methylene chloride(10 ml) were dissolved the alcohol compound(18) synthesized in Production Example 6-i)[606 mg (2 mmol.)] and pyridine[0.324 ml(4 mmol.)]. To the solution was added, under ice-cooling, phenyl chlorocarbonate[0.301 ml (2.4 mmol.)]. The mixture was stirred at room temperature for 10 minutes. The reaction mixture was washed with a 5% aqueous solution of sodium hydrogencarbonate. The organic layer was dried over anhydrous sodium sulfate, then the solvent was distilled off under reduced pressure to leave a crude carbonate compound(1.056 g).

To this crude carbonate compound was added N-anilinoethanol [354 ml(2.8 mmol.)], and the mixture was heated at 90° C. for two hours. The reaction mixture was cooled, and the resulting crude product was purified by means of a column chromatography(silica gel: 30 g; eluent: hexane/ethyl acetate=1/1.5) to obtain the object compound(210)[411 mg(42.3%, colorless solid)].

TLC(Silica Gel; hexane/AcOEt=1/1.5): Rf=0.37.

NMR(90 MHz, CDCl$_3$) δ2.30(1H,br), 3.45(2H,t), 3.71(4H,m), 4.09(2H,m), 6.5 to 7.4(10H,m), 7.77(1H,m), 8.27(1H,br s), 8.50(1H,br s).

(ii) Synthesis of 5-bromo-3-[N-[2-[N'-(2-naphthylcarbamoyloxyethyl)-N'-phenyl]carbamoyloxy]ethyl-N-phenyl]carbamoylpyridine (211)

In pyridine(7 ml) was dissolved the alcohol compound(211) synthesized in (i)[340 mg(0.7 mmol.)]. To the solution was added 1-naphthyl isocyanate [0.12 ml(0.84 mmol.)], and the mixture was stirred at room temperature for 20 hours. The reaction mixture was concentrated under reduced pressure, and the resulting crude product was purified by means of a column chromatography(silica gel: 25 g; eluent: hexane/ethyl acetate=1.5/1) to obtain the object compound(211)[408 mg (89.2%, colorless resinous substance).

TLC(Silica Gel; n-hexane/AcOEt=1.5/1): Rf=0.34.

NMR(90 MHz, CDCl$_3$) δ3.67(4H,m), 4.17(2H,m), 4.37(2H,t), 6.5 to 8.1(18H,m), 8.26(1H,d), 8.47(1H,d).

(ii) Synthesis of 5-bromo-3-[N-[2-[N'-(2-α-naphthylcarbamoyloxyethyl)-N'-phenyl]carbamoyloxy]ethyl-N-phenyl]carbamoyl-1-propylpyridinium chloride (212)

To the compound(211) synthesized in (ii) [392 mg(0.60 mmol.)] was added 1-iodopropane(15 ml). The mixture was heated under reflux for 53 hours in nitrogen streams while shielding light. The reaction mixture was cooled and concentrated under reduced pressure to obtain a crude product, which was dissolved in 70% methanol/water(80 ml). The solution was processed with IRA-410(Cl$^-$)[100 ml], followed by further purification by means of a column chromatography(silica gel: 20 g; eluent: chloroform/methanol=8/1) to obtain the object compound(212) [399 mg(90.8%, pale yellow powder)].

TLC(Silica Gel; CHCl₃/MeOH=6/1): Rf=0.20.

NMR(90 MHz, CDCl₃) δ0.52(3H,t), 1.54(2H,m), 3.4 to 4.5 (8H,m), 4.61(2H,m), 6.5 to 8.4(18H,m), 9.27(1H,m), 9.67(1H,m).

IR(KBr) cm⁻¹: 3422, 2966, 1716, 1655, 1597, 1543, 1504, 1399, 1220.

PRODUCTION EXAMPLE 83

5-Bromo-3-[N-[2-[2-(N'-methoxycarbonyl-N'-phenylamino)ethyl]carbamoyloxy]ethyl-N-phenyl]carbamoyl-1-propylpyridinium chloride (215)

(i) Synthesis of 5-bromo-3-[N-[2-[2-(N'-phenylamino)ethyl]carbamoyloxy]ethyl-N-phenyl]carbamoylpyridine (213)

In methylene chloride(20 ml) were dissolved the alcohol compound(18) synthesized in Production Example 6-i)[1.927 g (6 mmol.)] and pyridine[0.971 ml(12 mmol.)]. To the solution was added, under ice-cooling, phenyl chlorocarbonate[0.903 ml (7.2 mmol.)], and the mixture was stirred at room temperature for 10 minutes. The reaction mixture was washed with a 5% aqueous solution of sodium hydrogencarbonate. The organic layer was dried over anhydrous sodium sulfate, then the solvent was distilled off under reduced pressure to leave a crude carbonate compound(2.65 g).

To this crude carbonate compound was added N-phenylethylene diamine[1.099 ml(8.4 mmol.)], and the mixture was heated at 90° C. for two hours. The reaction mixture was cooled, and the resulting crude product was purified by means of a column chromatography(silica gel: 120 g; eluent: hexane/ethyl acetate=½) to obtain the object compound(213)[2.783 g (96%, colorless solid)]

TLC(Silica Gel; n-hexane/AcOEt=½): Rf=0.43.

NMR(90 MHz, CDCl₃) δ3.26(4H,m), 3.8 to 4.5(5H,m), 5.06 (1H,m), 6.63(3H,m), 6.9 to 7.4(7H,m), 7.81(1H,t), 8.29(1H,d), 8.48(1H,d).

(ii) Synthesis of 5-bromo-3-[N-[2-[2-(N'-methoxycarbonyl-N'-phenylamino)ethyl]carbamoyloxy]ethyl-N-phenyl]carbamoylpyridine(214)

In methylene chloride(10 ml) were dissolved the amino compound(213) synthesized in (i)[580 mg(1.2 mmol.)] and pyridine [0.914 ml(2.4 mmol.)]. To the solution was added, under ice-cooling, methyl chlorocarbonate[0.111 ml(1.44 mmol.)], and the mixture was stirred at room temperature for 10 minutes. The reaction mixture was washed with a 5% aqueous solution of sodium hydrogencarbonate. The organic layer was dried over anhydrous sodium sulfate, then the solvent was distilled off under reduced pressure. The resulting crude product was purified by means of a column chromatography(silica gel: 25 g; eluent: hexane/ethyl acetate=1/2.5) to obtain the object compound(214)[650 mg(100%, colorless resinous substance)].

TLC(Silica Gel; n-hexane/AcOEt=1/2.5): Rf=0.32.

NMR(90 MHz, CDCl₃) δ3.29(2H,q), 3.67(3H,s), 3.75(2H,t), 4.0 to 4.4(4H,m), 5.15(1H,m), 6.9 to 7.5(10H,m), 7.81(1H,m), 8.32(1H,br s), 8.51(1H,br s).

(ii) Synthesis of 5-bromo-3-[N-[2-[2-(N'-methoxycarbonyl-N'-phenylamino)ethyl]carbamoyloxy]ethyl-N-phenyl]carbamoyl-1-propylpyridinium chloride (215)

To the compound(214) synthesized in (ii) [541 mg(1.0 mmol.)] was added 1-iodopropane(20 m0), and the mixture was heated under reflux for 72 hours in nitrogen streams while shielding light. The reaction mixture was cooled and concentrated under reduced pressure, and the resulting crude product was dissolved in 70% methanol/water(50 ml). The solution was processed with IRA-410(Cl⁻)[70 ml], which was further subjected to purification by means of column chromatography (silica gel: 20 g; eluent: chloroform/methanol=6/1) to obtain the object compound(215)[586 mg(94.5%, pale yellow powder)].

TLC(Silica Gel; CHCl₃/MeOH=3/1): Rf=0.30.

NMR(90 MHz,CDCl₃) δ0.73(3H,t), 1.76(2H,m), 3.33(2H,m), 3.63(3H,s), 3.80(2H,t), 4.16(4H,m), 4.94(2H,m), 7.0 to 7.5 (10H,m), 8.32(1H,br s), 9.71(1H,br s), 9.83(1H,br s).

IR(KBr) cm⁻¹: 3420, 2964, 1708, 1659, 1595, 1495, 1458, 1392, 1252, 756, 702.

PRODUCTION EXAMPLE 84

5-Bromo-3-[N-[2-[[2-methyl-2-(1,2,3,4-tetrahydroisoquinolyl)carbonyloxy]ethyl]carbamoyloxy]ethyl-N-phenyl]carbamoyl-1-propylpyridinium chloride (217)

(i) Synthesis of 5-bromo-3-[N-[2-[[2-methyl-2-(1,2,3,4-tetrahydroisoquinolyl)carbonyloxy]ethyl]carbamoyloxy]ethyl-N-phenyl]carbamoylpyridine (216)

In methylene chloride(7 ml) were dissolved the alcohol compound(182) synthesized in Production Example 70-i)[538 mg (1.27 mmol.)] and pyridine[0.206 ml(2.55 mmol.)]. To the solution was added, under ice-cooling, phenyl chlorocarbonate [0.192 ml(1.53 mmol.)] and the mixture was stirred at room temperature for 30 minutes. The reaction mixture was washed with a 5% aqueous solution of sodium hydrogencarbonate. The organic layer was dried over anhydrous sodium sulfate, then the solvent was distilled off under reduced pressure to obtain a crude carbonate compound.

To this crude carbonate compound was added 1,2,3,4-tetrahydroisoqunioline [0.191 ml (1.53 mmol.)], and the mixture was heated at 90° C. for 1.5 hour. The reaction mixture was cooled, and the resulting crude product was purified by means of a column chromatography(silica gel: 20 g; eluent: hexane/ethyl acetate=½) to obtain the object compound(216)[500 mg(67.5%, colorless resinous substance].

TLC(Silica Gel; n-hexane/AcOEt=½): Rf=0.31.

NMR(90 MHz, CDCl₃) δ1.13(3H,d), 2.82(2H,t), 3.66(2H,t), 3.8 to 4.5(7H,m), 4.60(2H,s), 5.00(1H,m), 7.00 to 7.5(9H,m), 7.80(1H,m), 8.32(1H,m), 8.52(1H,m).

IR(Neat) cm⁻¹: 3334, 2974, 1704, 1651, 1595, 1532, 1494, 1431, 1297, 1230.

(ii) Synthesis of 5-bromo-3-[N-[2-[[2-methyl-2-(1,2,3,4-tetrahydroisoquinolyl)carbonyloxy]ethyl]carbamoyloxy]ethyl-N-phenyl]carbamoyl-1-propylpyridinium chloride (217)

To the compound(216) synthesized in (i)[407 mg(0.7 mmol.)] was added 1-iodopropane(20 ml), and the mixture was heated under reflux for 72 hours in nitrogen streams while shielding light. The reaction mixture was cooled and concentrated under reduced pressure. The resulting crude product was dissolved in 70% methanol/water(50 ml), which was processed with IRA-410(Cl⁻)[50 ml], followed by further purification by means of a column chromatography(silica gel: 20 g; eluent: chloroform/methanol=6/1) to obtain the object compound(217)[413 mg (89,4%, pale yellow powder)].

TLC(Silica Gel; CHCl$_3$:/MeOH=6/1): Rf=0.30.

NMR(90 MHz, CDCl$_3$) δ0.73(3H,m), 1.23(3H,d), 1.80(2H,m), 3.66(2H,t), 3.8 to 4.5(7H,m), 4.58(1H,s), 4.95(2H,m), 6.76 (1H,m), 6.9 to 7.6(9H,m), 8.30(1H,br s), 9.67(1H,br), 9.76 (1H,br).

IR(KBr) cm$^{-1}$: 3380, 2965, 1700, 1660, 1592, 1535, 1495, 1430, 1230, 750.

PRODUCTION EXAMPLE 85

5-Bromo-3-[N-[2-[[2-phenyl-2-(1,2,3,4-tetrahydroisoquinolyl)carbonyloxy]ethyl]carbamoyloxy]ethyl-N-phenyl]carbamoyl-1-propylpyridinium chloride (219)

(i) Synthesis of 5-bromo-3-[N-[2-[[2-phenyl-2-(1,2,3,4-tetrahydroisoquinolyl)carbonyloxy]ethyl]carbamoyloxy]ethyl-N-phenyl]carbamoylpyridine (218)

In methylene chloride(7 ml) were dissolved the alcohol compound(177) synthesized in Production Example 68-i)[609 mg (1.26 mmol.)] and pyridine[0.203 ml(2.51 mmol.)] To the solution was added, under ice-cooling, phenyl chlorocarbonate[0.189 ml(1.51 mmol.)], and the mixture was stirred at room temperature for 30 minutes. The reaction mixture was washed with a 5% aqueous solution of sodium hydrogencarbonate. The organic layer was dried over anhydrous sodium sulfate, then the solvent was distilled off under reduced pressure to leave a crude carbonate compound.

To this crude carbonate compound was added 1,2,3,4-tetrahydroisoquinoline[0.189 ml(1.51 mmol.)]. The mixture was heated at 90° C. for 3.5 hours. The reaction mixture was cooled, and the resulting crude product was purified by means of a column chromatography(silica gel: 20 g; eluent: hexane/ethyl acetate =½) to obtain the object compound(218)[621 mg(76.8%, colorless resinous substance)].

TLC(Silica Gel; n-hexane/AcOEt=½): Rf=0.47.

NMR(90 MHz, CDCl$_3$) δ2.83(2H,t), 3.2 to 3.8(4H,m), 3.9 to 4.4(4H,m), 4.63(2H,s), 5.07(1H,m), 5.79(1H,t), 6.9 to 7.5 (14H,m), 7.80(1H,t), 8.30(1H,d), 8.48(1H,d).

IR(KBr) cm$^{-1}$: 3342, 3062, 2936, 1706, 1650, 1595, 1527, 1494, 1431, 1297, 1230.

(ii) Synthesis of 5-bromo-3-[N-[2-[[2-phenyl-2-(1,2,3,4-tetrahydroisoquinolyl)carbonyloxy]ethyl]carbamoyloxy]ethyl-N-phenyl]carbamoyl-1-propylpyridinium chloride (219)

(i) To the compound(218) synthesized in (i)[515 mg(0.8 mmol.)] was added 1-iodopropane(20 ml). The mixture was heated under reflux for 72 hours in nitrogen streams while shielding light. The reaction mixture was, after cooling, concentrated under reduced pressure. The resulting crude product was dissolved in 70% methanol/water(50 ml), and the solution was processed with IRA-410(Cl$^-$)[50 ml], followed by further purification by means of a column chromatography(silica gel: 20 g; eluent: chloroform/methanol=6/1) to obtain the object compound(219)[367 mg(63.5%, pale yellow powder)].

TLC(Silica Gel; CHCl$_3$/MeOH=6/1): Rf=0.35 .

NMR(90 MHz, CDCl$_3$) δ0.71 (3H,t), 1.78(2H,m), 2.82(2H,m), 3.2 to 3.8(4H,m), 3.9 to 5.0(8H,m), 5.84(2H,t), 6.75(1H,m), 6.9 to 7.7(14H,m), 8.28(1H,m), 9.60(1H,m), 9.67(1H,m).

IR(KBr) cm$^{-1}$: 3400, 2955, 1702, 1658, 1594, 1493, 1430, 1228.

PRODUCTION EXAMPLE 86

5-Bromo-3-[N-[2-[[2-(9-fluorenylcarbamoyloxy)]ethyl]carbamoyloxy]ethyl-N-phenyl]carbamoyl-1-propylpyridinium chloride (221)

(i) Synthesis of 5-bromo-3-[N-[2-[[2-(9-fluorenylcarbamoyloxy)]ethyl]carbamoyloxy]ethyl-N-phenyl]carbamoylpyridine (220)

In methylene chloride(10 ml) were dissolved the alcohol compound(132) synthesized in Production Example 49-i)[613 mg (1.5 mmol.)] and pyridine[0.243 ml(3.0 mmol.) ]. To the solution was added, under ice-cooling, phenyl chlorocarbonate [0.226 ml(1.8 mmol.)], and the mixture was stirred at room temperature for 10 minutes. The reaction mixture was washed with a 5% aqueous solution of sodium hydrogen carbonate, and the organic layer was dried over anhydrous sodium sulfate. The solvent was then distilled off under reduced pressure to obtain a crude carbonate compound.

To this crude carbonate compound were added 9-aminoflurene [408 ml(2.25 mmol.)] and toluene(2 ml), and the mixture was heated for 12 hours at temperatures ranging from 60° C. to 90° C. To the reaction mixture was added, after cooling, chloroform, followed by washing with a 5% aqueous solution of sodium hydrogencarbonate. The organic layer was dried over anhydrous sodium sulfate, then the solvent was distilled off under reduced pressure. The resulting crude product was purified by means of a column chromatography(silica gel: 40 g; eluent: hexane/ethyl acetate=½) to obtain the object compound(220) [615 mg(66.6%, colorless powder)].

TLC(Silica Gel; n-hexane/AcOEt=1/2.5): Rf=0.35.

NMR(90 MHz, CDCl$_3$) δ3.41(2H,m), 3.9 to 4.4(6H,m), 5.12 (1H,br), 5.41(1H,d), 5.86(1H,d), 6.96 to 7.8(14H,m), 8.25 (1H,m), 8.35(1H,m).

IR(KBr) cm$^{-1}$: 3320, 1720, 1645, 1595, 1520, 1496, 1240, 748.

(ii) Synthesis of 5-bromo-3-[N-[2-[[2-(9-fluorenylcarbamoyloxy)]ethyl]carbamoyloxy]ethyl-N-phenyl]carbamoyl-1-propylpyridinium chloride (221)

To the compound(220) synthesized in (i)[339 mg(0.55 mmol.)] was added 1-iodopropane(20 ml). The mixture was heated under reflux for 68 hours in nitrogen streams while shielding light. The reaction mixture was cooled and concentrated under reduced pressure. The resulting crude product was dissolved in 70% methanol/water(50 ml), and the solution was processed with IRA-410(Cl$^-$)[50 ml], followed by purification by means of a column chromatography(silica gel: 20 g; eluent: chloroform/methanol=6/1) to obtain the object compound[347 mg (90.9%, pale yellow powder)].

TLC(Silica Gel; CHCl$_3$/MeOH=3/1): Rf=0.37.

NMR(90 MHz, CDCl$_3$) δ0.65(3H,t), 1.71(2H,m), 3.43(2H,m), 3.8 to 4.4(6H,m), 4.80(2H,m), 5.72(1H,d), 5.97(1H,br d), 6.9 to 7.7(13H,m), 8.16(1H, br s), 9.50(1H,br s), 9.73(1H,br s).

IR(KBr) cm$^{-1}$: 3330, 1710, 1655, 1590, 1520, 1490, 1450, 1400, 1300, 1240

PRODUCTION EXAMPLE 87

5-Bromo-3-[N-[2-[[2-(1,2,3,4-tetrahydroisoquinolyl)carbonyloxy]ethyl]carbamoyl]ethyl-N-phenyl]carbamoyl-1-propylpyridinium chloride (227)

(i) Synthesis of 1-t-butoxycarbonylamino-2-(1,2,3,4-tetrahydroisoquinolyl)carbonyloxyethane(222)

In methylene chloride(40 ml) was dissolved monoethanolamine[1.222 g(20 mmol.)]. To the solution was added, under ice-cooling, di-t-butyl dicarbonate[4.365 g(20 mmol.)]. The mixture was stirred at room temperature for two hours.

To the reaction solution was added pyridine[3.235 ml(40 mmol.)], to which was further added, under ice-cooling, phenyl chlorocarbonate[2.51 ml(20 mmol]. The mixture was then stirred at room temperature for 10 minutes. The reaction mixture was washed with a 5% aqueous solution of sodium hydrogencarbonate. The organic layer was dried over anhydrous sodium sulfate, and the solvent was distilled off under reduced pressure to obtain a crude carbonate compound. To this crude carbonate compound was added 1,2,3,4-tetrahydroisoquinoline[2.75 ml(22 mmol.). The mixture was heated at 90° C. for one hour, and the reaction mixture was cooled. The resulting crude product was purified by means of a column chromatography(silica gel: 200 g; eluent hexane/ethyl acetate=2/1 to 1/1) to obtain the object compound(222)[5.757 g(89.7%, white solid)].

TLC(Silica Gel; n-hexane/AcOEt=1/1): Rf=0.22.

NMR(90 MHz, CDCl$_3$) δ1.43(9H,s), 2.83(2H,t), 3.40(2H,q), 3.67(2H,t), 4.18(2H,t), 4.60(2H,s), 5.00(1H,br), 7.14(4H,s).

IR(KBr) cm$^{-1}$: 3340, 2970, 1710, 1670, 1520, 1478, 1430, 1365, 1290, 1230.

(ii) Synthesis of 2-(1,2,3,4-tetrahydroisoquinolyl)carbonyloxyethylamine(223)

In chloroform (15 ml) was dissolved the compound(222) synthesized in (i)[5.435 g(16.9 mmol.)]. To the solution was added HCl-saturated methanol(10 ml), and the mixture was stirred at room temperature for two hours. The reaction mixture was concentrated under reduced pressure. To the resulting crude product was added a 1N aqueous solution of sodium hydroxide (50 ml), and the mixture was subjected to extraction with chloroform. The organic layer was dried over anhydrous sodium sulfate, and the solvent was distilled off under reduced pressure to obtain the object compound(223)[3.72 g(100%, colorless oily substance)].

TLC(Silica Gel; MeOH/conc. NH$_4$OH=50/1): Rf=0.37.

NMR(90 MHz, CDCl$_3$) δ1.36(2H,s), 2.84(2H,t), 2.95(2H,t), 3.69(2H,t), 4.16(2H,t), 4.63(2H,s), 7.17(4H,s).

IR(Neat) cm$^{-1}$: 3360, 2940, 1690, 1580, 1430, 1295, 1230, 1120.

(iii) Synthesis of N-[2-(1,2,3,4-tetrahydroisoquinolyl)carbonyloxyethyl]-3-[(N'-t-butoxycarbonyl-N'-phenyl)amino]propanamide(224)

In methylene chloride(50 ml) were dissolved 3-(N-t-butoxy-carbonyl-N-phenyl)aminopropionic acid[3.714 g(14.0 mmol.)]and dicyclohexylcarbodiimide[3.177 g(15.4 mmol.)]. To the solution was added, under ice-cooling, the compound(223) synthesized in (ii)[3.084 g(14.0 mmol.)]. The mixture was cooled for 4 hours at room temperature. Resulting precipitates were filtered off, and the mother liquor was washed with a 1N aqueous solution of NaOH. The organic layer was dried over anhydrous potassium carbonate, then the solvent was distilled off under reduced pressure. The resulting crude product was purified by means of a column chromatography(silica gel: 200 g; eluent: hexane/ethyl acetate=3/7) to obtain the object compound(224)[5.00 g(76.4%, colorless resinous substance)].

TLC(Silica Gel; hexane/AcOEt=½): Rf=0.24.

NMR(90 MHz, CDCl$_3$) δ1.39(9H,s), 2.47(2H,t), 2.84(2H,t), 3.49(2H,q), 3.69(2H,t), 3.93(2H,t), 4.20(2H,t), 4.62(2H,s), 6.59(1H,br), 7.0 to 7.5(9H,m).

IR(Neat)cm$^{-1}$: 3320, 2980, 2930, 1710 to 1650, 1598, 1540, 1498, 1455, 1430, 1390, 1364, 1300, 1230, 1160

(iv) Synthesis of N-[2-(1,2,3,4-tetrahydroisoquinolyl)carbonyloxyethyl]-3-anilinopropanamide(225)

In a mixture of chloroform(10 ml) and methanol(10 ml) was dissolved the compound(224) synthesized in (ii)[4.675 g(10.0 mmol.)]. To the solution was added HCl-saturated methanol (20 ml), and the mixture was stirred for three hours at room temperature. The reaction mixture was concentrated under reduced pressure. To the resulting crude product was added a 1N aqueous solution of sodium hydroxide, followed by extraction with chloroform. The organic layer was dried over anhydrous potassium carbonate, then the solvent was distilled off under reduced pressure. The crude product thus obtained was purified by means of a column chromatography(silica gel: 80 g; eluent: hexane/ethyl acetate=1.6 to ½) to obtain the object compound(225)[3.158 g(85.9%, white solid)].

TLC(Silica Gel; hexane/AcOEt=1/6): Rf=0.28.

NMR(90 MHz, CDCl$_3$) δ2.45(2H,t), 2.80(2H,t), 3.3 to 3.8 (6H,m), 4.22(2H,t), 4.56(2H,s), 6.43(1H,br), 6.66(3H,m), 6.9 to 7.3(6H,s).

IR(KBr) cm$^{-1}$: 3310, 1690, 1660, 1560, 1460, 1443, 1430, 1299, 1282, 1240, 1230, 1130, 1115, 1095.

(v) Synthesis of 5-bromo-3-[N-[2-[[2-(1,2,3,4-tetrahydroisoquinolyl)carbonyloxy]ethyl]carbamoyl]ethyl-N-phenyl]carbamoylpyridine (226)

In chloroform(15 ml) were dissolved the compound(225) synthesized in (iv)[735 mg(2 mmol.)] and triethylamine[1.394 m (10 mmol.)]. To the solution was added, under ice-cooling, 5-bromonicotinic acid chloride hydrochloride[617 mg(2.4 mmol.)], and the mixture was stirred at room temperature for 1.5 hour. To the reaction mixture was added a 1N aqueous solution of NaOH, followed by extraction with chloroform. The organic layer was dried over anhydrous potassium carbonate, then the solvent was distilled off under reduced pressure. The crude product thus obtained was purified by means of a column chromatography(silica gel: 30 g; eluent: ethyl acetate) to obtain the object compound(226)[1.083 g(98.2%, white powder)].

TLC(Silica Gel; AcOEt): Rf=0.26.

NMR(90 MHz, CDCl$_3$) δ2.58(2H,t), 2.81(2H,t), 3.51(2H,q), 3.65 (2H,t), 4.20(4H,m), 4.58(2H,s), 6.79(1H,br t), 6.9 to 7.4(9H,m), 7.77(1H,t), 8.29(1H,br s), 8.47(1H,br s).

IR(Neat) cm$^{-1}$: 3320, 1710 to 1620, 1595, 1540, 1490, 1440, 1390, 1340, 1295, 1230, 1120, 1095.

(vi) Synthesis of 5-bromo-3-[N-[2-[[2-(1,2,3,4-tetrahydroisoquinolyl)carbonyloxy]ethyl]carbamoyl]ethyl-N-phenyl]-carbamoyl-1-propylpyridinium chloride (227)

To the compound(226) synthesized in (v)[827 mg(1.50 mmol.)] was added 1-iodopropane(25 ml), and the mixture was heated under reflux for 68 hours in nitrogen streams while shielding light. The reaction mixture was cooled and concentrated under reduced pressure. The resulting crude product was dissolved in 70% methanol/water(70 ml), and the solution was processed with IRA-410(Cl$^-$)[70 ml], followed by further purification by means of a column chromatography(silica gel: 35 g; eluent: chloroform/methanol=6/1) to obtain the object compound (227)[691 mg(73.1%, pale yellow powder)].

TLC(Silica Gel; CHCl$_3$/MeOH=6/1): Rf=0.30.

NMR(90 MHz, CDCl₃) δ0.76(3H,t), 1.85(2H,m), 2.81(4H,m), 3.43(2H,m), 3.65(2H,t), 4.15(4H,m), 4.58(2H,s), 4.85(2H,m), 7.0 to 7.5(9H,m), 8.09(1H,m), 8.35(1H,br s), 9.60(2H,br s).

IR(KBr) cm⁻¹: 3380, 3200, 2960, 1690, 1658, 1595, 1550, 1495, 1430, 1298, 1228, 1120, 745.

PRODUCTION EXAMPLE 88

5-Chloro-3-[N-[2-[[2-(1,2,3,4-tetrahydroisoquinolyl)carbonyloxy]ethyl]carbamoyl]ethyl-N-phenyl]carbamoyl-1-propylpyridinium chloride (229)

(i) Synthesis of 5-chloro-3-[N-[2-[[2-(1,2,3,4-tetrahydroisoquinolyl)carbonyloxy]ethyl]carbamoyl]ethyl-N-phenyl]carbamoylpyridine (228)

In chloroform(15 ml) were dissolved the compound(225) synthesized in Production Example 87-(iv) [735 mg(2 mmol.)] and triethylamine[1.394 ml(10 mmol.)]. To the solution was added, under ice-cooling, 5-chloro nicotinic acid chloride hydrochloride[637 mg(3 mmol.)], and the mixture was stirred at room temperature for one hour. To the reaction mixture was added a 1N aqueous solution of NaOH, followed by extraction with chloroform. The organic layer was dried over anhydrous potassium carbonate, then the solvent was distilled off under reduced pressure. The resulting crude product was purified by means of a column chromatography(silica gel: 45 g eluent: ethyl acetate/acetone=8/1) to obtain the object compound(228)[958 mg(63.0%, colorless resinous substance)].

TLC(Silica Gel; AcOEt/acetone=5/1): Rf=0.38.

NMR(90 MHz, CDCl₃) δ2.59(2H,t), 2.82(2H,t), 3.51(2H,q), 3.67(2H,t), 4.22(4H,m), 4.60(2H,s), 6.67(1H,br t), 6.9 to 7.4 (9H,m), 7.62(1H,t), 8.27(1H,br s), 8.39(1H,br s).

IR(Neat) cm⁻¹: 3320, 1710 to 1620, 1590, 1545, 1490, 1425, 1385, 1295, 1220, 1120.

(ii) Synthesis of 5-chloro-3-[N-[2-[[2-(1,2,3,4-tetrahydroisoquinolyl)carbonyloxy]ethyl]carbamoyl]ethyl-N-phenyl]carbamoyl-1-propylpyridinium chloride (229)

To the compound(228) synthesized in (i)[760 mg(1.50 mmol.)] was added 1-iodopropane(250 ml), and the mixture was heated under reflux for 68 hours in nitrogen streams while shielding light. The reaction mixture was cooled and concentrated under reduced pressure, and the resulting crude product was dissolved in 70% methanol/water(70 m()). The solution was processed with IRA-410(Cl⁻)[70 ml], followed by purification by means of a column chromatography(silica gel: 35 g; eluent: chloroform/methanol=6/1) to obtain the object compound(229)[664 mg (75.6%, pale yellow powder)].

TLC(Silica Gel; CHCl₃/MeOH=6/1): Rf=0.30.

NMR(90 MHz, CDCl₃) δ0.74(3H,t), 1.85(2H,m), 2.5 to 3.2 (4H,m), 3.42(2H,q), 3.65(2H,t), 4.14(4H,m), 4.57(2H,s), 4.85 (2H,m), 7.0 to 7.5(9H,m), 8.14(1H,m), 8.22(1H,br s), 9.55 (1H,br s), 9.60(1H,br s).

IR(KBr) cm⁻¹: 3400, 3050, 2960, 1690, 1655, 1590, 1492, 1430, 1222, 745.

PRODUCTION EXAMPLE 89

5-Bromo-3-[N-[2-[2-(4-phenylpiperidinocarbonyloxy)ethyl]carbamoyloxy]ethyl-N-phenyl]carbamoyl-1-propylpyridinium chloride (231)

(i) Synthesis of 5-bromo-3[N-[2-[2-(4-phenylpiperidinocarbonyloxy)ethyl]carbamoyloxy]ethyl-N-phenyl]carbamoylpyridine-(230)

In methylene chloride(10 ml) were dissolved the alcohol compound(132)[530 mg(1.3 mmol.)] and pyridine[0.21 m((2.6 mmol.)]. To the solution was added, under ice-cooling, phenyl chlorocarbonate[0.195 ml(1.56 mmol.)], and the mixture was stirred at room temperature for 30 minutes. The reaction mixture was washed with a 5% aqueous solution of sodium hydrogencarbonate. The organic layer was dried over anhydrous sodium sulfate, then the solvent was distilled off under reduced pressure to obtain a crude carbonate compound(929 mg).

To this crude carbonate compound was added 4-phenyl piperidine[251 mg(1.56 mmol.)], and the mixture was heated at 90° C. for 3 hours. The reaction mixture was cooled, and the crude product thus obtained was purified by means of a column chromatography(silica gel: 50 g; eluent: hexane/ethyl acetate=⅓) to obtain the object compound(230)[707 mg(91.3%, colorless resinous substance)].

TLC(Silica Gel; n-hexane/AcOEt=⅓): Rf=0.36.

NMR(90 MHz, CDC(₃) δ1.2 to 1.9(4H,m), 2.3 to 2.9(3H,m), 3.30(2H,m), 3.9 to 4.3(8H,m), 5.05(1H,br), 6.94 to 7.3(10H,m), 7.74(1H,m), 8.24(1H,d), 8.42(1H,m).

IR(Neat) cm⁻¹: 3335, 2940, 2855, 1700, 1650, 1595, 1538, 1495, 1440, 1390, 1300, 1280, 1222.

(ii) Synthesis of 5-bromo-3-[N-[2-[2-(4-phenylpiperidinocarbonyloxy)ethyl]carbamoyloxy]ethyl-N-phenyl]carbamoyl-1propylpyridinium chloride (231)]

To the compound(230) synthesized in (i)[616 mg(1.04 mmol)] was added 1-iodopropane(25 ml), and the mixture was heated under reflux for 70 hours in nitrogen streams while shielding light. The reaction mixture was cooled and then concentrated under reduced pressure. The resulting crude product was dissolved in 70% methanol/water(70 ml), which was processed with IRA-410(Cl⁻)[70 ml], followed by further purification by means of a column chromatography(silica gel: 20 g; eluent: chloroform/methanol=6/1) to obtain the object compound(231) [644 mg(92.0%, pale yellow powder)].

TLC(Silica Gel; CHCl₃/MeOH=3/1): Rf=0.33.

NMR(90 MHz, CDCl₃) δ0.75(3H,t), 1.3 to 2.0(6H,m), 2.3 to 3.0(3H,m), 3.43(6H,m), 3.8 to 4.4(8H,m), 4.78(2H,m), 6.9 to 7.5(11H,m), 8.33(1H,br s), 9.77(2H,br s).

IR(KBr) cm⁻: 3350, 3220, 2940, 1695, 1660, 1595, 1535, 1495, 1430, 1260, 1220, 1122, 760, 701.

PRODUCTION EXAMPLE 90

5-Bromo-3-[N-[2-[2-(naphthylcarbamoyloxy)ethyl]carbamoyl]-ethyl-N-phenyl]carbamoyl-1-propylpyridinium chloride (236)

(i) Synthesis of 3-(N-t-butoxycarbonyl-N-phenyl)aminopropionic acid(232)

In chloroform(20 ml) was dissolved 2-anilinopropionic acid [1.65 g(10.0 mmol.)]. To the solution was added di-tertbutyl dicarbonate[2.18 g(10.0 mmol.)], and the mixture was stirred at room temperature for one day. The reaction mixture was subjected to extraction with a 1N aqueous solution of sodium hydroxide. The aqueous layer was washed with chloroform, which was rendered to pH 1 with 1N HCl under ice-cooling, followed by extraction with chloroform to obtain the compound (232)[1.71 g(64.4%, yellow oily product)].

IR(Neat) cm⁻¹: 3150, 1700(br), 1600

NMR(90 MHz, CDCl₃) δ1.41(9H,s), 2.56(2H,t, J=7Hz), 3.90 (2H,t, J=7Hz), 7.03 to 7.43(5H,m), 8.24(1H,m).

(ii) Synthesis of 2-[3-(N-t-butoxycarbonyl-N-phenyl-)aminopropaneamido]ethyl N-(1-naphthylcarbamate (233)

In chloroform(8 ml) was dissolved the compound(232) synthesized in (i)[1.60 g(6.03 mmol.)]. To the solution was added dicyclohexylcarbodiimide[1.37 g(6.03 mmol.)]dissolved in chloroform(2 ml). The mixture was stirred at room temperature for 30 minutes. To the reaction mixture was added 2-aminoethyl N-(1-naphthyl)carbamate[1.39 g(6.63 mmol.)], and the mixture was stirred at room temperature for one hour. Resulting precipitates were filtered off, and the filtrate was concentrated under reduced pressure. The concentrate was subjected to a silica gel column chromatography, eluting with hexane - ethyl acetate(1:1), to obtain the compound(233) [1.79 g(62.6%)] as a colorless substance.

IR(Neat) cm$^{-1}$: 3310(br), 3060, 1690(br), 1650(br), 1600

NMR(90 MHz, CDCl$_3$) δ: 1.37(9H,s), 2.41(2H,t,J=7Hz), 3.45 (2H,q,J=5Hz), 3.89(2H,t,J=5Hz), 4.20(2H,t,J=7Hz), 6.62(1H,br t,J=5Hz), 6.93 to 8.07(13H,m).

(iii) Synthesis of 2-(3-anilinopropaneamido)ethyl N-(1naphthyl)carbamate(234)

In methanol(10 ml) was dissolved the compound(233) synthesized in (ii) [1.68 g(3.52 mmol.)]. To the solution was added a 14M hydrogen chloride methanol solution(10 ml), and the mixture was stirred at room temperature all night long. The solvent was distilled off, and the residue was rendered to alkaline with a 1N aqueous solution of sodium hydroxide, which was subjected to extraction with ethyl acetate. The organic layer was separated and dried, then the solvent was distilled off to obtain the compound(234)[1.33 g(quant.)] as a yellow oily substance.

IR(Neat) cm$^{-1}$: 3310(br), 3050, 1710(br), 1650(br), 1600.

NMR(90 MHz, CDCl$_3$) δ: 2.34(2H,t,J=6Hz), 3.03 to 3.78(4H,m), 4.23(2H,t,J=6Hz), 6.14 to 8.10(14H,m).

(iv) Synthesis of 5-bromo-3-[N-[2-[2-(1-naphthylcarbamoyloxy)ethyl]carbamoyl]ethyl-N-phenyl]carbamoylpyridine (235)

In chloroform(6 ml) were dissolved the compound synthesized in (iii)[1.17 g(3.10 mmol.)] and triethyamine[0.86 ml(6.20 mmol.)]. To the solution was added, under ice-cooling, 5-bromo nicotinic acid chloride hydrochloride[876 mg(3.41 mmol.). The mixture was stirred at room temperature for 30 minutes washed with a 1N aqueous solution of sodium hydroxide and then dried. The solvent was distilled off under reduced pressure. The residue was subjected to silica gel column chromatography, eluting with ethyl nacetate, to obtain the compound(235)[1.10 g(63.2%)] as colorless powder.

IR(KBr) cm$^{-1}$: 3260(br), 3070, 1714, 1650(br), 1590.

NMR(90 MHz, CDCl$_3$+d$_4$-MeOH : 2.57(2H,t,J=7 Hz), 3.47(2H,m), 3.73 to 4.50(4H), 6.87 to 8.14(13H,m), 8.27(1H,br s), 8.46 (1H,br s).

(v) Synthesis of 5-bromo-3-[N-[2-[2-(1-naphthylcarbamoyloxy)ethyl]carbamoyl]ethyl-N-phenyl]carbamoyl-1-propylpyridinium chloride (236)

A solution of the compound(235) synthesized in (iv) [1.00 g (1.78 mmol.)] in propyl iodide(10 ml) was stirred at 110° C. for two days. Resulting precipitates were washed with ether to obtain a crude iodide compound(1.25 g) as yellow powder. The above-mentioned crude compound was dissolved in a mixture of methanol-water(7:3)(50 ml), and the solution was allowed to pass through anion-exchange resin(IRA-410[Cl$^-$]) (50 ml). The effluent thus obtained was concentrated under reduced pressure. The concentrate was subjected to a silica gel column chromatography, followed by elution with methanol-chloroform(1:10) to obtain the compound(236) [662 mg(58.1%)]as yellow powder.

IR(KBr) cm$^{-1}$: 3440(br), 3260(br), 3050, 1720(br), 1650(br), 1590.

NMR(90 MHz, CDCl$_3$+d$_4$MeOH) δ 0.50(3H,m), 1.53(2H,m), 2.73 (2H,m), 3.45(2H,m, 4.17(6H,m), 6.70 to 8.74(14H,m), 8.90(1H, br s), 9.04(1H,br s), 9.22(1H,br s).

PRODUCTION EXAMPLE 91

5-Bromo-3-N-[3-[2-(1-naphthylcarbamoyloxy)ethyl]carbamoyloxy]propyl-N-phenyl]carbamoyl-1-propylpyridinium chloride (239)

(i) Synthesis of 5-bromo-3-[N-(3-hydroxypropyl)-N-phenyl]carbamoylpyridine (237)

In dichloromethane(100 ml) were dissolved 3-anilinopropan-1-ol [1.8 g(12 mmol.)] and pyridine(5 g). To the solution was added, under ice-cooling, 5-bromonicotinic acid chloride hydrochloride [3.4 g(13 mmol.)], and the mixture was stirred for 30 minutes, followed by stirring for further one hour at room temperature. The reaction mixture was washed with an aqueous solution of sodirm carbonate, which was then dried, followed by distilling off the solvent under reduced pressure. The residue was subjected to a silica gel column chromatography, eluting with ethyl acetate:hexane (4:1), to obtain 2.1 g of the compound(237). m.p. 97° to 99° C.

IR(KBr)cm$^{-1}$: 3400, 3015, 2920, 1655, 1630, 1590, 1490, 1410.

Elemental Analysis for C$_{15}$H$_{15}$N$_2$O$_2$Br Calcd. C, 53.75, H, 4.511, N, 8.36, Found C, 53.81, H, 4.48, N, 8.29.

(ii) Synthesis of 5-bromo-3- [N- [3- 2-(1-naphthylcarbamoyloxy)ethyl]carbamoyloxy]propyl-N-phenyl]carbamoylpyridine (238)

To a solution of the compound(237) synthesized in (i) [1.42 g (4.00 mmol.)] and pyridine [0.65 ml(8.00 mmol.)] in chloroform (16 ml) was added dropwise, under ice-cooling while stirring, phenyl chloroformate [0.55 ml(4.40 mmol.)], and the mixture was stirred at room temperature for 10 minutes. The reaction mixture was washed with a 5% aqueous solution of sodium hydrogencarbonate, which was then dried, followed by distilling off the solvent. To the residue was added 2-aminoethyl N-1-naphthyl carbamide [1.01 g(4.40 mmol.)], and the mixture was heated at 80° C. for two hours. The reaction mixture was cooled and subjected to a silica gel column chromatography, eluting with hexane-ethyl acetate(1:2), to obtain the compound(238) [1.21 g (51.2%)] as a pale yellow oily substance.

IR(Neat)cm$^{-1}$: 3320(br), 3050, 1720(br), 1640(br), 1590.

NMR(90 MHz,CDCl$_3$) δ: 1.90(2H,quint,J=7 Hz), 3.45(2H,q.J=6 Hz), 3.97(2H,t,J=7 Hz), 4.13(2H,t,J=7 Hz), 4.26(2H,t,J=6 Hz), 5.28(1H, brt,J=6 Hz), 6.73 to 8.06(14H,m), 8.26(1H,d,J=2 Hz), 8.42(1H,d, J=2 Hz).

(iii) Synthesis of 5-bromo-3- [N- [3- [2-(1-naphthylcarbamoyloxy)ethyl]carbamoyloxy]propyl-N-phenyl]carbamoyl-1-propylpyridinium chloride(239)

A solution of the compound(238) synthesized in (ii) [1.11 g (1.88 mmol.)] in propyl iodide(10 ml) was stirred at 110° C. for two days. Resulting precipitates were washed with ether to obtain a crude iodide product(1.46 g) as a yellow powder.

The above-mentioned crude product was dissolved in methanol-water(7:3) [20 ml], and the solution was allowed to pass through anion-exchange resin(IRA-410[Cl$^-$])(20 ml). The effluent was concentrated under reduced pressure, and the concentrate was subjected to a silica gel column chromatography, eluting with methanol-chloroform(1:10), to obtain the compound(239) [798 mg (63.5%)] as a yellow powder.

IR(KBr)cm$^{-1}$: 3390(br), 3050, 1710(br), 1650(br), 1590.

NMR(90 MHz,CDCl$_3$) δ: 0.50(3H,m), 1.53(2H,m), 2.73(2H,m), 3.45(2H,m), 4.17(6H,m), 6.70 to 8.74(14H,m), 8.90(1H,br s), 9.04(1H,br s), 9.22(1H,br s).

PRODUCTION EXAMPLE 92

5-Bromo-3- [N-(3-fluorophenyl)-N- [2-[2-(1-naphthylcarbamoyloxy)ethyl]carbamoyloxy]ethyl]carbamoyl-1-propylpyridinium chloride(242)

(i) Synthesis of 2- [2- [(N-t-butoxycarbonyl)-N-(3-fluorophenyl)]aminoethoxycarbonyl]aminoethyl N-(1-naphthyl)carbamate (240)

To a solution of 2-(3-fluoroanilino)ethanol [3.05 g(19.7 mmol.)] in chloroform(30 ml) was added di tert-butyl dicarbonate [4.30 g (19.7 mmol.)], and the mixture was stirred for 3 days at room temperature. The reaction mixture was washed with hydrochloric acid cooled with ice then dried, followed by distilling off the solvent under reduced pressure to obtain a pale yellow oily product(5.46 g).

To a solution of the above-mentioned crude product(5.46 g) and pyridine [3.12 ml(38.6 mmol.)] in chloroform(20 ml) was added dropwise, while stirring under ice-cooling, phenyl chloroformate [2.72 ml(21.7 mmol.)], and the mixture was stirred for 30 minutes at room temperature. The reaction mixture was washed with a 5% aqueous solution of hydrogencarbonate and dried, followed by distilling off the solvent. To the residue was added 2-aminoethyl N-(1-naphthyl)carbamate [4.54 g(19.7 mmol.)], and the mixture was heated at 80° C. for two hours. The reaction mixture was cooled and subjected to a silica gel column chromatography, eluting with hexane-ethyl acetate(4:3), to obtain the compound(240) [1.94 g(23.9%)] as a pale brown oily product.

IR(Neat)cm$^{-1}$: 3310(br), 3060, 1700(br), 1590.

NMR(90 MHz,CDCl$_3$) δ: 1.08(9H,s), 3.40(2H,q,J=6 Hz), 3.81(2H, t,J=6 Hz), 4.22(4H,t,J=6 Hz), 5.15(1H,t,J=6 Hz), 6.67 to 8.07 (13H,m).

(ii) Synthesis of 5-Bromo-3- [N-(3-fluorophenyl)-N- [2-[2-(1-naphthylcarbamoyloxy)ethyl]carbamoyloxy]ethyl]carbamoylpyridine(241)

To a solution of the compound(240) synthesized in (i) [1.05 g (2.55 mmol.)] in methanol(5 ml) was added a 14M hydrogen chloride methanol solution(5 ml), and the mixture was stirred at room temperature for one day. The reaction mixture was rendered alkaline with a 1N aqueous solution of sodium hydroxide and subjected to extraction with chloroform. The organic layer was separated and dried, followed by distilling off the solvent under reduced pressure to obtain a yellow oily product(703 mg).

To a solution of the above-mentioned compound [703 mg(1.71 mmol.)] and triethylamine [0.72 ml(5.17 mmol.)] in chlorofrom (4 ml) was added, while stirring under ice-cooling, 5-bromonicotinic acid chloride hydrochloride [725 mg(2.82 mmol.)], and the mixture was stirred at room temperature for 30 minutes. The reaction mxiture was washed with a saturated aqueous solution of sodium hydrogencarbonate and then dried, followed by distilling off the solvent under reduced pressure. The residue was subjected to a silica gel colum chromatography, eluting with hexane-ethyl acetate (1:2), to obtain the compound (241) [720 mg(47.5% based on 240) as a colorless oily product.

IR(Neat)cm$^{-1}$: 3320(br), 3060, 1720(br), 1650(br), 1600.

NMR(90 MHz, CDCl$_3$) δ: 3.46(2H,m), 3.93 to 4.54(6H,m), 5.22 (1H,m), 6.64 to 8.91(15H,m).

(iii) Synthesis of 5-bromo-3- [N-(3-fluorophenyl-N- [2-[2-(1-naphthylcarbamoyloxy)ethyl]carbamoyloxy]ethyl]carbamoyl-1-propylpyridinium chloride (242)

A solution of the compound(241) synthesized in (ii) [611 mg (1.03 mmol.)] in propyl iodide (5 ml) was stirred at 110° C. for two days. Resulting precipitates were washed with ether to obtain a crude product of iodide(790 mg) as a brown powder.

The above-mentioned crude product was dissolved in methanol-water(7:3), and the solution was allowed to pass through anion-exchange resin(IRA-410[Cl$^-$]) (20 ml). The resulting effluent was concentrated under reduced pressure. The concentrate was subject to s silica gel column chromatography, eluting with methanol-chloroform(1:4), to obtain the compound (242) [529 mg(76.2%)] as a yellow powder.

IR(KBr)cm$^{-1}$: 3390(br), 3240(br), 3050, 1720(br), 1660(br), 1590.

NMR(90 MHz, CDCl$_3$) δ: 0.52(3H,t,J=7 Hz), 1.58(2H,m), 3.48 (2H,m), 4.15(6H,m), 4.55(2H,m) 6.66 to 8.33(13H,m),8.76 (1H,br s), 9.12(1H,br s), 9.80(1H,br s).

PRODUCTION EXAMPLE 93

5-Bromo-3- [N-2-fluorophenyl)-N- [2-[2-(1-naphthylcarbamoyl-oxy)ethyl]carbamoyloxy]ethyl]carbamoyl-1-propylpyridinium chloride(245)

(i) Synthesis of 2- [2- [(N-t-butoxycarbonyl)-N-(2-fluoro-phenyl)]aminoethoxycarbonyl]aminoethyl N-(1-naphthyl)carbamate (243)

To a solution of 2-(2-fluoranilino)ethanol [2.70 g(17.4 mmol.)] in chloroform(30 ml) was added di-tert-butyl dicarbonate [3.80 g (17.4 mmol.)], and the mixture was stirred at room temperature for three days. The reaction mixture was washed with hydrochloric acid cooled with ice, then dried, followed by distilling off the solvent under reduced pressure to obtain a pale yellow oily product (4.99 g).

To a solution of the above-mentioned crude product (4.99 g) and pyridine [2.81 ml(34.7 mmol.)] in chloroform(20 ml). To the solution was added dropwise, while stirring under ice-cooling, phenyl chloroformate [2.40 ml(19.1 mmol.)], and the mixture was stirred at room temperature for 30 minutes. The reaction mixture was washed with a 5% aqueous solution of sodium hydrogen-carbonate, then dried, followed by distilling off the solvent. To the residue was added 2-aminoethyl N-(1-naphthyl) carbamate [4.01 g(17.4 mmol.)], and the mixture was heated at 80° C. for two hours. The reaction mixture was cooled and subjected to a silica gel column chromatography, eluting with hexane-ethyl acetate(4:3) to obtain the compound(243) [998 mg (13.9%)] as a pale brown oily product.

IR(Neat)cm$^{-1}$: 3330(br), 3050, 1710(br), 1590.

NMR(90 MHz, CDCl₃) δ: 1.38(9H,S), 3.40(2H,q,J=6 Hz), 3.84 (2H,t,J=6 Hz), 4.20(4H,t,J=6 Hz), 5.12(1H,br t,J=6 Hz), 6.84 to 8.17(13H,m).

(ii) Synthesis of 5-bromo-3- [N-(2-fluorophenyl)-N- [2-[2-(1-naphthylcarbamoyloxy)ethyl]carbamoyloxy]ethyl]carbamoyl-pyridine(244)

To a solution of the compound (243) was synthesized in (i) [968 mg (2.35 mmol.)] in methanol (5 ml) was added a 14M hydrogen chloride methanol solution(5 ml), and the mixture was stirred at room temperature for one hour. The reaction mixture was rendered alkaline with 1N aqueous solution of sodium hydroxide, followed by extraction with chloroform. The organic layer was separated and dried. The solvent was distilled off under reduced pressure to obtain a yellow oily product(486 mg). To a solution of the above-mentioned compound [486 mg(1.18 mmol.)] and triethylamine [0.50 ml(3.59 mmol.)] in chloroform(2 ml) was added, while stirring under ice-cooling, 5-bromonicotinic acid chloride hydrochloride [501 mg(1.95 mmol.)], and the mixture was stirred at room temperature for 30 minutes. The reaction mixture was washed with a saturated aqueous solution of sodium hydrogencarbonate and dried, followed by distilling off the solvent under reduced pressure. The residue was subjected to a silica gel column chromatography, eluting with hexane-ethyl acetate(1:2) to obtain the compound(244) [190 mg (13.6% based on (243))] as a colorless oily product.

IR(KBr)cm⁻¹: 3410(br), 3050, 1710(br), 1650(br).

NMR(90 MHz,CDCl₃) δ: 3.42(2H,m), 3.80 to 4.54(6H,m), 5.17 (1H,m), 6.66 to 9.14(15H,m).

(iii) Synthesis of 5-bromo-3- [N-(2-fluorophenyl)-N- [2-[2-(1-naphthylcarbamoyloxy)ethyl]carbamoyloxy]ethyl]carbamoyl-1-propylpyridium chloride (245)

A solution of the compound(244) synthesized in (i) [150 mg (0.25 mmol.)] in propyl iodide(5 ml) was stirred at 110° C. for two days. Resulting precipitates were washed with ether to obtain a crude iodide compound(164 mg) as brown powder.

The above-mentioned compound was dissolved in a mixture of methanol-water (7:3)(20 ml), and the solution was allowed to pass through anion-exchange resin-(IRA-410[Cl⁻])(20 ml). The effluent was concentrated under reduced pressure, and the concentrate was subjected to a silica gel column chromatography, eluting with methanol-chlorofrom(1:4), to obtain the compound(245) [102 mg(60.0%)] as a yellow powder.

IR(KBr)cm⁻¹: 3390(br), 3240(br), 3050, 1710(br), 1670(br).

NMR(90 MHz,CDCl₃) δ: 0.48(3H,t,J=7 Hz), 1.53(2H,m), 3.53 (2H,m), 4.30(6H,m), 4.60(2H,m), 6.70 to 8.43(13H,m), 8.70 (1H,br s), 8.80 to 9.30(1H,m), 9.82(1H,br s).

PRODUCTION EXAMPLE 94

5-Bromo-3- [N-(3-methoxyphenyl)-N- [2-[2-(1-naphthylcarbamoyloxy)ethyl]carbamoyloxy]ethyl]carbamoyl-1-propylpyridinium chloride (248)

(i) Synthesis of 5-bromo- [N-(2-hydroxyethyl)-N-(3-methoxyphenyl)]nicotinamide(246)

To a solution of 2-(3-methoxyanilino)ethanol [2.09 g(12.5 mmol.)] and triethylamine [3.48 ml(25.0 mmol.)] in chloroform (25 ml) was added, while stirring under ice-cooling, 5-bromonicotinic acid chloride hydrochloride [3.53 g(13.7 mmol.)], and the mixture was stirred at room temperautre for 10 minutes. The reaction mixture was washed with a 1N aqueous solution of sodium hydroxide and then dried, followed by distilling off the solvent under reduced pressure. The residue was subjected to a silica gel column chromatography, eluting with hexane ethyl acetate(2:1) to obtain the compound(246) [3.03 g(69.0%)] as a pale yellow oily product.

IR(Neat)cm⁻¹: 3410(br), 3060, 1650(br), 1600.

NMR(90 MHz,CDCl₃) δ: 3.72(3H,S), 3.82(2H,q,J=6 Hz), 4.08 (2H,t,J=6 Hz), 6.50 to 6.88(3H,m), 7.00 to 7.40(1H,m), 7.90 (1H,t,J=2 Hz), 8.38(1H,d,J=2 Hz), 8.53(1H,d,J=2 Hz).

(ii) Synthesis of 5-bromo-3- [N-(3-methoxyphenyl)-N- [2- [2-(1-naphthylcarbamoyloxy)ethyl]carbamoyloxy]ethyl]carbamoylpyridine(247)

To a solution of the compound(246) synthesized in (i) [3.55 g (10.1 mmol.)] and pyridine [3.26 ml(40.4 mmol.)] in chloroform (40 ml) was added dropwise, while stirring under ice-cooling, phenyl chloroformate [2.78 ml(22.2 mmol.)], and the mixutre was stirred at rcom temperature for 30 minutes. The reaction mixture was washed with a 5% aqueous solution of sodium hydrogencarbonate and the'n dried, followed by distilling off the solvent. To the residue was added 2-(1-naphthyl)-carbamoyloxyethylamine [2.33 g(10.1 mmol.)], and the mixture was heated at 80° C. for two hours. The reaction mixture was cooled and subjected to a silica gel column chromatography, eluting with hexane-ethyl acetate(3:4), to obtain the compound(247) [2.65 g (43.2%)] as a pale yellow oily product.

IR(Neat)cm⁻¹: 3320(br), 3060, 3010, 1720(br), 1650, 1600.

NMR(90 MHz,CDCl₃) δ: 3.43(2H,m), 3.66(3H,s), 3.97 to 4.57 (6H,m), 5.40(1H,m), 6.32 to 8.08(13H,m), 8.34(1H,d,J=2 Hz), 8.45(1H,d,J=2 Hz).

(iii) Synthesis of 5-bromo-3- [N-(3-methoxyphenyl)-N- [2- [2-(1-naphthylcarbamoyloxy)ethyl]carbamoyloxy]ethyl]carbamoyl-1-propylpyridinium chloride (248)

A solution of the compound(247) synthesized in (ii) [2.65 g (4.36 mmol.)] in propyl iodide(20 ml) was stirred at 120° C. for two days. Resulting precipitates were washed with ether to give a crude iodide compound (3.49 g) as a yellow powder.

The above-mentioned crude product was dissolve in a mixture of methanol-water(7:3)(80 ml), and the solution was allowed to pass through anion-exchange resin-(IRA-410[C⁻]) [80 ml]. The effluent was concentrated under reduced pressure, and the concentrate was subjected to a silica gel column chromatography, eluting with methanol-chloroform(3:5) to obtain the compound (248) [1.38 g(46.1%)] as a yellow powder.

IR(KBr)cm⁻¹: 3410(br), 3270(br), 3050, 3010, 1710(br), 1660(br), 1600.

NMR(90 MHz,CDCl₃) δ: 0.49(3H,t,J=7 Hz), 1.56(2H,m), 3.47 (2H,m), 3.70(3H,S), 4.17(6H,m), 4.53(2H,m), 6.33 to 8.33(13H, m), 8.80(1H,br s), 9.10(1H,br s), 9.72(1H,br s).

PRODUCTION EXAMPLE 95

5-Bromo-3- [N-(3-bromophenyl)-N- [2-[2-(1-naphthylcarbamoyloxy)ethyl]carbamoyloxy]ethyl]carbamoyl-1-propylpyridinium chloride(251)

(i) Synthesis of 2- [N-(3-bromophenyl)-N-(t-butoxycarbonyl)]aminoethanol (249)

To a solution of 2-(3-bromoanilino)ethanol [3.10 g(14.3 mmol.)] in chloroform(28 ml) was added di-tert-butyl dicarbonate [3.12 g(14.3mmol.)]. The mixture was stirred at room temperature for three days and at 50° C. for one day. The solvent was distilled off under reduced pressure, and the residue was subjected to a silica gel column chromatography, eluting with hexane-ethyl acetate(2:1), to obtain the compound (249) [2.72 g(60.0%)] as a colorless oily product.

IR(Neat)cm$^{-1}$: 3450(br), 3060, 1700(br), 1590.

NMR(90 MHz,CDCl$_3$) δ: 1.42(9H,S), 3.72(4H,br s), 6.97 to 7.50(4H,m).

(ii) Synthesis of 5-bromo-3- [N-(3-bromophenyl)-N- [2-[2-(1-naphthylcarbamoyloxy)ethyl]carbamoyloxy]ethyl]carbamoyl pyridine(250)

To a solution of the compound(249) synthesized in (i) [2.70 (8.54 mmol.)] and pyridine [2.76 ml(34.2 mmol.)] in chloroform (17 ml) was added dropwise, while stirring under ice-cooling, phenyl chloroformate [2.36 ml(18.8 mmol.)], and the mixture was stirred at room temperature for 30 minutes. The reaction mixture was washed with a 5% aqueous solution of sodium hydrogencarbonate and then dried, followed by distilling off the solvent. To the residue was added 2-aminoethyl N-(1-naphthyl)carbamate [1.97 g(8.54 mmol.)], and the mixture was heated at 80° C. for two hours. The reaction mixture was cooled and subjected to a silica gel column chromatography, eluting with hexane-ethyl acetate(3:4), to obtain a yellow oily product(3.02 g).

To a solution of the above-mentioned crude product [2.79 g (4.87 mmol.)] in methanol(10 ml) was added 14M hydrogen chloride methanol solution(10 ml), and the mixture was stirred at room temperature for one hour. The solvent was distilled off, and the residue was processed with a 1N aqueous solution of sodium hydroxide, followed by extraction with ethyl acetate. The organic layer was separated and dried, then the solvent was distilled off under reduced pressure to obtain a pale yellow oily prodcut(2.12 g).

To a solution of the above-mentioned compound [2.11 g(4.47 mmol.)] and triethylamine [1.87 ml(13.4 mmol.)] in chloroform (20 ml) was added, while stirring under ice-cooling, 5-bromonicotinic acid chloride hydrochloride [1.72 g(6.70 mmol.)], and the mixture was stirred at room temperature for 30 minutes. The reaction mixture was washed with a 1N aqueous solution of sodium hydroxide, which was then dried, followed by distilling off the solvent under reduced pressure. The residue was subjected to a silica gel column chromatography, eluting with hexane-ethyl acetate(1:1), to obtain the compound(250) [1.37 g(46.7% based on (240))] as a pale yellow oily product.

IR(KBr)cm$^{-1}$: 3320(br), 3060, 1720(br), 1650(br), 1590.

NMR(90 MHz,CDCl$_3$) δ: 3.47(2H,m), 3.80 to 4.50(6H,m), 5.34 (1H,m), 6.77 to 8.00(13H,m), 8.32(1H,br s), 8.50(1H,br s).

(iii) Synthesis of 5-bromo-3- [N-(3-bromophenyl)-N- [2-[2-(1-naphthylcarbamoyloxy)ethyl]carbamoyloxy]ethyl]carbamoyl-1-propylpyridinium chloride(251)

A solution of the compound(250) synthesized in (ii) [1.33 g (2.03 mmol.)] in propyl iodide(10 ml) was stirred at 120° C. for two days. Resulting precipitates were washed with ether to obtain a crude iodide(1.75 g) as a yellow powder.

The above-mentioned crude prodcut was dissolved in a mixture of methanol-water(7:3)(40 ml), and the solution was allowed to pass through anion-exchange resin-(IRA-410[Cl$^-$])(40 ml). The effluent was concentrated under reduced pressure, and the concentrate was subjected to a silica gel column chromatography, eluting with methanol-chloroform(1:8), to obtain the compound(251) [437 mg(29.3%)] as a yellow powder.

IR(KBr)cm$^{-1}$: 3400(br), 3240(br), 3050, 1710(br), 1660(br), 1590.

MNR(90 MHz,CDCl$_3$) δ: 0.48(3H,t,J=7 Hz), 1.52(2H,m), 3.44 (2H,m), 4.19(6H,m), 4.50(2H,m), 6.80 to 8.44(13H,m), 6.74 (1H,br s), 9.00(1H,br s), 9.78(1H,br s).

PRODUCTION EXAMPLE 96

5-Bromo-3- [N- [3- [N-[2-(1-naphthylcarbamoyloxy)ethyl]-N-benzoyl]amino]-propyl-N-phenyl]carbamoyl-1-propylpyridinium chloride(258)

(i) Synthesis of tert-butyl N- [2-(2-hydroxyethylcarbamoyl)ethyl]-N-phenylcarbamate(252)

To a solution of the compound(232) synthesized in Production Example 90-(i) [5.30 g(20.0 mmol.)] in chloroform(160 ml) was added a solution of dicyclohexylcarbodiimide [4.12 g(20.0 mmol.)] in chloroform(40 ml), and the mixture was stirred at room temperature for 30 minutes. To the mixture was added, while stirring under ice-cooling, monoethanolamine [1.22 g(20.0 mmol.)], and ir was stirred at room temperature for one hour. Resulting precipitates were separated, and the filtrate was concentrated under reduced pressure. The concentrate was subjected to a silica gel column chromatography, eluting with ethyl acetate, to obtain the compound(252) [5.37 g(87.1 %)] as a pale yellow oily product.

IR(Neat)cm$^{-1}$: 3170(br), 3070, 1700(br), 1670(br), 1600.

NMR(90 MHz,CDCl$_3$) δ: 1.37(9H,S), 2.41(2H,t,J=7 Hz), 3.27 (2H,q,J=5 Hz), 3.58(2H,q,J=5 Hz), 3.88(2H,t,J=7 Hz), 6.88(1H, brt,J=5 Hz), 7.00 to 7.44(5H,m).

(ii) Synthesis of t-butyl N- [3-(2-hydroxyethylamino)]propyl-N-phenyl carbamate(253)

To a solution of the compound(252) synthesized in (i) [5.02 g (16.3 mmol.)] in anhydrous tetrahydrofuran(100 ml) was added, while stirring under ice-cooling, a solution of diborane in 1M tetrahydrofuran [23.2 ml(23.2 mmol.)]. The reaction mixture was heated under reflux for 4 hours, and there was added 1N hydrochloric acid cooled with ice, and the aqueous layer was washed with ethyl acetate. The aqueous layer was made alkaline by the addition of 1N aqueous solution of sodium hydroxide, followed by extraction with ethyl acetate. The extract was dried, then the solvent was distilled off to obtain the compound(253) [2.53 g(52.8%)] as a pale yellow oily product.

IR(Neat)cm$^{-1}$: 3310(br), 3070, 1700(br), 1600.

NMR(90 MHz, CDCl$_3$) δ: 1.40(9H,S), 1.69(2H,quint.,J=7 Hz), 2.63(2H,t,J=7 Hz). 2.70(2H,t,J=5 Hz), 3.60(2H,t,J=5 Hz), 3.69 (2H,t,J=7 Hz), 7.03 to 7.47(5H,m).

(iii) Synthesis of t-butyl [N- [3- [N-(2-hydroxyethyl)-N-benzoyl]amino]propyl-N-phenyl]carbamate(254)

To a solution of the compound(253) synthesized in (ii) [1.19 g (40.4 mmol.)] and triethylamine [0.62 ml(4.44 mmol)] in dichloromethane(8 ml) was added, while stirring under ice-cooling, benzoyl chloride [0.47 ml(4.04 mmol.)], and the mixture was stirred at room temperature for one hour. The reaction mixture was washed with a 1N aqueous solution of sodium hydroxide, and then dried, followed by distilling off the solvent under reduced pressure. The residue was subjected to a silica gel column chromatography, eluting with hexaneethyl acetate (1:5), to obtain the compound(254) [825 mg(51.2%)] as a pale yellow oily product.

IR(Neat)cm$^{-1}$: 3410(br), 3060, 1700(br), 1630(br), 1610.

NMR(90 MHz,CDCl$_3$) δ: 1.24(9H,S), 1.79(2H,m), 2.90 to 3.8 (8H,m), 6.67 to 7.53(10H,m).

(iv) Synthesis of t-butyl [N- [3- [N- [2-(1-naphthylcarbamoyloxy)ethyl]-N-benzoyl]amino]propyl-N-phenyl]-carbamate(255)

To a solution of the compound(254) synthesized in (iii) [446 mg(1.12 mmol.)] in pyridine(4 ml) was added 1-naphthylisocyanate [0.25 ml(1.76 mmol.)], and the mixture was stirred for one hour. To the reaction mixture was added chloroform, which was washed with 1N hydrochloric acid cooled with ice. The resultant was dried, and the solvent was distilled off under reduced pressure. The residue was subjected to a silica gel column chromatography, eluting with hexane-ethyl acetate (1:1), to obtain the compound(255) [501 mg(78.9%)] as a pale yellow oily product.

IR(Neat)cm$^{-1}$: 3290(br), 3060, 1730(br), 1690(br), 1630 (br), 1600.

NMR(90 MHz,CDCl$_3$) δ: 1.30(9H,S), 1.81(2H,m), 3.10 to 3.90 (6H,m), 4.35(2H, m), 6.67 to 8.08(18H,m).

(v) Synthesis of 2- [N-(3-anilinopropyl)-N-benzoyl-]aminoethyl N-(1-naphthyl)carbamate (256)

To a solution of the compound(255) synthesized in (iv) [451 mg(0.79 mmol.)] in methanol(4 ml) was added a 14M hydrogen chloride methanol solution(4 ml). The solution was stirred at room temperature all the night through. The solvent was distilled off, and the residue was processed with a 1N aqueous solution of sodium hydroxide, followed by extraction with ethyl acetate. The organic layer was separated and dried. The solvent was distilled off under reduced pressure to obtain the compound(256) [337 mg(91.2%)] as a yellow oily product.

IR(Neat)cm$^{-1}$: 3310(br), 3270(br), 3050, 1720(br), 1620(br), 1600.

NMR(90 MHz;CDCl$_3$) δ: 1.78(2H,m), 2.96(2H,m), 3.43(2H,m), 3.64(2H,m), 4.33(2H,m), 6.18 to 8.00(18H,m).

(vi) Synthesis of 5-bromo-3- [N- [3- [2-(1-naphthylcarbamoyloxy)ethyl-N-benzoyl]amino]propyl-N-phenyl]-carbamoylpyridine (257)

To a solution of the compound(256) [256 mg(0.55 mmol)] and triethylamine [0.15 ml(1.10 mmol.)] in chloroform (4ml) was added, while stirring under ice-cooling, 5-bromonicotinic acid chloride hydrochloride [155 mg(0.61 mmol.)]. The mixture was stirred at room temperature for 30 minutes. The reaction mixture was washed with a 1N aqueous solution of sodium hydroxide, which was then dried, followed by distilling off the solvent under reduced pressure. The residue was subjeted to a silica gel column chromatography, eluting with hexane-ethyl acetate (1:2), to obtain the compound(257) [303 mg(84.9% based on (255))] as a pale yellow oily product.

IR(Neat)cm$^{-1}$: 3280(br), 3060, 1730(br), 1640(br), 1600.

NMR(90 MHz,CDCl$_3$) δ: 1.98(2H,m), 3.70(6H,m), 4.37(2H,m), 6.60 to 8.09(19H,m), 8.18(1H,br s), 8.44(1H,d,J=2 Hz).

(vii) Synthesis of 5-bromo-3- [N- [3- [N- [2-(1-naphthylcarbamoyloxy)ethyl]-N-benzoyl]amino]propyl-N-phenyl]carbamoyl-1-propylpyridinium chloride(258)

A solution of the compound(257) synthesized in (vi) [226 mg (0.35 mmol.)] in propyl iodide(5 ml) was stirred at 120° C. for two days. Resulting precipitates were washed with ether to obtain a crude iodide compound(283 mg) as a brown powder. The above-mentioned crude product was dissolved in a mixture of methanol-water(7:3)(20 ml), and the solution was allowed to pass through anion-exchange resin(IRA-410[Cl$^-$])(20 ml). The effluent was concentrated under reduced pressure, and the concentrate was subjected to a silica gel column chromatography, eluting with methanol-chloroform(1:4), to obtain the compound(258) [102 mg(39.9%)] as a pale yellow oily product.

IR(Neat)cm$^{-1}$: 3370(br), 3040, 1720(br), 1650(br), 1590.

MNR(90 MHz,CDCl$_3$) δ: 0.66(3H,t,J=7 Hz), 1.44 to 2.24(2H,m), 2.95(2H,m), 3.17(2H,m), 3.70 to 4.30(2H,m), 4.50(2H,m), 4.81 (2H,m), 7.00 to 8.14(18H,m), 8.40(1H,br s), 9.32(1H,br s), 9.73 (1H,br s).

PRODUCTION EXAMPLE 97

5-Bromo-3- [N- [2-[2-(1-naphthylcarbamoyloxy)ethyl]carbamoyl]ethyl-N-(3-chlorophenyl)]carbamoyl-1-propylpyridiniun chloride (262)

(i) 3- [N-t-Butoxycarbonyl-N-(m-chlorophenyl)]aminopropionic acid

In dichloromethane(200 ml) were dissolved 3-(m-chloroanilino)propionic acid(11.1 g) and di-t-butyl dicarbonate(14 g). The solution was heated under reflux for 4 days, and the reaction mixture was concentrated. The concentrate was purified by means of a silica gel chromatography(silica gel: 300 g ; developing solvent-:ethyl acetate) to obtain the object compound as an oily product.

IR(Neat cm$^{-1}$: 2960, 1680, 1585, 1360, 1140.

(ii) Synthesis of 2- [3- [N-t-butoxycarbonyl-N-(3-chlorophenyl)]aminopropaneamido]ethyl N-(1-naphthyl)carbamate(260)

To a solution of the compound(259) synthesized in (i) [1.02 g (4.41 mmol.)] in chloroform(20 ml) was added a solution of dicyclohexyl carbodiimide [1.00 g(4.85 mmol.)] in chloroform (10 ml), and the mixture wa stirred at room temperature for 30 minutes. To the reaction mixture was added 2-aminoethyl N-1-naphthyl carbamate [1.32 g(4.40 mmol.)], which was stirred for 30 minutes at room temperature. Resulting precipitates were filtered off, and the filtrate was concentrated under reduced pressure. The concentrate was subjected to a silica gel column chromatography, eluting with hexane ethyl acetate(1:2) to obtain the compound(260) [1.88 g(82.9%)] as a pale yellow oily product.

IR(Neat)cm$^{-1}$: 3320(br), 3060, 1700(br), 1660(br), 1600.

NMR(90 MHz,CDCl$_3$) δ: 1.48(9H,S), 2.42(2H,t,J=7 Hz), 3.48 (2H,t,J=6 Hz), 3.89(2H,t,J=7 Hz), 4.23(2H,t,J=6 Hz), 6.53(1H,m), 6.90 to 8.07(12H,m).

(iii) Synthesis of 5-bromo-3- [N-(3-chlorophenyl)-N- [2-[2-(1-naphthylcarbamoyloxy)ethyl]carbamoyl]ethyl]-carbamoylpyridine (261)

To a solution of the compound(260) synthesized in (ii) [1.81 g (3.54 mmol.)] in methanol(10 ml) was added a 14M hydrogen chlororide methanol solution(10 ml), and the mixture was stirred at room temperature for two hours. The solvent was distilled off, and the residue was processed with a 1N aqueous solution of sodium hydroxide, followed by extraction with ethyl acetate. The organic layer was separated and dried, then the solvent was distilled off under reduced pressure to obtain a pale yellow oily product(1.46 g).

To a solution of the above-mentioned compound [1.46 g(3.54 mmol.)] and triethylamine [1.98 ml(14.2 mmol.)] in chloroform (40 ml) was added, while stirring under ice-cooling, 5-bromonicotinic acid chloride hydrochloride [2.00 g(7.78 mmol.)]. The mixture was stirred at room temperature for 30 minutes. The reaction mixture was washed with a 1N aqueous solution of sodium hydroxide and dried, followed by distilling off the solvent under reduced pressure. The crystals thus obtained were washed with ether to obtain the compound(261) [1.57 g (74.5% based on (258))] as a colorless powder.

IR(KBr)cm$^{-1}$: 3250(br), 3090, 1720, 1650(br), 1590.

NMR(90 MHz,CDCl$_3$) δ: 2.48(2H,t,J=7 Hz), 3.57(2H,q,J=6 Hz), 4.18(2H,t,J=7 Hz), 4.35(2H,t,J=6 Hz), 6.50(1H,m), 6.73 to 8.06 (13H,m), 8.34(1H,br s 8.51(1H,br s).

(iv) Synthesis of 5-bromo-3- [N- [2-(1-naphthylcarbamoyloxy)ethyl]carbamoyl]ethyl-N-(3-chlorophenyl)-]carbamoyl-1-propyl pyridinium chloride(262)

A solution of the compound(261) synthesized in (iii) [1.50 g (2.52 mmol.)] in propyl iodide(10 ml) was stirred at 110° C. for two days. Resulting precipitates were washed with ether to obtain a crude iodide compound(2.27 g) as yellow powder. The above-mentioned crude product was dissolved in a mixture of methanol-water(7:3)(20 ml), and the solution was allowed to pass through anion-exchange resin(IRA-410[Cl$^-$])(20 ml). The effluent was concentrated under reduced pressure, and the concentrate was subjected to a silica gel column chromatography, eluting with methanol-chloroform(1:8) to obtain the compound(262) [814 mg(47.9%)] as a yellow powder.

IR(KBr)cm$^{-1}$: 3400(br), 3250(br), 3050, 1720(br), 1660(br), 1590.

NMR(90 MHz,CDCl$_3$) δ: 0.48(3H,t,J=7 Hz), 1.47(2H,m), 2.75 (2H,m), 3.47(2H,m), 4.18(6H,m), 6.34 to 8.96(15H,m), 9.76 (1H,br s).

PRODUCTION EXAMPLE 98

5-Bromo-3- [N- [2- [2-(2-naphthylsulfonamidoethyl]carbamoyl]ethyl-N-phenyl]carbamoyl-1-propylpyridinium chloride (267)

(i) Synthesis of 2-(2-naphthylsulfonamido)ethylamine(263)

In dichloromethane(200 ml) was dissolved ethylenediamine [4.8 g(80 mmol.)]. To the solution was added, while stirring under ice-cooling, 2-naphthylsulfonyl chloride [4.52 g(20 mmol.)]. The mixture was stirred for one hour under ice-cooling and for one further hour at room temperature. To the reaction mixture was added dilute hydrochloric acid to make it acid, and the aqueous layer was separated. A small amount of insolubles was filtered off, and the filtrate was washed with dichloromethane, which was neutralized with conc. ammonia water. Thus-neutralized solution was subjected to extraction with dichloromethane, and the dichloromethane layer was dried over anhydrous sodium sulfate, followed by concentration. To the concentrate was added ether(100 ml) to obtain the object compound (263) as crystals, m.p. 125° to 126° C.

Elemental Analysis for C$_{12}$H$_{14}$N$_2$O$_2$S: Calcd.: C, 57.58, H, 5.61, N, 11.19. Found: C, 57.54, H, 5.57, N, 11.17.

(ii) Synthesis of t-butyl N- [2- [2-(2-naphthylsulfonamido)ethyl carbamoyl]ethyl]-N-phenyl carbamate (264)

To a solution of the compound(232) synthesized in Production Example 90-(i) in chloroform(20 ml) was added dicyclohexylcarbodiimide [1.13 g(5.50 mmol.)] dissolved in chloroform(10 ml), and the mixture was stirred for 30 minutes at room temperature. To the reaction mixture was added the compound(263) synthesized in (i) [1.25 g(5.00 mmol.)], and the mixture was stirred for 30 minutes at room temperature. Resulting precipitates were filtered off, and the filtrate was concentrated under reduced pressure. The cc,ncentrate was was subjected to a silica gel column chromatography, eluting with hexane-ethyl acetate (1:2) to obtain the compound(264) [1.81 g(72.8%)] as a yellow oily product.

IR(Neat)cm$^{-1}$: 3320(br), 3060, 1680(br), 1600, 1330(br), 1160(br).

NMR(90 MHz,CDCl$_3$) δ: 1.34(9H,S), 2.47(2H,t,J=7 Hz), 3.07 (2H,q,J=6 Hz), 3.30(2H,q,J=6 Hz), 3.86(2H,t,J=7 Hz), 6.07(1H, brt,J=6 Hz), 6.68(1H,brt,J=6 Hz), 7.00 to 8.10(11H,m), 8.43 (1H,br s).

(iii) Synthesis of N- [2-(2-naphthylsulfonamido)ethyl]-3-anilinopropionamide(265)

To a solution of the compound(264) synthesized in (ii) [1.80 g(3.62 mmol.)] in methanol(6 ml) was added a 14M hydrogen chloride methanol solution(6 ml), and the mixture was stirred for one hour at room temperature. The reaction mixture was made alkaline with a 1N aqueous solution of sodium hydroxide, followed by extraction with ethyl acetate. The organic layer was separated and dried, then the solvent was distilled off under reduced pressure to obtain the compound(265) [1.30 g (90.4%)] as a colorless powder.

IR(KBr)cm$^{-1}$: 3390, 3260(br), 3070, 1650, 1600, 1320, 1150.

NMR(90 MHz,CDCl$_3$) δ: 2.43(2H,t,J=7 Hz), 3.05(2H,m), 3.35 (4H,q,J=6 Hz), 6.34 to 8.16(13H,m), 8.43(1H, br S).

(iv) Synthesis of 5-bromo-3- [N- [2- [2-(2-naphthylsulfonamido)ethyl]carbamoyl]ethyl-N-phenyl]carbamoyl-pyridine(266)

To a solution of the compound synthesized in (ii) [1.29 g (3.25 mmol.)] and triethylamine [1.55 ml( 11.1 mmol.)] in chloroform(15 ml) was added, while stirring under ice-cooling, 5-bromonicotinic acid chloride hydrochloride [1.42 g(5.53 mmol.)]. The mixture was stirred at room temperature for 15 minutes. The reaction mixture was washed with a 1N aqueous solution of sodium hydroxide, and dried, followed by distilling off the solvent under reduced pressure. The residue was subjected to a silica gel column chromatography, eluting with hexane ethyl acetate(1:10) to obtain the compound(266) [595 mg(31.5%)] as a pale yellow oily product.

IR(Neat)cm$^{-1}$: 3280(br), 3060, 1650(br), 1590, 1330(br), 1150.

NMR(90 MHz,CDCl$_3$) δ: 2.53(2H,t,J=7 Hz), 3.12(2H,q,J=6 Hz), 3.38(2H,q,J=6 Hz), 4.20(2H,t,J=7 Hz), 6.37(1H,t,J=6 Hz), 6.86 to 8.68(16H,m).

(v) Synthesis of 5-bromo-3- [N- [2- [2-(2-naphthylsulfonamide)ethyl]carbamoyl]ethyl-N-phenyl]carbamoyl-1-propylpyridinium 7 chloride(267)

A solution of the compound(266) synthesized in (iv) [565 mg (0.97 mmol.)] in propyl iodide(10 ml) was stirred at 110° C. for 3 days. Resulting precipitates were washed with ether to obtain a crude iodide product(533 mg) as a pale yellow powder.

The above-mentioned crude product was dissolved in a mixture of methanol-water(7:3)(100 ml), to which was added anion-exchange resin(IRA-410[Cl$^-$])(100 ml), and the mixture was stirred for 4 hours. The resin was filtered off. The filtrate was concentrated under reduced pressure. The concentrate was subjected to a silica gel column chromatography, eluting with methanolchlorofrom(1:3), to obtain the compound(267) [533 mg(83.1%)] as pale yellow powder.

IR(KBr)cm$^{-1}$: 3390(br), 3250(br), 3060(br), 1650(br), 1590, 1320(br), 1150.

NMR(90 MHz,CDCl$_3$) δ: 0.72(3H,t,J=7 Hz), 1.82(2H, sext,J=7 Hz), 2.69(2H,m), 3.07(2H,m), 3.23(2H,m), 4.17(2H,m), 4.82(2H,brt, J=7 Hz), 6.68 to 8.67(15H,m), 9.38(1H,brs), 9.68(1H,brs).

PRODUCTION EXAMPLE 99

5-Bromo-3- [N- [2- [2-(2-napthylsulfonamido)ethyl]carbamoyloxy]ethyl-N-phenyl]carbamoyl-1-propylpyridinium chloride (269)

(i) Synthesis of 5-bromo-3- [N- [2- [2-(2-naphthylsulfonamido)ethyl]carbamoyloxy]ethyl-N-phenyl]carbamoyl pyridine(268)

A solution of the carbonate compound [882 mg (2.00 m mol)], which was prepared by the same procedure as described in Production Example 6-(ii) from phenyl chlorocarbonate, pyridine and the alcohol compound synthesized in Production Example 6-(i), and the compound (263) synthesized in Production Example 98-(i) [500 mg (2.00 mmol)] in pyridine (4 ml) was heated for 3 hours at 120° C., then the solvent was distilled off. The residue was subjected to a silica gel column chromatography, eluting with hexane-ethyl acetate(1:2), to obtain the compound(268) [820 mg(43.3%)] as a pale yellow oily product IR(KBr)cm$^{-1}$: 3250(br), 3060, 1720(br), 1640(br), 1590, 1320(br), 1150(br).

NMR(90 MHz,CDCl$_3$) δ: 3.19(4H,m), 4.18(4H,m), 5.47(1H,brt, J=6 Hz), 6.19(1H,brt,J=6 Hz), 6.94 to 8.13(14H,m), 8.35(1H,br s), 8.43(1H,br s), 8.49(1H,br s).

(ii) Synthesis of 5-bromo-3- [N- [2- [2-(2-naphthylsulfonamido)ethyl]carbamoyloxy]ethyl-N-phenyl]carbamoyl-1-propylpyridinium chloride(269)

A solution of the compound(268) synthesized in (i) [80 mg (1.34 mmol.)] in propyl iodide(10 ml) was stirred at 120° C. for two days. Resulting precipitates were washed with ether to obtain a crude iodide compound(1.00 g) as a yellow powder.

The above crude product was dissolved in a mixture of methanol-water(7:3), to which was added anion-exchange resin (IRA-410[Cl$^-$])(100 ml), and the mixture was stirred. The resin was filtered off, and the filtrate was concentrated under reduced pressure The concentrate was subjected to a silica gel column chromatography, eluting with methanolchloroform(1:7), to obtain the compound(269) [708 mg(78.2%)] as a yellow powder.

IR(KBr)cm$^{-1}$: 3390(br), 3230(br), 3050(br), 1710(br), 1660(br), 1590, 1320(br), 1160.

NMR(90 MHz,CDCl$_3$) δ: 0.80(3H,t,J=7 Hz), 1.90(2H,sext.,J=7 Hz), 3.19(4H,brs), 4.14(4H,br s), 4.98(2H,t,J=7 Hz), 7.00 to 8.53 (14H,m), 8.50(1H,brs), 9.30(1H,br s), 9.86(1H,br s).

PRODUCTION EXAMPLE 100

5-Bromo-3- [N- [2- [2-(1-naphthylcarbamoyloxy)ethyl]aminosulfonyl]ethyl-N-phenyl]carbamoyl-1-propylpyridinium chloride (273)

(i) Synthesis of 2-(vinyl sulfonamido)ethyl N-(1-naphthyl)carbamate

To a solution of 2-aminoethyl N-(1-naphthyl)carbamate [2.30 g(10.0 mmol.)] and triethylamine [1.53 ml(11.0 mmol.)] in chloroform(20 ml) was added, while stirring under ice-cooling, 2-chloroethanesulfonyl chloride [1.06 ml(10.0 mmol.)]. The mixture was stirred for 30 minutes under ice-cooling. The reaction mixture was washed with a 1N aqueous solution of sodium hydroxide, and dried, followed by distilling off the solvent under reduced pressure. The residue was subjected to a silica gel colum chromatography, eluting with hexane-ethyl acetate(1:1) to obtain the compound(270) [1.50 g(46.9%)] as a yellow oily product.

IR(Neat)cm$^{-1}$: 3300(br), 3050, 1710(br), 1590, 1330(br), 1130(br).

NMR(90 MHz,CDCl$_3$) δ: 3.22(2H,q,J=6 Hz), 4.24(2H,t,J=6 Hz), 5.44(1H,brt,J=6 Hz), 5.79(1H,d,J=10 Hz), 6.13(1H,d,J=16 Hz), 6.44(1H,dd,J=10,16 Hz), 7.14 to 8.04(8H,m).

(ii) Synthesis of 2-(2-anilinoethylsulfonamido)ethyl N-(1-naphthyl)carbamate(271)

A mixture of the compound(270) synthesized in (i) [1.46 g (4.56 mmol.)] and aniline [0.75 g(8.18 mmol.)] was heated at 120° C. for 15 hours. The reaction mixture was cooled, then resulting crude product was purified by means of a silica gel column chromatography, eluting with hexane-ethyl acetate (1:1), to obtain the compound(271) [970 mg(51.6%)] as a pale brown powder.

IR(KBr)cm$^{-1}$: 3390, 3370(br), 3310(br), 3050, 1710(br), 1600, 1320(br), 1130(br).

NMR(90 MHz,DMSO-d$^6$) δ: 3.30(6H,m), 4.16(2H,t,J=6 Hz), 5.60 (1H,m), 6.37 to 6.80(3H,m), 7.13(2H,t,J=8 Hz), 7.23 to 8.24 (7H,m), 9.55(1H,br s).

(iii) Synthesis of 5-bromo-3- [N- [2- [2-(1-naphtylcarbamoyloxy)ethyl]aminosulfonyl]ethyl-N-phenyl]carbamoylpyridine (272)

To a solution of the compound(271) synthesized in (ii) [315 mg (0.76 mmol.)] and triethylamine [0.42 ml(3.04 mmol.)] in chloroform(6 ml) was added, while stirring under ice-cooling, 5-bromonicotinic acid chloride hydrochloride [392 mg(1.52 mmol.)]. The mixture was stirred at room temperature for 30 minutes. The reaction mixture was washed with a saturated aqueous solution of sodium hydrogencarbonate, then dried, followed by distilling off the solvent under reduced pressure. The residue was subjected to a silica gel column chromatography, eluting with hexane-ethyl acetate(1:1), to obtain the compound(272) [380 mg(83.5%)] as a colorless oily product.

IR KBr)cm$^{-1}$: 3300(br), 3060, 1730(br), 1640(br), 1590, 1320(br), 1130(br).

NMR(90 MHz,CDCl$_3$) δ: 3.39(2H,t,J=7 Hz), 3.50(2H,q,J=6 Hz), 4.34(2H,t,J=7 Hz), 4.40(2H,t,J=6 Hz), 6.00(1H,t,J=6 Hz), 6.90 to 8.07(14H,m), 8.25(1H,d,J=2 Hz), 8.48(1H,d,J=2 Hz).

(iv) Synthesis of 5-bromo-3- [N- [2- [2-(1-naphthylcarbamoyloxy)ethyl]aminosulfonyl]ethyl-N-phenyl]carbamoyl-1-propylpyridinium chloride (273)

A solution of the compound(272) synthesized in (ii) [380 mg (0.64 mmol.)] in propyl iodide(10 ml) was stirred at 110° C. for two days. Resulting precipitates were washed with ether to obtain a crude iodide compound(525 mg) as a brown powder.

The above-mentioned crude product was dissolved in a mixture of methanol-water(7:3)(20 ml). To the solution was added anion-exchange resin(IRA-410[Cl−])(40 ml), and the mixture was stirred for 4 hours. The resin was filtered off, and the filtrate was concentrated under reduced pressure. The concentrate was subjected to a silica gel column chromatography, eluting with methanol-chloroform(1:10), to obtain the compound (273) [333 mg(77.5%)] as a yellow powder.

IR(KBr)cm$^{-1}$: 3390(br), 3300(br), 3050, 1720(br), 1650(br), 1590, 1320(br), 1130(br).

NMR(90 MHz,CDCl$_3$) δ: 0.66(3H,m), 1.27(2H,m), 3.44(4H,m), 4.30(6H,m), 6.20 to 8.68(17H,m).

PRIODUCTION EXAMPLE 101

5-Bromo-3- [N- [2-[3-(1-naphthylcarbamoyl)propionyl]amino]ethyl-N-phenyl]carbamoyl-1-propylpyridinium chloride (279)

(i) Synthesis of t-butyl N-(2-anilinoethyl)carbamate(274)

To a solution of N-phenylethylenediamine [10.3 g(75.4 mmol.)] in chloroform(120 ml) was added di-tert-butyl dicarbonate [16.5 g(75.4 mmol.)], and the mixture was stirred for two hours at room temperature. The solvent was distilled off to leave a powdery product, which was washed with hexane and dried to obtain the compound(274) [17.3 g(97.0%)] as pale yellow powder.

IR(KBr)cm$^{-1}$: 3390(br), 1680(br), 1610.

NMR(90 MHz,CDCl$_3$) δ: 1.50(9H,s), 3.25(2H,m), 3.71(2H,m), 4.90(1H,m), 6.47 to 7.33(5H,m).

(ii) Synthesis of 3-bromo-5- [N- [2-(t-butoxycarbonylamino)ethyl]-N-phenyl]carbamoylpyridine(275)

To a solution of the compound(274) synthesized in (i) [9.45 g (40.0 mmol.)] and triethylamine [11.6 ml(80.0 mmol.)] in chloroform(80 ml) was added, while stirring under ice-cooling, 5-bromonicotinic acid chloride hydrochloride [10.3 g(40.0 mmol.)]. The mixture was stirred at room temperature for 30 minutes. The reaction mixture was washed with a 1N aqueous solution of sodium hydroxide, then dried, followed by distilling off the solvent under reduced pressure. The residue wa subjected to a silica gel column chromatography, eluting with hexane-ethyl acetate(1:1) to obtain the compound(275) [13.8 g (82.1%)] as colorless powder.

IR(KBr)cm$^{-1}$: 3270(br), 1700(br), 1650, 1600.

NMR(90 MHz,CDCl$_3$) δ: 1.40(9H,s), 3.42(2H,m), 4.02(2H,t, J=7 Hz), 5.05(1H,m, 6.98 to 7.44(5H,m), 7.83(1H,t,J=2 Hz), 8.33(1H,d,J=2 Hz), 8.50(1H,d,J=2 Hz).

(iii) Synthesis of 5-bromo-3- [N-(2-aminoethyl)-N-phenyl]carbamoylpyridine(276)

To a solution of the compound(275) synthesized in (ii) [13.5 g (32.1 mmol.)] in methanol(60 ml) was added a 14M hydrogen chloride methanol solution(30 ml), and the mixture was stirred for two hours at room temperature. The solvent was distilled off to leave a crystalline product, which was washed with ethyl acetate to obtain hydrochloride(13.3 g). This hydrochloride was processed with a 1N aqueous solution of sodium hydroxide, followed by extraction with ethyl acetate. The organic layer was separated and dried, then the solvent was distilled off to obtain the compound(276)[10.3 g(quant.) as colorless prisms.

IR(KBr)cm$^{-1}$: 3380(br), 3050, 3020, 1640(br), 1600.

NMR(90 MHz,CDCl$_3$) δ: 3.38(2H,t,J=7 Hz), 3.68(2H,q,J=7 Hz), 6.40 to 6.97(3H,m), 7.20(2H,q,J=8 Hz), 8.20(1H,t,J=2 Hz), 8.77 (1H,d,J=2 Hz), 8.84(1H,d,J=2 Hz).

(iv) Synthesis of 5-bromo-3-[N-[2-(3-carboxypropionyl)amino]-ethyl-N-phenyl]carbamoylpyridine(277)

To a solution of the compound(276) synthesized in (iii) [1.50 g (4.68 mmol.)] in anhydrous tetrahydrofuran (20 ml) was added maleic anhydride[938 mg(9.37 mmol.)], and the mixture was heated for 18 hours under reflux. The solvent was distilled off, and the residue was washed with ether, followed by dissolving in chloroform. The chloroform solution was washed with water and dried. The solvent was distilled off to obtain the compound(277)[1.77 g(89.9%)] as anhydrous powder.

IR(KBr)cm$^{-1}$: 3300 to 2300(br), 3280(br), 1710(br), 1640(br), 1590.

NMR(90 MHz,d$^6$-DMSO) δ: 1.94 to 2.60(4H,m), 3.40(2H,q,J=6 Hz), 3.82(2H,t,J=6 Hz), 7.43(5H,br s), 8.29(1H,t,J=2 Hz), 8.87(3H,m), 12.4(1H,m).

(v) Synthesis of 5-bromo-3-[N-[2-[3-(1-naphthylcarbamoyl)propionyl]amino]ethyl-N-phenyl]carbamoylpyridine(278)

To a solution of the compound(277) synthesized in (iv) [625 mg(1.49 mmol.)] in chloroform(5 ml) was added a solution of dicyclohexylcarbodiimide[307 mg(1.49 mmol.)] in chloroform (5 ml), and the mixture was stirred at room temperature for 30 minutes. To the reaction mixture was added 1-naphthylamine[213 mg(1.49 mmol.)], which was stirred for 30 minutes at room temperature. Resulting precipitates were separated by filtration, and the filtrate was washed with a 1N aqueous solution of sodium hydroxide, which was then dried, followed by concentration under reduced pressure. The concentrate was subjected to a silica gel column chromatography, eluting with hexane - ethyl acetate(1:1) to obtain the compound(278) [375 mg(46.2%) as a colorless oily product.

IR(KBr)cm$^{-1}$: 3400(br), 3290(br), 3050, 1650(br), 1590

NMR(90 MHz,CDCl$_3$) δ: 2.62(2H,m), 2.73(2H,m), 3.46(2H,q, J=6 Hz), 4.03(2H,t,J=6 Hz), 6.33 to 8.10(14H,m), 8.27(1H,br s), 8.49(1H,br s), 8.95(1H,m).

(vi) Synthesis of 5-bromo-3-[N-[2-[3-(1-naphthylcarbamoyl)propionyl]amino]ethyl-N-phenyl] carbamoyl-1-propylpyridinium chloride (279)

A solution of the compound(278) synthesized in (v)[350 mg (0.64 mmol.)]in propyl iodide(10 ml) was stirred at 110° C. for two days. Resulting precipitates were washed with ether to obtain a crude iodide compound(511 mg) as yellow powder.

The above-mentioned crude compound was dissolved in a mixture of methanol-water(7:3)(20 ml). To the solution was added anion exchange resin(IRA-410[Cl−])(20 ml), and the mixture was stirred. The resin was filtered off, and the filtrate was concentrated under reduced pressure. The concentrate was subjected to a silica gel column chromatography, eluting with methanol-chloroform(1:10), to obtain the compound(279)[40 mg(10.0%)] as yellow powder.

IR(KBr)cm$^{-1}$: 3430(br), 3240(br), 3050, 1660(br), 1590.

NMR(90 MHz,CDCl$_3$)δ:0.46(3H,t,J=7 Hz), 1.54(2H, m), 2.60 (2H,m), 2.84(2H,m), 3.54(2H,m), 3.97(2H,m), 4.35(2H,br t, J=6 Hz), 6.92 to 8.54(13H,m), 8.87(1H,m), 9.33(1H,br s), 9.70 (1H,br s), 9.91(1H,br s).

PRODUCTION EXAMPLE 102

5-Bromo-3-[N-[2-[3-[2-(1-naphthylcarbamoyloxy)ethyl-]ureido]ethyl]-N-phenyl]carbamoyl-1-propyl-pyridinium chloride(281)

(i) Synthesis of 5-bromo-3-[N-[2-[3-[2-(1-naphthylcarbamoyloxy)ethyl]ureido]ethyl]-N-phenyl]carbamoyl-pyridine(280)

To a solution of trichloromethylformate[0.36 ml(3.00 mmol.)]in toluene(30 ml) was added 2-aminoethyl 1-naphthylcarbamate [691 mg(3.00 mmol.)]. The mixture was stirred for 10 minutes at room temperature, followed by stirring, in nitrogen streams, at 80° C. for 4 hours. The solvent was distilled off, and the residual crude product was dissolved in chloroform(15 ml). To the solution was added a solution of the compound(276) synthesized in Production Example 101-iii) in chloroform(15 ml), while stirring under ice-cooling. The mixture was stirred at room temperature for 4 hours. The solvent was distilled off, and the residue was purified by means of a silica gel column chromatography, eluting with ethyl acetate, to obtain the compound (280)[791 mg(45.7%)]as a colorless oily product.

IR(Neat)cm$^{-1}$: 3290(br), 3060, 1720(br), 1650(br), 1600.

NMR(90 MHz,CDCl$_3$) δ: 3.51(4H,m), 3.90(2H,m), 4.26(2H,t, J=6 Hz), 4.80(1H,t,J=6 Hz), 6.90 to 8.03(13H,m), 8.27 to 8.50 (2H,m), 8.72(1H,br s), 9.06(1H,br s).

(ii) Synthesis of 5-bromo-3-[N-[2-[3-[2-(1-naphthylcarbamoyloxy)ethyl]ureido]ethyl]-N-phenyl]carbamoyl-1-propyl pyridinium chloride(281)

A solution of the compound(280) synthesized in i)[540 mg (0.94 mmol.)]in propyl iodide(10 ml) was stirred at 110° C for two days. Resulting precipitates were washed with ether to obtain a crude iodide compound(710 mg) as yellow powder.

The above-mentioned crude product was dissolved in a mixture of methanol-water(7:3), to which was added anion-exchange resin (IRA-410[Cl$^-$]) (30 ml). The mixture was stirred for 3 hours, then the resin was filtered off, and the filtrate was concentrated under reduced pressure. The concentrate was subjected chloroform(1:8), to obtain the compound(281)[470 mg(76.3%)] as yellow powder.

IR(KBr)cm$^{-1}$: 3390(br), 3210(br), 3050, 1720(br), 1660(br), 1600.

NMR(90 MHz,CDCl$_3$) δ: 0.84(3H,t,J=7 Hz), 1.94(2H,m), 3.28 (2H,m), 3.53(2H,m), 3.90(2H,m), 4.10(2H,m), 4.59(2H,t,J=7 Hz), 4.92(1H,m), 7.00 to 8.20(12H,m), 8.24(1H,br s), 8.97(1H,br s), 9.38(1H,br s), 10.00(2H,m).

PRODUCTION EXAMPLE 103

5-Bromo-3-[N-[2-[3-(1-naphthoylamino)propionyl-]amino]ethyl-N-phenyl]carbamoyl-1-propylpyridinium chloride(285)

(i) Synthesis of 5-bromo-3-[N-[2-[3-(t-butoxycarbonylamino)propionyl] amino]ethyl-N-phenyl]carbamoyl pyridine(282)

To a solution of the compound(276) synthesized in Production Example 101-iii)[1.89 g(10.0 mmol.)]in chloroform(20 ml) was added dicyclohexyl carbodiimide[2.39g(11.0 mmol.)]. To the mixture was then added 3-t-butoxycarbonylaminopropionic acid [1.89 g(10.0 mmol.)], which was stirred at room temperature for 30 minutes. Resulting precipitates were filtered off, and the filtrate was concentrated under reduced pressure. Resulting crystals were washed with hexane - ethyl acetate(1:2) to obtain the compound(282)[4.36 g(88.7%)] as colorless crystals.

IR(KBr)cm$^{-1}$: 3310(br), 3050, 1680, 1650, 1640, 1590.

NMR(90 MHz,CDCl$_3$) δ: 1.39(9H,s), 2.24(2H,t,J=6 Hz), 3.36 (2H,q,J=6 Hz), 3.49 to 3.80(2H,m), 3.80 to 4.10(2H,m), 5.17(1H, br t,J=6 Hz), 7.00 to 7.63(5H,m), 7.93(1H,m), 8.31(1H,t,J=2 Hz), 8.77(1H,d,J=2 Hz), 8.97(1H,d,J=2 Hz).

(ii) Synthesis of 5-bromo-3-[N-[2-(3-aminopropionyl-)amino]-ethyl-N-phenyl]carbamoylpyridine(283)

To a solution of the compound(282) synthesized in (i)[3.00 g (61.1 mmol.)] in methanol(20 ml) was added 14M hydrogen chloride methanol solution(20 ml). The mixture was stirred for 18 hours at room temperature. The solvent was distilled off, and the residue was made alkaline with a 1N aqueous solution of sodium hydroxide, followed by extraction with ethyl acetate. The organic layer was separated and dried, then the solvent was distilled off under reduced pressure. The residue was subjected to a silica gel column chromatography, eluting with conc.-ammoniacal water-methanol(1:100), to obtain the compound(283) [2.27 g(95.0%)] as a yellow oily product.

IR(Neat)cm$^{-1}$:3300(br), 3060, 1650(br), 1590.

NMR(90 MHz,CDCl$_3$)δ: 2.18(2H,t,J=6 Hz), 2.87(2H,t,J=6 Hz), 3.40 to 3.89(2H,m), 3.89 to 4.23(2H,m), 7.00 to 7.62(5 Hmm), 8.13(1H,m), 8.31(1H,t,J=2 Hz), 8.77(1H,d,J=2 Hz), 8.98(1H,d,j=2 Hz).

(iii) Synthesis of 5-bromo-[N-[2-[3-(1-naphthoylamino)-propionyl]amino]ethyl-N-phenyl]carbamoyl-pyridine(284)

To a solution of the compound (283) synthesized in (ii) [670 mg (1.71 mmol.)] and triethylamine[0.29 ml(2.05 mmol.)] in chloroform (4 ml) was added, while stirring under ice-cooling, 1-naphthoyl chloride [0.28 ml(1.88 mmol.)]. The 151 mixture was washed with a saturated aqueous solution of sodium hydrogen-carbonate, then the solvent was distilled off under reduced pressure. The residue was subjected to a silica gel column chromatography, eluting with ethyl acetate, to obtain the compound(284) [720 mg(77.1%] as a colorless oily product.

IR(KBr)cm$^{-1}$: 3290(br), 3060, 1640(br), 1590.

NMR(90 MHz,CDCl$_3$)δ:2.40(2H,t,J=6 Hz), 3.30 to 3.79(4H,m), 3.79 to 4.20(2H,m), 6.89(1H,br t,J=6 Hz), 7.07 to 8.05(12H,m), 8.05 to 8.37(2H,m), 8.59(1H,br s), 88.5(1H,br s).

(iv) Synthesis of 5-bromo-3-[N-[2-[3-(1-naphthoylamino)propionyl]amino]ethyl-N-phenyl]carbamoyl-1-propylpyridinium chloride(285)

A solution of the compound(284) synthesized in (iii) [680 mg (1.25 mmol.)] in propyl iodide(5 ml) was stirred at 110° C. for two days. Resulting precipitates were washed with ether to obtain a crude iodide compound(95λ9 mg) as yellow powder.

The above-mentioned crude product was dissolved in a mixture of methanol-water(7:3)(100 ml). To the solution was added anion-exchange resin(IRA-410[Cl$^-$])(40 ml), and the mixture was stirred for 18 hours, and the resin was filtered off. The filtrate was concentrated under reduced pressure, and the concentrate was subjected to a silica gel column chromatography, eluting with methanol-chloroform(1:7) to obtain the compound (285)[440 mg(56.6%)] as yellow powder.

IR(KBr)cm$^{-1}$: 3420(br), 3210(br), 3040, 1650(br), 1580.

NMR(90 MHz,CDCl$_3$) δ: 0.84(3H,t,J=9 Hz), 1.90(2H,sext,J=7 Hz), 2.45(2H,t,J=5 Hz), 3.58(4H,m), 3.96(2H,m), 4.42(2H,t,J=7 Hz), 6.33 to 8.40(13H,m), 8.93(1H,br s), 9.00(1H,br s), 10.0(1H,m), 10.17(1H,br s).

PRODUCTION EXAMPLE 104

5-Bromo-3-[N-[2-[3-(1-naphthylsulfonylamino)propionyl]amino]-ethyl-N-phenyl]carbamoyl-1-propylpyridinium chloride(287)

(i) Synthesis of 5-bromo-3-[N-[2-[3-(1-naphthylsulfonylamino)propionyloxy] amino] ethyl-N-phenyl]carbamoylpyridine(286)

To a solution of the compound(283) synthesized in Production Example 103-ii [770 mg(1.97 mmol.)]and triethylamine[0.33 ml (2.36 mmol.)]in chloroform(4 ml) was added, while stirring under ice-cooling, 1-naphthalenesulfonyl chloride[491 mg(2.17 mmol.)]. The mixture was stirred for 30 minutes under ice-cooling. The reaction mixture was washed with a saturated aqueous solution of sodium hydrogencarbonate, then dried, followed by distilling off the solvent under reduced pressure. The residue was subjected to a silica gel column chromatography, eluting with hexane - ethyl acetate(1:10) to obtain the compound (286)[869 mg(75.9%)].

IR(KBr)cm$^{-1}$: 3310(br), 3050, 1650(br), 1590, 1320, 1150.

NMR(90 MHz,CDCl$_3$) δ: 2.05(2H,t,J=6 Hz), 3.18(2H,q,J=6 Hz), 3.57(2H,q,J=6 Hz), 3.83(2H,t,J=6 Hz), 6.32(1H,t,J=6 Hz), 6.67 to 8.33(13H,m), 8.50 to 8.82(1H,m), 8.73(1H,d,J=2 Hz), 8.93 (1H,br s).

(ii) Synthesis of 5-bromo-3-[N-[2-[3-(1-naphthylsulfonylamino]ethyl-N-phenyl]carbamoyl-1-propyl-pyridinium chloride (287)

A solution of the compound(286) synthesized in (i) in propyl iodide(5 ml) was stirred for two days at 110° C. Resulting precipitates were washed with ether to obtain a crude iodide compound(1.14 mg) as yellow powder.

The above-mentioned crude product was dissolved in methanol -water(7:3)(100 ml), to which was added anion-exchange resin (IRA-410[Cl$^-$])(40 ml), and the mixture was stirred for 18 hours. The resin was filtered off, and the filtrate was concentrated under reduced pressure. The concentrate was subjected to a silica gel column chromatography, eluting with methanol-chloroform(1: 8), to obtain the compound(287)[718 mg(76.3%)] as yellow powder.

IR(KBr)cm$^{-1}$: 3430(br), 3190(br), 3050, 1670(br), 1580, 1320(br), 1150.

NMR(90 MHz,CDCl$_3$) δ: 0.92(3H,t,J=7 Hz), 2.112(4H,m), 3.03(2H,m), 3.55(2H,m), 3.85(2H,m), 4.80(2H,t,7 Hz), 6.67 to 8.27(12H,m), 8.43 to 8.87(1H,m), 9.10(1H,br s), 9.20(1H, br s), 10.30(2H, br s).

PRODUCTION EXAMPLE 105

5-Bromo-3-[N-[2-[3-[3-(1-naphthyl)ureido]propionyl]amino]-ethyl-N-phenyl]carbamoyl-1-propylpyridinium chloride(289)

(i) Synthesis of 5-bromo-3-[N-[2-[3-[3-(1-naphthyl)ureido]propionyl]amino]ethyl-N-phenyl]carbamoyl pyridine(288)

To a solution of the compound(283) synthesized in Production Example 103-iii)[633 mg(1.62 mmol.)] in chloroform(4 ml) was added 1-naphthyl isocyanate[0.28 ml(1.94 mmol.)], and the mixture was stirred at room temperature for 30 minutes. The solvent was distilled off under reduced pressure, and the residue was subjected to a silica gel column chromatography, eluting with methanol - ethyl acetate(1:100) to obtain the compound(288)[580 mg(64.0%)] as colorless powder.

IR(KBr)cm$^{-1}$: 3300(br), 3050, 1640, 1580

NMR(90 MHz,d$^6$-DMSO) δ: 2.20(2H,m), 3.00 to 3.61(4H,m), 3.84(2H,t,J=6 Hz), 6.65(1H,t,J=6 Hz), 7.17 to 8.22(13H,m), 8.29(1H,t,J=2 Hz), 8.53(1H,br s), 8.67 to 9.00(2H,m).

(ii) Synthesis of 5-bromo-3-[N-[2-[3-(1-naphthyl)ureido]-propionyl]amino]ethyl-N-phenyl]carbamoyl-1-propylpyridinium chloride(289)

A solution of the compound(288) synthesized in (i)[540 mg (0.96 mmol.)] in propyl iodide(5 ml) was heated at 110° C for two days. Resulting precipitates were washed with ether to obtain a crude iodide compound(828 mg) as brown powder.

The above-mentioned crude product was dissolved in a mixture of methanol-water(7:3)(100 ml), to which was added anion-exchange resin(IRA-410[Cl$^-$])(40 ml). The mixture was stirred for 18 hours at room temperature. Then, the resin was filtered off, and the filtrate was concentrated under reduced pressure. The concentrate was subjected to a silica gel column chromatography, eluting with methanol-chloroform(1:8), to obtain the compound (289)[391 mg(63.5%)] as yellow powder.

IR(KBr)cm$^{-1}$: 3410(br), 3260(br), 3050, 1670(br), 1590.

NMR(90 MHz,CDCl$_3$) δ: 0.76(3H,t,J=7 Hz), 1.84(2H,sext,J=7 Hz), 2.38(2H,m), 3.58(4H,m), 3.97(2H,m), 4.31(2H,t,J=7 Hz), 6.33 to 8.54(13H,m), 8.63(1H,br s), 8.90(2H,br s), 9.90(1H,br s), 10.00 (1H,m)

PRODUCTION EXAMPLE 106

5-Bromo-3-[N-[2-(1-naphthylmethyl)carbamoyl]ethyl-N-phenyl]-carbamoyl-1-propylpyridinium chloride (295)

(i) Synthesis of methyl 3-anilinopropionate(290)

To a solution of 2-anilinopropionic acid[4.95. g(30 mmol.)]in methanol(10 ml) was added a 14M hydrogen chloride methanol solution(30 ml), and the mixture was stirred at room temperature for one hour. Methanol was distilled off under reduced pressure. The residue was made alkaline with a saturated aqueous solution of sodium hydrogencarbonate, followed by extraction with ethyl acetate. The extract was washed with water and dried, then the solvent was distilled off to obtain the compound (290)[3.80 g(70.7%)] as yellow powder.

IR(KBr)cm$^{-1}$: 3400, 3050, 3030, 1720, 1600.

NMR(CDCl$_3$;90 Mz) δ: 2.59(2H,t,J=7 Hz), 3.42(2H,t,7 Hz), 3.67 (3H,s), 6.47 to 6.87(3H,m), 6.96 to 7.37(2H,t,J=8 Hz).

(ii) Synthesis of 5-bromo-3-[N-(2-methoxycarbonyl)ethyl-N-phenyl]carbamoylpyridine(291)

To a solution of the compound(290) synthesized in (i)[10.24 g (57.2 mmol.)] and triethylamine[7.5 ml(126 mmol.)]in chloroform (120 ml) was added 5-bromonicotinic acid chloride hydrochloride [16.2 g(62.9 mmol.)] while stirring under ice-cooling. The mixture was stirred at room temperature for 30 minutes. The reaction mixture was washed with a saturated aqueous solution of sodium hydrogencarbonate and dried, then the solvent was distilled off under reduced pressure. The residue was washed with hexane to obtain the compound(291)[18.2 g(87.7%)] as pale brown powder.

IR(KBr)cm$^-$: 3040, 1700, 1660, 1590.

NMR(CDCl₃;90 MHz) δ: 2.67(2H,t,J=7 Hz), 3.60(3H,s), 4.20 (2H,t,J=7 Hz), 6.90 to 7.57(5H,m), 7.82(1H,t,J=2 Hz), 8.32 (1H,d,J=2 Hz), 8.52(1H,d,J=2 Hz).

(iii) Synthesis of 5-bromo-3-[N-(2-carboxy)ethyl-N-phenyl]carbamoylpyridine(292)

To a solution of the compound(291) synthesized in (ii)[18.0 g (49.6 mmol.)] in methanol(200 ml) was added 1N aqueous solution of sodium hydroxide, and the mixture was stirred for one hour at room temperature. The reaction mixture was neutralized with 1N hydrochloric acid, followed by distilling off methanol. The residue was made acid with 1N hydrochloric acid and subjected to extraction with ethyl acetate. The organic layer was washed with water and dried, then the solvent was distilled off under reduced pressure. The residue was washed with ether to obtain the compound(292) [15.5 g(90%)] as pale yellow powder.

IR(KBr)cm⁻¹: 3220(br), 3030, 1730, 1660, 1580.

NMR(CDCl₃;90 Mz) δ: 2.74(2H,t,J=7 Hz), 4.24(2H,t,J=7 Hz), 6.83 to 7.56(5H,m), 7.88(1H,J=2 Hz), 8.36(1H,d,J=2 Hz), 8.54 (1H,d,J=2 Hz), 10.13(1H,m).

(iv) Synthesis of 5-bromo-3-[N-(2-chloroformyl)ethyl-N-7 phenyl]carbamoylpyridine hydrochloride(293)

In oxalyl chloride(10 ml) was suspended the compound(292) synthesized in ii)[2.13 g(6.10 mmol.)]. The suspension was heated under reflux for one hour. The reaction mixture was cooled, and the excess oxalyl chloride was distilled off. The residue was washed with anhydrous ether to obtain the compound(293)[1.78 g(72.2%)]as pale brown powder.

NMR(CDCl₃;90 MHz) δ3.31(2H,t,J=7 Hz), 4.27(2H,t,J=7 Hz), 7.37(5H,m), 8.25(1H,br s), 8.62(1H, br s), 8.77(2H,br s).

(v) Synthesis of 5-bromo-3-[N-[2-(1-naphthyl)carbamoyl]ethyl-N-phenyl]carbamoylpyridine(294)

To a solution of 1-naphthylmethylamine[0.12 ml(0.76 mmol.)] and triethylamine[0.23 ml(1.68 mmol.)] in chloroform(3 ml) was added, while stirring under ice-cooling, the compound(293) synthesized in (iv)[340 mg(0.84 mmol.)]. The mixture was stirred for 30 minutes at room temperature. The reaction mixture was washed with 1N aqueous solution of sodium hydroxide cooled with ice then with water, then dried, followed by distilling off the solvent under reduced pressure. The residue was subjected to a silica gel column chromatography, eluting with hexane - ethyl acetate(1:5), to obtain the compound(294)[312 mg (84.1%)]as colorless powder.

IR(KBr)cm⁻¹: 3410(br), 3300(br), 3040(br), 1650(br), 1590

NMR(CDCl₃;90 MHz) δ : 2.57(2H,t,J=7 Hz), 4.19(2H,t,J=7 Hz), 4.87(2H,d,J=6 Hz), 6.66(1H,br t,J=6 Hz), 6.76 to 8.23(15H,m).

(vi) Synthesis of 5-bromo-3-[N-[2-(1-naphthylmethyl)carbamoyl] ethyl-N-phenyl]-1-propylpyridinium chloride(295)

A solution of the compound(294) synthesized in v)[280 mg (0.57 mmol.)]in propyl iodide(5 ml) was stirred at 110° C. for two days. Resulting precipitates were washed with ether to obtain a crude iodide compound(344 mg) as yellow powder.

The above-mentioned crude product was dissolved in a mixture of methanol-water(7:3)(100 ml), to which was added anion-exchange resin IRA-410[Cl⁻])(50 m%). The mixture was stirred for 3 hours. The resin was filtered off, and the filtrate was concentrated under reduced pressure. The concentrate was subjected to a silica gel column chromatography, eluting with methanol-chloroform(1: 8) to obtain the compound(295)[249 mg(76.6%)]as pale yellow powder.

IR(KBr)cm⁻¹: 3410(br), 3210(br), 3040(br), 1650(br), 1590.

NMR(CDCl₃;90 MHz) δ: 0.56(3H,t,J=7 Hz), 1.62(2H,m), 2.71 (2H,m), 4.13(2H,m), 4.62(2H,m), 4.77(2H,d,J=6 Hz), 6.77 to 8.67 (14H,m), 9.47(2H,br s).

PRODUCTION EXAMPLE 107

5-Bromo-3-[N-[2-(1,2,3,4-tetrahydroisoquinolyl)carbonyl]-ethyl-N-phenyl]carbamoyl-1-propylpyridinium chloride(297)

(i) Synthesis of 5-bromo-3-[N-[2-(1,2,3,4-tetrahydroisoquinolyl)carbonyl]ethyl-N-phenyl]carbamoylpyridine(296)

To a solution of 1,2,3,4-tetrahydroisoquinoline[0.1 4 ml (1.12 mmol.)] and triethylamine[0.35 ml(2.48 mmol.)- ]in chloroform(6 m%) was added, while stirring under ice-cooling, the compound(293) synthesized in Production Example 106-ii)[500 mg (1.24 mmol.)], and the mixture was washed with a 1N aqueous solution of sodium hydroxide and then dried, followed by distilling off the solvent under reduced pressure. The residue was subjected to a silica gel column chromatography, eluting with hexane - ethyl acetate(1:5) to obtain the compound(296) [418 mg(72.7%)]as a pale yellow oily product.

IR(Neat)cm⁻¹: 3050, 1640(br), 1590

NMR(CDCl₃) δ: 2.88(4H,m), 3.78(2H,t,J=6 Hz), 4.25(2H,t,J=8 Hz), 4.68(2H,s), 7.17(9H,m), 7.24(1H,t,J=2 Hz), 8.35(1H,br s), 8.54 (1H,br s)

(ii) Synthesis of 5-bromo-3-[N-[2-(1,2,3,4-tetrahydroisoquinolyl)carbonyl]ethyl-N-phenyl] carbamoylpyridine(297)

A solution of the compound(296) synthesized in (i)[378 mg (0.81 mmol.)] in propyl iodide(8 ml) was stirred for two days at 110° C. Resulting precipitates were washed with ether to obtain a crude iodide compound(534 mg) as yellow powder.

The above-mentioned crude product was dissolve in a mixture of methanol-water(7:3)(100 ml). To the solution was added anion-exchange resin(IRA-410[Cl⁻])(50 ml), and the mixture was stirred for 3 hours. The resin was filtered off, and the filtrate was concentrated under reduced pressure. The concentrate was subjected to a silica gel column chromatography, eluting with methanol-chloroform(1:8) to obtain the compound (297)[245 mg(55.4%)] as pale yellow powder.

IR(KBr)cm⁻¹: 3420(br), 1650(br), 1590

NMR(CDCl₃;90 MHz) δ: 0.76(3H,t,7 Hz), 1.80(2H,m), 2.58 to 3.15 (4H,m), 3.68(2H,m), 4.22(2H,m), 4.66(2H,s), 4.99(2H,br t,J=7 Hz), 6.77 to 7.83(9H,m), 8.30(1H,m), 9.45(1H,m), 9.84(1H,m).

PRODUCTION EXAMPLE 108

5-Bromo-3-[N-[2-[2-(1-naphthoylamino)ethyl]carbamoyl]ethyl-N-phenyl]carbamoyl-1-propylpyridinium chloride(300)

(i) Synthesis of 2-(1-naphthoylamino)ethylamine(298)

To a solution of ethylenediamine[5.35 ml(80 mmol.)] in chloroform(200 ml) was added, while stirring under ice-cooling, 1-naphthoyl chloride[3.01 ml(20 mmol.)], and the mixture was stirred at room temperature for one hour. The reaction mixture was made acid with 1N hydrochloric acid cooled with ice. The aqueous layer was washed with chloroform, to which was added concentrated ammonia to make it alkaline, followed by extraction with chloroform. The extract was dried, and the solvent was distilled off to leave the compound(298)[3.08 g(71.9%)] as a yellow oily product.

IR(Neat)cm$^{-1}$: 3260(br), 3050, 1640(br), 1590.

NMR(CDCl$_3$;90 MHz) δ: 2.82(2H,t,J=6 Hz), 3.44(2H,t,J=6 Hz), 6.78(1H,m), 7.00 to 8.40(7H,m)

(ii) Synthesis of 5-bromo-3-[N-[2-[2-(1-naphthoylamino)ethyl]carbamoyl]ethyl-N-phenyl]carbamoylpyridine(299)

To a solution of the compound(298) synthesized in (i)[240 mg (1.12 mmol.)] and triethylamine[0.35 ml(2.48 mmol.)]in chloroform(6 ml) was added, while stirring under ice-cooling, the compound synthesized in Production Example 106-iv) [500 mg(1.24 mmol.)]. The mixture was stirred at room temperature for 30 minutes. The reaction mixture was washed with a 1N aqueous solution of sodium hydroxide and then dried, followed by distilling off the solvent under reduced pressure. The residue was subjected to a silica gel column chromatography, eluting with methanol - ethyl acetate(1:20) to obtain the compound (299)[402 mg(65.8%) as colorless powder.

IR(KBr)cm$^{-1}$: 3290(br), 3040, 1680, 1660, 1630, 1590.

NMR(CDCl$_3$; 90 MHz) δ: 2.48(2H,t,J=7 Hz), 3.48(4H,m), 4.10 (2H,t,J=7 Hz), 6.65 to 8.60(14H,m), 8.25(2H,m), 8.46(1H,d,J=2 Hz).

(iii) Synthesis of 5-bromo-3-[N-[2-[2-(1-naphthoylamino)ethyl]carbamoyl]ethyl-N-phenyl]carbamoyl-1-propylpyridinium chloride (300)

A solution of the compound(299) synthesized in (ii) [365 mg (0.67 mmol.)] in propyl iodide(7 ml) was stirred at 110° C. for two days. Resulting precipitates were washed with ether to obtain a crude iodide compound(510 mg) as yellow powder.

The above-mentioned crude product was dissolved in a mixture of methanol-water(7:3)(100 ml). To the solution was added anion-exchange resin(IRA-410[Cl$^-$]) (50 ml), and the mixture was stirred for 6 hours. The resin was filtered off, and the filtrate was concentrated under reduced pressure. The concentrate was subjected to a silica gel column chromatography, eluting with methanol-chloroform(1:4), to obtain the compound(300) [303 mg(72.6%)] as pale yellow powder.

IR(KBr)cm$^{-1}$: 3420(br), 3240(br), 3040, 1650(br), 1590.

NMR(CDCl$_3$;90 MHz) δ: 0.67(3H,t,J=7 Hz), 1.78(2H, quint., J=7 Hz), 2.66(2H,m), 3.00(2H,m), 3.20(2H,m), 4.14(2H,m), 4.78 (2H,m), 6.83 to 8.97(15H,m), 9.16(1H,br s), 9.82(1H, br s).

PRODUCTION EXAMPLE 109

5-Bromo-3-[N-[2-[2-(1-naphthylsulfonamide)ethyl]carbamoyl]-ethyl-N-phenyl]carbamoyl-1-propylpyridinium chloride(303)

(i) Synthesis of 2-(1-naphthylsulfonamide)ethylamine(301)

To a solution of ethylenediamine[5.35 ml(80 mmol.)] in dichloromethane(200 ml) was added, while stirring under ice-cooling, 1-naphthylsulfonyl chloride[4.53 g(20 mmol.)]. The mixture was stirred at room temperature for one hours. The reaction mixture was subjected to extraction with 1N hydrochloric acid. The extract solution was washed with chloroform, which was made alkaline with a concentrated aqueous solution of ammonia, followed by extraction with chloroform. The extract was dried, then the solvent was distilled off under reduced pressure to leave a residue. The residue was washed with ether to obtain the compound(301)[4.10 g(81.9%)] as colorless powder.

IR(KBr)cm$^{-1}$: 3350, 3300, 3050(br), 1600, 1310, 1160.

NMR(CDCl$_3$;90 MHz) δ: 2.20 to 3.20(4H,m), 7.14 to 8.40(7H,m), 8.86 to 8.88(1H,m).

(ii) Synthesis of 5-bromo-3-[N-[2-[2-(1-naphthylsulfonamido)ethyl]carbamoyl]ethyl-N-phenyl]carbamoylpyridine(302)

To a solution of the compound(301) synthesized in (i)[280 mg (1.12 mmol.)] and triethylamine[0.35 ml(2.48 mmol.)]in chloroform(6 ml) was added, while stirring under ice-cooling, the compound(293) synthesized in Production Example 106-iv)[500 mg(1.24 mmol.)], and the mixture was stirred at room temperature for 30 minutes. The reaction mixture was washed with a 1N aqueous solution of sodium hydroxide, which was then dried, followed by distilling off the solvent under reduced pressure. The residue was subjected to a silica gel column chromatography, eluting with ethyl acetate, to obtain the compound(302)[511 mg (78.6%)] as pale yellow powder.

IR(KBr)cm$^{-1}$: 3280(br), 1650(br), 1320, 1160.

NMR(CDCl$_3$;90Mz) 6 : 2.42(2H,t,J=7 Hz), 3.05(2H,m), 3.25(2H,m), 4.16(2H,t,J=7 Hz), 6.37(1H,t,J=6 Hz), 6.73(1H,br t,J=6 Hz), 6.90 to 6.84(15H,m).

(iii) Synthesis of 5-bromo-3-[N-[2-[2-(1-naphthylsulfonamido)ethyl]carbamoyl]ethyl-N-phenyl]carbamoyl-1-propylpyridinium chloride(303)

A solution of the compound(302) synthesized in (ii)[477 mg (0.82 mmol.)]in propyl iodide(8 ml) was stirred at 110° C. for two days. The resulting precipitates were washed with ether to obtain a crude iodide compound(604 mg) as yellow powder.

The above-mentioned crude product was dissolved in a mixture of methanol-water(7:3)(100 ml). To the solution was added anion-exchange resin(IRA-410[Cl$^-$])(50 ml), and the mixture was stirred for 6 hours. The resin was filtered off, and the filtrate was concentrated under reduced pressure. The concentrate was subjected to a silica gel column chromatography, eluting with methanol-chloroform(1:4) to obtain the compound(303)[505 mg(93.3%)] as yellow powder.

IR(KBr)cm$^{-1}$: 3400(br), 3240(br), 3060, 1660(br), 1590, 1320, 1160.

NMR(CDCl$_3$;90Mz) δ: 0.50(3H,t,J=7 Hz), 1.54(2H,m), 2.71 (2H,m), 3.54(4H,m), 4.14(4H,m), 6.93 to 8.44(15H,m), 8.73 (1H,br s), 9.80(1H,br s).

PRODUCTION EXAMPLE 110

5-Bromo-3-[N-[2-[2-(1-naphthylcarbamoyl)ethyl]carbamoyl]-ethyl-N-phenyl]carbamoyl-1-propylpyridinium chloride(307)

(i) Synthesis of 1-(t-butoxycarbonylamino)-2-(1-naphthylcarbamoyl)ethane(304)

To a solution of 3-t-butoxycarbonyl aminopropionic acid [3.78 g(20.0 mmol.)]in chloroform(40 m%) was added dicyclohexyl carbodiimide[4.56 g(21.0 mmol.)], and the mixture was stirred at room temperature for one hour. To the reaction mixture was added 1-naphthylamine[2.86 g(20.0 mmol.)], which was stirred at room temperature for one hour. Resulting precipitates were filtered off, and the filtrate was washed with a saturated aqueous solution of sodium hydrogencarbonate, 1N hydrochlorie acid and water, successively, followed by concentration under reduced pressure. The concentrate was washed with hexane to obtain the compound(304)[6.01 g(95.6%) as a pale yellow oily product.

IR(KBr)cm$^{-1}$: 3320, 3270, 3040, 1680, 1650

NMR(CDCl$_3$;90 MHz)δ: 1.42(9H,s), 2.65(2H,m), 3.45(2H,m), 5.37(1H,m), 7.14 to 8.55(8H,m).

(ii) Synthesis of 2-(1-naphthylcarbamoyl)ethylamine(305)

To a solution of the compound(304) synthesized in (i) [5.00 g(15.9 mmol.)] in methanol(100 ml) was added a 10M hydrogen chloride methanol solution(20 ml). The mixture was stirred at room temperature for one hour, then the solvent was distilled off. To the residue was added water, and the mixture was washed with ethyl acetate, followed by making the system alkaline with a 1N aqueous solution of sodium hydroxide. The resultant was subjected to extraction with ethyl acetate. The organic layer was separated and dried, then the solvent was distilled off under reduced pressure. The residue was washed with hexane to obtain the compound(305)[2.50 g(85.6%)] as pale yellow powder.

IR(KBr)cm$^{-1}$: 3440(br), 3330, 3270, 1670.

NMR(CDCl$_3$;90 MHz) δ: 2.55(2H,t,J=6 Hz), 3.15(2H,t,J=6 Hz), 7.10 to 8.43(8H,m).

(iii) Synthesis of 5-bromo-3-[N-[2-[2-(1-naphthylcarbamoyl)ethyl]carbamoyl]ethyl-N-phenyl]carbamoylpyridine(306)

To a solution of the compound(305) synthesized in (ii)[280 mg (1.30 mmol.)] and triethylamine[0.40 ml(2.88 mmol.)]in chloroform (6 ml) was added, while stirring under ice-cooling, the compound (293) synthesized in Production Example 106-(iv)[580 mg(1.44 mmol.)], and the mixture was stirred at room temperature for 30 minutes. The reaction mixture was washed with a 1N aqueous solution of sodium hydroxide and dried, then the solvent was distilled off under reduced pressure. The residue was subjected to a silica gel column chromatography, eluting with methanolethyl acetate(1:20) to obtain the compound(306)[510 mg(71.9%)] as colorless powder.

IR(KBr)cm$^{-1}$: 3430(br), 3270(br), 1640(br), 1590.

NMR(CDCl$_3$;90 MHz) δ: 2.43(2H,t,J=7 Hz), 2.67(2H,m), 3.52 (2H,m), 4.13(2H,t,J=7 Hz), 6.67 to 8.13(14H,m), 8.26(1H,d, J=2 Hz), 8.45(1H,d,J=2 Hz), 8.64(1H,m).

(iv) Synthesis of 5-bromo-3-[N-[2-[2-(1-naphthylcarbamoyl)ethyl]carbamoyl]ethyl-N-phenyl]carbamoyl-1-propylpyridinium chloride (307)

A solution of the compound(306) synthesized in (ii)[440 mg (0.81 mmol.)] in propyl iodide(10 ml) was stirred at 110° C. for two hours. Resulting precipitates were washed with ether to obtain a crude iodide compound(524 mg) as yellow powder. The above-mentioned product was dissolved in a mixture of methanol-water(7:3)(100 ml). To the solution was added anion-exchange resin(IRA-410[Cl$^-$])(50 ml), and the mixture was stirred for 6 hours. The resin was filtered off, and the filtrate was concentrated under reduced pressure. The concentrate was subjected to a silica gel column chromatography, eluting with methanol-chloroform(1:6) to obtain the compound(307)[354 mg (70.3%)] as yellow powder.

IR(KBr)cm$^{-1}$: 3240(br), 3050(br), 1650(br), 1590

NMR(d$^4$-MeOH,90 MHz) δ: 0.62(3H,t,J=7 Hz), 1.72(2H,m), 2.23 to 2.94(4H,m), 2.34(2H,m), 4.10(2H,br t,J=6 Hz), 4.45(2H,br t, J=6 Hz), 6.87 to 8.50(15H,m), 8.78(1H, br s), 9.24(1H, br s)

PRODUCTION EXAMPLE 111

5-Bromo-3-[N-[2-[2-(1-naphthylcarbamoyloxy)ethyl]-carbamoyl]-propyl-N-phenyl]carbamoyl-1-propyl-pyridinium chloride(312)

(i) Synthesis of 5-bromo-3-[N-(2-methoxycarbonyl)propyl-N-phenyl]carbamoyl pyridine(308)

To a solution of N-(2-methoxycarbonyl)propyl aniline[2.58 g (13.4 mmol.)] and triethylamine[4.10 ml(29.4 mmol.)]in chloroform(30 ml) was added, while stirring under ice-cooling, 5-bromonicotinic acid chloride hydrochloride[3.78 g(14.7 mmol.)]. The mixture was stirred at room temperature for 30 minutes. The reaction mixture was washed with a saturated aqueous solution of hydrogencarbonate and dried, and then the solvent was distilled off under reduced pressure. The residue was subjected to a silica gel column chromatography, eluting with hexane - ethyl acetate(2:1), to obtain the compound(308) [3.50 g(69.5%)] as pale yellow powder.

IR(KBr)cm$^{-1}$: 3430(br), 1730, 1660, 1590

NMR(CDCl$_3$; 90 MHz) δ: 1.20(3H,d,J=7 Hz), 2.89(1H,sextet, J=7 Hz), 3.57(3H,s), 3.98(1H,dd,J=6,14 Hz), 4.12(1H,dd,J=10, 14 Hz), 6.87 to 7.48(5H,m), 7.77(1H,t,J=2 Hz), 8.28(1H,d,J=2 Hz), 8.48(1H,d,J=2 Hz).

(ii) Synthesis of 5-bromo-3-[N-(2-carboxy)propyl-N-phenyl]carbamoylpyridine(309)

To a solution of the compound(308) synthesized in (i)[2.24 g (5.94 mmol.)] in methanol(80 ml) was added a 1N aqueous solution of sodium hydroxide(40 ml), and the mixture was stirred at room temperature for one hour. The reaction mixture was neutralized with 1N hydrochloric acid, followed by distilling off methanol under reduced pressure. The residue was made acid with 1N hydrochloric acid and subjected to extraction with ethyl acetate. The organic layer was washed with water, dried and then the solvent was distilled off under reduced pressure. The residue was washed with ether to obtain the compound(309)[1.70 g(78.8%)] as a yellow oily product.

NMR(CDCl$_3$; 90 MHz) δ: 1.18(3H,d,J=7 Hz), 2.80(2H,m), 4.84 (1H,dd,J=6,15 Hz), 4.37(1H,dd,J=9, 15 Hz), 6.87 to 7.50(5H,m), 7.86(1H,t,J=2 Hz), 8.28(1H,br s), 8.47(1H,d,J=2 Hz).

(iii) Synthesis of 5-bromo-3-[N-(2-chloroformyl)propyl-N-phenyl]carbamoylpyridine hydrochloride (310)

In oxalyl chloride(10 ml) was suspended the compound(309) synthesized in (ii)[1.47 g(4.05 mmol.)], which was heated for one hour under reflux. The reaction mixture was cooled, and then excess volume of oxalyl chloride was distilled off. The residue was washed with anhydrous ether to obtain the compound (310)[1.36 g(80.4%)]as pale brown powder. NMR(CDCl$_3$;90 MHz) δ: 1.22(3H,d,J=7 Hz), 2.87(1H,quint,J=7 Hz), 3.95(1H,dd,J=7, 14 Hz), 4.21(1H,dd,J=9, 14 Hz), 6.90 to 7.53(5H,m) 8.05(1H, br s), 8.43(1H, m), 8.67(1H, m)

(iv) Synthesis of 5-bromo-3-[N-[2-[2-(1-naphthylcarbamoyloxy)ethyl]carbamoyl]propyl-N-phenyl]carbamoylpyridine(311)

To a solution of 2-(1-naphthylcarbamoyloxy)ethylamine[536 mg (2.33 mmol.)] and triethylamine[0.71ml(5.12 mmol.)]in chloroform(10 ml) was added, while stirring under ice-cooling, the compound(310) synthesized in (ii)[1.07 g(2.56 mmol.)], and the mixture was stirred at room temperature for 30 minutes. The reaction mixture was washed with a 1N aqueous solution of sodium hydroxide, which was then dried, followed by distilling off the solvent under reduced pressure. The residue was subjected to a silica gel column chromatography, eluting with ethyl acetate, to obtain the compound(311)[1.10 g(82.0%)] as yellow powder.

IR(KBr)cm$^{-1}$: 3300(br), 1730(br), 1650(br), 1590.

NMR(CDCl$_3$;90 MHz) δ: 1.12(3H,d,J=7 Hz), 2.88(1H,quint,J=7 Hz), 3.51(2H,m), 3.88(1H,dd,J=6, 14 Hz), 4.05(1H,dd,J=8, 14 Hz), 4.30 (2H,t,J=7 Hz), 6.65(1H,m), 6.90 to 8.07(14H,m), 8.37(2H,br s).

(v) Synthesis of 5-bromo-3-[N-[2-[2-(1-naphthylcarbamoyloxy)ethyl]carbamoyl]propyl-N-phenyl]carbamoyl-1-propylpyridinium chloride(312)

A solution of the compound(311) synthesized in iv) [900 mg (1.56 mmol.)]in propyl iodide(10 ml) was stirred at 110° C. for two days. Resulting precipitates were washed with ether to obtain a crude iodide compound(1.01 g) as yellow powder. The above-mentioned crude product was dissolved in a mixture of methanol-water(7:3)(100 ml). To the solution was added anion-exchange resin(IRA-410[Cl$^-$])(50 ml), and the mixture was stirred for 6 hours. The resin was filtered off, and the filtrate was concentrated under reduced pressure. The concentrate was subjected to s silica gel column chromatography, eluting with methanol-chloroform(1:8), to obtain the compound(312)[316 mg (30.9%)] as yellow powder.

IR(KBr)cm$^{-1}$: 3420(br), 3240(br), 3050, 1720(br), 1660(br), 1590.

NMR(CDCl$_3$; 90 MHz) δ: 0.43(3H,t,J=7 Hz), 1.15(3H,d,J=7 Hz), 1.46(2H,m), 2.67(1H,m), 2.83 to 3.86(4H,m), 4.15(4H,m), 6.70 to 8.75(14H,m), 8.77(2H,br s), 9.70(1H,br s).

PRODUCTION EXAMPLE 112

3-[N-[2-[2,5-Dioxo-1-[(2-methoxy-3-octadecylcarbamoyloxy)propyl]imidazolidin-3-yl]ethyl]]carbamoyl-1-ethyl pyridinium iodide (315)

(i) Synthesis of 2,5-dioxo-1-[(2-methoxy-3-octadecylcarbamoyloxy)propyl]-3-(2-aminoethyl)imidazolidine(313)

In dimethyl sulfoxide(0.5 ml) was dissolved 2,5-dioxo-1-[(2-methoxy-3-octadecylcarbamoyloxy)propyl]-3-(iodoethyl)imidazolidine[300 mg(0.47 mmol.)]. To the solution was added potassium phthalimide[174 mg(0.94 mmol.)], and the mixture was heated at 130° C for one hour in nitrogen streams. The reaction mixture was cooled, to which was added water, followed by extraction with ether. The organic layer was dried over anhydrous sodium sulfate, then the solvent was distilled off under reduced pressure.

The residue was dissolved in methanol(5 ml), to which was added hydrazine hydrate(0.1ml), and the mixture was heated under reflux for one hour in nitrogen streams. The reaction mixture was concentrated under reduced pressure. To the residue was added chloroform, and insolubles were filtered off, followed by concentration of the filtrate under reduced pressure. The crude product thus obtained was purified by means of a column chromatography(silica gel : 10 g; eluent : 0.1% conc. ammonia water/methanol) to obtain the object compound(313)[213 mg(86.0%), a pale yellow oily substance].

TLC(Silica Gel; 0.1% conc.NH$_4$OH/MeOH) : Rf=0.16.

NMR(90 MHz, CDCl$_3$)δ:0.87(3H,t), 1.25(32H,s), 2.93(2H,t), 3.13 (2H,q), 3.41(3H,s), 3.5 to 3.7(5H,m), 4.00(2H,s), 4.15 (2H,br d), 5.05(1H,br).

IR(Neat)cm$^{-1}$: 3350, 2920, 2850, 1757, 1690, 1530, 1465.

(ii) Synthesis of 3-[N-[2-[2,5-dioxo-1-[(2-methoxy-3-octadecylcarbamoyloxy)propyl]imidazolidin-3-yl]ethyl]carbamoyl pyridine (314)

To a solution of the compound(313) synthesized in (i)[100 mg (0.19 mmol.)] and triethylamine[0.159 ml(1.14 mmol.)] in chloroform(5 ml) was added nicotinic acid chloride hydrochloride[68 mg(0.38 mmol.)]. The mixture was stirred for 30 minutes at room temperature. To the reaction mixture was added a 1N aqueous solution of sodium hydroxide(4 ml), followed by extraction with chloroform. The organic layer was dried over anhydrous potassium carbonate, and then the solvent was distilled off under reduced pressure to leave a crude product, which was purified by means of a column chromatography(silica gel : 5 g ; eluent : chloroform-/methanol=19/1) to obtain the object compound(314)[81 mg(67.5%, white solid)].

TLC(Silica Gel; AcOEt/acetone=2/1) : Rf=0.27.

NMR(CDCl$_3$,90 MHz) 6 : 0.87(3H,t), 1.25(32H s), 3.14(2H,q), 3.39(3H,s), 3.4 to 3.9(7H,m), 4.03(2H,s) 4.11(2H,m), 5.17 (1H,br), 7.35(1H,m), 7.48(1H,br), 8.13(1H,m), 8.68(1H,m), 9.02 (1H,br s).

IR(KBr)cm$^-$: 3320, 2920, 2850, 1765, 1700, 1635, 1590, 1543, 1480, 1268

(iii) Synthesis of 3-[N-[2-[2,5-dioxo-1-[(2-methoxy-3-octadecylcarbamoyloxy)propyl]imidazolidin-3-yl]ethyl]]carbamoyl1-ethylpyridinium iodide(315)

The compound(314) synthesized in (ii) [79 mg(0.125 mmol.)] was dissolved in iodoethane(3 ml). The solution was heated under reflux in nitrogen streams for 4 days while shielding light. The reaction mixture was concentrated under reduced pressure, and the crude product thus obtained was recrystallized from acetone/ethyl ether to obtain the object compound (315)[81 mg(82.3%, yellow crystals)].

TLC(silica gel; CHCl$_3$/MeOH/H$_2$O=65/25/4) : Rf=0.33.

NMR(90 MHz,CDCl$_3$)δ: 0.87(3H,t), 1.24(32H,s), 1.77(3H,t), 3.12 (2H,q), 3.41(3H,s), 3.4 to 3.9(7H,m), 4.13(4H,m), 4.7 to 5.1 (3H,m), 8.15(1H,dd), 8.8 to 9.2(2H,m), 9.83(1H,br s).

PRODUCTION EXAMPLE 113

2-[N-[2-[2,5-Dioxo-1-[(2-methoxy-3-octadecylcarbamoyloxy)propyl]imidazolidin-3-yl]ethyl]]carbamoyl-1-ethylpyridinium iodide (317)

(i) Synthesis of 2-[N-[2-[2,5-Dioxo-1-[(2-methoxy-3-octadecylcarbamoyloxy)propyl]imidazolidin-3-yl]ethyl]]carbamoylpyridine (316)

To a solution of the compound(313) synthesized in Production Example 112(-ii) [100 mg(0.19 mmol.)]and triethylamine[0.159 ml (1.14 mmol.)]in chloroform(5 ml) was added picolinoyl chloride hydrochloride[68 mg(0.38 mmol.)], and the mixture was stirred at room temperature for 30 minutes. To the reaction mixture was added a 1N aqueous solution of sodium hydroxide, which was subjected to extraction with chloroform. The organic layer was dried over anhydrous potassium carbonate, then the solvent was distilled off. The crude product thus obtained was purified by means of a column chromatography(silica gel : 5 g ; eluent : ethyl acetate) to afford the object compound (316)[103 mg(85.8%, white solid)].

TLC(Silica Gel;AcOEt) : Rf=0.32.

NMR(90 MHz,CDCl$_3$) δ: 0.87(3H,t), 1.23(32H,s), 3.14(2H,q), 3.38(3H,s), 3.4 to3.9(7H,m), 3.97(2H,s), 4.11(2H,m), 7.37 (1H,m), 7.80(1H,d,t), 8.15(1H,d), 8.34(1H,br), 8.55(1H,d).

IR(KBr)cm$^{-}$: 3320, 2920, 2850, 1764, 1702, 1528, 1462, 1238.

(ii) Synthesis of 2-[N-[2-[2,5-dioxo-1-[(2-methoxy-3-octadecylcarbamoyloxy)propyl]imidazolidin-3-yl]ethyl]]carbamoyl1-ethylpyridinium iodide (317)

A solution of the compound(316) synthesized in (i)[100 mg (0.158 mmol.)]in iodoethane(3 ml) was heated under reflux for 4 days in nitrogen streams while shielding light. The reaction mixture was concentrated under reduced pressure, and the crude product thus obtained was purified by means of a column chromatography(silica gel : 6 g ; eluent : ethyl acetate chlorofrom/methanol=19/1→chloroform/methanol/water=65/25/1) to obtain the object compound(317)[47 mg(37.8%,yellow powder)].

TLC(Silica Gel; CHCl$_3$/MeOH/H$_2$O=65/25/1) : Rf=0.32.

PRODUCTION EXAMPLE 114

3-[2-[(2-methoxy-3-octadecylcarbamoyloxy)propoxycarbonyl]aminoethyloxy]carbonyl-1-ethylpyridinium iodide (319)

(i) Synthesis of 3-[2-[(2-methoxy-3-octadecylcarbamoyloxy)propoxycarbonyl]aminoethyloxy]carbonylpyridine (318)

To a solution of 3-(hydroxyethyl)carbamoyl-2-methyl-loctadecyl carbamoyl glycerine[977 mg(2 mmol.)]in triethylamine(20 ml) was added, under ice-cooling, nicotinic acid chloride hydrochloride[427 mg(2.4 mmol.)]. The mixture was stirred at room temperature for two hours. The reaction mixture was concentrated under reduced pressure. To the concentrate was added a 5% aqueous solution of sodium hydrogencarbonate, followed by extraction with chloroform. The organic layer was dried over anhydrous sodium sulfate, then the solvent was distilled off under reduced pressure. The crude product thus obtained was purified by means of a column chromatography (silica gel : 50 g ; eluent : n-hexane/ethyl acetate =1/3) to obtain the object compound(318)[1.036 g(87.2%, white solid)].

TLC(Silica Gel;n-hexane/AcOEt=1/3) : Rf=0.28.

NMR(90 MHz,CDCl$_3$) δ: 0.87(3H,t), 1.26(32H,s), 3.14(2H,q), 3.42(3H,s), 3.47 to 3.7(3H,m), 4.15(4H,m), 4.44(2H,t), 4.97 (1H,br), 5.31(1H,br), 7.41(1H,dd), 8.31(1H,m), 8.81(1H,m), 9.25(1H,br s).

Synthesis of 3-[2-[(2-methoxy-3-octadecyl carbamoyloxy)propoxy carbonyl]aminoethyloxy]carbonyl-1-ethylpyrdinium 7 iodide (319)

A solution of the compound(318) synthesized in (i)[594 mg (1 mmol.)]in iodoethane(8 ml) was heated under reflux for 84 hours in nitrogen streams while shielding light. The reaction mixture was concentrated under reduced pressure to obtain the object compound(319)[750 mg(100%, yellow powder)].

TLC(Silica Gel;CHCl$_3$)/MeOH=3/1) : Rf =0.17.

NMR(90 MHz,CDCl$_3$) δ: 0.88(3H,t), 1.26(32H,s), 1.76(3H,t), 3.13 (2H,q), 3.43(3H,s), 3.63(3H,m), 4.15(4H,m), 4.52(2H,br t), 5.04(1H,br), 5.18(2H,q), 6.55(1H,br), 8.33(1H,dd), 9.07(1H,m), 9.67(1H,m), 10.05(1H,br s).

PRODUCTION EXAMPLE 115

5-Bromo-3-[N-[2-[[2-(1-indolinyl)carbonyloxy]ethyl]-carbamoyl]ethyl-N-phenyl]carbamoyl-1-propyl-pyridinium chloride(323)

(i) Synthesis of 1-(N-t-butoxycarbonyl-N-benzyl)amino-2-(1-indolinyl)carbonyloxyethane (320)

In methylene chloride(70 ml) was dissolved N-benzylethanolamine[2.57 g(17 mmol.)], to which was added, under ice-cooling, di-t-butyl dicarbonate[3.71 g(17 mmol.)]. The mixture was stirred at room temperature for two hours, and the reaction mixture was concentrated under reduced pressure.

To the concentrate were added trietylamine[2.606 ml(18.7 mmol.)] and methylene chloride(100 ml). To the mixture was further added, under ice-cooling, diphosgene[2.257 ml(18.7 mmol.)], which was stirred at 0° C. for 45 minutes and then at room temperature for 1.5 hour. The reaction mixture was washed with water, and the organic layer was dried over anhydrous sodium sulfate, then the solvent was distilled off under reduced pressure to obtain a crude carbonic acid ester (5.487 g). To this crude carbonic acid ester[1.238 g(3 mmol.)] was added indoline[358 mg(3 mmol.)], and the mixture was left standing for 30 minutes at room temperature. To the reaction mixture was added chloroform, which was washed with water, followed by drying the organic layer over anhydrous sodium sulfate. The solvent was distilled off under reduced pressure to obtain a crude product, which was purified by means of a column chromatography(silica gel : 50 g ; eluent : hexane/ ethyl acetate=4/1) to obtain the object compound(320)[869 mg (73.1%, a pale yellow oily product)].

TLC(Silica Gel ; n-hexane/AcOEt=3/1) : Rf =0.39

NMR(90 MHz,CDCl$_3$) δ: 1.44(9H,s), 3.05(2H,t), 3.51(2H,m), 3.94(2H,t), 4.30(2H,t), 4.51(2H,s), 6.8 to 7.4(9H,m).

IR(Neat)cm$^{-1}$: 2975, 1700, 1601, 1490, 1410, 1140.

(ii) Synthesis of 2-(1-indolinyl)carbonyloxyethylamine(321)

To a solution of the compound(320) synthesized in (i)[849 mg(2.14 mmol.)]in chloroform(10 ml) was added methanol saturated with hydrochloric acid. The mixture was stirred at room temperature for 20 minutes, and the reaction mixture was concentrated under reduced pressure.

The crude product thus obtained was dissolved in a 90% aqueous solution of acetic acid. The solution was subjected to catalytic reduction in the presence of 5% Pd/C (1 g). The reaction mixture was subjected to filtration, and the filtrate was concentrated under reduced pressure. The concentrate was dissolved in chloroform, which was washed with water. The organic layer was dried over anhydrous potassium carbonate. The solvent was then distilled off under reduced pressure. The crude product thus obtained was purified by means of a column chromatography(silica gel : 15 g ; eluent : methanol/ conc. ammoniacal water =100/1) to obtain the object compound (321)[336 mg(76.1%, a colorless oily product)].

TLC(Silica Gel; MeOH/conc.NH$_4$OH=50/1): Rf=0.45.

. NMR(90 MHz, CDCl$_3$) δ: 1.46(2H,br s), 3.01(2H,t), 3.10(2H,t), 4.03(2H,t), 4.27(2H,t), 6.8 to 7.3(4H,m).

IR(Neat)cm$^{-}$: 3365, 2950, 1700, 1600, 1490, 1410, 1335, 1292, 1140.

(iii) Synthesis of 5-bromo-3-[N-[2-[[2-(1-indolinyl)carbonyl oxy]ethyl]carbamoyl]ethyl-N-phenyl]carbamoylpyridine (322)

In chloroform(10 ml) were dissolved the compound(321) synthesized in [289 mg(1.4 mmol.)]and triethylamine[0.976 ml(7.0 mmol.)]. To the solution was added, under ice-cooling, the acid chloride(293)[679 mg(1.68 mmol.)], and the mixture was stirred at room temperature for one hour. The reaction mixture was washed with a 1N aqueous solution of NaOH, and the organic layer was dried over anhydrous potassium carbonate, then the solvent was distilled off under reduced pressure. The crude product thus obtained was purified by means of a column chromatography(silica gel: 30 g; eluent: ethyl acetate/acetone=19/1) to obtain the object compound(322) [487 mg(64.7%, a colorless resinous product)].

TLC(Silica Gel; AcOEt) : Rf=0.23

NMR(90MHz,CDCl$_3$) δ: 2.59(2H,t), 3.05(2H,t), 3.56(2H,q), 3.98(2H,t), 4.0 to 4.4(4H,t), 6.71(1H,br), 6.8 to 7.3(9H,m), 7.76(1H,t), 8.26(1H,d), 8.45(1H,d).

Synthesis of 5-bromo-3-[N-[2-[[2-(1-indolinyl)carbonyloxy]ethyl]carbamoyl]ethyl-N-phenyl]carbamoyl-1-propylpyridinium chloride (323)

To the compound(322) synthesized in (ii)[446 mg(0.83 mmol.)]was added 1-iodo propane(15 ml), and the mixture was heated under reflux for 64 hours in nitrogen streams while shielding light. The reaction mixture was cooled and concentrated under reduced pressure. The crude product thus obtained was dissolved in 70% methanol/water(70 ml). The solution was processed with IRA-410(Cl$^-$)(70 ml) and then purified by means of a column chromatography(silica gel : 20 g ; eluent : chloroform/methanol=6/1) to obtain the object compound(323)[350 mg(68.5%, pale yellow powder)].

TLC(Silica Gel ; CHCl$_3$:/MeOH=3/1) : Rf=0.23.

NMR(90MHz,CDCl$_3$) δ: 0.71(3H,t), 1.81(2H,m), 2.74(2H,m), 3.04(2H,t), 3.47(2H,m), 3.8 to 4.4(6H,m), 4.82(2H,m), 6.8 to 7.8(9H,m), 8.3 to 8.7(2H, m), 9.67(1H,br), 9.74(1H,br).

IR(KBr)cm$^{-1}$: 3410, 2960, 1700, 1655, 1595, 1490, 1415.

Production Example 116

5-Bromo-3-[N-[2-[[2-(1,2,3,4-tetrahydroquinolyl)carbonyloxy]ethyl]carbamoyl]ethyl-N-phenyl]carbamoyl-1-propylpyridinium chloride (327)

i) Synthesis of 1-(N-t-butoxycarbonyl-N-benzyl)amino-2-(1,2,3,4-tetrahydroquinolyl)carbonyloxyethane (324)

In methylene chloride(70 ml) was dissolved N-benzylethanolamine[2.57 g(17 mmol.)]. To the solution was added, under ice-cooling, di-t-butyl dicarbonate[3.71 g(17 mmol.)], and the mixture was stirred at room temperature for two hours, then the reaction mixture was concentrated under reduced pressure. To the concentrate were added triethylamine[2.606 ml(18.7 mmol.)-]and methylene chloride(100 ml). To the mixture was further added, under ice-cooling, diphosgene[2.257 ml(18.7 mmol.)], then the mixture was stirred at 0° C. for 45 minutes and at room temperature for 1.5 hour. The reaction mixture was washed with water, and the organic layer was dried over anhydrous sodium sulfate. The solvent was then distilled off under reduced pressure to obtain a crude carbonic acid ester(5.487 g). To this crude carbonic acid ester[1.238 g (3 mmol.)]was added tetrahydroquinoline[400 mg(3 mmol.)], and the mixture was left standing at room temperature for 30 minutes. To the reaction mixture was added chloroform and then was washed with water. The organic layer was then dried over anhydrous sodium: sulfate, and the solvent was distilled off under reduced pressure. The crude product thus obtained was purified by means of a column chromatography(silica gel: 50 g; eluent:hexane/ethyl acetate=4/1) to obtain the object compound(324)[1.018 g(82.7%, a colorless oily product)].

TLC(Silica Gel; n-hexane/AcOEt=3/1): Rf=0.34.

NMR(90MHz,CDCl$_3$) δ: 1.45(9H,s), 1.92(2H,m), 2.76(2H,t), 3.49(2H,m), 3.73(2H,t), 4.28(2H,t), 4.47(2H,s), 6.9 to 7.4 (9H,m), 7.70(1H,d).

IR(Neat)cm$^{-1}$: 2970, 1700, 1601, 1580, 1492, 1400, 1260, 1242, 1172, 1140.

(ii) Synthesis of 2-(1,2,3,4-tetrahydroquinolyl)carbonyloxy ethylamine(325)

In chloroform(10 ml) was dissolved the compound (324) synthesized in i)[1.00 g(2.436 mmol.)]. To the solution was added methanol saturated with hydrochloric acid(10 ml), and the mixture was stirred at room temperature for 20 minutes. The reaction mixture was concentrated under reduced pressure. The crude product thus obtained was dissolved in a 90% aqueous solution of acetic acid, which was subjected to catalytic reduction in the presence of 5% Pd/C(lg). The reaction mixture was subjected to filtration, and the filtrate was concentrated under reduced pressure. The concentrate was dissolved in chloroform and washed with water. The organic layer was dried over anhydrous potassium carbonate, then the solvent was distilled off under reduced pressure. The crude product thus obtained was purified by means of a column chromatography(silica gel: 15 g; eluent:methanol/conc. ammoniacal water=100/1) to obtain the object compound (325)[454 mg(84.6%, a colorless oily product)].

TLC(Silica Gel; MeOH/Conc.NH$_4$OH=50/1): Rf=0.49.

NMR(90MHz,CDCl$_3$); δ: 1.30(2H,br s), 1.93(2H,quint), 2.77 (2H,t , 2.97(2H,t), 3.77(2H,t), 4.21 2H,t), 6.8 to 7.3(3H,m), 7.69(1H,d).

IR(Neat)cm$^{-1}$: 3370, 2975, 1700, 1600, 1580, 1490, 1390, 1320, 1260, 1204, 1138.

(iii) Synthesis of 5-bromo-3-[N-[2-[[2-(1,2,3,4-tetrahydroquinolyl)carbonyloxy]ethyl]carbamoyl]ethyl-N-phenyl]carbamoyl pyridine(326)

In chloroform(10 ml) were dissolved the compound(325) synthesized in (ii) [352 mg(1.6 mmol.)]and triethylamine[1.115 ml (8.0 mmol.)]. To the solution was added, under ice-cooling, the acid chloride compound(293)[776 mg(1.92 mmol.)], followed by stirring at room temperature for one hour. The reaction mixture was washed with a 1N aqueous solution of NaOH. The organic layer was dried over anhdyrous potassium carbonate, and the solvent was distilled off under reduced pressure. The crude product thus obtained was purified by means of a column chromatography(silica gel: 30 g; eluent:ethyl acetate/acetone= 19/1) to obtain the object compound(326)[479 mg (54.3%, a colorless resinous product)].

TLC(Silica Gel ; AcOEt): Rf=0.24.

NMR(90MHz,CDCl$_3$) δ: 1.19(2H,quint), 2.57(2H,t), 2.74(2H,t), 3.53(2H,q), 3.73(2H,t), 4.0 to 4.4(4H,t), 6.56(1H,br), 6.9 to 7.3(8H,m), 7.65(1H,m), 7.80(1H,t), 8.29(1H,d), 8.47(1H,d).

(iv) Synthesis of 5-bromo-3-[N-[2-[[2-(1,2,3,4-tetrahydroquinolyl)carbonyloxy]ethyl]carbamoyl]ethyl-N-phenyl]carbamoyl-1-propylpyridinium chloride (327)

To the compound(326) synthesized in i)[438 mg(0.79 mmol.)]was added 1-iodo propane(15 ml), and the mixture was heated under reflux for 64 hours in nitrogen streams while shielding light. The reaction mixture was cooled and concentrated under reduced pressure. The crude product thus obtained was dissolved in 70% methanol/water(70 ml). The solution was processed with IRA-410(Cl−)[70 ml], followed by further purification by means of a column chromatography(silica gel: 20 g; eluent: chloroform/methanol=6/1) to obtain the object compound(327) [317 mg(63.7%, pale yellow powder)].

TLC(Silica Gel; CHCl$_3$/MeOH=3/1): Rf=0.26.

NMR (90MHz,CDCl$_3$) δ: 0.69(3H,t), 1.83(4H,m), 2.70(4H,m), 3.3 to 3.8(4H,m), 4.19(4H,m), 4.78(2H,m), 6.9 to 7.5(8H,m), 7.65(1H,d), 8.1 to 8.4(2H,m), 9.62(2H,br s).

IR(KBr)cm$^{-1}$: 3425, 2960, 1690, 1660, 1595, 1495, 1400.

Production Example 117

3-[N-[2-[[2-(1,2,3,4-tetrahydroisoquinolyl)carbonyloxy]ethyl]carbamoyl]ethyl-N-phenyl]aminosulfonyl-1-propylpyridinium chloride(329)

(i) Synthesis of 3-[N-[2-[[2-(1,2,3,4-tetrahydroisoquinolyl)carbonyloxy]ethyl]carbamoyl]ethyl-N-phenyl]aminosulfonyl pyridine (328)

At 180° C. were heated 3-pyridine sulfonic acid[7.96 g(50.0 mmol.)]and phosphorus pentachloride[20.8 g(100 mmol.)]for two hours. The reaction mixture was cooled, there was added benzene, and then insolubles were filtered off. The filtrate was concentrated under reduced pressure to obtain the sulfonyl chloride compound(226)(10.0 g). To a solution of the compound(225) synthesized in Production Example 87-v)[300 mg(0.82 mmol.)]and triethylamine[0.35 ml (2.80 mmol.)]in chloroform(5 ml) was added the sulfonyl chloride compound(226)[300 mg(1.40 mmol.)], and the mixture was stirred for 30 minutes. The reaction mixture was washed with a 1N aqueous solution of sodium hydroxide cooled with ice, then washed with water, then dried, followed by distilling off the solvent under reduced pressure. The residue was subjected to a silica gel column chromatography, eluting with ethyl acetate, to obtain the compound(328)[240 mg(57.8%)]as colorless powder.

IR(Neat)cm$^{-1}$: 3320(br), 3060, 1700, 1670, 1350, 1170.

NMR(90MHz;CDCl$_3$) δ: 2.43(2H,t,J=7Hz), 2.83(2H,t,J=6Hz), 3.46(2H,q,J=6Hz), 3.67(2H,t,J=6Hz), 3.87(2H,t,J=7Hz), 4.20 (2H,t,J=6Hz), 4.60(2H,s), 6.30(1H,br t,J=6Hz), 6.73 to 7.67 (11H,m), 7.84(1H,d,J=8Hz), 8.74(1H,m).

(ii) Synthesis of 3-[N-[2-[[2-(1,2,3,4-tetrahydroisoquinolyl)carbonyloxy]ethyl]carbamoyl]ethyl-N-phenyl]aminosulfonyl-1-propylpyridinium chloride (329)

A solution of the compound(328)[180 mg(0.35 mmol synthesized in i) in isopropyl iodide(10 ml) was heated under reflux over night. Resulting crystals(256 mg) were separated and dissolved in 70% methanol(50 ml). To the solution was added IRA-410[Cl−](25 ml), and the mixture was stirred for 4 hours. The resin was filtered off, and the filtrate was concentrated under reduced pressure. The concentrate was subjected to a silica gel column chromatography, eluting with chloroform-methanol [4:1(v/v)], to obtain the compound(328)[140 mg(67.4%)]as pale yellow powder.

IR(KBr)cm$^{-1}$: 3420(br), 3050, 1690(br), 1660(br), 1370, 1160.

NMR(90MHz;CDCl$_3$) δ: 0.98(3H,t,J=7Hz), 2.07(2H,quint,J=7Hz), 2.47(2H,t,J=6Hz), 2.80(2H,t,J=6Hz), 3.47(4H,m), 3.64(2H,t, J=6Hz), 4.13(4H,m), 4.57(2H,s), 5.00(1H,br t,J=6Hz), 6.64 to 7.50(8H,m), 7.70(1H,m), 8.20 to 8.67(2H,m), 9.39(1H, br s), 9.74(1H, br d,J=3Hz).

Production Example 118

1-Benzyl-3-[N-[2-[2-methoxy-3-octadecyl carbamoyloxy propoxycarbonyl]aminoethyl]-N-methyl]carbamoyl-pyridinium 7 chloride (330)

In acetone(10 ml) was dissolved the compound(4) synthesized in Production Example 1-iv)[303 mg(0.5 mmol.)]. To the solution was added benzyl bromide[0.144 ml(1.2 mmol.), and the mixture was heated under reflux for 24 hours in nitrogen streams while shielding light. The reaction mixture was cooled and concentrated under reduced pressure. The crude product thus obtained was recrystallized from ethyl acetate to afford the object compound[332 mg(85.4%,white powder)].

TLC(Silica Gel ; CHCl$_3$:/MeOH=3/1): Rf=0.31.

NMR(90MHz,CDCl$_3$) δ: 0.87(3H,t), 1.26(32H,s), 3.08(2H,m), 3.13(3H,s), 3.2 to 3.7(8H,m), 4.17(4H,m), 5.18(1H,br), 6.12 (2H,m), 6.92(1H,br), 7.3 to 7.8(5H,m), 8.08(1H,m), 8.45(1H,m), 8.9 to 9.4(2H,m).

Production Example 119

1-Benzyl-3-[N-[2-[2-methoxy-3-octadecylcarbamoyloxypropoxycarbonyl]aminoethyl]]carbamoylpyridinium chloride (331)

In acetone(10 ml) was dissolved the compound(167) synthesized in Production Example 63-i)[242 mg(0.408 mmol.)]. To the solution was added benzyl bromide[140 mg(0.816 mmol.)], and the mixture was heated under reflux for 24 hours in nitrogen streams while shielding light. The reaction mixture was cooled, and resulting precipitates were collected by filtration and dried to obtain the object compound(331) [285 mg(91.5%, white powder)].

TLC(Silica Gel; CHCl$_3$/MeOH=3/1): Rf=0.33.

NMR(90MHz,CDCl$_3$) δ: 0.87(3H,t), 1.25(32H,s), 3.10(2H,q), 3.40(3H,s), 3.53(5H,m), 4.13(4H,br d), 5.60(1H,br), 6.09 (2H,s), 6.57(1H,br), 7.44(3H,m), 7.67(2H,m), 8.11(1H,m), 9.12(1H,m), 9.33(1H,m), 10.37(1H,br).

Production Example 120

5-Bromo-3-[N-[2-[[2-methoxy-3-(1,2,3,4-tetrahydroisoquinolyl)carbonyloxy]propyl]carbamoyl]ethyl-N-phenyl]carbamoyl-1-propylpyridinium chloride (335)

(i) Synthesis of 3-(1,2,3,4-tetrahydroisoquinolyl)carbonyl-2-methyl glycerine (332)

In methylene chloride(15 ml) were dissolved 3-benzoyl-2-methyl glycerine[1.051 g(5 mmol.)]and pyridine[0.809 ml(10 mmol.)]. To the solution was added, under ice-cooling, phenyl chlorocarbonate[0.69 ml(5.5 mmol.)], and the mixture was stirred at room temperature for 10 minutes. The reaction mixture was washed with a 5% aqueous solution of sodium hydrogen carbonate. The organic layer was dried over anhdyrous sodium sulfate, then the solvent was distilled off under reduced pressure to obtain a crude carbonate product and there was added 1,2,3,4-tetrahydroisoquinoline[733 mg(5.5 mmol.)]. The mixture was heated at 90° C. for 40 minutes, to which was added, after cooling, chloroform, followed by washing with water. The organic layer was dried over anhydrous sodium sulfate, then the solvent was distilled off under reduced pressure. The crude product thus obtained was dissolved in methanol(30 ml). To the solution was added a 1N NaOH aqueous solution(10 ml), and the mixture was stirred at room temperature for 10 minutes. After completion of the reaction, the reaction mixture was concentrated under reduced pressure. To the concentrate was added water, which was subjected to extraction with chloroform. The organic layer was dried over anhydrous sodium sulfate, then the solvent was distilled off under reduced pressure. The crude product thus obtained was purified by means of a column chromatography(silica gel: 60 g; eluent ethyl acetate) to afford the object compound(332)]1.118 g (84.3%, colorless liquid).

TLC(Silica Gel; AcOEt); δRf=0.42. NMR(90MHz,CDCl₃) δ: 2.65(1H,t), 2.84(2H,t), 3.46(3H,s), 3.69(4H,m), 4.29(2H,d), 4.62(2H,s), 7.13(4H,s).

IR(KBr)cm⁻¹: 3425, 2930, 1700, 1430, 1230, 1120, 1092.

(ii) Synthesis of 2-methoxy-3-(1,2,3,4-tetrahydroisoquinolyl)carbonyloxy propylamine (333)

In anhydrous tetrahydrofuran(20 ml) were dissolved the compound(332) synthesized in i)[1.10 g(4.416 mmol.)], triphenyl phosphine[2.175 g(8.292 mmol.)]and phthalimide[1.22 g (8.292 mmol.)]. To the solution was added, under ice-cooling, diethyl diaza-carboxylate[1.278 ml(8.292 mmol.)]. The mixture was stirred at room temperature for two hours. The reaction mixture was concentrated under reduced pressure, and the resulting crude product was purified by means of a column chromatography(silica gel: 140 g; eluent:hexane/ethyl acetate=1/1) to obtain a crude product(2.636 g). This crude product was dissolved in methanol(20 ml), to which was added hydrazine hydrate(1 ml), and the mixture was heated for one hour under reflux. The reaction mixture was cooled and concentrated under reduced pressure. To the concentrate was added chloroform, and then insolubles were filtered off. The filtrate was concentrated under reduced pressure to obtain a crude product, which was subjected to purification by means of a column chromatography(silica gel: 140 g; eluent:methanol (333)[1.046 g(95.4%, a colorless oily product)]. TLC(Silica Gel ; MeOH/conc.N-H₄OH=200/1): Rf=0.24.

NMR(90MHz,CDCl₃) δ: 1.42(2H,br), 2.84(4H,t), 3.37(1H, quint), 3.47(3H,s), 3.69(2H,t), 4.23(2H,d), 4.63(2H,s), 7.18 (4H,s).

IR(Neat)cm⁻¹: 3360, 2935, 1700, 1430, 1230, 1123, 1098.

(iii) Synthesis of 5-bromo-3-[N-[2-[[2-methoxy-3-(1,2,3,4-tetrahydroisoquinolyl)carbonyloxy]propyl]carbamoyl]ethyl-N-phenyl]carbamoyl pyridine (334)

In chloroform(20 ml) were dissolved the compound(333) synthesized in (ii) [527 mg(1.994 mmol.)]and triethylamine [1.39 ml(9.97 mmol.)]. To the solution was added, under ice-cooling, the acid chloride(293)[886 mg(2.193 mmol.)], and the mixture was stirred at room temperature for 50 minutes. The reaction mixture was washed with a 1N NaOH aqueous solution. The organic layer was dried over anhydrous potassium carbonate, then the solvent was distilled off under reduced pressure. The crude product thus obtained was purified by means of a column chromatography(silica gel: 40 g; eluent:ethyl acetate/acetone=10/1) to obtain the object compound(334)[645 mg(54.3%, a colorless resinous product)].

TLC(Silica Gel ; AcOEt/acetone=10/1): Rf=0.34.

NMR(90MHz,CDCl₃) δ: 2.60(2H,t), 2.83(2H,t), 3.2 to 3.6 (3H,s), 3 46(3H,S), 3.69(2H,t), 4.23(4H,m), 4.63(2H.s), 6.44(1H,br), 7.0 to 7.4(9H,m), 7.83(1H,t), 8.33 1H,d), 8.51{1H,d)

iv) Synthesis of 5-bromo-3-[N-[2-[[2-methoxy-3-(1,2,3,4-tetrahydroisoquinolyl)carbonyloxy]propyl]carbamoyl]ethyl-N-phenyl]carbamoyl-1-propylpyridinium chloride(335)

To the compound(334) synthesized in (i)[595 mg(1 mmol.)]was added 1-iodopropane(20 ml), and the mixture was heated for 60 hours under reflux in nitrogen streams while shielding light. The reaction mixture was cooled and concentrated under reduced pressure. The crude product thus obtained was dissolved in 70% methanol/water(70 ml). The solution was processed with IRA-410(Cl⁻¹)[70 ml], and further purified by means of a column chromatography(silica gel: 20 g; eluent: chloroform/methanol=6/1) to obtain the object compound(335) [409 mg(60.7%, pale yellow powder)].

TLC(Silica Gel; CHCl₃/MeOH=3/1): Rf=0.25.

NMR(90MHz,CDCl₃) δ: 0.74(3H,t), 1.80(2H,m), 2.5 to 3.1 (4H,m), 3.2 to 3.8(5H,m), 3.40(3H,s), 4.16(4H,m), 4.57(2H,s), 4.88(2H,m), 6.9 to 7.5(9H,m), 7.80(1H,br), 8.36(2H,br s), 9.64(1H,br s), 9.77(1H,br s).

IR(KBr)cm⁻¹: 3425, 2925, 1695, 1655, 1590, 1495, 1426, 1225.

Production Example 121

5-Bromo-3-[N-phenyl-N-[2-[[3-(1,2,3,4-tetrahydroisoquinolyl)carbonyloxy]propyl]carbamoyl]ethyl]-carbamoyl-1-propylpyridinium chloride (339)

(i) Synthesis of 1-t-butoxycarbonylamino-3-(1,2,3,4-tetrahydroquinolyl)carbonyloxypropane(336)

In methylene chloride(20 ml) was dissolved 3-aminopropanol [751 mg(10 mmol.)]. To the solution was added, under icecooling, di-t-butyl dicarbonate[2.183 g(10 mmol.)], and the mixture was stirred at room temperature for two hours.

To the above-mentioned reaction mixture was added pyridine [1.618 ml(20 mmol.)] and there was further added, under ice-cooling, phenyl chlorocarbonate[1.254 ml(10 mmol.)] followed by stirring for 10 minutes at room temperature. The reaction mixture was washed with a 5% aqueous solution of sodium hydrogencarbonate. The organic layer was dried over anhydrous sodium sulfate, then the solvent was distilled off under reduced pressure to obtain a crude carbonate product. To this crude carbonate product was added 1,2,3,4-tetrahydroisoquinoline[377 ml(11 mmol.)],and the mixture was heated at 90° C. for one hour and then cooled. The resulting crude product was purified by means of a column chromatography (silica gel: 100 g; eluent:hexane/ethyl acetate=1.5/1) to obtain the object compound(336)[2.868 g(85.8%, a colorless oily product).

TLC(Silica Gel; n-hexane/AcOEt=1.5/1): Rf=0.35 NMR(

NMR(90MHz,CDCl₃) δ: 1.44(9H,s), 1.83(2H,quint), 2.83 (2H,t), 3.22(2H,q), 3.68(2H,t), 4.20(2H,t), 4.62(2H,s), 4.84 (1H,br), 7.17(4H,s).

IR(Neat)cm$^{-1}$: 3350, 2970, 1700, 1520, 1432, 1362, 1232, 1070, 1020.

(ii) Synthesis of 3-(1,2,3,4-tetrahydroisoquinoyl)carbonyloxy propylamine (337)

To a solution of the compound(336) synthesized in i) [2.675 g(8 mmol.)]in chloroform(10 ml) was added HCl-saturated methanol(5 ml), and the mixture was stirred at room temperature for 1.5 hour. The reaction mixture was concentrated under reduced pressure. To the crude product thus obtained was added a 1N aqueous solution of sodium hydroxide (25 ml), followed by extraction with chloroform. The organic layer was dried over anhydrous potassium carbonate, then the solvent was distilled off under reduced pressure to obtain the object compound(337)[1.874 g(100%, a pale yellow oily product)].

TLC(Silica Gel; MeOH/conc.NH.OH=50/1): Rf=0.29

NMR(90MHz,CDCl$_3$) δ: 1.30(2H,s), 1.79(2H,quint), 2.80(4H,m), 3.67(2H,t), 4.21(2H,t), 4.60(2H,s), 7.14(4H,s).

IR(Neat)cm$^{-1}$: 3365, 2925, 1690, 1580, 1430, 1298, 1230, 1120.

(iii) Synthesis of 5-bromo-3-[N-[2-[3-(1,2,3,4-tetrahydroisoquinolyl)carbonyloxy]propyl]carbamoyl]ethyl-N-phenyl]carbamoylpyridine (338)

In chloroform(10 ml ) were dissolved the compound(337) synthesized in ii) [585 mg(2.5 mmol.)]and triethylamine[1.742 ml (12.5 mmol.)]. To the solution was added, under ice-cooling, the acid chloride compound(293)[1.212 g(3 mmol.)], and the mixture was stirred at room temperature for one hour. The reaction mixture was washed with a 1N aqueous solution of NaOH, and the organic layer was dried over anhydrous potassium carbonate, followed by distilling off the solvent under reduced pressure. The crude product thus obtained was purified by means of a column chromatography(silica gel: 60 g; eluent:ethyl acetate/acetone=5/1) to obtain the object compound(338) [722 mg(51.1%, a colorless resinous product)].

TLC(Silica Gel ; AcOEt/acetone=5/1): Rf=0.32.
NMR(90MHz,CDCl$_3$)δ: 1.82(2H,quint),2.57(2H,t),2.83(2H,t), 3.30(2H,q),3.67(2H,t),4.21(4H,m),4.61(2H,s),6.49(1H,br), 7.17(9H,m), 7.80(1H,t), 8.31(1H,d), 8.50(1H,d)

(iv) Synthesis of 5-bromo-3-[N-phenyl-N-[2-[[3-(1,2,3,4-tetrahydroisoquinolyl)carbonyloxy]propyl]carbamoyl]ethyl]carbamoyl-1-propylpyridinium chloride(339)

To the compound(338) synthesized in iii)[565 mg(1 mmol.)]was added 1-iodopropane(20 ml). The mixture was heated under reflux for 38 hours in nitrogen streams while shielding light. The reaction mixture was cooled and concentrated under reduced pressure. The crude product thus obtained was dissolved in 70% methanol/water(70 ml), and the solution was processed with IRA-410(Cl$^-$)[70 ml], followed by further purification by means of a column chromatography(silica gel: 30 g; eluent:chloroform/methanol=6/1) to obtain the object compound(339)[457 mg(71.0%, pale yellow powder)].

TLC(Silica Gel;CHCl$_3$/MeOH=3/1): Rf=0.28.
NMR(90MHz,CDCl$_3$) 6: 0.77(3H,t), 1.87(4H,m), 2.82(4H,m), 3.24(2H,m), 3.65(2H,t), 4.13(4H,m), 4.58(2H,s), 4.90(2H,m), 7.0 to 7.6(9H,m), 8.23(1H,br), 8.41(1H,br s), 9.77(2H,br s).

IR(KBr)cm$^{-1}$: 3410, 2955, 1690, 1655, 1590, 1430, 1228.

Production Example 122

5-Bromo-3-[N-phenyl-N-[2-[2-(1,2,3,4-tetrahydroisoquinolyl)carbonyloxy]ethoxy]ethylcarbamoyl]ethyl]carbamoyl-1-propylpyridinium chloride (343)

(i) Synthesis of 1-t-butoxycarbonylamino-2-[2-(1,2,3,4-tetrahydroisoquinolyl)carbonyloxy]ethoxyethane(340)

To a solution of 2-(2-aminoethoxy)ethanol[1.051 g(10 mmol.)]in methylene chloride (20 ml) was added, under ice-cooling, di-t-butyl dicarbonate[2.183 g(10 mmol.)], and the mixture was stirred at room temperature for two hours.

To the above-mentioned reaction mixture was added pyridine [1.618 ml(20 mmol.)]and there was further added, under ice-cooling, phenyl chlorocarbonate[1.254 ml(10 mmol.)], followed by stirring at room temperature for 15 minutes. The reaction mixture was washed with a 5% aqueous solution of sodium hydrogencarbonate, and the aqueous layer was dried over anhydrous sodium sulfate, followed by distilling off the solvent under reduced pressure to give a crude carbonate. To this crude carbonate was added 1,2,3,4-tetrahydroisoquinoline[1.377 ml(11 mmol.)], and the mixture was heated at 90° C for one hour. The reaction mixture was cooled, and the crude product thus obtained was purified by means of a column chromatography(silica gel: 100 g; eluent:hexane/ethyl acetate=1/1) to afford the object compound (340)[3.577 g(98.2%, a colorless oily product)].

TLC(Silica Gel ; n-hexane/AcOEt=1/1): Rf=0.23.
NMR(90MHz,CDCl$_3$) δ: 1.33(9H,s), 2.75(2H,t), 3.21(2H,q), 3.41 to 3.68(6H,m), 4.21(2H,m), 4.56(2H, s), 4.88(1H,br), 7.12(4H,s).

IR(Neat)cm$^{-1}$: 3350, 2975, 1700, 1510, 1430, 1362, 1298, 1235, 1172, 1120, 1100.

(ii) Synthesis of 1-amino-2-[2-(1,2,3,4-tetrahydroisoquinolyl)carbonyloxy]ethoxyethane(341)

To a solution of the compound(340) synthesized in i) [2.915 g(8 mmol.)]in chloroform(10 ml) was added HCl-saturated methanol(5 ml), and the mixture was stirred at room temperature for 1.5 hour. The reaction mixture was concentrated under reduced pressure. To the crude product thus obtained was added a 1N aqueous solution of sodium hydroxide(25 ml), followed by extraction with chloroform. The organic layer was dried over anhydrous potassium carbonate, and the solvent was distilled off under reduce pressure to obtain the object compound(341)[2.114 g(100%, a pale yellow oily product)].

TLC(Silica Gel; MeOH/conc.NH$_4$OH=50/1): Rf=0.35.
NMR(90MHz,CDCl$_3$) δ: 1.37(2H,s), 2.83(4H,t), 3.50(2H,t), 3.68(4H,m), 4.29(2H,m), 4.61(2H,s), 7.14(4H,s).

IR(Neat)cm$^{-1}$: 3375, 2860, 1700, 1430, 1295, 1230, 1120, 1098.

(iii) Synthesis of 5-bromo-3-[N-phenyl-N-[2-[2-(1,2,3,4-tetrahydroisoquinolyl)carbonyloxy]ethoxy]ethylcarbamoyl]ethyl]carbamoyl pyridine (342)

In methylene chloride(10 ml) were dissolved the compound (292) synthesized in Production Example 106-iii)[1.048 g (3 mmol.)]DCC[681 mg(3.3 mmol.)]and N-hydroxysuccinimide [414 mg(3.6 mmol.)]. To the solution was added the compound (341) synthesized in ii) above[661 mg(2.5 mmol.)], and the mixture was stirred at room temperature for 1.5 hour. The reaction mixture was washed with a 1N NaOH aqueous solution.

The organic layer was dried over anhydrous potassium carbonate, then the solvent was distilled off under reduced pressure. The crude product thus obtained was purified by means of a column chromatography(silica gel: 60 g; eluent:ethyl acetate/acetone=5/1) to obtain the object compound(342)[1.37 g (92.0%, a colorless resinous product)].

TLC(Silica Gel ; AcOEt/acetone=5/1): Rf=0.26.

NMR(90MHz,CDCl$_3$) δ: 2.60(2H,t), 2.84(2H,t), 3.2 to 3.8 (8H,m), 4.22(4H,m), 4.62(2H,s), 6.50(1H,br), 6.9 to 7.4(9H,m), 7.79(1H,t), 8.30(1H,br), 8.47(1H,br).

iv) Synthesis of 5-bromo-3-[N-phenyl-N-[2-[2-[2-(1,2,3,4-tetrahydroisoquinolyl)carbonyloxy]ethoxy]ethylcarbamoyl]ethyl]carbamoyl-1-propylpyridinium chloride (343)

To the compound(342) synthesized in iii)[893 mg(1.5 mmol.)]was added 1-iodopropane(30 ml), and the mixture was heated under reflux for 38 hours in nitrogen streams while shielding light. The reaction mixture was cooled and concentrated under reduced pressure. The crude product thus obtained was dissolved in 70% methanol/water(70 ml). The solution was processed with IRA-410(Cl$^-$)[70 ml], followed by further purification by means of a column chromatography(silica gel: 30 g; eluent:chloroform/methanol=6/1) to obtain. the object compound(343)[514 mg(50.8%, pale yellow powder)].

TLC(Silica Gel ; CHCl$_3$:/MeOH=3/1): Rf=0.24.

NMR(90MHz,CDCl$_3$) δ: 0.76(3H,t), 1.85(2H,m), 2.82(4H,m), 3.1 to 3.7(8H,m), 4.22(4H,m), 4.61(2H,s), 4.90(2H,m), 6.9 to 7.5(9H,m), 8.40(1H,br), 9.70(1H,br), 9.87(1H,br)

IR(KBr)cm$^{-1}$: 3415, 1690, 1658, 1595, 1430, 1230, 1120

Production Example 123

5-Bromo-3-[N-phenyl-N-[2-[[2,2-dimethyl-3-(1,2,3,4-tetrahydroisoquinolyl)carbonyloxy]propyl]carbamoyl]ethyl]carbamoyl-1-propylpyridinium chloride (347)

(i) Synthesis of 1-t-butoxycarbonylamino-2,2-dimethyl-3-(1,2,3,4-tetrahydroisoquinolyl)carbonyloxy propane(344)

To a solution of 3-amino-2,2-dimethyl-1-propanol[1.032 g (10 mmol.)]in methylene chloride(20 ml) was added, under ice-cooling, di-t-butyl dicarbonate[2.183 g(10 mmol.)], and the mixture was stirred at room temperature for two hours.

To the above-mentioned reaction mixture was added pyridine [1.618 ml(20 mmol.)] and there was further added, under ice-cooling, phenyl chlorocarbonate[1.254 ml(10 mmol.)], and the mixture was stirred at room temperature for 10 minutes. The reaction mixture was washed with a 5% aqueous solution of sodium hydrogencarbonate. The organic layer was dried over anhydrous sodium sulfate, followed by distilling off the solvent under reduced pressure to obtain a crude carbonate. To this crude carbonate was added 1,2,3,4-tetrahydroisoquinoline [1.377 ml(11 mmol.)], and the mixture was heated at 90° C for one hour. The reaction mixture was cooled, and the crude product thus obtained was purified by means of a column chromatography(silica gel: 120 g; eluent:hexane/ethyl acetate=2.5/1) to afford the object compound(344)[3.417 g (94.3%, a colorless oily product).

TLC(Silica Gel ; n-hexane/AcOEt=2.5/1): Rf=0.35.

NMR(90MHz,CDCl$_3$) δ: 0.91 6H,s), 1.43(9H,s), 2.84(2H,t), 3.02(2H,d), 3.68(2H,t), 3.90(2H,s), 4.63(2H,s), 5.05(1H,br), 7.19(4H,s).

IR(Neat)cm$^-$: 3350, 2970, 1700, 1510, 1470, 1455, 1430, 1392, 1365, 1232, 1170, 1120.

(ii) Synthesis of 1-amino-2,2-dimethyl-3-[(1,2,3,4-tetrahydroisoquinolyl)carbonyloxy]propane(345)

To a solution of the compound(344) synthesized in i) [2.900 g(8 mmol.)]in chloroform(5 ml) was added HCl-saturated methanol(5 ml), and the mixture was stirred at room temperature for 1.5 hour. The reaction mixture was concentrated under reduced pressure to obtain a crude product, to which was added a 1N aqueous solution of sodium hydroxide(25 ml), followed by extraction with chloroform. The organic layer was dried over anhydrous potassium carbonate, then the solvent was distilled off under reduced pressure to obtain the object compound(345)[2.099 g(100%, a pale yellow oily product)].

TLC(Silica Gel ; MeOH/conc. NH$_4$OH=50/1): Rf=0.59

NMR(90MHz,CDCl$_3$) δ: 0.92(6H,s), 1.18(2H,br s), 2.54(2H,s), 2.83(2H,t), 3.68(2H,t), 3.92(2H,s), 4.62(2H,s), 7.14(4H,s). IR(Neat)cm$^-$: 3380, 2950, 1698, 1470, 1450, 1430, 1230, 1120.

(iii) Synthesis of 5-bromo-3-[N-phenyl-N-[2-[[2,2-dimethyl3-(1,2,3,4-tetrahydroisoquinolyl)carbonyloxy]-propyl]carbamoyl]ethyl]carbamoylpyridine (346)

In methylene chloride(10 ml) were dissolved the compound(292) synthesized in Production Example 106-iii)[1.048 g(3 mmol.)], DCC[681 mg(3.3 mmol.)]and N-hydroxysuccinimide[414 mg(3.6 mmol.)]. To the solution was added the compound(345) synthesized in ii) above[656 mg(2.5 mmol.)], and the mixture was stirred at room temperature for one hour. The reaction mixture was washed with a 1N NaOH aqueous solution, and the organic layer was dried over anhdyrous potassium carbonate, followed by distilling off the solvent under reduced pressure. The crude product thus obtained was purified by means of a column chromatography(silica gel: 75 g ; eluent: ethyl acetate/acetone=5/1) to obtain the object compound(346)[1.161 g(78.2%, a colorless resinous product)].

TLC(Silica Gel ; AcOEt): Rf=0.37.

NMR(90MHz,CDCl$_3$) δ: 0.91(6H,s), 2.61(2H,t), 2.84(2H,t),
3.07(2H,d), 3.68(2H,t), 3.89(2H,s), 4.21(2H,t), 4.61(2H,s), 6.67(1H,br t), 6.9 to 7.3(9H,m), 7.78(1H,t), 8.30(1H,br), 8.47(1H,br), (iv) Synthesis of 5-bromo-3-[N-phenyl-N-[2-[[2,2-dimethyl-3-(1,2,3,4-tetrahydroisoquinolyl)carbonyloxy]propyl]carbamoyl]ethyl]carbamoyl-1-propyl-pyridinium chloride (347)

To the compound(346) synthesized in i)[890 mg(1.5 mmol.)]was added 1-iodepropane(30 ml), and the mixture was heated for 64 hours under reflux in nitrogen streams while shielding light. The reaction mixture was cooled and concentrated under reduced pressure, and the resulting crude product was dissolved in 70% methanol/water(70 ml). The solution was processed with IRA-410(Cl$^-$)[70 ml], which was further purified by means of a column chromatography(silica gel: 30 g; eluent:chloroform/methanol=6/1) to obtain the object compound (347)[693 mg(68.7%, pale yellow powder)].

TLC(Silica Gel; CHCl$_3$/MeOH=6/1): Rf=0.30.

NMR(90MHz,CDCl$_3$) δ: 0.76(3H,t), 0.94(6H,s), 1.81(2H,m), 2.6 to 2.9(4H,m), 3.07(2H,d), 3.67(2H,t), 3.87(2H,s), 4.18 (2H,m), 4.60(2H,s), 4.91(2H,m), 6.9 to 7.4(9H,m), 7.67(1H,m), 8.34(1H,br s), 9.64(1H,br s), 9.90(1H,br s).

IR(KBr)cm$^{-}$: 3400, 2955, 1690, 1658, 1595, 1492, 1425, 1225.

Production Example 124

5-Fluoro-3-[N-[2-[[2-(1,2,3,4-tetrahydroisoquinolyl)carbonyloxy]ethyl]carbamoyl]ethyl-N-phenyl]carbamoyl-1-propyl pyridinium chloride(351)

(i) Synthesis of 2,2-dichloro-5-fluoro-3-[N-phenyl-N-[2-[(2-hydroxy)ethyl]carbamoyl]ethyl]carbamoyl-pyridine(348)

To a solutice of the compound(252) synthesized in Production Example 96-i)[1.984 g(6.434 mmol.)]in chloroform/methanol (1/1)(20 ml) was added HCl-saturated methanol(15 ml), and the mixture was stirred at room temperature for one hour. The reaction mixture was concentrated under reduced pressure to give a crude product, to which was added a 1N NaOH-aqueous solution, followed by extraction with ethyl acetate. The organic layer was dried over anhydrous sodium sulfate, then the solvent was distilled off under reduced pressure. The crude product thus obtained was purified by means of a column chromatography(silica gel: 45 g; eluent:ethyl acetate/acetone=2/1) to obtain the object amino compound[1.107 g (82.6%, a white resinous product)].

TLC(Silica Gel; AcOEt/acetone=2/1): Rf=0.25.

In chloroform:(20 ml) were dissolved the above-mentioned amino compound[756 mg(3.63 mmol.)]and triethylamine[2.3 ml (16.5 mmol.)]. To the solution was added, under ice-cooling, an acid chloride synthesized from 2,6-dichloro-5-fluoronicotinic acid[693 mg(3.3 mmol.)]and thionyl chloride(1.2 ml), and the mixture was stirred at room temperature for one hour. The reaction mixture was washed with a 1N NaOH aqueous solution, and the organic layer was dried over anhydrous potassium carbonate, then the solvent was distilled off under reduced pressure. The crude product thus obtained was subjected to purification by means of a column chromatography(silica gel: 40 g; eluent:ethyl acetate/acetone=3/1) to obtain the object compound(348)[576 mg(43.6%, a white resinous product)].

TLC(Silica Gel; ACOEt/acetone=3/1): Rf=0.22.

NMR(90MHz,CDCl$_3$) δ: 2.60(2H,t), 3.37(2H,q), 3.67(2H,t), 4.18(2H,t), 6.85(1H,br t), 7.23(5H,s), 7.40(1H,d)

IR(KBr)cm$^{-}$: 3432, 1660, 1635, 1593, 1397

(ii) Synthesis of 5-fluoro-3-[N-phenyl-N-[2-[(2-hydroxy)ethyl]carbamoyl]ethyl]carbamoylpyridine (349)

To a solution of the compound(348) synthesized in i)[526 mg (1.314 mmol.)]in methanol(20 ml) were added triethylamine [366 mg(2.628 mmol.)]and 5% Pd/C(500 mg). The mixture was subjected to catalystic reduction at room temperature for two days. The reaction mixture was subjected to filtration, and the filtrate was concentrated under reduced pressure. The crude product thus obtained was purified by means of a column chromatography(silica gel: 19 g; eluent:ethyl acetate/acetone=1/2) to obtain the object compound(349) [136 mg(31.2%, a white resinous product)].

TLC(Silica Gel; AcOEt/acetone=1/2): Rf=0.30.

NMR(90MHz,CDCl$_3$) δ: 2.58(2H,t), 3.35(2H,m), 3.64(2H,m), NMR(90MHz,CDCl$_3$) δ: 2.58(2H,t) 4.21(2H,t), 6.88(1H,br), 7.0 to 7.5(6H,m), 8.26(2H,br s).

IR(Neat)cm$^{-}$: 3320, 1663, 1632, 1598, 1500, 1420, 1400, 1302, 1248.

(iii) Synthesis of 5-fluoro-3-[N-[2-[[2-(1,2,3,4-tetrahydroisoquinolyl)carbonyloxy]ethyl]carbamoyl]ethyl-N-phenyl]carbamoylpyridine (350)

In methylene chloride were dissolved the alcohol compound (349) synthesized in ii)[126 mg(0.38 mmol.)]and pyridine [0.061 ml(0.76 nol.)]. To the solution was added, under ice-cooling, phenyl chlorocarbonate[0.057 ml(0.456 mmol.)], and the mixture was stirred at room temperature for 10 minutes. The reaction mixture was washed with a 5% aqueous solution of sodium hydrogencarbonate, then the organic layer was dried over anhydrous sodium sulfate, followed by distilling off the solvent under reduced pressure to obtain a crude carbonate compound. To this crude carbonate compound was added 1,2,3,4-tetrahydroisoquinoline[0.057 ml(1.53 mmol. , and the n1ixture was heated at 90° C. for one hour. The reaction mixture was cooled, and the crude product thus obtained was purified by means of a column chromatography(silica gel: 15 g; eluent:ethyl acetate/acetone=6/1) to obtain the object compound(350)[163 mg (87.4%,a colorless resinous product)].

TLC(Silica Gel; AcOEt/acetone=6/1): Rf=0.25.

NMR(90MHz,CDCl$_3$) δ: 2.59(2H,d), 2.82(2H,t), 3.50(2H,q), 3.66(2H,t), 4.22(4H,m), 4.61(2H,s), 6.62(1H,br), 6.8 to 7.5 (10H,m), 8.28(2H,m).

IR(Neat)cm$^{-}$: 3325, 1700, 1655, 1598, 1498, 1428, 1235.

(iv) Synthesis of 5-fluoro-3-[N-[2-[[2-(1,2,3,4-tetrahydroisoquinolyl)carbonyloxy]ethyl]carbamoyl]ethyl-N-phenyl]carbamoyl-1-propylpyridinium chloride (351)

To the compound(350) synthesized in ii)[153 mg(0.312 mmol.)]was added i-iodopropane(10 ml), and the mixture was heated under reflux for 72 hours in nitrogen streams while shielding light. The reaction mixture was cooled and concentrated under reduced pressure. The crude product thus obtained was dissolved in 70% methanol/water(30 ml), and the solution was processed with IRA-410(Cl$^-$)[30 ml], which was subjected to further purification by means of a column chromatography(silica gel: 7 g; eluent:chloroform/methanol=6/1) to obtain the object compound(351)[118 mg(66.5%, pale yellow powder)].

NMR(90MHz,CDCl$_3$) δ: 0.67(3H,t), 1.76(2H,m), 2.5 to 2.8 (4H,m), 3.2 to 3.8(4H,m), 3.8 to 4.4(4H,m), 4.54(2H,s), 4.77 (2H,m), 7.0 to 7.7(9H,m), 7.9 to 8.4(2H,m), 9.31(1H,br s), 9.64(1H,br s).

Production Example 125

5-Bromo-3-[N-[2-[(2-benzylcarbamoyloxy)ethyl]carbamoyl]ethyl-N-phenyl]carbamoyl-1-propylpyridinium chloride (355) i) Synthesis of 5-Bromo-3-[N-[2[(2-hydroxy)ethyl]carbamoyl]ethyl-N-phenyl]carbamoylpyridine (352)

To a solution of the compound (292) synthesized in Production Example 106-iii) [28.0 g (80.2 mmol]and N-hydroxysuccinimide [12.0 g (104 mmol)]in methylene chloride (400 ml) was added 1-ethyl-3-(3-dimethylaminopropyl)carbodiimide hydrochloride [18.5 g (96.5 mmol)]with stirring at 0° C. The mixture was stirred for 1 hr at room temperature. Ethanolamine [4.84 ml (80.2 mmol)]was added to the mixture. Then, the whole was stirred for 2 hr. The resulting precipitate was removed by decantation, the solution was washed with water, and dried over K$_2$CO$_3$. The solvent was evaporated under reduced pressure and the residue was chromatographed on silica gel using ethyl acetate-acetone (2:1) as eluent, to obtain the compound (352) [21.0 g (66.8%)]as a yellow oil.

IR (Neat) cm$^{-1}$: 3310, 3060, 2940, 1650, 1590.

NMR (200 MHz, CDCl$_3$) δ: 2.60 (2H,t,J=7Hz), 3.41 (2H,q,J=6Hz), 3.72 (2H,q,J=6Hz), 4.25 (2H,t,J=7Hz), 6.22 (1H,br t,J=6Hz), 7.00-7.40 (5H,m), 7.80 (1H,t,J=2Hz), 8.30 (1H,d,J=2Hz), 8.51 (1H,d,J=2Hz).

ii) Synthesis of 5-Bromo-3-[N-[2-[(2-phenoxycarbonyloxy)ethyl]carbamoyl]ethyl-N-phenyl]carbamoylpyridine (353)

In chloroform (300 ml) were dissolved the alcohol compound (352) synthesized in i) [21.0 g (53.5 mmol.)]and pyridine [4.33 ml (53.5 mmol.)]. To the solution was added, under ice-cooling, phenyl chlorocarbonate [13.4 ml (107 mmol.)], and the mixture was stirred at room temperature for 10 minutes. The reaction mixture was washed with 5% aqueous solution of sodium hydrogencarboante, then the organic layer was dried over anhydrous sodium sulfate, followed by distilling off the solvent under reduced pressure. The residue was chromatographed on silica gel using ethyl acetate as eluent, to obtain the compound (353) [20.0 g (72.9%)]as a colorless powder.

IR (KBr) cm$^{-1}$: 3340, 3090, 2930, 1770, 1670, 1630, 1590.

NMR (200 MHz, CDCl$_3$) δ: 2.16 (2H,t,J=7Hz , 3.64 (2H,q,J=6Hz), 4.27 (2H,t,J=7Hz), 4.35 (2H,t,J=6Hz), 6.48 (1H,br t,J=6Hz), 7.00-7.46 (10H,m), 7.85 (1H,t,J=2Hz), 8.32 (1H,d,J=2Hz), 8.50 (1H,d,J=2Hz).

(iii) Synthesis of 5-Bromo-3-[N-[2-[(2-benzylcarbamoyloxy)ethyl]carbamoyl]ethyl-N-phenyl]carbamoylpyridine (354)

A mixture of the carbonate compound (353) synthesized in (ii) [700 mg (1.37 mmol.)]and benzylamine [0.16 ml (1.50 mmol)]was heated at 120° C for 4 hours. After cooling, the crude product was chromatographed on silica gel using ethyl acetate as eluent, to obtain the compound (354) [596 mg (83.0%)]as a pale yellow foam.

IR (KBr) cm$^{-1}$: 3300, 3050, 2950, 1700, 1650, 1640, 1590.

NMR (90 MHz, CDCl$_3$)δ: 2.55 (2H,t,J=7Hz), 3.44 (2H,q,J=6Hz), 4.17 (4H,t,J=7Hz), 4.30 (2H,d,J=6Hz), 5.50 (1H,m), 6.55 (1H,m), 6.80-7.50 (10H,m), 7.78 (1H,t,J=2Hz), 8.30 (1H,d,J=2Hz), 8.44 (1H,d,J=2Hz).

iv) Synthesis of 5-Bromo-3-[N-[2-[(2-benzylcarbamoyloxy)ethyl]carbamoyl]ethyl-N-phenyl]carbamoyl-1-propylpyridinium chloride (355)

To the compound (354) synthesized in iii) [500 mg (0.95 mmol.)]was added n-iodopropane (10 ml), and the mixture was heated under reflux for 18 hours in nitrogen streams while shielding light. The reaction mixture was cooled and concentrated under reduced pressure. The crude product thus obtained was dissolved in 70% methanol/water (50 ml), and the solution was processed with IRA-410 (Cl$^-$) [50 ml], after it was subjected to further purification by means of a column chromatography (silica gel: 50 g; eluent:chloroform/methanol=8/1) to obtain the object compound (355) [418 mg (72.7%)]as a pale yellow powder. IR KBr) cm$^{-1}$: 3420, 3270, 3060, 2920, 1710, 1660, 1590. NMR (200 MHz, CDCl$_3$)δ: 0.73 (3H,t,J=7Hz), 1.80 (2H,m), 2.76 (2H,m), 3.38 (2H,m), 4.08 (2H,m), 4.20 (2H,m), 4.32 (2H,d,J=6Hz), 4.69 (2H,m), 6.56 (1H,m), 6.93-7.57 (10H,m), 8.13 (1H,m), 8.24 (1H,br s), 8.89 (1H,br s), 9.83 (1H,br s).

The carbonate compound (353) synthesized in Product Example 125-ii) was allowed to react with various amines

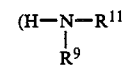

wherein R$^9$ and R$^{11}$ are of the same meaning as defined above) shown in Table 4 by the same procedure as described in Product Example 125-iii), followed by the same treatment as described in Product Example 125-iv), to obtain products (356)-(365) shown in Table 4. The spectra data of these products (356)-(365) are shown in Table 4.

TABLE 4

| Amine used | Product Compound Name | Spectra Data |
|---|---|---|
| diallylamine | 5-Bromo-3-[N-[2-[(2-diallylcarbamoyloxy)ethyl]-carbamoyl]ethyl-N-phenyl]-carbamoyl-1-propylpyridinium chloride (356) | NMR(200 MHz, CDCl$_3$)δ: 0.80 (3H, t, J=7Hz), 1.62-2.00(2H, m), 2.50(2H, t, J=7Hz), 3.48 (2H, q, J=5Hz), 3.86(4H, m), 3.97-4.30(4H, m), 4.80(2H, t, J=6Hz), 4.95-5.37(4H, m), 5.64-5.93(2H, m), 6.79(1H, m), 6.90-7.56(5H, m), 7.70 (1H, m), 8.26(1H, br s), 9.22(1H, br s), 9.69(1H, br s). IR(KBr)cm$^{-1}$: 3300(br), 3250(br), 3060, 1700(br), 1660(br), 1590. |
| allylamine | 5-Bromo-3-[N-[2-[(2-allylcarbamoylocy)ethyl;]-carbamoyl]ethyl-N-phenyl]-carbamoyl-1-propylpyridinium chloride (357) | NMR(200 MHz, CDCl$_3$)δ: 0.78 (3H, m), 1.90(2H, m), 2.75(2H, m), 3.38(2H, m), 3.73(2H, m), 4.08 (2H, m), 4.20(2H, m), 4.82(2H, m), 4.95-5.30(3H, m), 5.80(1H, m), 6.10 (1H, m), 6.90-7.54(5H, m), 8.12 (1H, m), 8.30(1H, br s), 9.18(1H, br s), 9.80(1H, br s). IR(KBr)cm$^{-1}$: 3420(br), 3260(br), 3060, 1710(br), 1660(br), 1600. |
| 2,3,4,5,6-pentafluoroamine | 5-Bromo-3-[N-[2-[[2-(2,3,4,5,6-pentafluorobenzyl)carbamoyloxy]-ethyl]carbamoyl]ethyl-N-phenyl]carbamoyl-1-propyl-pyridinium chloride (358) | NMR(200 MHz, CDCl$_3$)δ: 0.84 (3H, t, J=7Hz), 1.94(2H, m), 2.28 (2H, t, J=6Hz), 3.34(2H, q, J=6Hz), 4.03(2H, d, J=6Hz), 4.22 (2H, t, J=6Hz), 4.42(2H, t, J=6Hz), 4.80(2H, t, J=7Hz), 7.02(1H, m), 7.10-7.56(5H, m), 8.10(1H, m), 8.23 |

TABLE 4-continued

| Amine used | Product Compound Name | Spectra Data |
|---|---|---|
| | | (1H, br s), 8.88(1H, br s), 9.97(1H, br s).<br>IR(KBr)cm$^{-1}$: 3310(br), 3060, 1720 (br), 1650(br), 1590. |
| hexylamine | 5-Bromo-3-[N-[2-[(2-hexycarbamoyloxy)ethyl]carbamoyl]ethyl-N-phenyl]carbamoyl-1-propylpyridinium chloride (359) | NMR(90MHz, CDCl$_3$) δ0.63–0.92(6 H, m)1.27(8H, br s)1.86(2H, m)2,72(2H, m)3.08(2H, t)3.39(2H, m)4.10(4H, m)4.86(2H, t)5.74(1H, br s) 7.2–7.5(5H, m)8.04(1H, br s)8.37(1H, br s)9.43(1H, br s)9.74(1H, br s)<br>IR(KBr) cm$^{-1}$:3358, 2930, 1710, 1655, 1599, 1539, 1495, 1443, 1251 |
| dioctylamine | 5-Bromo-3-[N-[2-[(2-dioctylcarbamoyloxy)ethyl]carbamoyl]ethyl-N-phenyl]carbamoyl-1-propylpyridinium chloride (360) | NMR(90MHz, CDCl$_3$) δ0.7–1.0(9H, m)1.26(24H, br s)1.90(2H, m)2.65(2H, m)3.15(4H, m)3.42(2H, m)4.09(4H, m)4.87(2H, m)7.1–7.5(5H, m) 7.81(1H, br s)8.33(1H, br s)9.50(1H, br s)9.73(1H, br s)<br>IR(KBr) cm$^{-1}$:3313, 3200, 2922, 1687, 1651, 1593, 1553, 1494, 1424, 1230 |
| butylmethylamine | 5-Bromo-3-[N-[2-[(2-butylmethylcarbamoyloxy)ethyl]carbamoyl]ethyl-N-phenyl]carbamoyl-1-propylpyridinium chloride (361) | NMR(90MHz, CDCl$_3$) δ0.76(3H, t) 0.88(3H, t)1.37(4H, m)1.86(2H, m) 2.76(2H, m)2.84(3H, s)3.19(2H, t) 3.38(2H, m)4.13(4H, m)4.88(2H, t) 7.2–7.5(5H, m)8.07(1H, m)8.39(1 H, br s)9.72(2H, br s)<br>IR(KBr)cm$^{-1}$:3429, 3278, 2932, 1854, 1593, 1550, 1495, 1457, 1223 |
| 3,3-dimethylbutylamine | 5-Bromo-3-[N-[2-[[2-(3,3-dimethylbutyl)carbamoyloxy]ethyl]carbamoyl]ethyl-N-phenyl]carbamoyl-1-propylpyridinium chloride (362) | NMR(90MHz, CDCl$_3$) δ0.77(3H, t) 0.90(9H, s)1.34(2H, m)1.86(2H, m) 2.70(2H, t)3.10(2H, m)3.34(2H, m) 4.07(4H, m)4.86(2H, t)5.67(1H, b r s)7.2–7.5(5H, m)8.06(1H, br s) 8.35(1H, br s)9.47(1H, br s)9.78(1H, br s)<br>IR(KBr)cm$^{-1}$:3371, 3281, 2957, 1704, 1655, 1599, 1539, 1494, 1402, 1245 |
| 1,1-dimethylpropylamine | 5-Bromo-3-[N-[2-[[2-(1,1-dimethylpropyl)carbamoyloxy]ethyl]carbamoyl]ethyl-N-phenyl]carbamoyl-1-propylpyridinium chloride (363) | NMR(90MHz, CDCl$_3$) δ0.66–0.82(6 H, m)1.22(6H, s)1.45–1.97(4H, m) 2.71(2H, m)3.35(2H, m)3.98(2H, m) 4.15(2H, m)4.85(2H, t)5.27(1H, b r s)7.2–7.5(5H, m)8.03(1H, br s) 8.41(1H, br s)9.50(1H, br s)9.72(1H, br s)<br>IR(KBr) cm$^{-1}$:3410, 3284, 2935, 1708, 1653, 1593, 1539, 1494, 1400, 1260 |
| 1,5-dimethylhexylamine | 5-Bromo-3-[N-[2-[[2-(1,5-dimethylhexyl)carbamoyloxy]ethyl]carbamoyl]ethyl-N-phenyl]carbamoyl-1-propylpyridinium chloride (364) | NMR(90MHz, CDCl$_3$) δ0.76(3H, m) 0.84(6H, d)1.09(3H, d)1.27(7H, m) 1.86(2H, m)2.73(2H, m)3.36(2H, m) 3.60(1H, m)4.31(4H, m)4.86(2H, t) 5.35(1H, br s)7.2–7.5(5H, m)8.03(1H, br s)8.36(1H, br s)9.50(1H, br s)9.66(1H, br s)<br>IR(KBr) cm$^{-1}$:3365, 3239, 2932, 1701, 1652, 1593, 1530, 1495, 1456, 1239 |
| butylphenylamine | 5-Bromo-3-[N-[2-[(2-butylphenylcarbamoyloxy)ethyl]carbamoyl]ethyl-N-phenyl]carbamoyl-1-propylpyridinium chloride (365) | NMR(90MHz, CDCl$_3$) δ0.75(3H, t) 0.90(3H, t)1.1–2.0(6H, m)2.70(2 H, m)3.33(6H, m)4.13(2H, m)4.78(2 H, t)6.5–7.4(10H, m)8.02(1H, br s) 8.27(1H, br s)9.23(1H, br s)9.68(1H, br s)<br>IR(KBr) cm$^{-1}$:3400, 3250, 2962, 1653, 1594, 1543, 1495, 1442, 1225 |

What is claimed is:

1. A compound of the formula (I):

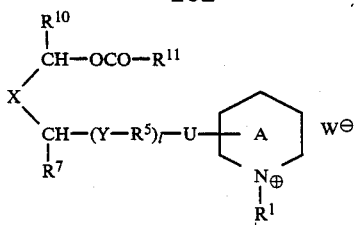

wherein

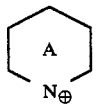

is a pyridinium ring unsubstituted or substituted by one to four members selected from the class consisting of a halogeno group, a lower alkyl group, a lower alkoxy group, a nitro group, a cyano group, a lower alkoxycarbonyl group, a carbamoyl group and lower alkyl carbamoyl group;
$R^1$ is a lower alkyl group, a phenyl-lower alkyl group or a naphthyl-lower alkyl group;
$R^7$ and $R^{10}$ are independently hydrogen, a lower alkyl group, a phenyl-lower alkyl group, a naphthyl-lower alkyl group or aromatic hydrocarbon group selected from the class consisting of phenyl, naphthyl, phenanthryl and anthryl;
p is 0 or 1;
$R^5$ is a phenylene group or an alkylene group unsubstituted or substituted by a lower alkyl group;
$R^{11}$ is a 1,2,3,4-tetrahydro-2-isoquinolyl, 1,2,3,4-tetrahydro-1-quinolyl or 1,2,3,4-tetrahydro-2-quinolyl group;
X is a group of the formula: $-CH_2OCH_2-$ or a group of the formula:

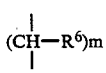

wherein $R^6$ is hydrogen, a lower alkyl or a lower alkoxy group, and m is an integer of 0 to 3;
U is a group of the formula:

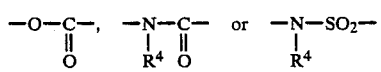

wherein $R^4$ is hydrogen, a lower alkyl group, a phenyl-lower alkyl group, a naphthyl-lower alkyl group or aromatic hydrocarbon group selected from the class consisting of phenyl, naphthyl, phenanthryl and anthryl;
Y is a divalent chain group consisting of one to six members selected from the class consisting of groups of the formulae:

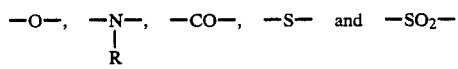

wherein R is hydrogen, a lower alkyl group, acyl group or aromatic hydrocarbon group selected from the class consisting of phenyl, naphthyl, phenanthryl and anthryl, and at least one of which is a group of the formula:

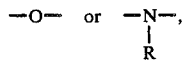

with the proviso that the R groups may be the same or different from each other and
$W^\ominus$ is a pharmacologically acceptable anion selected from the class consisting of chloride ion, bromide ion, iodide ion, sulfate ion, nitrate ion, phosphate ion, acetate ion, tosylate ion and mesylate ion.

2. A compound according to claim 1, wherein

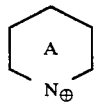

is a pyridinium ring which is substituted by one to two members selected from the class consisting of a halogeno group, a lower alkyl group, a lower alkoxy group, a nitro group, a cyano group, a lower alkoxy carbonyl group, a carbamoyl group and lower alkyl carbamoyl group.

3. A compound according to claim 1, wherein

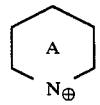

is a pyridinium ring which is substituted by one halogeno group at the 5-position.

4. A compound according to claim 1, wherein U is bonded to the 2- to 4-position of the pyridinium ring.

5. A compound according to claim 1, wherein U is bonded to the 3-position of the pyridinium ring.

6. A compound according to claim 1, wherein Y is a group of the formula:

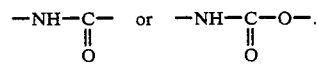

7. A compound according to claim 1, wherein $R^1$ is a lower alkyl group.

8. A compound according to claim 1, wherein U is a group of the formula:

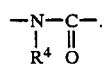

9. A compound according to claim 8, wherein $R^4$ is a phenyl group unsubstituted by a halogeno group.

10. A compound according to claim 1, wherein l is 1.

11. A compound according to claim 1, wherein $R^5$ is an alkylene group unsubstituted or substituted by a lower alkyl group.

12. A compound according to claim 1, wherein $R^5$ is an ethylene group or trimethylene group.

13. A compound according to claim 1, wherein $R^7$ is hydrogen.

14. A compound according to claim 1, wherein $R^{10}$ is hydrogen.

15. A compound according to claim 1, wherein X is a group of the formula: —(CH$_2$)$_m$— wherein m is 0 or 1.

16. A compound according to claim 1, wherein w$^\ominus$ is a halogeno ion.

17. A compound according to claim 1, wherein R$^1$ is a lower alkyl group, U is a group of the formula:

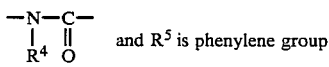 and R$^5$ is phenylene group or alkylene group.

18. A compound according to claim 1, which is a compound of the formula:

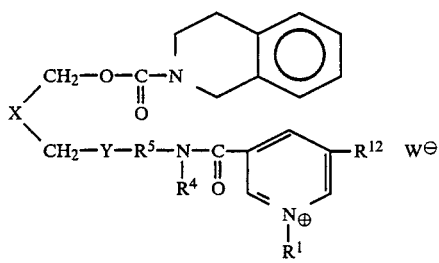

wherein

R$^1$ is a lower alkyl group;

R$^4$ is a phenyl group unsubstituted or substituted by a halogen group;

R$^5$ is ethylene group or trimethylene group;

R$^{12}$ is a halogeno group;

X is a group of the formula: —(CH$_2$)$_m$— wherein m is 0 or 1 W$\theta$ is a halogeno ion;

Y is a group of the formula:

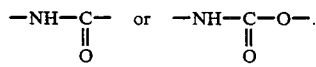

19. A compound according to claim 1, which is 5-bromo-3-[N-[2-[[2-(1,2,3,4-tetrahydroisoquinolyl)carbonyloxy]ethyl]carbamoyl]ethyl-N-phenyl]carbamoyl-1-propylpyridinium chloride.

20. A compound according to claim 1, which is 5-chloro-3-[N-[2-[[2-(1,2,3,4-tetrahydroisoquinolyl)carbonyloxy]ethyl]carbamoyl]ethyl-N-phenyl]carbamoyl-1-propylpyridinium chloride.

21. A compound according to claim 1, wherein Y is a divalent chain group selected from the class consisting of groups of the formulae:

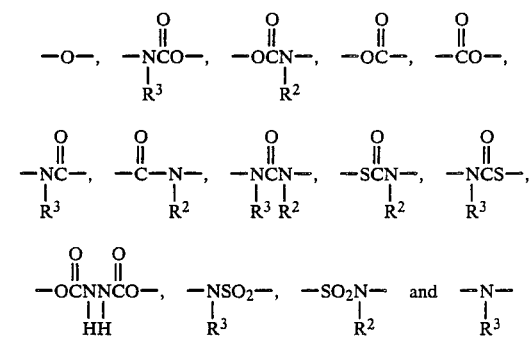

wherein R$^2$ and R$^3$ are independently hydrogen, a lower alkyl group, acyl group or aromatic hydrocarbon group selected from the class consisting of phenyl, naphthyl, phenanthryl and anthryl.

22. A compound according to claim 21, wherein an acyl group represented by R$^2$ and R$^3$ is a lower alkanoyl group or benzoyl.

23. A pharmaceutical composition suitable for inhibiting activity of platelet activating factor which comprises
   (a) as the active ingredient, an amount effective to inhibit activity of platelet activating factor of a compound as claimed in claim 1 and
   (b) a pharmaceutically acceptable carrier or excipient therefor.

24. A method for inhibiting activities of platelet activating factor in a mammal, which comprises administering to said mammal an amount effective to inhibit activities of platelet activating factor of a compound as claimed in claim 1.

* * * * *